US012640231B2

(12) United States Patent
Mueller

(10) Patent No.: US 12,640,231 B2
(45) Date of Patent: May 26, 2026

(54) CELL-FREE DETECTION OF METHYLATED BREAST TUMOR

(71) Applicants: QUEEN'S UNIVERSITY AT KINGSTON, Kingston (CA); INSTITUT CURIE, Paris (FR); INSTITUT NATIONAL DE LA SANTE ET DE LA RECHERCHE MEDICALE (INSERM), Paris (FR)

(72) Inventor: Christopher R. Mueller, Kingston (CA)

(73) Assignees: QUEEN'S UNIVERSITY AT KINGSTON, Kingston (CA); INSTITUT CURIE, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 18/632,749

(22) Filed: Apr. 11, 2024

(65) Prior Publication Data

US 2024/0274232 A1      Aug. 15, 2024

Related U.S. Application Data

(63) Continuation of application No. 16/098,455, filed as application No. PCT/CA2017/000111 on May 4, 2017, now Pat. No. 12,300,356.

(60) Provisional application No. 62/331,585, filed on May 4, 2016.

(51) Int. Cl.
| | |
|---|---|
| *C12Q 1/6886* | (2018.01) |
| *C12Q 1/6827* | (2018.01) |
| *G16B 25/00* | (2019.01) |
| *G16B 25/10* | (2019.01) |
| *G16B 30/00* | (2019.01) |
| *G16B 35/00* | (2019.01) |
| *G16B 99/00* | (2019.01) |

(52) U.S. Cl.
CPC ........... *G16B 30/00* (2019.02); *C12Q 1/6827* (2013.01); *C12Q 1/6886* (2013.01); *G16B 25/00* (2019.02); *G16B 25/10* (2019.02); *G16B 35/00* (2019.02); *G16B 99/00* (2019.02); *C12Q 2600/106* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 6,582,908 | B2 | 6/2003 | Fodor et al. |
| 2009/0075260 | A1 | 3/2009 | Distler et al. |
| 2009/0305256 | A1 | 12/2009 | Pfeifer et al. |
| 2012/0064521 | A1 | 3/2012 | Yen et al. |
| 2012/0219946 | A1 | 8/2012 | Laird et al. |
| 2013/0084328 | A1 | 4/2013 | Perera |
| 2015/0119350 | A1 | 4/2015 | Kebebew et al. |

FOREIGN PATENT DOCUMENTS

| | | |
|---|---|---|
| WO | 2013/177265 A1 | 11/2013 |
| WO | 2014/043763 A1 | 3/2014 |
| WO | 2014/164874 A2 | 10/2014 |
| WO | 2015/159292 A2 | 10/2015 |

OTHER PUBLICATIONS

Office Action issued Dec. 20, 2023 in European patent application No. 17 801 856.0.
Office Action issued Feb. 21, 2023 in European Patent Application No. 17 801 856.0.
Office Action issued Nov. 19, 2021 in European Patent Application No. 17 801 856.0.
Office Action issued Oct. 2, 2020 in European Patent Application No. 17 801 856.0.
International Search Report issued Aug. 29, 2017 in PCT/CA2017/000111.
Written Opinion of the International Searching Authority, issued Aug. 29, 2017 in PCT/CA2017/000111.
Office Action issued Apr. 4, 2023 in Canadian Patent Application No. 3,023,335.
Carson, et al., "Development and initial clinical correlation of a DNA methylation-based blood test for prostate cancer," *The Prostate*, 2020, 80: 1038-1042.
Cristall, et al., "A DNA methylation-based liquid biopsy for triple-negative breast cancer," *Precision Oncology*, (2021) 5:53.
Walsh et al. (Genes & Development (1999) vol. 13, pp. 26-36) (Year: 1999).
Zhang et al. (Hepatol Int 2013 vol. 7 p. 893) (Year: 2013).
Feng (PNAS 2010 vol. 107 No. 19 pp. 8689-8694) (Year: 2010).

(Continued)

*Primary Examiner* — Katherine D Salmon
(74) *Attorney, Agent, or Firm* — Greenblum & Bernstein, P.L.C.

(57) ABSTRACT

Provided herein is a method for detecting a tumour that can be applied to cell-free samples, to cell-free detect circulating tumour DNA. The method utilizes detection of adjacent methylation signals within a single sequencing read as the basic positive tumour signal, thereby decreasing false positives. The method comprises extracting DNA from a cell-free sample obtained from a subject, bisulphite converting the DNA, amplifying regions methylated in cancer (CpG islands, CpG shores, and/or CpG shelves), generating sequencing reads, and detecting tumour signals. To increase sensitivity, biased primers designed based on bisulphite converted methylated sequences can be used. Target methylated regions can be selected from a pre-validated set according to the specific aim of the test. Absolute number, proportion, and/or distribution of tumour signals may be used for tumour detection or classification. The method is also useful in, predicting, prognosticating, and/or monitoring response to treatment, tumour load, relapse, cancer development, or risk.

3 Claims, 35 Drawing Sheets

Specification includes a Sequence Listing.

(56) References Cited

OTHER PUBLICATIONS

Legendre et al., Whole-genome bisulfate sequencing of cell-free DNA identifies signature associated with metastatic breast cancer, *Clinical Epigenetics*, 2015, vol. 7, No. 100.

Farkas et al., "Genome-wide DNA methylation assay reveals novel candidate biomarker genes in cervical cancer," *Epigenetics*, Nov. 2013, vol. 8, No. 11, pp. 1213-1225.

Haldrup et al., "DNA Methylation Signatures for of Biochemical Recurrence After Radical Prostatectomy of Clinically Localized Prostate Cancer," *J. Clin Oncol*, Sep. 10, 2013, vol. 31, No. 26, pp. 3250-3258.

Tommasi et al., "Methylation of homeobox genes is a frequent and early epigenetic event in breast cancer," *Breast Cancer Research*, Feb. 27, 2009, vol. 11, No. 1.

Fackler et al., "Novel Methylated Biomarkers and a Robust Assay to Detect Circulating Tumor DNA in Metastatic Breast Cancer," *Cancer Research*, Oct. 17, 2014, vol. 74, No. 8, pp. 2160-2170.

Ellinger et al., "CpG Island Hypermethylation in Cell-Free Serum DNA Identifies Patients With Localized Prostate Cancer," *The Prostate*, 2008, vol. 68, pp. 42-49.

Schwarzenbach et al., "Circulating DNA as biomarker in breast cancer," *Breast Cancer Research*, 2015, vol. 17, No. 136.

Lehmann-Wermann et al., "Identification of tissue-specific cell death using methylation patterns of circulating DNA," *Proceedings of the National Academy of Sciences*, vol. 113, No. 13, pp. E1826-E1834, Mar. 14, 2015.

Anonymous, "Infinium(R) HumanMethylation450 BeadChip," Mar. 9, 2012.

Office Action issued Sep. 2, 2024 in European patent application No. 17801856.0.

| | Area | Std. Error | 95% CI | P value |
|---|---|---|---|---|
| cg03257575 | 0.8773 | 0.01278 | 0.8523 to 0.9024 | < 0.0001 |
| cg25764893 | 0.96 | 0.008397 | 0.9336 to 0.9664 | < 0.0001 |
| cg25191618 | 0.9281 | 0.01008 | 0.9084 to 0.9458 | < 0.0001 |
| cg22336008 | 0.9088 | 0.01063 | 0.8882 to 0.9305 | < 0.0001 |
| cg12071888 | 0.9168 | 0.01006 | 0.8971 to 0.9365 | < 0.0001 |
| cg04550737 | 0.9012 | 0.01089 | 0.8799 to 0.9225 | < 0.0001 |
| cg22677509 | 0.8984 | 0.01146 | 0.8769 to 0.9209 | < 0.0001 |
| cg17816394 | 0.9136 | 0.01019 | 0.8936 to 0.9336 | < 0.0001 |
| cg05099508 | 0.9182 | 0.01046 | 0.8977 to 0.9387 | < 0.0001 |
| cg22831607 | 0.8864 | 0.01502 | 0.8569 to 0.8958 | < 0.0001 |
| cg21384402 | 0.8963 | 0.01125 | 0.8742 to 0.9183 | < 0.0001 |
| cg15556502 | 0.9087 | 0.01014 | 0.8888 to 0.9286 | < 0.0001 |
| cg19697940 | 0.8473 | 0.01317 | 0.8214 to 0.8731 | < 0.0001 |
| cg13691247 | 0.8976 | 0.01212 | 0.8738 to 0.9213 | < 0.0001 |
| cg13879483 | 0.9415 | 0.008398 | 0.9250 to 0.9579 | < 0.0001 |
| cg01940855 | 0.8454 | 0.0144 | 0.8171 to 0.8736 | < 0.0001 |
| cg27398263 | 0.865 | 0.01322 | 0.8391 to 0.8909 | < 0.0001 |
| cg13631572 | 0.8666 | 0.01321 | 0.8297 to 0.8815 | < 0.0001 |
| cg04368094 | 0.8967 | 0.01107 | 0.8750 to 0.9184 | < 0.0001 |
| cg05527869 | 0.8242 | 0.01534 | 0.7941 to 0.8543 | < 0.0001 |
| cg03348978 | 0.8991 | 0.01093 | 0.8776 to 0.9205 | < 0.0001 |
| cg20945565 | 0.8479 | 0.01321 | 0.8220 to 0.8738 | < 0.0001 |
| cg15146859 | 0.9161 | 0.01115 | 0.8942 to 0.9379 | < 0.0001 |
| cg06537894 | 0.9344 | 0.00961 | 0.9055 to 0.9433 | < 0.0001 |
| cg22473620 | 0.8525 | 0.01338 | 0.8263 to 0.8787 | < 0.0001 |
| cg00778995 | 0.8738 | 0.01229 | 0.8497 to 0.8979 | < 0.0001 |
| cg13356895 | 0.8288 | 0.01579 | 0.7969 to 0.8578 | < 0.0001 |
| cg23448584 | 0.8714 | 0.01422 | 0.8435 to 0.8993 | < 0.0001 |
| cg09260891 | 0.9309 | 0.00953 | 0.9122 to 0.9495 | < 0.0001 |
| cg19127283 | 0.8919 | 0.01179 | 0.8688 to 0.9150 | < 0.0001 |
| cg00442112 | 0.8498 | 0.014 | 0.8223 to 0.8772 | < 0.0001 |
| cg14866200 | 0.8071 | 0.01626 | 0.7753 to 0.8390 | < 0.0001 |
| cg24154833 | 0.958 | 0.00663 | 0.9450 to 0.9710 | < 0.0001 |
| cg03205103 | 0.9322 | 0.009127 | 0.9143 to 0.9501 | < 0.0001 |
| cg18148997 | 0.9154 | 0.01079 | 0.8942 to 0.9365 | < 0.0001 |
| cg08516513 | 0.9184 | 0.01039 | 0.8980 to 0.9387 | < 0.0001 |
| cg05766140 | 0.908 | 0.01147 | 0.8855 to 0.9305 | < 0.0001 |
| cg14151259 | 1 | 0 | 1.000 to 1.000 | < 0.0001 |
| cg00124375 | 0.8782 | 0.01189 | 0.8529 to 0.8995 | < 0.0001 |
| cg25459558 | 0.8939 | 0.01131 | 0.8718 to 0.9161 | < 0.0001 |
| cg27363327 | 0.8514 | 0.01377 | 0.8244 to 0.8784 | < 0.0001 |
| cg13315970 | 0.8697 | 0.01282 | 0.8446 to 0.8948 | < 0.0001 |
| cg21684012 | 0.8854 | 0.01139 | 0.8631 to 0.9078 | < 0.0001 |
| cg16924337 | 0.8455 | 0.01437 | 0.8173 to 0.8736 | < 0.0001 |
| cg14045873 | 0.8401 | 0.01494 | 0.8108 to 0.8694 | < 0.0001 |
| cg00158528 | 0.8997 | 0.01093 | 0.8782 to 0.9211 | < 0.0001 |
| cg25832771 | 0.8648 | 0.01255 | 0.8398 to 0.8893 | < 0.0001 |

Fig. 3

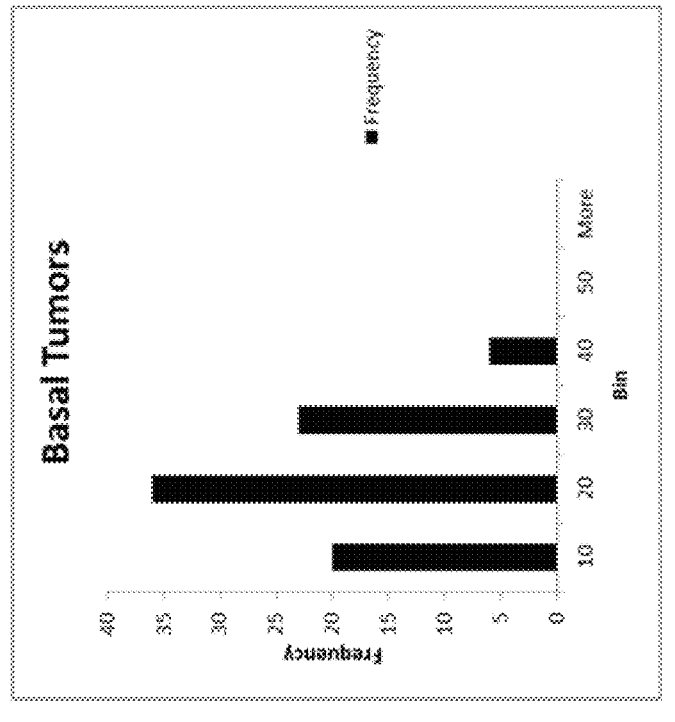
Panel B
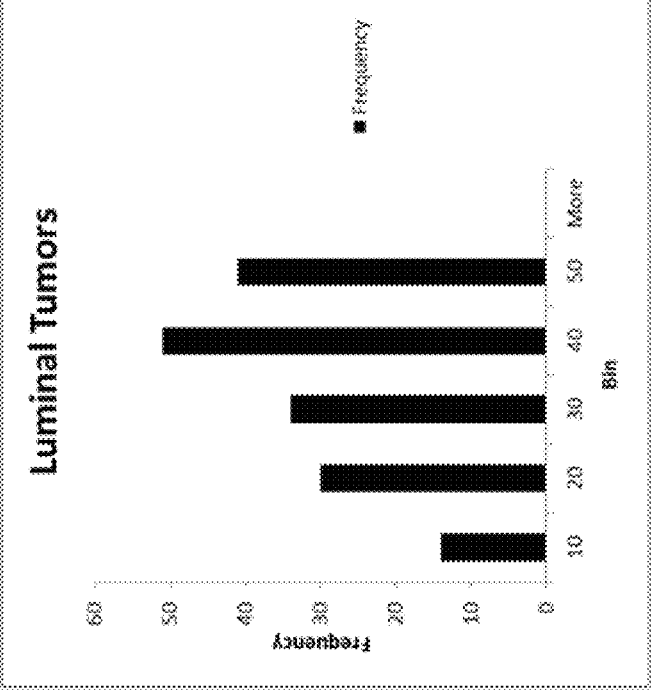
Panel A
Fig. 4

| Reference | MCF7 # Reads | MCF7 Mean Me | SKBR3 # Reads | SKBR3 Mean Me | T47D # Reads | T47D Mean Me | MDA MB 231 # Reads | MDA MB 231 Mean Me | MCF10A # Reads | MCF10A Mean Me | hTert # Reads | hTert Mean Me |
|---|---|---|---|---|---|---|---|---|---|---|---|---|
| ADCYFtrim | 204 | 0.968 | 351 | 0.975 | 334 | 0.965 | 40 | 0.781 | 603 | 0.475 | 175 | 0.548 |
| ADCYGtrim | 121 | 0.975 | 219 | 0.981 | 218 | 0.967 | 30 | 0.862 | 427 | 0.522 | 121 | 0.627 |
| ADCYHtrim | 0 | 0 | 0 | 0 | 0 | 0 | 0 | 0 | 0 | 0 | 0 | 0 |
| C1Dtrim | 1597 | 0.942 | 1184 | 0.922 | 1047 | 0.832 | 418 | 0.916 | 215 | 0.575 | 104 | 0.933 |
| C1Etrim | 1423 | 0.784 | 1976 | 0.68 | 726 | 0.762 | 746 | 0.999 | 2289 | 0.675 | 118 | 0.149 |
| C1Ftrim | 1545 | 0.937 | 1156 | 0.919 | 995 | 0.8 | 418 | 0.916 | 214 | 0.758 | 100 | 0.917 |
| C1Gtrim | 1477 | 0.615 | 1980 | 0.646 | 890 | 0.529 | 568 | 0.928 | 700 | 0.501 | 158 | 0.032 |
| MIRBtrim | 300 | 0.783 | 383 | 0.024 | 315 | 0.711 | 311 | 0.78 | 507 | 0.251 | 458 | 0.073 |
| MIRCtrim | 374 | 0.916 | 448 | 0.565 | 471 | 0.884 | 118 | 0.559 | 858 | 0.49 | 929 | 0.643 |
| MIRDtrim | 145 | 0.954 | 6 | 0.148 | 258 | 0.856 | 118 | 0.989 | 134 | 0.189 | 10 | 0.126 |
| MIREtrim | 2078 | 0.976 | 524 | 0.614 | 1295 | 0.965 | 536 | 0.946 | 1818 | 0.484 | 172 | 0.305 |
| MIRFtrim | 170 | 0.895 | 68 | 0.196 | 115 | 0.798 | 14 | 0.801 | 144 | 0.279 | 167 | 0.397 |
| VWCJtrim | 635 | 0.915 | 195 | 0.239 | 1329 | 0.633 | 205 | 0.903 | 261 | 0.622 | 102 | 0.281 |
| VWCKtrim | 44 | 0.975 | 23 | 0.279 | 98 | 0.764 | 7 | 0.971 | 114 | 0.599 | 15 | 0.603 |
| VWCLtrim | 1786 | 0.909 | 747 | 0.472 | 2805 | 0.733 | 125 | 0.896 | 4493 | 0.806 | 2253 | 0.566 |
| VWCMtrim | 952 | 0.964 | 632 | 0.275 | 943 | 0.784 | 1051 | 0.788 | 1408 | 0.767 | 63 | 0.67 |
| VWCNtrim | 1062 | 0.934 | 220 | 0.254 | 1764 | 0.603 | 291 | 0.855 | 326 | 0.659 | 111 | 0.39 |
| CHSAtrim | 223 | 0.914 | 66 | 0.012 | 259 | 0.485 | 7 | 0.048 | 191 | 0.009 | 52 | 0.007 |
| CHSBtrim | 1387 | 0.928 | 5 | 0.02 | 1840 | 0.776 | 0 | 0 | 2 | 0 | 30 | 0 |
| CHSCtrim | 1847 | 0.918 | 108 | 0.016 | 2421 | 0.772 | 59 | 0.006 | 205 | 0.007 | 220 | 0.021 |
| CHSDtrim | 1357 | 0.928 | 5 | 0.02 | 1761 | 0.778 | 0 | 0 | 3 | 0 | 30 | 0 |
| DMBAtrim | 0 | 0 | 0 | 0 | 2 | 0.269 | 0 | 0 | 0 | 0 | 0 | 0 |
| DMBBtrim | 1120 | 0.965 | 113 | 0.098 | 1117 | 0.956 | 885 | 0.955 | 1792 | 0.803 | 2976 | 0.515 |
| DMBCtrim | 795 | 0.971 | 105 | 0.162 | 874 | 0.959 | 814 | 0.964 | 1404 | 0.799 | 2324 | 0.553 |
| FOXAtrim | 481 | 0.871 | 417 | 0.636 | 362 | 0.741 | 169 | 0.001 | 280 | 0.512 | 50 | 0.143 |
| FOXBtrim | 30 | 0.878 | 0 | 0 | 123 | 0.79 | 39 | 0.043 | 4 | 0.167 | 49 | 0.418 |
| FOXCtrim | 0 | 0 | 0 | 0 | 0 | 0 | 1 | 0 | 0 | 0 | 0 | 0 |
| FOXDtrim | 316 | 0.97 | 321 | 0.9 | 496 | 0.885 | 450 | 0.329 | 259 | 0.696 | 627 | 0.783 |
| FOXEtrim | 636 | 0.98 | 1040 | 0.951 | 938 | 0.956 | 800 | 0.88 | 588 | 0.881 | 1128 | 0.906 |
| HOXAAtrim | 1969 | 0.949 | 1561 | 0.088 | 2319 | 0.726 | 796 | 0.902 | 1639 | 0.678 | 1911 | 0.734 |
| HOXABtrim | 2006 | 0.958 | 1703 | 0.305 | 2460 | 0.802 | 780 | 0.924 | 1676 | 0.714 | 1943 | 0.775 |
| HOXACtrim | 13 | 0.85 | 48 | 0.246 | 81 | 0.749 | 135 | 0.841 | 79 | 0.744 | 44 | 0.934 |
| HOXADtrim | 469 | 0.935 | 1108 | 0.395 | 701 | 0.829 | 173 | 0.911 | 543 | 0.295 | 497 | 0.368 |
| SFRAtrim | 594 | 0.901 | 220 | 0.123 | 667 | 0.884 | 662 | 0.978 | 641 | 0.565 | 491 | 0.252 |
| SFRBtrim | 1061 | 0.959 | 0 | 0 | 1046 | 0.946 | 325 | 0.997 | 778 | 0.719 | 629 | 0.4 |
| SFRCtrim | 1256 | 0.984 | 173 | 0.306 | 1254 | 0.968 | 1292 | 0.998 | 853 | 0.689 | 458 | 0.633 |
| SFRDtrim | 643 | 0.867 | 231 | 0.023 | 728 | 0.823 | 731 | 0.926 | 666 | 0.49 | 503 | 0.219 |
| SFREtrim | 1195 | 0.955 | 0 | 0 | 1170 | 0.936 | 307 | 0.997 | 875 | 0.62 | 815 | 0.137 |
| TTBAtrim | 419 | 0.968 | 100 | 0.04 | 674 | 0.77 | 400 | 0.766 | 205 | 0.206 | 478 | 0.343 |
| TTBBtrim | 381 | 0.946 | 0 | 0 | 457 | 0.74 | 242 | 0.933 | 9 | 0.4 | 383 | 0.134 |
| TTBCtrim | 198 | 0.967 | 1 | 1 | 199 | 0.64 | 59 | 0.844 | 15 | 0.4 | 42 | 0.291 |
| TTBDtrim | 656 | 0.974 | 4 | 0.2 | 557 | 0.866 | 377 | 0.957 | 19 | 0.649 | 25 | 0.874 |
| 4th Generation | | | | | | | | | | | | |
| mbBARHL2 Trim | 73 | 0.968 | 50 | 0.515 | | | 76 | 0.961 | 811 | 0.883 | 159 | 0.976 |
| mbBOLL Trim | 46 | 0.974 | 53 | 0.954 | | | 16 | 0.935 | 234 | 0.759 | 54 | 0.873 |
| mbC5orf Trim | 26 | 0.832 | 14 | 0.842 | | | 15 | 0.886 | 1077 | 0.983 | 661 | 0.745 |
| mbCDO Trim | 44 | 0.95 | 59 | 0.556 | | | 48 | 0.988 | 523 | 0.517 | 373 | 0.95 |
| mbCOL1 Trim | 297 | 0.966 | 522 | 0.857 | | | 496 | 0.984 | 917 | 0.841 | 348 | 0.552 |
| mbCYTL Trim | 23 | 0.804 | 3 | 0.778 | | | 4 | 0.25 | 251 | 0.561 | 118 | 0.164 |
| mbDDAH Trim | 5 | 0.4 | 0 | 0 | | | 0 | 0 | 59 | 0.571 | 1 | 0.4 |
| mbDMRTA Trim | 48 | 0.964 | 59 | 0.199 | | | 106 | 0.907 | 517 | 0.811 | 346 | 0.714 |
| mbEGFLAM Trim | 76 | 0.936 | 11 | 0 | | | 66 | 0.867 | 826 | 0.632 | 15 | 0.35 |
| mbGABRA A Trim | 1 | 0.909 | 0 | 0 | | | 11 | 0.873 | 15 | 0.713 | 4 | 0.907 |
| mbGABRA B Trim | 55 | 0.786 | 26 | 0.433 | | | 54 | 0.854 | 557 | 0.682 | 78 | 0.451 |
| mbGNG Trim | 67 | 0.971 | 45 | 0.859 | | | 44 | 0.966 | 222 | 0.931 | 131 | 0.974 |
| mbID4 Trim | 40 | 0.967 | 111 | 0.81 | | | 42 | 0.607 | 264 | 0.909 | 91 | 0.6 |
| mbIRF Trim | 151 | 0.953 | 0 | 0 | | | 112 | 0.895 | 593 | 0.731 | 81 | 0.318 |
| mbNTSE Trim | 136 | 0.957 | 63 | 0.695 | | | 3 | 0.6 | 502 | 0.757 | 0 | 0 |
| mbPDE4 Trim | 58 | 0.922 | 25 | 0.485 | | | 40 | 1 | 503 | 0.691 | 93 | 0.625 |
| mbPOU3F Trim | 178 | 0.776 | 122 | 0.432 | | | 132 | 0.59 | 1439 | 0.695 | 382 | 0.656 |
| mbRUSC Trim | 18 | 0.902 | 71 | 0.902 | | | 27 | 0.984 | 916 | 0.946 | 136 | 0.514 |
| mbSCAND Trim | 111 | 0.014 | 116 | 0.022 | | | 249 | 0.808 | 463 | 0.044 | 238 | 0.039 |

Fig. 12A

| Reference | MCF7 Reads Exp. | MCF7 Mn. Meth. | SKBR3 Reads Exp. | SKBR3 Mn. Meth. | T47D Reads Exp. | T47D Mn. Meth. | MDA MB 231 Reads Exp. | MDA MB 231 Mn. Meth. | MCF10A Reads Exp. | MCF10A Mn. Meth. | hTert Reads Exp. | hTert Mn. Meth. |
|---|---|---|---|---|---|---|---|---|---|---|---|---|
| mbSHISA Trim | 208 | 0.958 | 0 | 0 | | | 0 | 0 | 648 | 0.786 | 7 | 0.167 |
| mbSIM A Trim | 144 | 0.966 | 219 | 0.928 | | | 53 | 0.997 | 374 | 0.848 | 228 | 0.742 |
| mbSIM B Trim | 45 | 0.978 | 103 | 0.728 | | | 113 | 0.997 | 293 | 0.944 | 334 | 0.652 |
| mbSLC Trim | 236 | 0.96 | 38 | 0.23 | | | 8 | 0 | 740 | 0.938 | 52 | 0.976 |
| mbTAL Trim | 300 | 0.939 | 115 | 0.467 | | | 84 | 0.699 | 351 | 0.664 | 411 | 0.772 |
| mbTBX15 Trim | 51 | 0.954 | 9 | 0.358 | | | 41 | 0.897 | 144 | 0.516 | 76 | 0.505 |
| mbTRIM A Trim | 21 | 0.939 | 40 | 0.619 | | | 23 | 0.664 | 77 | 0.608 | 65 | 0.422 |
| mbTRIM B Trim | 118 | 0.97 | 167 | 0.892 | | | 95 | 0.915 | 298 | 0.735 | 133 | 0.619 |
| pbBARHL Trim | 55 | 0.932 | 69 | 0.222 | | | 94 | 0.83 | 515 | 0.762 | 138 | 0.779 |
| pbBOLL Trim | 35 | 0.942 | 18 | 0.719 | | | 18 | 0.681 | 151 | 0.803 | 336 | 0.66 |
| pbCDO Trim | 56 | 0.852 | 81 | 0.149 | | | 62 | 0.824 | 176 | 0.244 | 147 | 0.569 |
| pbCOL1 Trim | 302 | 0.965 | 522 | 0.867 | | | 496 | 0.985 | 890 | 0.863 | 348 | 0.615 |
| pbCYTL Trim | 39 | 0.842 | 29 | 0.913 | | | 7 | 0.25 | 207 | 0.239 | 60 | 0.104 |
| pbCorf Trim | 26 | 0.86 | 21 | 0.838 | | | 13 | 0.904 | 1171 | 0.979 | 785 | 0.687 |
| pbDDAH Trim | 5 | 0.4 | 0 | 0 | | | 0 | 0 | 60 | 0.585 | 1 | 0 |
| pbDMRTA Trim | 61 | 0.956 | 31 | 0.276 | | | 46 | 0.977 | 83 | 0.583 | 64 | 0.732 |
| pbEGFLAM Trim | 43 | 0.944 | 0 | 0 | | | 40 | 0.879 | 256 | 0.664 | 13 | 0.528 |
| pbGABRA Trim | 161 | 0.717 | 68 | 0.222 | | | 114 | 0.849 | 1092 | 0.686 | 156 | 0.417 |
| pbGNG Trim | 125 | 0.952 | 116 | 0.869 | | | 48 | 1 | 359 | 0.794 | 107 | 0.988 |
| pbID4 A Trim | 44 | 0.96 | 104 | 0.911 | | | 36 | 0.847 | 562 | 0.944 | 242 | 0.805 |
| pbID4 B Trim | 70 | 0.929 | 159 | 0.909 | | | 4 | 0.663 | 318 | 0.977 | 43 | 0.902 |
| pbIRF4 Trim | 79 | 0.96 | 0 | 0 | | | 36 | 0.961 | 392 | 0.847 | 211 | 0.703 |
| pbPDE4 Trim | 33 | 0.735 | 20 | 0 | | | 22 | 0.659 | 720 | 0.638 | 149 | 0.675 |
| pbPOU3F Trim | 196 | 0.696 | 135 | 0.056 | | | 144 | 0.184 | 1591 | 0.241 | 427 | 0.289 |
| pbRUSC Trim | 19 | 0.885 | 73 | 0.907 | | | 23 | 0.981 | 1131 | 0.942 | 172 | 0.526 |
| pbSCAND Trim | 108 | 0.012 | 117 | 0.019 | | | 248 | 0.809 | 461 | 0.044 | 236 | 0.037 |
| pbSHISA Trim | 205 | 0.945 | 0 | 0 | | | 0 | 0 | 611 | 0.868 | 8 | 0 |
| pbSIM A Trim | 210 | 0.97 | 330 | 0.943 | | | 58 | 1 | 699 | 0.969 | 520 | 0.726 |
| pbSIM B Trim | 55 | 0.919 | 75 | 0.673 | | | 35 | 0.932 | 261 | 0.897 | 128 | 0.879 |
| pbSIM C Trim | 165 | 0.953 | 261 | 0.89 | | | 49 | 0.995 | 936 | 0.582 | 701 | 0.512 |
| pbSLC Trim | 70 | 0.952 | 38 | 0.553 | | | 0 | 0 | 297 | 0.76 | 226 | 0.965 |
| pbTAL Trim | 100 | 0.952 | 8 | 0 | | | 78 | 0.752 | 326 | 0.513 | 138 | 0.443 |
| pbTBX15 Trim | 1 | 0.875 | 0 | 0 | | | 0 | 0 | 4 | 0.975 | 0 | 0 |
| pbTRIM Trim | 133 | 0.967 | 200 | 0.957 | | | 112 | 0.907 | 689 | 0.822 | 221 | 0.603 |

Fig. 12B

| Reference | A02324 T HER2 + # Reads | A02324 T HER2 + Mean Me | A02324 N HER2 + # Reads | A02324 N HER2 + Mean Me | A02354 T TRIPLE - # Reads | A02354 T TRIPLE - Mean Me | A02354 N TRIPLE - # Reads | A02354 N TRIPLE - Mean Me | B02275 T TRIPLE - GR + # Reads | B02275 T TRIPLE - GR + Mean Me | B02275 N TRIPLE - GR + Mean Me | 802275 N TRIPLE - GR + Mean Me |
|---|---|---|---|---|---|---|---|---|---|---|---|---|
| ADCYFtrim | 16 | 0.991 | 0 | 0 | 0 | 0 | 4 | 1 | 125 | 0.791 | 251 | 0.529 |
| ADCYGtrim | 10 | 0.987 | 0 | 0 | 0 | 0 | 3 | 1 | 96 | 0.832 | 210 | 0.62 |
| ADCYHtrim | 0 | 0 | 0 | 0 | 0 | 0 | 0 | 0 | 0 | 0 | 0 | 0 |
| C1Dtrim | 344 | 0.843 | 45 | 0.776 | 0 | 0 | 0 | 0 | 955 | 0.912 | 556 | 0.549 |
| C1Etrim | 393 | 0.347 | 728 | 0.036 | 193 | 0.007 | 1 | 0 | 663 | 0.778 | 753 | 0.359 |
| C1Ftrim | 331 | 0.741 | 51 | 0.912 | 0 | 0 | 0 | 0 | 913 | 0.889 | 550 | 0.501 |
| C1Gtrim | 378 | 0.439 | 73 | 1 | 0 | 0 | 0 | 0 | 504 | 0.892 | 246 | 0.581 |
| MIRBtrim | 557 | 0.099 | 485 | 0.031 | 136 | 0.001 | 499 | 0.027 | 253 | 0.471 | 247 | 0.054 |
| MIRCtrim | 23 | 0.64 | 286 | 0.084 | 175 | 0.094 | 9 | 0 | 130 | 0.735 | 328 | 0.242 |
| MIRDtrim | 0 | 0 | 0 | 0 | 63 | 0 | 31 | 0 | 213 | 0.868 | 144 | 0.287 |
| MIREtrim | 248 | 0.996 | 80 | 1 | 0 | 0 | 191 | 0.026 | 475 | 0.944 | 685 | 0.355 |
| MIRFtrim | 88 | 0.214 | 92 | 0.012 | 112 | 0.044 | 603 | 0.082 | 30 | 0.383 | 39 | 0.061 |
| VWCJtrim | 1 | 0 | 78 | 0.55 | 32 | 0.071 | 2 | 0.5 | 604 | 0.879 | 351 | 0.3 |
| VWCKtrim | 0 | 0 | 9 | 0.269 | 0 | 0 | 0 | 0 | 248 | 0.915 | 39 | 0.62 |
| VWCLtrim | 0 | 0 | 3 | 0 | 339 | 0.011 | 0 | 0 | 697 | 0.925 | 476 | 0.47 |
| VWCMtrim | 0 | 0 | 0 | 0 | 92 | 0.153 | 0 | 0 | 454 | 0.981 | 234 | 0.673 |
| VWCNtrim | 1 | 0.2 | 93 | 0.658 | 34 | 0.273 | 2 | 0.6 | 809 | 0.912 | 403 | 0.425 |
| CHSAtrim | 77 | 0.006 | 27 | 0 | 44 | 0.004 | 2 | 0 | 378 | 0.748 | 279 | 0.047 |
| CHSBtrim | 0 | 0 | 0 | 0 | 0 | 0 | 0 | 0 | 1039 | 0.946 | 240 | 0.34 |
| CHSCtrim | 125 | 0.256 | 46 | 0 | 36 | 0.046 | 583 | 0.748 | 1396 | 0.921 | 337 | 0.176 |
| CHSDtrim | 0 | 0 | 0 | 0 | 0 | 0 | 0 | 0 | 1037 | 0.946 | 241 | 0.339 |
| DMBAtrim | 0 | 0 | 0 | 0 | 0 | 0 | 0 | 0 | 0 | 0 | 0 | 0 |
| DMBBtrim | 1078 | 0.876 | 586 | 0.386 | 559 | 0.935 | 219 | 0.486 | 1078 | 0.887 | 544 | 0.373 |
| DMBCtrim | 1000 | 0.891 | 564 | 0.399 | 530 | 0.939 | 202 | 0.461 | 1014 | 0.889 | 506 | 0.399 |
| FOXAtrim | 205 | 0.745 | 12 | 0 | 0 | 0 | 0 | 0 | 240 | 0.232 | 51 | 0.093 |
| FOXBtrim | 155 | 0.355 | 32 | 0.078 | 54 | 0.09 | 2363 | 0.159 | 6 | 0.056 | 12 | 0.069 |
| FOXCtrim | 0 | 0 | 0 | 0 | 0 | 0 | 21 | 0.179 | 0 | 0 | 0 | 0 |
| FOXDtrim | 806 | 0.918 | 0 | 0 | 0 | 0 | 0 | 0 | 44 | 0.023 | 38 | 0 |
| FOXEtrim | 1139 | 0.956 | 0 | 0 | 185 | 0.072 | 173 | 0.888 | 341 | 0.157 | 268 | 0.173 |
| HOXAAtrim | 905 | 0.824 | 536 | 0.376 | 1899 | 0.696 | 781 | 0.589 | 1076 | 0.199 | 1163 | 0.178 |
| HOXABtrim | 896 | 0.824 | 529 | 0.466 | 1877 | 0.764 | 770 | 0.7 | 1079 | 0.225 | 1153 | 0.265 |
| HOXACtrim | 31 | 0.987 | 78 | 0.379 | 190 | 0.668 | 67 | 0.973 | 107 | 0.055 | 118 | 0.469 |
| HOXADtrim | 189 | 0.181 | 189 | 0.056 | 299 | 0.294 | 121 | 0.671 | 750 | 0.124 | 639 | 0.026 |
| SFRAtrim | 353 | 0.351 | 798 | 0.094 | 410 | 0.104 | 192 | 0.089 | 520 | 0.61 | 403 | 0.339 |
| SFRBtrim | 836 | 0.667 | 0 | 0 | 0 | 0 | 583 | 0.998 | 591 | 0.94 | 168 | 0.72 |
| SFRCtrim | 331 | 0.633 | 700 | 0.277 | 370 | 0.282 | 1830 | 0.937 | 1006 | 0.671 | 468 | 0.557 |
| SFRDtrim | 375 | 0.232 | 881 | 0.027 | 458 | 0.028 | 212 | 0.018 | 553 | 0.636 | 435 | 0.326 |
| SFREtrim | 831 | 0.508 | 0 | 0 | 0 | 0 | 595 | 0.999 | 578 | 0.927 | 169 | 0.58 |
| TTBAtrim | 35 | 0 | 12 | 0.15 | 157 | 0.276 | 163 | 0.79 | 434 | 0.691 | 150 | 0.098 |
| TTBBtrim | 1 | 0.4 | 0 | 0 | 0 | 0 | 125 | 0.95 | 131 | 0.937 | 62 | 0.21 |
| TTBCtrim | 0 | 0 | 0 | 0 | 1 | 0.333 | 1 | 0.25 | 69 | 0.782 | 8 | 0.588 |
| TTBDtrim | 0 | 0 | 0 | 0 | 0 | 0 | 0 | 0 | 361 | 0.888 | 126 | 0.484 |

Fig. 13A

| Reference | D01333 T ER+ PR+ # Reads | D01333 T ER+ PR+ Mean Me | D01333 N ER+ PR+ # Reads | D01333 N ER+ PR+ Mean Me | D02291 T ER+ PR+ GR+ # Reads | D02291 T ER+ PR+ GR+ Mean Me | D02291 N ER+ PR+ GR+ # Reads | D02291 N ER+ PR+ GR+ Mean Me | D02610 T ER+ PR+ # Reads | D02610 T ER+ PR+ Mean Me | D02610 N ER+ PR+ # Reads | D02610 N ER+ PR+ Mean Me |
|---|---|---|---|---|---|---|---|---|---|---|---|---|
| ADCYFtrim | 33 | 0.896 | 5 | 0.92 | 30 | 0.966 | 0 | 0 | 216 | 0.776 | 13 | 0 |
| ADCYGtrim | 21 | 0.905 | 4 | 1 | 23 | 0.98 | 0 | 0 | 131 | 0.84 | 14 | 0.217 |
| ADCYHtrim | 0 | 0 | 0 | 0 | 0 | 0 | 0 | 0 | 0 | 0 | 0 | 0 |
| C1Dtrim | 170 | 0.923 | 14 | 0.99 | 342 | 0.967 | 27 | 0.425 | 1009 | 0.968 | 35 | 0.095 |
| C1Etrim | 355 | 0.802 | 77 | 0.148 | 529 | 0.943 | 82 | 0.032 | 808 | 0.906 | 506 | 0.621 |
| C1Ftrim | 165 | 0.926 | 13 | 0.981 | 326 | 0.964 | 26 | 0.506 | 986 | 0.97 | 40 | 0 |
| C1Gtrim | 218 | 0.578 | 14 | 0.381 | 332 | 0.981 | 0 | 0 | 409 | 0.882 | 0 | 0 |
| MIRBtrim | 103 | 0.611 | 435 | 0.121 | 156 | 0.061 | 8 | 0 | 530 | 0.077 | 65 | 0.005 |
| MIRCtrim | 103 | 0.724 | 47 | 0.049 | 87 | 0.918 | 28 | 0.257 | 231 | 0.621 | 5 | 0 |
| MIRDtrim | 91 | 0.782 | 10 | 0.017 | 52 | 0.775 | 0 | 0 | 159 | 0.31 | 70 | 0.149 |
| MIREtrim | 203 | 0.924 | 5 | 0 | 208 | 0.832 | 0 | 0 | 393 | 0.925 | 184 | 0.836 |
| MIRFtrim | 27 | 0.446 | 36 | 0.052 | 3 | 0.167 | 24 | 0.063 | 112 | 0.04 | 56 | 0 |
| VWCJtrim | 56 | 0.969 | 3 | 0.051 | 184 | 0.758 | 0 | 0 | 48 | 0.174 | 6 | 0.013 |
| VWCKtrim | 30 | 0.98 | 0 | 0 | 29 | 0.914 | 0 | 0 | 0 | 0 | 0 | 0 |
| VWCLtrim | 399 | 0.976 | 0 | 0 | 422 | 0.901 | 0 | 0 | 245 | 0.766 | 0 | 0 |
| VWCMtrim | 70 | 0.977 | 3 | 0.267 | 243 | 0.65 | 0 | 0 | 50 | 0.242 | 6 | 0.217 |
| VWCNtrim | 275 | 0.852 | 0 | 0 | 335 | 0.339 | 4 | 0.175 | 477 | 0.505 | 2 | 0 |
| CHSAtrim | 486 | 0.973 | 0 | 0 | 588 | 0.739 | 0 | 0 | 125 | 0.802 | 0 | 0 |
| CHSBtrim | 572 | 0.968 | 3 | 0 | 702 | 0.763 | 0 | 0 | 330 | 0.751 | 4 | 0 |
| CHSCtrim | 483 | 0.972 | 0 | 0 | 589 | 0.737 | 0 | 0 | 125 | 0.802 | 0 | 0 |
| CHSDtrim | 0 | 0 | 0 | 0 | 0 | 0 | 0 | 0 | 0 | 0 | 0 | 0 |
| DMBAtrim | 500 | 0.896 | 175 | 0.65 | 424 | 0.97 | 4 | 0 | 1359 | 0.745 | 0 | 0 |
| DMBBtrim | 470 | 0.909 | 147 | 0.61 | 400 | 0.976 | 4 | 0 | 1291 | 0.771 | 0 | 0 |
| DMBCtrim | 216 | 0.906 | 32 | 0.503 | 382 | 0.906 | 0 | 0 | 401 | 0.714 | 0 | 0 |
| FOXAtrim | 4 | 0.333 | 70 | 0.19 | 12 | 0.417 | 35 | 0.01 | 53 | 0.305 | 1 | 0 |
| FOXBtrim | 0 | 0 | 1 | 0 | 0 | 0 | 0 | 0 | 0 | 0 | 0 | 0 |
| FOXCtrim | 100 | 0.96 | 0 | 0 | 371 | 0.91 | 0 | 0 | 499 | 0.878 | 0 | 0 |
| FOXDtrim | 213 | 0.978 | 9 | 0.667 | 511 | 0.966 | 0 | 0 | 908 | 0.93 | 0 | 0 |
| FOXEtrim | 291 | 0.704 | 277 | 0.205 | 748 | 0.776 | 3 | 0.133 | 1055 | 0.118 | 67 | 0.051 |
| HOXAAtrim | 292 | 0.753 | 277 | 0.423 | 746 | 0.796 | 3 | 0.25 | 1052 | 0.25 | 66 | 0.078 |
| HOXABtrim | 43 | 0.738 | 19 | 0.189 | 194 | 0.61 | 0 | 0 | 296 | 0.453 | 0 | 0 |
| HOXACtrim | 106 | 0.619 | 34 | 0.306 | 245 | 0.614 | 3 | 0.293 | 518 | 0.224 | 60 | 0.003 |
| HOXADtrim | 308 | 0.685 | 104 | 0.078 | 447 | 0.649 | 48 | 0.082 | 594 | 0.339 | 0 | 0 |
| SFRAtrim | 320 | 0.967 | 79 | 0.881 | 438 | 0.742 | 0 | 0 | 534 | 0.825 | 0 | 0 |
| SFRBtrim | 407 | 0.811 | 87 | 0.238 | 726 | 0.907 | 45 | 0.237 | 1050 | 0.682 | 0 | 0 |
| SFRCtrim | 328 | 0.627 | 117 | 0.016 | 485 | 0.613 | 52 | 0.017 | 617 | 0.278 | 0 | 0 |
| SFRDtrim | 314 | 0.966 | 80 | 0.83 | 428 | 0.665 | 0 | 0 | 524 | 0.755 | 0 | 0 |
| SFREtrim | 221 | 0.553 | 54 | 0.119 | 240 | 0.408 | 1 | 0 | 178 | 0.036 | 15 | 0 |
| TTBAtrim | 60 | 0.81 | 0 | 0 | 138 | 0.527 | 0 | 0 | 39 | 0.046 | 0 | 0 |
| TTBBtrim | 116 | 0.355 | 0 | 0 | 79 | 0.417 | 0 | 0 | 1 | 0.25 | 0 | 0 |
| TTBCtrim | 106 | 0.751 | 0 | 0 | 155 | 0.5 | 0 | 0 | 0 | 0 | 0 | 0 |
| TTBDtrim | 341 | 0.963 | 0 | 0 | 356 | 0.995 | 0 | 0 | 0 | 0 | 0 | 0 |

Fig. 13B

| Reference | DU145 # Reads | DU145 Mean Me | PC3 # Reads | PC3 Mean Me | LNCAP # Reads | LNCAP Mean Me | RWPE # Reads | RWPE Mean Me |
|---|---|---|---|---|---|---|---|---|
| ADCYFtrim | 216 | 0.916 | 213 | 0.459 | 199 | 0.903 | 71 | 0.297 |
| ADCYGtrim | 146 | 0.917 | 188 | 0.611 | 161 | 0.921 | 46 | 0.416 |
| ADCYHtrim | 4 | 0.847 | 0 | 0 | 5 | 0.795 | 0 | 0 |
| C1Dtrim | 548 | 0.916 | 616 | 0.95 | 941 | 0.954 | 58 | 0.063 |
| C1Etrim | 621 | 0.74 | 585 | 0.943 | 2458 | 0.956 | 292 | 0.023 |
| C1Ftrim | 526 | 0.93 | 591 | 0.936 | 872 | 0.942 | 61 | 0.049 |
| C1Gtrim | 736 | 0.78 | 523 | 0.721 | 1583 | 0.786 | 0 | 0 |
| MIRBtrim | 187 | 0.096 | 745 | 0.824 | 994 | 0.169 | 775 | 0.032 |
| MIRCtrim | 265 | 0.387 | 461 | 0.876 | 369 | 0.564 | 81 | 0.019 |
| MIRDtrim | 155 | 0.152 | 0 | 0 | 289 | 0.092 | 24 | 0.071 |
| MIREtrim | 566 | 0.377 | 1110 | 0.97 | 1190 | 0.547 | 31 | 0.032 |
| MIRFtrim | 56 | 0.1 | 173 | 0.873 | 62 | 0.095 | 200 | 0.021 |
| VWCJtrim | 494 | 0.948 | 891 | 0.676 | 766 | 0.836 | 379 | 0.103 |
| VWCKtrim | 208 | 0.956 | 44 | 0.911 | 36 | 0.877 | 8 | 1 |
| VWCLtrim | 1041 | 0.923 | 746 | 0.911 | 1419 | 0.851 | 675 | 0.405 |
| VWCMtrim | 1071 | 0.922 | 917 | 0.867 | 1083 | 0.88 | 1 | 0 |
| VWCNtrim | 657 | 0.938 | 1120 | 0.736 | 992 | 0.853 | 425 | 0.268 |
| CHSAtrim | 56 | 0.003 | 986 | 0.482 | 945 | 0.524 | 1194 | 0.194 |
| CHSBtrim | 111 | 0.585 | 734 | 0.931 | 1944 | 0.746 | 1463 | 0.367 |
| CHSCtrim | 345 | 0.246 | 1074 | 0.927 | 2539 | 0.762 | 1983 | 0.218 |
| CHSDtrim | 113 | 0.592 | 730 | 0.93 | 1933 | 0.745 | 1467 | 0.367 |
| DMBAtrim | 0 | 0 | 0 | 0 | 0 | 0 | 0 | 0 |
| DMBBtrim | 1046 | 0.977 | 1388 | 0.967 | 2759 | 0.892 | 3164 | 0.175 |
| DMBCtrim | 1026 | 0.98 | 1282 | 0.974 | 2597 | 0.911 | 3049 | 0.218 |
| FOXAtrim | 1663 | 0.946 | 670 | 0.876 | 710 | 0.619 | 1722 | 0.3 |
| FOXBtrim | 7 | 1 | 4 | 0.667 | 70 | 0.607 | 90 | 0.259 |
| FOXCtrim | 0 | 0 | 0 | 0 | 0 | 0 | 0 | 0 |
| FOXDtrim | 387 | 0.873 | 510 | 0.958 | 964 | 0.919 | 1974 | 0.438 |
| FOXEtrim | 1547 | 0.975 | 1336 | 0.964 | 1619 | 0.903 | 3207 | 0.709 |
| HOXAAtrim | 2289 | 0.965 | 2522 | 0.056 | 1952 | 0.46 | 2234 | 0.135 |
| HOXABtrim | 2298 | 0.972 | 2505 | 0.142 | 1939 | 0.598 | 2216 | 0.199 |
| HOXACtrim | 302 | 0.906 | 38 | 0 | 286 | 0.355 | 116 | 0.016 |
| HOXADtrim | 710 | 0.971 | 1741 | 0.134 | 603 | 0.607 | 1313 | 0.051 |
| SFRAtrim | 452 | 0.357 | 374 | 0.872 | 562 | 0.092 | 920 | 0.101 |
| SFRBtrim | 330 | 0.784 | 531 | 0.855 | 0 | 0 | 855 | 0.609 |
| SFRCtrim | 817 | 0.672 | 933 | 0.932 | 506 | 0.246 | 1400 | 0.133 |
| SFRDtrim | 484 | 0.283 | 412 | 0.832 | 611 | 0.021 | 1006 | 0.081 |
| SFREtrim | 321 | 0.719 | 514 | 0.896 | 18 | 0.993 | 846 | 0.428 |
| TTBAtrim | 823 | 0.673 | 351 | 0.63 | 1197 | 0.6 | 1262 | 0.111 |
| TTBBtrim | 301 | 0.752 | 374 | 0.818 | 343 | 0.822 | 295 | 0.723 |
| TTBCtrim | 161 | 0.678 | 29 | 0.548 | 453 | 0.483 | 51 | 0.634 |
| TTBDtrim | 890 | 0.693 | 428 | 0.854 | 845 | 0.799 | 508 | 0.809 |

Fig. 14

Tumour Volume  483 cm³  Unknown

| Name | Chromosome | Nucleotide | Basal | Her2 | LumA | LumB | Normal-Lik | Tissue |
| --- | --- | --- | --- | --- | --- | --- | --- | --- |
| | | | 82 | 31 | 280 | 127 | 17 | 29 # Tumours |
| CTSA,NEURL2 | chr20 | 43552039 | 0.30 | 0.71 | 0.89 | 0.91 | 0.24 | 0.01 |
| CHR5:43054200 | chr5 | 43054200 | 0.15 | 0.77 | 0.87 | 0.90 | 0.35 | 0.06 |
| ADCY4 | chr14 | 23873713 | 0.26 | 0.84 | 0.83 | 0.90 | 0.41 | 0.06 |
| DDAH2 | chr6 | 31906357 | 0.18 | 0.61 | 0.81 | 0.84 | 0.18 | 0.00 |
| USP44 | chr12 | 94467032 | 0.43 | 0.90 | 0.80 | 0.95 | 0.35 | 0.01 |
| L3TD1 | chr1 | 52435212 | 0.95 | 0.90 | 0.78 | 0.94 | 0.35 | 0.03 |
| PROM1S | chr21 | 42110155 | 0.37 | 0.74 | 0.78 | 0.79 | 0.53 | 0.02 |
| HOXD11 | chr2 | 176850809 | 0.20 | 0.65 | 0.76 | 0.89 | 0.35 | 0.03 |
| GNG4 | chr1 | 235880693 | 0.35 | 0.57 | 0.75 | 0.91 | 0.24 | 0.02 |
| COL18A3 | chr1 | 31942288 | 0.24 | 0.84 | 0.75 | 0.92 | 0.18 | 0.00 |
| TAL1 | chr1 | 47470935 | 0.77 | 0.87 | 0.74 | 0.90 | 0.35 | 0.02 |
| CDH23 | chr10 | 73825383 | 0.11 | 0.81 | 0.73 | 0.83 | 0.24 | 0.01 |
| SHF | chr15 | 43267047 | 0.21 | 1.00 | 0.72 | 0.91 | 0.53 | 0.03 |
| CHST11 | chr12 | 103376969 | 0.12 | 0.62 | 0.72 | 0.77 | 0.18 | 0.01 |
| PRKCB | chr16 | 23795067 | 0.32 | 0.68 | 0.71 | 0.83 | 0.12 | 0.00 |
| AFF3 | chr2 | 99542136 | 0.00 | 0.61 | 0.71 | 0.57 | 0.18 | 0.04 |
| ATP9B2 | chr12 | 51357357 | 0.40 | 0.74 | 0.70 | 0.89 | 0.12 | 0.03 |
| CHR19:51073789 | chr19 | 51073789 | 0.34 | 0.97 | 0.70 | 0.83 | 0.24 | 0.02 |
| C1orf114 | chr1 | 167665259 | 0.61 | 0.90 | 0.69 | 0.88 | 0.24 | 0.00 |
| CHR1:90967747 | chr1 | 90967747 | 0.52 | 0.74 | 0.68 | 0.80 | 0.12 | 0.03 |
| NT5E | chr6 | 86215916 | 0.45 | 0.61 | 0.68 | 0.79 | 0.12 | 0.01 |
| PLTP | chr20 | 43973373 | 0.20 | 0.84 | 0.68 | 0.82 | 0.18 | 0.00 |
| MAST1 | chr19 | 12839811 | 0.59 | 0.87 | 0.67 | 0.88 | 0.29 | 0.00 |
| ITPRIPL1 | chr2 | 96954841 | 0.61 | 0.90 | 0.67 | 0.84 | 0.12 | 0.00 |
| KIAA1751 | chr1 | 1925149 | 0.18 | 0.71 | 0.66 | 0.70 | 0.18 | 0.01 |
| ACVRL1 | chr12 | 50587172 | 0.31 | 0.81 | 0.66 | 0.89 | 0.18 | 0.02 |
| GABRA4 | chr4 | 46690498 | 0.33 | 0.52 | 0.66 | 0.85 | 0.06 | 0.00 |
| TOB2P1 | chr6 | 28263425 | 0.77 | 0.65 | 0.65 | 0.80 | 0.18 | 0.00 |
| FLI1 | chr11 | 128068895 | 0.12 | 0.61 | 0.65 | 0.77 | 0.06 | 0.00 |
| CD38 | chr4 | 15388836 | 0.21 | 0.77 | 0.65 | 0.79 | 0.18 | 0.00 |
| HOTAIR | chr12 | 53648064 | 0.84 | 1.00 | 0.64 | 0.77 | 0.53 | 0.04 |
| PROM1S | chr6 | 100167882 | 0.74 | 0.81 | 0.64 | 0.82 | 0.24 | 0.00 |
| HNF1B | chr17 | 33177343 | 0.30 | 0.65 | 0.64 | 0.75 | 0.06 | 0.00 |
| RGS17 | chr6 | 153494417 | 0.10 | 0.77 | 0.64 | 0.79 | 0.24 | 0.02 |
| COL11A2 | chr6 | 33269254 | 0.07 | 0.55 | 0.64 | 0.70 | 0.18 | 0.01 |
| CHR11:68379305 | chr11 | 68379315 | 0.16 | 1.00 | 0.63 | 0.87 | 0.18 | 0.03 |
| RUNX1T1 | chr8 | 93188836 | 0.35 | 0.42 | 0.63 | 0.80 | 0.18 | 0.01 |
| YWC1 | chr7 | 49783645 | 0.11 | 0.65 | 0.63 | 0.76 | 0.18 | 0.00 |
| RTN4RL1 | chr17 | 1827755 | 0.46 | 0.52 | 0.62 | 0.76 | 0.12 | 0.03 |
| CHR17:89463208 | chr17 | 89463208 | 0.35 | 0.90 | 0.62 | 0.79 | 0.18 | 0.01 |
| TMEM132C | chr12 | 127317993 | 0.78 | 0.71 | 0.62 | 0.73 | 0.12 | 0.00 |
| C19orf41 | chr19 | 55258360 | 0.39 | 0.45 | 0.61 | 0.77 | 0.12 | 0.00 |
| SHISA3 | chr4 | 42094500 | 0.04 | 0.26 | 0.61 | 0.75 | 0.18 | 0.00 |
| SOX2OT | chr3 | 18291839 | 0.56 | 0.77 | 0.60 | 0.80 | 0.18 | 0.01 |
| ALX4 | chr11 | 44289229 | 0.08 | 0.68 | 0.60 | 0.79 | 0.41 | 0.03 |
| HLA-F | chr6 | 29798979 | 0.06 | 0.42 | 0.60 | 0.62 | 0.29 | 0.02 |
| KCNJ2 | chr17 | 65676379 | 0.10 | 0.65 | 0.60 | 0.76 | 0.06 | 0.00 |
| ERNA4 | chr1 | 153110087 | 0.59 | 0.90 | 0.60 | 0.78 | 0.12 | 0.01 |
| HIF3A | chr19 | 51491904 | 0.09 | 0.55 | 0.59 | 0.71 | 0.12 | 0.01 |
| CHR8:95315690 | chr8 | 95315690 | 0.57 | 0.84 | 0.59 | 0.80 | 0.29 | 0.02 |
| GIPC2 | chr1 | 78284188 | 0.60 | 0.77 | 0.59 | 0.78 | 0.24 | 0.04 |
| CRYM | chr16 | 21203755 | 0.39 | 0.58 | 0.59 | 0.83 | 0.29 | 0.01 |
| HIVEP3 | chr1 | 41903042 | 0.00 | 0.35 | 0.59 | 0.80 | 0.24 | 0.01 |
| SLC2A2 | chr3 | 172228901 | 0.40 | 0.68 | 0.58 | 0.80 | 0.12 | 0.00 |
| CYTL1 | chr4 | 5072014 | 0.13 | 0.58 | 0.58 | 0.78 | 0.06 | 0.00 |
| PON3 | chr7 | 94986672 | 0.33 | 0.55 | 0.58 | 0.64 | 0.32 | 0.00 |

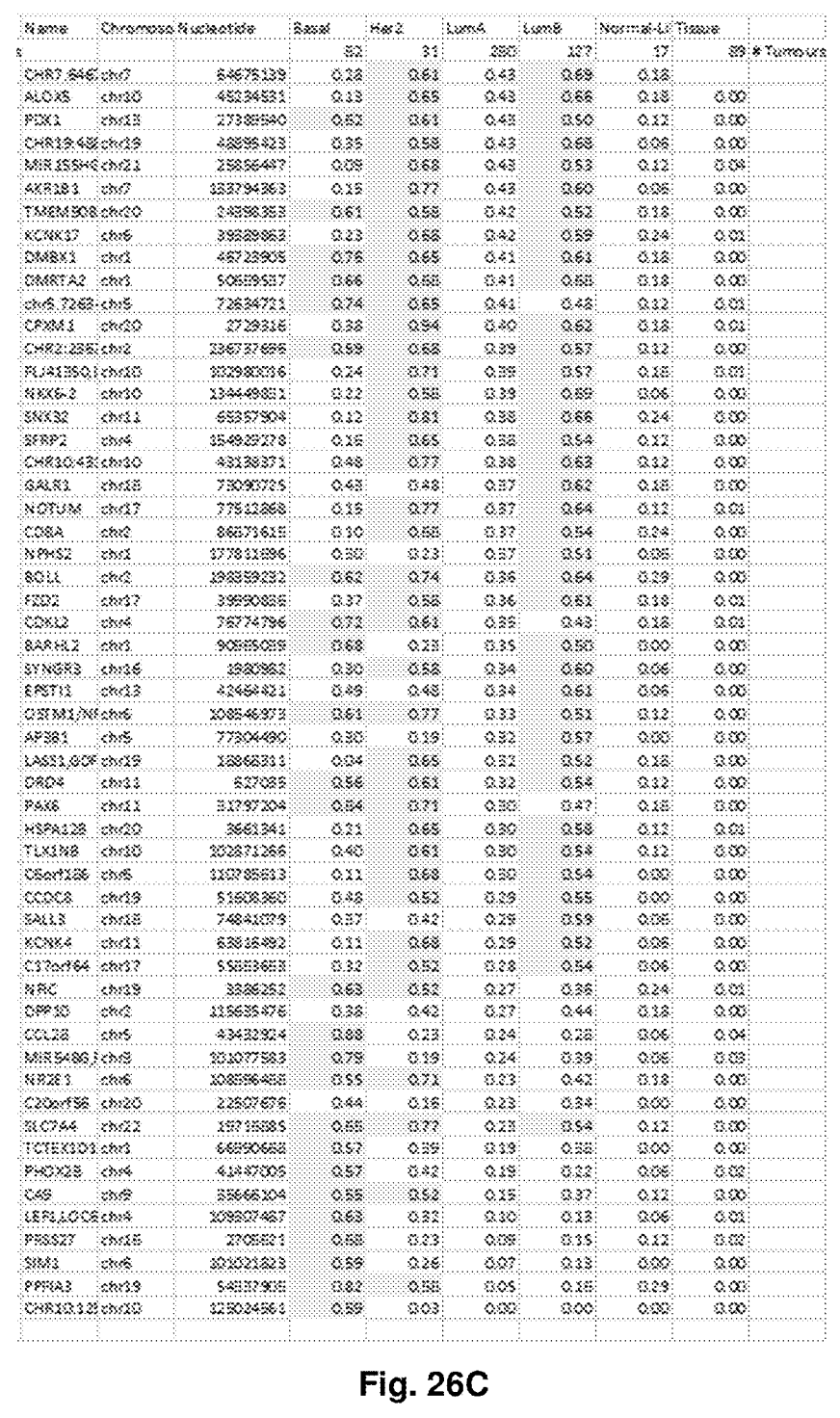

| Name | Chromoso | Nucleotide | Basal | Her2 | Lum4 | Lum8 | Normal-Li | Tissue | |
|------|----------|-----------|-------|------|------|------|-----------|--------|---|
| | | | 82 | 31 | 280 | 127 | 17 | 89 | # Tumours |
| CHR7.646 | chr7 | 64675139 | 0.28 | 0.61 | 0.43 | 0.69 | 0.18 | | |
| ALOX5 | chr10 | 45234531 | 0.13 | 0.65 | 0.43 | 0.66 | 0.18 | 0.00 | |
| PDX1 | chr13 | 27385940 | 0.61 | 0.61 | 0.43 | 0.50 | 0.12 | 0.00 | |
| CHR19.48 | chr19 | 48895423 | 0.35 | 0.58 | 0.43 | 0.68 | 0.06 | 0.00 | |
| MIR155HG | chr21 | 25856447 | 0.09 | 0.68 | 0.43 | 0.53 | 0.12 | 0.04 | |
| AKR1B1 | chr7 | 133794363 | 0.15 | 0.77 | 0.43 | 0.60 | 0.06 | 0.00 | |
| TMEM908 | chr20 | 34898355 | 0.61 | 0.58 | 0.42 | 0.52 | 0.18 | 0.00 | |
| KCNK17 | chr6 | 39289862 | 0.23 | 0.68 | 0.42 | 0.59 | 0.24 | 0.01 | |
| DMBX1 | chr1 | 46723905 | 0.76 | 0.65 | 0.41 | 0.61 | 0.18 | 0.00 | |
| CMRTA2 | chr1 | 50699517 | 0.66 | 0.68 | 0.41 | 0.58 | 0.18 | 0.00 | |
| chr6.7262 | chr6 | 72634721 | 0.74 | 0.65 | 0.41 | 0.48 | 0.12 | 0.01 | |
| CPXM1 | chr20 | 2729316 | 0.38 | 0.54 | 0.40 | 0.62 | 0.18 | 0.01 | |
| CHR2.236 | chr2 | 236737696 | 0.59 | 0.68 | 0.39 | 0.57 | 0.12 | 0.00 | |
| RUA15Q1 | chr18 | 83298306 | 0.14 | 0.71 | 0.39 | 0.57 | 0.18 | 0.03 | |
| NKX6-2 | chr10 | 134449811 | 0.22 | 0.58 | 0.39 | 0.69 | 0.06 | 0.00 | |
| SNX32 | chr11 | 65357904 | 0.12 | 0.81 | 0.38 | 0.66 | 0.24 | 0.00 | |
| SFRP2 | chr4 | 154829278 | 0.16 | 0.65 | 0.38 | 0.54 | 0.12 | 0.00 | |
| CHR10.43 | chr10 | 43138371 | 0.48 | 0.77 | 0.38 | 0.63 | 0.12 | 0.00 | |
| GALR1 | chr18 | 73090725 | 0.43 | 0.48 | 0.37 | 0.62 | 0.18 | 0.00 | |
| NOTUM | chr17 | 77512868 | 0.19 | 0.77 | 0.37 | 0.64 | 0.12 | 0.01 | |
| CO8A | chr2 | 86871615 | 0.10 | 0.68 | 0.37 | 0.54 | 0.24 | 0.01 | |
| NPHS2 | chr1 | 177811996 | 0.30 | 0.23 | 0.37 | 0.51 | 0.06 | 0.00 | |
| SOLL | chr4 | 198859232 | 0.62 | 0.74 | 0.36 | 0.64 | 0.29 | 0.00 | |
| FLD2 | chr17 | 39990885 | 0.37 | 0.58 | 0.36 | 0.61 | 0.18 | 0.01 | |
| COX12 | chr4 | 76774796 | 0.72 | 0.61 | 0.35 | 0.43 | 0.18 | 0.03 | |
| BARHL2 | chr1 | 90865089 | 0.68 | 0.23 | 0.35 | 0.58 | 0.00 | 0.01 | |
| SYNGR3 | chr16 | 1980982 | 0.30 | 0.58 | 0.34 | 0.60 | 0.06 | 0.00 | |
| EPSTI1 | chr13 | 42464421 | 0.49 | 0.48 | 0.34 | 0.61 | 0.06 | 0.00 | |
| GRM1/N | chr6 | 108846973 | 0.61 | 0.77 | 0.33 | 0.51 | 0.12 | 0.01 | |
| AP3B1 | chr5 | 77304490 | 0.30 | 0.19 | 0.32 | 0.57 | 0.00 | 0.00 | |
| LASS1/GOF | chr19 | 18865311 | 0.04 | 0.65 | 0.32 | 0.52 | 0.18 | 0.00 | |
| OR04 | chr11 | 627085 | 0.56 | 0.61 | 0.32 | 0.54 | 0.12 | 0.00 | |
| PAX6 | chr11 | 31797204 | 0.54 | 0.71 | 0.30 | 0.47 | 0.18 | 0.00 | |
| HSPA12B | chr20 | 3661341 | 0.21 | 0.65 | 0.30 | 0.58 | 0.12 | 0.03 | |
| TLX1NB | chr10 | 102871266 | 0.40 | 0.61 | 0.30 | 0.54 | 0.12 | 0.00 | |
| C6orf126 | chr6 | 119785613 | 0.11 | 0.68 | 0.30 | 0.54 | 0.00 | 0.00 | |
| CCDC8 | chr19 | 51608360 | 0.48 | 0.52 | 0.29 | 0.55 | 0.00 | 0.00 | |
| SALL3 | chr18 | 74841079 | 0.37 | 0.42 | 0.29 | 0.59 | 0.06 | 0.00 | |
| KCNK4 | chr11 | 63816492 | 0.11 | 0.68 | 0.29 | 0.52 | 0.06 | 0.00 | |
| C17orf64 | chr17 | 55856653 | 0.32 | 0.52 | 0.28 | 0.54 | 0.06 | 0.00 | |
| NRC | chr19 | 3386252 | 0.68 | 0.52 | 0.27 | 0.38 | 0.24 | 0.01 | |
| OPP10 | chr2 | 115635476 | 0.38 | 0.42 | 0.27 | 0.44 | 0.18 | 0.00 | |
| CCL28 | chr5 | 43432924 | 0.88 | 0.23 | 0.24 | 0.28 | 0.06 | 0.04 | |
| MIR5486 | chr8 | 101077583 | 0.79 | 0.19 | 0.24 | 0.39 | 0.06 | 0.03 | |
| NR2E1 | chr6 | 108896488 | 0.55 | 0.71 | 0.23 | 0.42 | 0.18 | 0.01 | |
| C20orf56 | chr20 | 22507676 | 0.44 | 0.16 | 0.23 | 0.34 | 0.00 | 0.00 | |
| SLC7A4 | chr22 | 19715885 | 0.55 | 0.77 | 0.23 | 0.54 | 0.12 | 0.00 | |
| ICTEK3D1 | chr3 | 66890668 | 0.57 | 0.39 | 0.19 | 0.58 | 0.00 | 0.01 | |
| PHOX2B | chr4 | 41447009 | 0.57 | 0.42 | 0.19 | 0.52 | 0.06 | 0.02 | |
| C4S | chr9 | 35666104 | 0.55 | 0.52 | 0.19 | 0.37 | 0.12 | 0.00 | |
| LEFL1/OC | chr4 | 109807487 | 0.63 | 0.32 | 0.30 | 0.13 | 0.06 | 0.01 | |
| PRSS27 | chr16 | 2705821 | 0.56 | 0.23 | 0.09 | 0.35 | 0.12 | 0.02 | |
| SIM1 | chr6 | 101021823 | 0.59 | 0.26 | 0.07 | 0.13 | 0.00 | 0.00 | |
| PFPA3 | chr19 | 54557905 | 0.82 | 0.58 | 0.05 | 0.16 | 0.29 | 0.03 | |
| CHR10.12 | chr10 | 125024561 | 0.59 | 0.03 | 0.02 | 0.00 | 0.00 | 0.00 | |

Fig. 26C

CELL-FREE DETECTION OF METHYLATED BREAST TUMOR

CROSS-REFERENCE TO RELATED APPLICATIONS

This application is a continuation of U.S. application Ser. No. 16/098,455, which is a U.S. National Stage entry of PCT/CA2017/000111, filed May 4, 2017, which claims the benefit of U.S. Provisional App. No. 62/331,585, filed May 4, 2016. The disclosure of each of the above applications is herein incorporated by reference in its entirety.

The instant application contains a Sequence Listing which has been submitted electronically in XML file format and is hereby incorporated by reference in its entirety. Said XML copy, created on Apr. 1, 2024, is named "P70051_SL.xml" and is 891,946 bytes in size.

FIELD

This disclosure relates generally to tumour detection. More particularly, this disclosure relates to tumour-specific DNA methylation detection.

BACKGROUND

Cancer screening and monitoring has helped to improve outcomes over the past few decades simply because early detection leads to a better outcome as the cancer can be eliminated before it has spread. In the case of breast cancer, for instance, physical breast exams, mammography, ultrasound and MRI (in high risk patients) have all played a role in improving early diagnosis. The cost/benefit of these modalities for general screening, particularly in relatively younger women, has been controversial.

A primary issue for any screening tool is the compromise between false positive and false negative results (or specificity and sensitivity) which lead to unnecessary investigations in the former case, and ineffectiveness in the latter case. An ideal test is one that has a high Positive Predictive Value (PPV), minimizing unnecessary investigations but detecting the vast majority of cancers. Another key factor is what is called "detection sensitivity", to distinguish it from test sensitivity, and that is the lower limits of detection in terms of the size of the tumour. Screening mammography in breast cancer, for instance, is considered to have a sensitivity from 80 to 90% with a specificity of 90%. However the mean size of tumours detected by mammography remains in the range of 15 to 19 mm. It has been suggested that only 3-13% of women derive an improved treatment outcome from this screening suggesting that the detection of smaller tumours would provide increased benefit. For women at high risk of developing breast cancer the use of MRI has offered some benefit with sensitivities in the range of 75 to 97% and specificities in the area of 90 to 96% and in combination with mammography offering 93-94% sensitivity and 77 to 96% specificities. However, MRI is acknowledged to have a poor PPV, in the area of 10-20%, leading to a large number of false positives and as a consequence unnecessary invasive investigations. All of these screens have likely reached their limit of detection sensitivity (or size of the tumour) and in the case of mammography still involve exposure to radiation, which may be of particular concern in women with familial mutations which render them more sensitive to radiation damage. There are no effective blood based screens for breast cancer based on circulating analytes.

While the above discussion focusses on breast cancer as an example, many of the same challenges exist for other types of cancers as well.

The detection of circulating tumour DNA is increasingly acknowledged as a viable "liquid biopsy" allowing for the detection and informative investigation of tumours in a non-invasive manner. Typically using the identification of tumour specific mutations these techniques have been applied to colon, breast and prostate cancers. Due to the high background of normal DNA present in the circulation these techniques can be limited in sensitivity. As well, the variable nature of tumour mutations in terms of occurrence and location (such as p53 and KRAS mutations) has generally limited these approaches to detecting tumour DNA at 1% of the total DNA in serum. Advanced techniques such as BEAMing have increased sensitivity, but are still limited overall. Even with these limitations the detection of circulating tumour DNA has recently been shown to be useful for detecting metastasis in breast cancer patients.

The detection of tumour specific methylation in the blood has been proposed to offer distinct advantages over the detection of mutations[1-5]. A number of single or multiple methylation biomarkers have been assessed in cancers including lung[6-10], colon[11,12] and breast[13-16]. These have suffered from low sensitivities as they have tended to be insufficiently prevalent in the tumours. Several multi-gene assays have been developed with improved performance. A more advanced multi-gene system using a combination of 10 different genes has been reported and uses a multiplexed PCR based assay[17]. It offers combined sensitivity and specificity of 91% and 96% respectively, due to the better coverage offered and it has been validated in a small cohort of stage IV patients. However, it has a very high background in normal blood which will limit its detection sensitivity. Methylated markers have been used to monitor the response to neoadjuvant therapy[18,19], and recently a methylation gene signature associated with metastatic tumours has been identified[20].

There remains a need for more sensitive and specific screening tools, as well as for straightforward tests that allow for the assessment of tumour burden, chemotherapy response, detection of residual disease, relapse and primary screening in high risk populations.

SUMMARY

It is an object of this disclosure to obviate or mitigate at least one disadvantage of previous approaches.

In a first aspect, this disclosure provides a method for detecting a tumour, comprising: extracting DNA from a cell-free sample obtained from a subject, bisulphite converting at least a portion of the DNA, amplifying regions methylated in cancer from the bisulphite converted DNA, generating sequencing reads from the amplified regions, and detecting tumour signals comprising at least two adjacent methylated sites within a single sequencing read, wherein the detection of at least one of the tumour signals is indicative of a tumour.

In another aspect, there is provided a use of the method for determining response to treatment.

In another aspect, there is provided a use of the method for monitoring tumour load.

In another aspect, there is provided a use of the method for detecting residual tumour post-surgery.

In another aspect, there is provided a use of the method for detecting relapse.

In another aspect, there is provided a use of the method as a secondary screen.

In another aspect, there is provided a use of the method as a primary screen.

In another aspect, there is provided a use of the method for monitoring cancer development.

In another aspect, there is provided a use of the method for monitoring cancer risk.

In another aspect, there is provided a kit for detecting a tumour comprising reagents for carrying out the method, and instructions for detecting the tumour signals.

Other aspects and features of this disclosure will become apparent to those ordinarily skilled in the art upon review of the following description of specific embodiments in conjunction with the accompanying figures.

BRIEF DESCRIPTION OF THE DRAWINGS

Embodiments of this disclosure will now be described, by way of example only, with reference to the attached Figures.

FIG. 3 lists 47 CpG targets selected to identify differentially methylated regions, and shows the results of Receiver Operator Curve (ROC) analysis.

FIG. 4 depicts histograms showing the frequency of patients binned according to positive (methylated) probe frequency. Panel A depicts results for luminal tumours. Panel B depicts results for basal tumours.

FIG. 5 depicts sequencing results to assess methylation status of a region near the CHST11 gene (CHST11 Probe C) in breast cancer cell lines.

FIG. 8 depicts sequencing results to assess methylation status of CHST Probe A and Probe B in prostate cancer cell lines.

FIG. 9 depicts sequencing results to assess methylation status of FOXA Probe A in prostate cancer cell lines.

FIGS. 12A and 12B depict a numerical summary of validation data generated for 98 different probes by bisulphite sequencing six different cell lines. #Reads is indicative of the number of reads exported, and Mean Me is indicative of the mean methylation.

FIGS. 13A and 13B depict a numerical summary of generated methylation data for tumour samples. #Reads is indicative of the number of reads exported, and Mean Me is indicative of the mean methylation.

FIG. 14 depicts a numerical summary generated methylation data for prostate cell lines. #Reads is indicative of the number of reads exported, and Mean Me is indicative of the mean methylation.

In FIG. 19A the patient was retested after seven months and the tumour at that time was assessed as being 0.5 cm$^3$ in volume. In FIG. 19B the patient was retested after four months where the initial tumour volume was 483 cm$^3$.

FIGS. 26A, 26B, and 26C are charts showing regions used to develop a breast cancer test according to one embodiment. The chromosomal location and nucleotide position of the first CpG residue in the region is indicated. The TCGA breast cancer cohort was divided into sub-groups based on PAM-50 criteria. The fraction of each group that is positive for that probe is indicated. "Tissue" indicates results from normal tissue samples.

DETAILED DESCRIPTION

Figure 1:
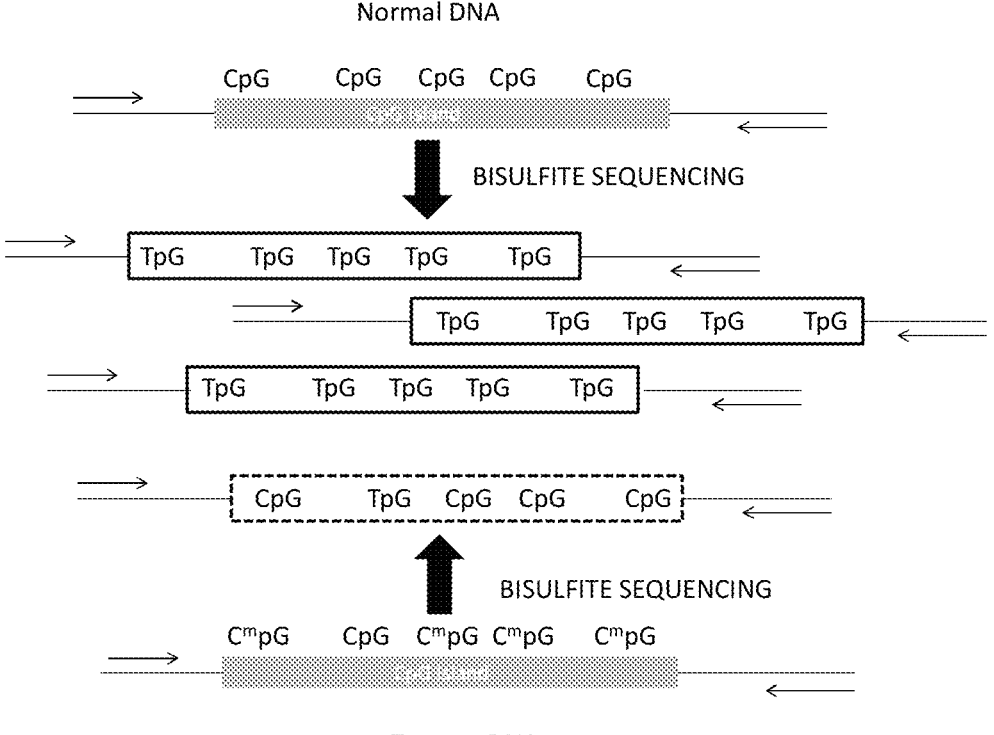
FIG. 1 depicts a schematic of the method.

Generally, this disclosure provides a method for detecting a tumour that can be applied to cell-free samples, e.g., to detect cell-free circulating tumour DNA. The method utilizes detection of adjacent methylation signals within a single sequencing read as the basic "positive" tumour signal.

In one aspect, there is provided a method for detecting a tumour, comprising: extracting DNA from a cell-free sample obtained from a subject, bisulphite converting at least a portion of the DNA, amplifying regions methylated in cancer from the bisulphite converted DNA, generating sequencing reads from the amplified regions, and detecting tumour signals comprising at least two adjacent methylated sites within a single sequencing read, wherein the detection of at least one of the tumour signals is indicative of a tumour.

By "cell-free DNA (cfDNA)" is meant DNA in a biological sample that is not contained in a cell. cfDNA may circulate freely in in a bodily fluid, such as in the bloodstream.

"Cell-free sample", as used herein, is meant a biological sample that is substantially devoid of intact cells. This may be a derived from a biological sample that is itself substantially devoid of cells, or may be derived from a sample from which cells have been removed. Example cell-free samples include those derived from blood, such as serum or plasma; urine; or samples derived from other sources, such as semen, sputum, feces, ductal exudate, lymph, or recovered lavage.

"Circulating tumour DNA", as used herein, accordingly refers to cfDNA originating from a tumour.

By "region methylated in cancer" is meant a segment of the genome containing methylation sites (CpG dinucleotides), methylation of which is associated with a malignant cellular state. Methylation of a region may be associated with more than one different type of cancer, or with one type of cancer specifically. Within this, methylation of a region may be associated with more than one subtype, or with one subtype specifically.

The terms cancer "type" and "subtype" are used relatively herein, such that one "type" of cancer, such as breast cancer, may be "subtypes" based on e.g., stage, morphology, histology, gene expression, receptor profile, mutation profile, aggressiveness, prognosis, malignant characteristics, etc. Likewise, "type" and "subtype" may be applied at a finer level, e.g., to differentiate one histological "type" into "subtypes", e.g., defined according to mutation profile or gene expression.

By "adjacent methylated sites" is meant two methylated sites that are, sequentially, next to each other. It will be understood that this term does not necessarily require the sites to actually be directly beside each other in the physical DNA structure. Rather, in a sequence of DNA including spaced apart methylation sites A, B, and C in the context A-(n)n-B-(n)n-C, wherein (n)n refers to the number of base pairs (bp) (e.g., up to 300 bp), sites A and B would be recognized as "adjacent" as would sites B and C. Sites A and C, however, would not be considered to be adjacent methylated sites.

In one embodiment, the regions methylated in cancer comprise CpG islands.

"CpG islands" are regions of the genome having a high frequency of CpG sites. CpG islands are usually 300-3000 bp in length and are found at or near promotors of approximately 40% of mammalian genes. They show a tendency to occur upstream of so-called "housekeeping genes". A concrete definition is elusive, but CpG islands may be said to have an absolute GC content of at least 50%, and a CpG dinucleotide content of at least 60% of what would be statistically expected. Their occurrence at or upstream of the 5' end of genes may reflect a role in the regulation of transcription, and methylation of CpG sites within the promoters of genes may lead to silencing. Silencing of tumour suppressors by methylation is, in turn, a hallmark of a number of human cancers.

In one embodiment, the regions methylated in cancer comprise CpG shores.

"CpG shores" are regions extending short distances from CpG islands in which methylation may also occur. CpG shores may be found in the region 0 to 2 kb upstream and downstream of a CpG island.

In one embodiment, the regions methylated in cancer comprise CpG shelves.

"CpG shelves" are regions extending short distances from CpG shores in which methylation may also occur. CpG shelves may generally be found in the region between 2 kb and 4 kb upstream and downstream of a CpG island (i.e., extending a further 2 kb out from a CpG shore).

In one embodiment, the regions methylated in cancer comprise CpG islands and CpG shores.

In one embodiment, the regions methylated in cancer comprise CpG islands, CpG shores, and CpG shelves.

In one embodiment, the regions methylated in cancer comprise CpG islands and sequences 0 to 4 kb upstream and downstream. The regions methylated in cancer may also comprise CpG islands and sequences 0 to 3 kb upstream and downstream, 0 to 2 kb upstream and downstream, 0 to 1 kb upstream and downstream, 0 to 500 bp upstream and downstream, 0 to 400 bp upstream and downstream, 0 to 300 bp upstream and downstream, 0 to 200 bp upstream and downstream, or 0 to 100 bp upstream and downstream.

In one embodiment, the step of amplifying is carried out with primers designed to anneal to bisulphite converted target sequences having at least one methylated site therein. Bisulphite conversion results in unmethylated cytosines being converted to uracil, while 5-methylcytosine is unaffected. "Bisulphite converted target sequences" are thus understood to be sequences in which cytosines known to be methylation sites are fixed as "C" (cytosine), while cytosines known to be unmethylated are fixed as "U" (uracil; which can be treated as "T" (thymine) for primer design purposes). Primers designed to target such sequences may exhibit a degree of bias towards converted methylated sequences. However, in one embodiment, the primers are designed without preference as to location of the at least one methylated site within target sequences. Often, to achieve optimal discrimination, it may be desirable to place a discriminatory base at the ultimate or penultimate 3' position of an oligonucleotide PCR primer. In this embodiment, however, no preference is given to the location of the discriminatory sites of methylation, such that overall primer design is optimized based on sequence (not discrimination). This results in a degree of bias for some primer sets, but usually not complete specificity towards methylated sequences (some individual primer pairs, however, may be specific if a discriminatory site is fortuitously placed). As will be described herein, this permits some embodiments of the method to be quantitative or semi-quantitative.

In one embodiment, the PCR primers are designed to be methylation specific. This may allow for greater sensitivity in some applications. For instance, primers may be designed to include a discriminatory nucleotide (specific to a methylated sequence following bisulphite conversion) positioned to achieve optimal discrimination, e.g. in PCR applications. The discriminatory may be positioned at the 3' ultimate or penultimate position.

In one embodiment, the primers are designed to amplify DNA fragments 75 to 150 bp in length. This is the general size range known for circulating DNA, and optimizing primer design to take into account target size may increase the sensitivity of the method according to this embodiment. The primers may be designed to amplify regions that are 50 to 200, 75 to 150, or 100 or 125 bp in length.

In some embodiments, concordant results provide additional confidence in a positive tumour signal. By "concordant" or "concordance", as used herein, is meant methylation status that is consistent by location and/or by repeated observation. As has already been stated, the basic "tumour signal" defined herein comprises at least two adjacent methylated sites within a single sequencing read. However, additional layers of concordance can be used to increase confidence for tumour detection, in some embodiments, and not all of these need be derived from the same sequencing read. Layers of concordance that may provide confidence in tumor detection may include, for example:

(a) detection of methylation of at least two adjacent methylation sites;

(b) detection of methylation of more than two adjacent methylation sites;

(c) detection of methylation at adjacent sites within the same section of a target region amplified by one primer pair;

(d) detection of methylation at non-adjacent sites within the same section of a region amplified by one primer pair;

(e) detection of methylation at adjacent sites within the same target region;

(f) detection of methylation at non-adjacent sites within the same target region;

(g) any one of (a) to (f) in the same sequencing read;

(h) any one of (a) to (f) in at least two sequencing reads;

(i) any one of (a) to (f) in a plurality of sequencing reads;

(j) detection over methylation at sets of adjacent sites that overlap;

(k) repeated observation of any one of (a) to (j); or (l) any combination or subset of the above.

In one embodiment, each of the regions is amplified in sections using multiple primer pairs. In one embodiment, these sections are non-overlapping. The sections may be immediately adjacent or spaced apart (e.g. spaced apart up to 10, 20, 30, 40, or 50 bp). Since target regions (including CpG islands, CpG shores, and/or CpG shelves) are usually longer than 75 to 150 bp, this embodiment permits the methylation status of sites across more (or all) of a given target region to be assessed.

A person of ordinary skill in the art would be well aware of how to design primers for target regions using available tools such as Primer3, Primer3Plus, Primer-BLAST, etc. As discussed, bisulphite conversion results in cytosine converting to uracil and 5'-methyl-cytosine converting to thymine. Thus, primer positioning or targeting may make use of bisulphite converted methylate sequences, depending on the degree of methylation specificity required.

Target regions for amplification are designed to have at least two CpG dinucleotide methylation sites. In some embodiments, however, it may be advantageous to amplify regions having more than one CpG methylation site. For instance, the amplified regions may have 3, 4, 5, 6, 7, 8, 9, 10, 11, 12, 13, 14, or 15 CpG methylation sites. In one embodiment, the primers are designed to amplify DNA fragments comprising 3 to 12 CpG methylation sites. Overall this permits a larger number of adjacent methylation sites to be queried within a single sequencing read, and provides additional certainty (exclusion of false positives) because multiple concordant methylations can be detected within a single sequencing read. In one embodiment, the tumour signals comprise more than two adjacent methylation sites within the single sequencing read. Detecting more than two adjacent methylation sites provides additional concordance, and additional confidence that the tumour signal is not a false positive in this embodiment. For example, a tumour signal may be designated as 3, 4, 5, 6, 7, 8, 9, 10 or more adjacent detected methylation sites within a single sequencing read. In one embodiment, the detection of more than one of the tumour signals is indicative of a tumour. Detection of multiple tumour signals, in this embodiment, can increase confidence in tumour detection. Such signals can be at the same or at different sites. In one embodiment, the detection of more than one of the tumour signals at the same region is indicative of a tumour. Detection of multiple tumour signals indicative of methylation at the same site in the genome, in this embodiment, can increase confidence in tumour detection. So too can detection of methylation at adjacent sites in the genome, even if the signals are derived from different sequencing reads. This reflects another type of concordance. In one embodiment, the detection of adjacent or overlapping tumour signals across at least two different sequencing reads is indicative of a tumour. In one embodiment, the adjacent or overlapping tumour signals are within the same CpG island. In one embodiment, the detection of 5 to 25 adjacent methylated sites is indicative of a tumour.

Methylated regions can be selected according to the purpose of the intended assay. In one embodiment, the regions comprise at least one region listed Table 1 and/or Table 2. In one embodiment, the regions comprise all regions listed in Table 1 and/or Table 2.

Likewise, primer pairs can be designed based on the intended target regions.

In one embodiment, the step of amplification is carried out with more than 100 primer pairs. The step of amplification may be carried out with 10, 20, 30, 40, 50, 60, 70, 80, 90, 100, 110, 120, 130, 140, 150, or more primer pairs. In one embodiment, the step of amplification is a multiplex amplification. Multiplex amplification permits large amount of methylation information to be gathered from many target regions in the genome in parallel, even from cfDNA samples in which DNA is generally not plentiful. The multiplexing may be scaled up to a platform such as ION AmpliSeq™, in which, e.g. up to 24,000 amplicons may be queried simultaneously. In one embodiment, the step of amplification is nested amplification. A nested amplification may improve sensitivity and specificity.

The nested reaction may be part of a next generation sequencing approach. Barcode and/or sequencing primers may be added in the second (nested) amplification. Alternatively, these may added in the first amplification.

In one embodiment, the method further comprises quantifying the tumour signals, wherein a number in excess of a threshold is indicative of a tumour. In one embodiment, the steps of quantifying and comparing are carried out independently for each of the sites methylated in cancer. Accordingly, a count of positive tumour signals may be established for each site. In one embodiment, the method further comprises determining a proportion of the sequencing reads containing tumour signals, wherein the proportion in excess of a threshold is indicative of a tumour. In one embodiment, the step of determining is carried out independently for each of the sites methylated in cancer.

By "threshold", as used herein, is meant a value that is selected to discriminate between a disease (e.g., malignant) state, and a non-disease (e.g., healthy) state. Thresholds can be set according to the disease in question, and may be based on earlier analysis, e.g., of a training set. Thresholds may also be set for a site according to the predictive value of methylation at a particular site. Thresholds may be different for each methylation site, and data from multiple sites can be combined in the end analysis.

Various design parameters may be used to select the regions subject to amplification in some embodiments. In one embodiment, the regions are not methylated in healthy tissue. Healthy tissue would be understood to be non-malignant. Healthy tissue is often selected based on the origin of the corresponding tumour.

Regions may be selected based on desired aims or required specificity, in some embodiments. For instance, it may be desirable to screen for more than one cancer type. Thus, in one embodiment, the regions are collectively methylated in more than one tumour type. It may be desirable to include regions methylated generally in a group of cancers, and regions methylated in specific cancers in order to provide different tiers of information. Thus, in one embodiment, the regions comprise regions that are specifically methylated in specific tumours, and regions that are methylated in more than one tumour type. Likewise, it may be desirably to include a second tier of regions that can differentiate between tumour types. In one embodiment, the regions specifically methylated in specific tumours comprise a plurality of groups, each specific to one tumour type. However, it may be desirable in some contexts to have a test that is focused on one type of cancer. Thus, in one embodiment, the regions are methylated specifically in one tumour type. In one embodiment, the regions are selected from those listed in Table 3 and the tumour is one carrying a BRCA1 mutation.

More specifically, in some embodiments regions may be selected that are methylated in particular subtypes of a cancer exhibiting particular histology, karyotype, gene expression (or profile thereof), gene mutation (or profile thereof), staging, etc. Accordingly, the regions to be amplified may comprise one or more groups of regions, each being established to be methylated in one particular cancer subtype. In one embodiment the regions to be amplified may be methylated in a cancer subtype bearing particular mutations. With breast cancer in mind, one example subtype defined by mutation is cancer bearing BRCA1 mutations. Another subtype is cancer bearing BRCA2 mutations. Other breast cancer subtypes for which methylated regions may be determined include Basal, Luminal A, Luminal B, HER2 and Normal-like tumours. For uveal melanoma, for example, subtypes may include tumours that have retained or lost chromosome 3 (monosomy 3).

Within the context of such a test of some embodiments, information about not only the presence, but also the pattern and distribution of tumour signals both within specific regions and between different regions may help to detect or validate the presence of a form of cancer. In one embodiment, the method further comprises determining a distribution of tumour signals across the regions, and comparing the distribution to at least one pattern associated with a cancer, wherein similarity between the distribution and the pattern is indicative of the cancer.

"Distribution", as used herein in this context, is meant to indicate the number and location of tumour signals across the regions. Statistical analysis may be used to compare the observed distribution with, e.g., pre-established patterns (data) associated with a form of cancer. In other embodiments, the distribution may be compared to multiple patterns. In one embodiment, the method further comprises determining a distribution of tumour signals across the regions, and comparing the distribution to a plurality of patterns, each one associated with a cancer type, wherein similarity between the distribution and one of the plurality of patterns is indicative of the associated cancer type.

In one embodiment, the step of generating sequencing reads is carried out by next generation sequencing. This permits a very high depth of reads to be achieved for a given region. These are high-throughput methods that include, for example, Ilumina (Solexa) sequencing, Roche 454 sequencing, Ion Torrent sequencing, and SOLID sequencing. The depth of sequencing reads may be adjusted depending on desired sensitivity.

In one embodiment, the step of generating sequencing reads is carried out simultaneously for samples obtained from multiple patients, wherein the amplified CpG islands from is barcoded for each patient. This permits parallel analysis of a plurality of patients in one sequencing run.

A number of design parameters may be considered in the selection of regions methylated in cancer, according to some embodiments. Data for this selection process may be from a variety of sources such as, e.g., The Cancer Genome Atlas (TCGA) (http://cancergenome.nih.gov/), derived by the use of, e.g., Illumina Infinium HumanMethylation450 BeadChip (http://www.illumina.com/products/methylation_450_bea-dchip kits.html) for a wide range of cancers, or from other sources based on, e.g., bisulphite whole genome sequencing, or other methodologies. For instance, "methylation value" (understood herein as derived from TCGA level 3 methyl-ation data, which is in turn derived from the beta-value, which ranges from −0.5 to 0.5) may be used to select regions. In one embodiment, the step of amplification is carried out with primer sets designed to amplify at least one methylation site having a methylation value of below −0.3 in normal issue. This can be established in a plurality of normal tissue samples, for example 4. The methylation value may be at or below −0.1, −0.2, −0.3, −0.4, or −0.5. In one embodiment, the primer sets are designed to amplify at least one methylation site having a difference between the aver-age methylation value in the cancer and the normal tissue of greater than 0.3. The difference may be greater than 0.1, 0.2, 0.3, 0.4, or 0.5. Proximity of other methylation sites that meet this requirement may also play a role in selecting regions, in some embodiments. In one embodiment, the primer sets include primer pairs amplifying at least one methylation site having at least one methylation site within 200 bp that also has a methylation value of below −0.3 in normal issue, and a difference between the average meth-ylation value in the cancer and the normal tissue of greater than 0.3. In another embodiment the adjacent site having these features may be 300 bp. The adjacent site may be within 100, 200, 300, 400, or 500 bp.

In some embodiments, target regions may be selected for amplification based on the number of tumours in the vali-dation set having methylation at that site. For example, a region may be selected if it is methylated in at least 50%, 55%, 60%, 65%, 70%, 75%, 80, 85%, 90, or 95% of tumours tested. For example, regions may be selected if they are methylated in at least 75% of tumours tested, including within specific subtypes. For some validations, it will be appreciated that tumour-derived cell lines may be used for the testing.

In another embodiment, the method further comprises oxidative bisulphite conversion. In addition to the analysis of methylation of CpG residues, additional information that may be of clinical significance may be derived from the analysis of hydroxymethylation. Bisulphite sequencing results in the conversion of unmethylated cytosine residues into uracil/thymidine residues, while both methylated and hydroxymethylated cytosines remain unconverted. How-ever, oxidative bisulphite treatment allows for the conver-sion of hydroxymethylated cytosines to uracil/thymidine allowing for the differential analysis of both types of modi-fications. By comparison of bisulphite to oxidative bisul-phite treatments the presence of hydroxymethylation can be deduced. This information may be of significance as its presence or absence may be correlated with clinical features of the tumor which may be clinically useful either as a predictive or prognostic factor. Accordingly, in some embodiments, information about hydroxymethylation could additionally be used in the above-described embodiments.

In one aspect, the presence of specific patterns of meth-ylation is linked to underlying characteristics of particular tumours. In these cases, the methylation patterns detected by the method are indicative of clinically relevant aspects of the tumours such as aggressiveness, likelihood of recurrence, and response to various therapies. Detection of these pat-terns in the blood may thus provide both prognostic and predictive information related to a patient's tumor.

In another aspect, the forgoing method may be applied to clinical applications involving the detection or monitoring of cancer.

In one embodiment, the forgoing method may be applied to determine and/or predict response to treatment.

In one embodiment, the forgoing method may be applied to monitor and/or predict tumour load.

In one embodiment, the forgoing method may be applied to detect and/or predict residual tumour post-surgery.

In one embodiment, the forgoing method may be applied to detect and/or predict relapse.

In one aspect, the forgoing method may be applied as a secondary screen.

In one aspect, the forgoing method may be applied as a primary screen.

In one aspect, the forgoing method may be applied to monitor cancer development.

In one aspect, the forgoing method may be applied to monitor and/or predict cancer risk.

In another aspect, there is provided a kit for detecting a tumour comprising reagents for carrying out the aforemen-tioned method, and instructions for detecting the tumour signals. Reagents may include, for example, primer sets, PCR reaction components, and/or sequencing reagents.

In one embodiment of the forgoing methods, the regions comprise C2CD4A, COL19A1, DCDC2, DHRS3, GALNT3, HES5, KILLIN, MUC21, NR2E1/OSTM1, PAMR1, SCRN1, and SEZ6, and the tumour is uveal melanoma. In one embodiment, the probes comprise C2C5F, COL2F, DCD5F, DGR2F, GAL1F, GAL3F, HES1F, HES3F, HES4F, KIL5F, KIL6F, MUC2F, OST3F, OST4F, PAM4F, SCR2F, SEZ3F, and SEZ5F.

In one embodiment, the regions comprise ADCY4, ALDH1L1, ALOX5, AMOTL2, ANXA2, CHST11, EFS, EPSTI1, EYA4, HAAO, HAPLN3, HCG4P6, HES5, HIF3A, HLA-F, HLA-J, HOXA7, HSF4, KLK4, LOC376693, LRRC4, NBR1, PAH, PON3, PPM1H, PTRF, RARA, RARB, RHCG, RND2, TMP4, TXNRD1, and ZSCAN12, and the tumour is prostate cancer. In one embodiment, the probes comprise ADCY4-F, ALDH1L1-F, ALOX5-F, AMOTL2-F, ANXA2-F, CHST11-F, EFS-F, EPSTI1-F, EYA4-F, HAAO-F, HAPLN3-F, HCG4P6-F, HES5-F, HIF3A-F, HLA-J-F, HLA-J-1-F, HLA-J-2-F, HOXA7-F, HSF4-F, KLK4-F, LOC376693-F, LRRC4-F, NBR1-F, PAH-F, PON3-F, PPM1H-F, PTRF-F, RARA-F, RARB-F, RHCG-F, RND2-F, TMP4-F, TXNRD1-F, and ZSCAN12-F. In one embodiment, the probes additionally include C1Dtrim, C1 Etrim, CHSAtrim, DMBCtrim, FOX-Atrim, FOXEtrim, SFRAtrim, SFRCtrim, SFREtrim, TTBAtrim, VWCJtrim, and VWCKtrim.

In one embodiment, the regions comprise ASAP1, BC030768, C18orf62, C6orf141, CADPS2, CORO1C, CYP27A1, CYTH4, DMRTA2, EMX1, HFE, HIST1H3G/1H2BI, HMGCLL1, KCNK4, KJ904227, KRT78, LINC240, Me3, MIR1292, NBPF1, NHLH2, NRN1, PPM1H, PPP2R5C, PRSS3, SFRP2, SLCO4C1, SOX2OT, TUBB2B, USP44, Intergenic (Chr1), Intergenic (Chr2), Intergenic (Chr3), Intergenic (Chr4), Intergenic (Chr8), and Intergenic (Chr10), and the tumour is aggressive prostate cancer. In one embodiment, the aggressive prostate cancer has a Gleason Score greater than 6. In one embodiment, the aggressive prostate cancer has a Gleason Score of 9 or greater. In one embodiment, the probes comprise ASAP1/p, BC030768/p, C18orf62/p, C6orf141/p-1, C6orf141/p-2, CADPS2/p, CORO1C/p-1, CORO1C/p-2, CYP27A1/p, CYTH4/p, DMRTA2/p, EMX1/p, HFE/p-1, HFE/p-2, HIST1H3G/1H2BI/p, HMGCLL1/p, KCNK4/p, KJ904227/ p, KRT78/p, LINC240/p-1, LINC240/p-2, Me3/p-1, Me3/p-2, MIR129, NBPF1/p, NHLH2/p, NRN1/p, PPM1H/p-1, PPM1H/p-2, PPP2R5C/p, PRSS3/p, SFRP2/p-1, SFRP2/p-2, SLCO4C1/p, SOX2OT/p, TUBB2B/p, USP44/p, Chr1/p-1, Chr2/p-1, Chr3/p-1, Chr4/p-1, Chr8/p-1, and Chr10/p-1.

In one embodiment, the regions comprise the regions depicted in FIGS. 26A, 26B, and 26C, and the tumour is breast cancer.

In one embodiment, the regions comprise ALX1, ACVRL1, BRCA1,C1orf114, CA9, CARD11, CCL28, CD38, CDKL2, CHST11, CRYM, DMBX1, DPP10, DRD4, ERNA4, EPSTI1, EVX1, FABP5, FOXA3, GALR3, GIPC2, HINF1B, HOXA9, HOXB13, Intergenic5, Intergenic 8, IRF8, ITPRIPL1, LEF1, LOC641518, MAST1, BARHL2, BOLL, C5orf39, DDAH2, DMRTA2, GABRA4, ID4, IRF4, NT5E, SIM1, TBX15, NFIC, NPHS2, NR5A2, OTX2, PAX6, GNG4, SCAND3, TAL1, PDX1, PHOX2B, POU4F1, PFIA3, PRDM13, PRKCB, PRSS27, PTGDR, PTPRN2, SALL3, SLC7A4, SOX2OT, SPAG6, TCTEX1D1, TMEM132C, TMEM90B, TNFRSF10D, TOP2P1, TSPAN33, TTBK1, UDB, and VWC2, and the tumour is triple negative breast cancer (TNBC). In one embodiment, the probes comprise ALX1, AVCRL1, BRCA1-A, C1Dtrim, C1Etrim, CA9-A, CARD11-B, CCL28-A, CD38, CDKL2-A, CHSAtrim, CRYM-A, DMBCtrim, DMRTA2exp-A, DPP10-A, DPP10-B, DPP10-C,DRD4-A, EFNA4-B, EPSTI1, EVX1, FABP5, FOXAtrim, FOXEtrim, GALR3-A, GIPC2-A, HINF C trim, HOXAAtrim, HOXACtrim, HOXB13-A, Int5, Int8, IRF8-A, ITRIPL1, LEF1-A, MAST1 A trim, mbBARHL2 Trim, mbBOLL Trim, mbC5orf Trim, mbDDAH Trim, mbDMRTA Trim, mbGABRA A Trim, mbGABRA B Trim, mbGNG Trim, mbID4 Trim, mbIRF Trim, mbNT5E Trim, mbSIM A Trim, mbTBX15 Trim, NFIC-B, NFIC-A, NPSH2-B, NR5A2-B, OTX2-A, PAX6-A, pbDMRTA Trim, pbGNG Trim, pbSCAND Trim, pbTAL Trim, PDX1exp-B, PHOX2B-A, POU4F1 A trim, PPFIA3-A, PRDM13, PRKCB-A, PRKCB-C, PRSS27-A, PTGDR, PTPRN2-A, PTPRN2-B, SALL3-A, SALL3-B, SLC7A4-A, SOX2OT-B, SPAG6 A trim, TCTEX1D1-A, TMEM-A, TMEM-B, TMEM90B-A, TNFRSF10D, TOP2P1-B, TSPAN33-A, TTBAtrim, UBD-A, VWCJtrim, and VWCKtrim.

In one embodiment, each region is amplified with primer pairs listed for the respective region in Table 15.

In one embodiment, the method further comprises administering a treatment for the tumour detected.

In one aspect, there is provided a method for identifying a methylation signature indicative of a biological characteristic, the method comprising: obtaining data for a population comprising a plurality of genomic methylation data sets, each of said genomic methylation data sets associated with biological information for a corresponding sample, segregating the methylation data sets into a first group corresponding to one tissue or cell type possessing the biological characteristic and a second group corresponding to a plurality of tissue or cell types not possessing the biological characteristic, matching methylation data from the first group to methylation data from the second group on a site-by-site basis across the genome, identifying a set of CpG sites that meet a predetermined threshold for establishing differential methylation between the first and second groups, identifying, using the set of CpG sites, target genomic regions comprising at least two differentially methylated CpGs with 300 bp that meet said predetermined criteria, extending the target genomic regions to encompass at least one adjacent differentially methylated CpG site that does not meet the predetermined criteria, wherein the extended target genomic regions provide the methylation signature indicative of the biological trait.

In one embodiment, the method further comprises validating the extended target genomic regions by testing for differential methylation within the extended target genomic regions using DNA from at least one independent sample possessing the biological trait and DNA from at least one independent sample not possessing the biological sample.

In one embodiment, the step of identifying further comprises limiting the set of CpG sites to CpG sites that further exhibit differential methylation with peripheral blood mononuclear cells from a control sample.

In one embodiment, the plurality of tissue or cell types of the second group comprises at least some tissue or cells of the same type as the first group.

In one embodiment, the plurality of tissue or cell types of the second group comprises a plurality of non-diseased tissue or cell types.

In one embodiment, the predetermined threshold is indicative of methylation in the first group and non-methylation in the second group.

In one embodiment, the predetermined threshold is at least 50% methylation in the first group.

In one embodiment, the predetermined threshold is a difference in average methylation between the first and second groups of 0.3 or greater.

In one embodiment, the biological trait comprises malignancy.

In one embodiment, the biological trait comprises a cancer type.

In one embodiment, the biological trait comprises a cancer classification.

In one embodiment, the cancer classification comprises a cancer grade.

In one embodiment, the cancer classification comprises a histological classification.

In one embodiment, the biological trait comprises a metabolic profile.

In one embodiment, the biological trait comprises a mutation.

In one embodiment, the mutation is a disease-associated mutation.

In one embodiment, the biological trait comprises a clinical outcome.

In one embodiment, the biological trait comprises a drug response.

In one embodiment, the method further comprises designing a plurality of PCR primers pairs to amplify portions of the extended target genomic regions, each of the portions comprising at least one differentially methylated CpG site.

In one embodiment, the step of designing the plurality of primer pairs comprising converting non-methylated cytosines uracil, to simulate bisulphite conversion, and designing the primer pairs using the converted sequence.

In one embodiment, the primer pairs are designed to have a methylation bias.

In one embodiment, the primer pairs are methylation-specific.

In one embodiment, the primer pairs have no CpG residues within them having no preference for methylation status.

In one aspect, there is provided a method for synthesizing primer pairs specific to a methylation signature, the method comprising: carrying out the forgoing method, and synthesizing the designed primer pairs.

In one aspect, there is provided a non-transitory computer-readable medium comprising instructions that direct a processor to carry out the forgoing method.

In one aspect, there is provided a computing device comprising the computer-readable medium.

Example 1

Concept Summary

The embodiments detect circulating tumour DNA using a highly sensitive and specific methylation based assay with detection limits 100 times better than other techniques.

FIG. 1 depicts a schematic of the overall strategy. CpG dinucleotides are often clustered into concentrated regions in the genome referred to as CpG islands (grey box) and are often, but not always, associated with the promoter or enhancer regions of genes. These regions are known to become abnormally methylated in tumours (CmpG) as compared to normal tissue (CpG) which may be linked to the inactivation of tumour suppressor genes by this methylation event. Methylation of CpG islands and the boundary regions (CpG island shores) is extensive and co-ordinated such that most or all of the CpG residues in that region become methylated. The detection of this methylation typically involves bisulphite conversion, PCR amplification of the relevant region (arrows), and sequencing where un-methylated CpG residues are converted to TpG dinucleotides while methylated CpG residues are preserved as CpGs. Sequencing of these PCR-amplified "probes" (BISULFITE SEQUENCING) from tumour DNA (arrows) results in the detection of multiple CpG residues being methylated within the same DNA fragment (Dashed Box) which can easily be distinguished from DNA from normal tissue (Boxes). The co-ordinated/concordant nature of this methylation produces a strong signal which can be detected over random or background changes from DNA sequencing. This is accomplished by first identifying regions of tumour specific DNA methylation with multiple correlated CpG methylation sites within the same region.

Figure 30:
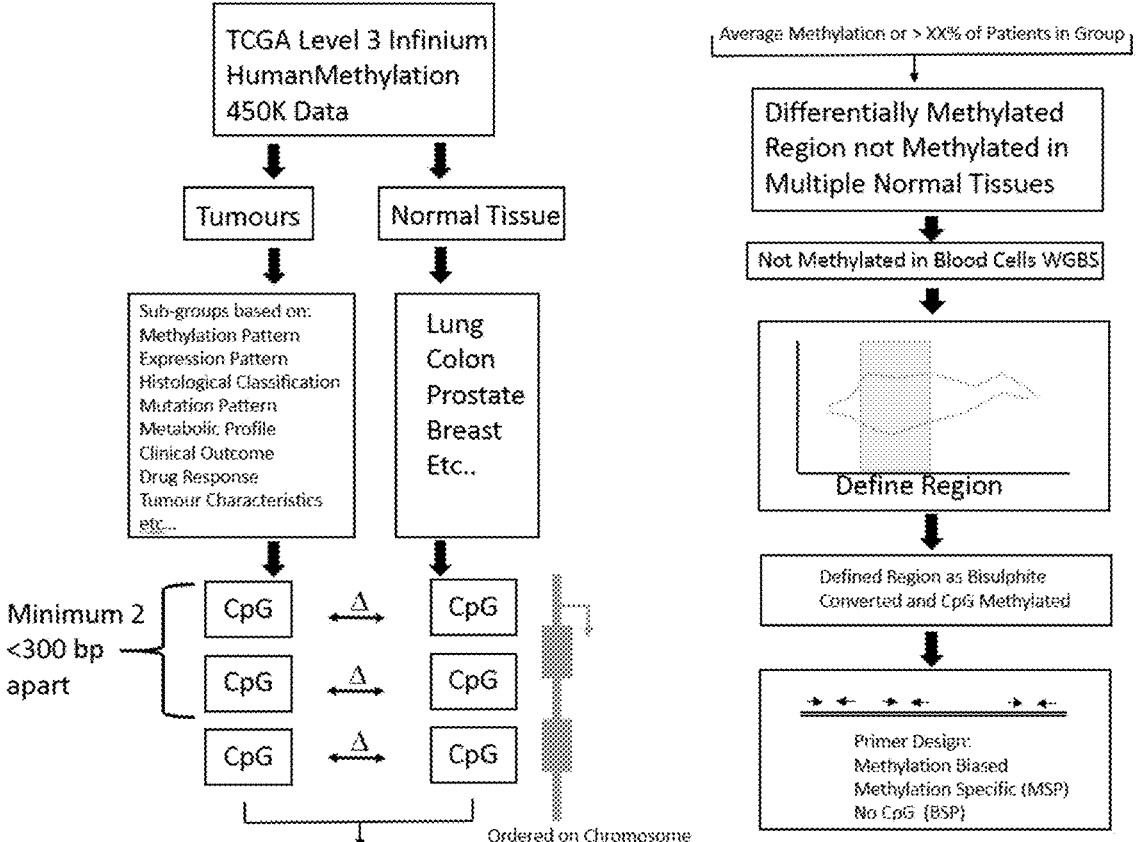
FIG. 30 is a flowchart illustrating a method for determining biological methylation signatures, and for developing probes for their detection.

FIG. 30 depicts a flowchart showing how a methylation signature for a biological trait may be determined. One or more steps of this method may be implemented on a computer. Accordingly, another aspect of this disclosure relates to a non-transitory computer-readable medium comprising instructions that direct a processor to carry out steps of this method.

Generally "probe" is used herein to refer to a target region for amplification and/or the ensuing amplified PCR product. It will be understood that each probe is amplified by a "primer set" or "primer pair".

Figure 2:
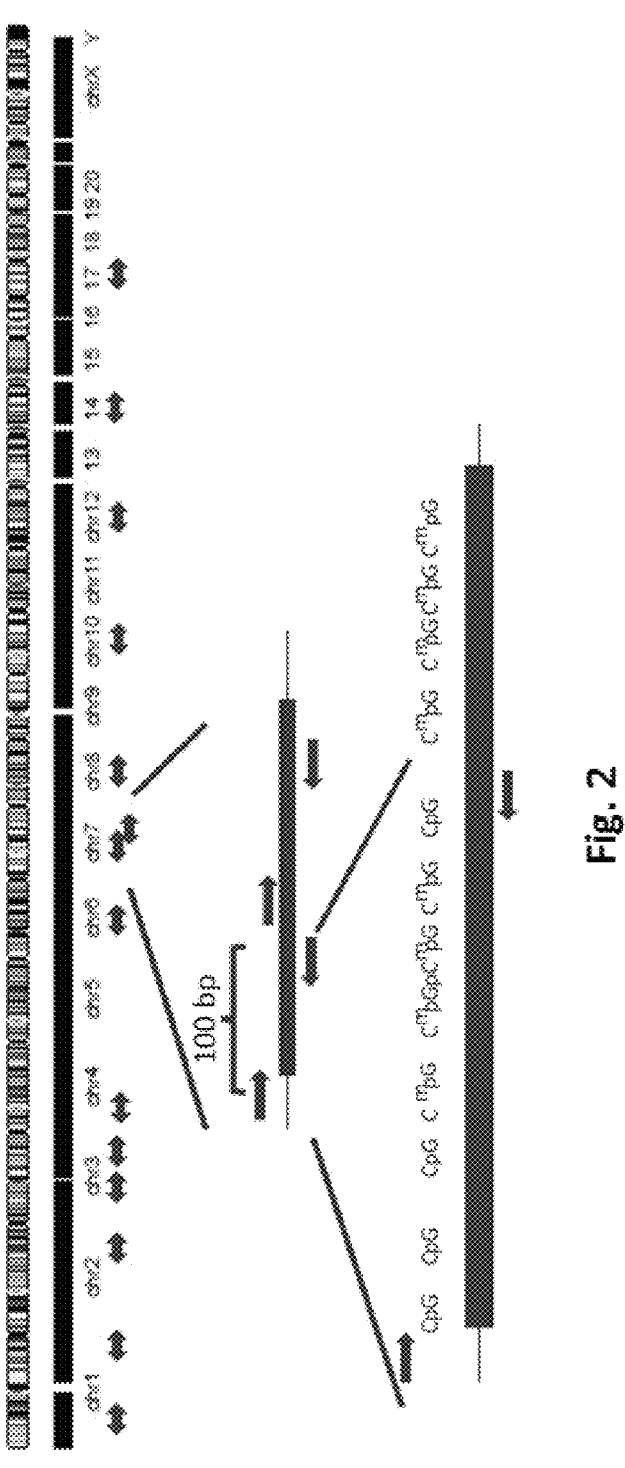
FIG. 2 depicts a schematic of the amplification of multiple target regions.

FIG. 2 depicts a schematic for amplification of target regions. Multiple regions from across the human genome have been identified as being differentially methylated in the DNA from various types of tumours compared to the normal DNA from a variety of different tissues. These regions can be fairly extensive spanning 100s to 1000s of base pairs of DNA. These target regions (black boxes, bottom) exhibit coordinated methylation where most or all of the CpG dinucleotides in these regions are methylated in tumour tissue with little or no methylation in normal tissues. As shown in FIG. 2, when sequencing across these regions (arrows) multiple CpG residues are seen to be methylated together in the tumour creating a concordant signal identifiable as being tumour specific. By targeting multiple PCR-amplified probes across individual regions (middle) and across the entire genome (top) large numbers of probes can be designed with the advantage that with more probes comes greater sensitivity due to the greater likelihood of detecting a tumour specific fragment in a given sample. Primers for these probes are designed to amplify regions from 75 to 150 bp in length, corresponding to the typical size of circulating tumour DNA. The primers may include CpG dinucleotides or not, which in the former case can make these primers biased towards the amplification of methylated DNA or exclusively amplify only methylated DNA.

Multiple methylation-biased PCR primer pairs can be created, which are able to preferentially amplify these regions. These multiple regions are sequenced using next generation sequencing (NGS) at a high read depth to detect multiple tumour specific methylation patterns in a single sample. As described herein, features have been incorporated into a blood based cancer detection system that provides advantages over other tests which have been developed, and provides an unprecedented level of sensitivity and specificity as well as enables the detection of minute quantities of DNA (detection sensitivity).

Example 2

Probe and Primer Set Development

The detection of circulating tumour DNA is hampered by both the presence of large amounts of normal DNA as well as by the very low concentrations of tumour DNA in the blood. Compounding this issue, both PCR and sequencing based approaches suffer from the introduction of single nucleotide changes due to the error prone nature of these processes. To deal with these issues, regions of the genome have been identified that exhibit concerted tumour specific methylation over a significant expanse of DNA so that each CpG residue is concordant[21]. Methylation-biased PCR primer pairs were designed for multiple segments of DNA across these regions each containing multiple CpG residues. Sample protocols for selection of differentially methylated regions and design of region specific PCR primers are provided.

Protocol for the Selection of Differentially Methylated Regions

Use of TCGA DATA for Identifying Breast Specific Probes

Level 3 (processed) Illumina Infinium HumanMethylation450 BeadChip array data (http://www.illumina.com/techniques/microarrays/methylation-arrays.html) was downloaded from The Tumour Genome Atlas (TCGA) site (https://tcga-data.nci.nih.gov/tcga/tcgaHome2.jsp) for the appropriate tumour types (e.g., breast, prostate, colon, lung, etc.). Tumour and normal samples were separated and the methylation values (from −0.5 to +0.5) for each group were averaged. The individual methylation probes were mapped to their respective genomic location. Probes that fulfilled the following example criteria were then identified:

1. The average methylation values for the normal breast, prostate, colon and lung tissues all below −0.3;
2. The difference between the average breast tumour and average breast normal values greater than 0.3, or at least 50% methylation in the tumour group; and
3. Two probes within 300 bp of each other fulfill criteria 1 and 2.

These criteria establish that the particular probe is not methylated in normal tissue, that the difference between the tumour and normal is significant, and that multiple probes in a relatively small area are co-ordinately methylated. Regions which had multiple positive consecutive probes (i.e., 3 or more) were prioritized for further analysis. Average values for approximately 10 other probes to either side of the positive region were plotted for all tumour and normal tissue samples to define the region exhibiting differential methylation. Regions exhibiting concerted differential methylation between tumour and normal for single or multiple tumour types were identified.

A secondary screen for a lack of methylation of these regions in blood was carried out by examining the methylation status of the defined regions in multiple tissues using nucleotide level genome wide bisulphite sequencing data. Specifically the UCSC Genome Browser (https://genome.ucsc.edu/) was used to examine methylation data from multiple sources.

Data was processed by the method described in Song Q, et al., A reference methylome database and analysis pipeline to facilitate integrative and comparative epigenomics. PLOS ONE 2013 8(12): e81148 (http://journals.plos.org/plosone/article?id=10.1371/journal.pone.0081148) for use in the UCSC Browser and to identify hypo-methylated regions (above blue lines).

The Following Data Sources were Used:

Gertz J, et al., Analysis of DNA methylation in a three-generation family reveals widespread genetic influence on epigenetic regulation. PLOS Genet. 2011 7(8):e1002228 (http://journals.plos.org/plosgenetics/article?id=10.1371/journal.pgen.1002228).

Heyn H, et al., Distinct DNA methylomes of newborns and centenarians. Proc. Natl. Acad. Sci. U.S.A. 2012 109(26): 10522-7 (http://www.pnas.org/content/109/26/10522).

Hon G C, et al., Global DNA hypomethylation coupled to repressive chromatin domain formation and gene silencing in breast cancer. Genome Res. 2012 22(2):246-58 (http://genome.cshlp.org/content/22/2/246).

Heyn H, et al., Whole-genome bisulfite DNA sequencing of a DNMT3B mutant patient. Epigenetics. 2012 7(6):542-50 (http://www.tandfonline.com/doi/abs/10.4161/epi.20523 #.VsS_gdIUVIw).

Hon G C, et al., Global DNA hypomethylation coupled to repressive chromatin domain formation and gene silencing in breast cancer. Genome Res. 2012 22(2):246-58 (http://genome.cshlp.org/content/22/2/246).

All of the regions identified exhibited hypo-methylation in normal blood cells including Peripheral Blood Mononuclear Cells (PBMC), the prime source of non-tissue DNA in plasma.

Protocol for the Design of Region Specific Primers for PCR Amplification and Next Generation Sequencing For regions identified as being differentially methylated in tumours, PCR primers were designed that are able to recognize bisulphite converted DNA which is methylated. Using Methyprimer Express™ or PyroMark™, or other web based programs, the DNA sequence of the region was converted to the sequence obtained when fully methylated DNA is bisulphite converted (i.e., C residues in a CpG dinucleotide remain Cs, while all other C residues are converted to T residues). The converted DNA was then analysed using PrimerBlast™ (http://www.ncbi.nlm.nih.gov/tools/primer-blast/) to generate optimal primers. Primers were not expressly selected to contain CpG residues but due to the nature of the regions, generally CpG islands, most had 1 to 3 CpGs within them. This renders them biased towards the amplification of methylated DNA but in many cases they do they recognize and amplify non-methylated DNA as well. The region between the primers includes 2 or more CpG residues. Primers were chosen to amplify regions from 75 to 150 base pairs in size with melting temperatures in the range of 52-68° C. Multiple primers were designed for each region to provide increased sensitivity by providing multiple opportunities to detect that region. Adapter sequences (CS1 and CS2) were included at the 5' end of the primers to allow for barcoding and for sequencing on multiple sequencing platforms by the use of adaptor primers for secondary PCR.

Primers were characterized by PCR amplification of breast cancer cell line DNA and DNA from various primary tumours. PCR amplification was done with individual sets of primers and Next Generation Sequencing carried out to characterize the methylation status of specific regions. Primer sets exhibiting appropriate tumour specific methylation were then combined into a multiplex PCR reaction containing many primers.

Results

FIG. 3 lists the 47 CpG probes used to identify differentially methylated regions. These were analyzed by Receiver Operator Curve analysis (ROC). Normal and tumour samples from the entire TCGA breast cancer database were compared. The Area Under the Curve (AUC) analysis for each probe is shown with the standard error, 95% confidence interval and P-value. All of them where shown to have excellent discriminatory capabilities.

FIG. 4 depicts the results of analysis methylation level for each patient in the TCGA database for the 47 CpG. Those exceeding the threshold of −0.1 were considered to be positive for methylation in that patient. The number of probes exceeding this methylation threshold were calculated for each patient. Patients were divided into those with Luminal A and B subtypes (Luminal Tumours; FIG. 4, Panel A) and those with Basal cancers (Basal Tumours; FIG. 4, Panel B) or and the number of patients with a specific range of positive probes was calculated. The histogram shows the frequency of patents within each range of positive probes. While these probes give excellent coverage in both populations, there are more positive probes amongst the Luminal tumours than the Basal tumours. Additional probes specific to the different breast cancer subtypes have been identified and appropriate probe development and validation is underway.

Example 3

Selection of Regions for Cancer and Cancer Types

For breast cancer, 52 regions in the genome were identified that are highly methylated in tumours but where multiple normal tissues do not exhibit methylation of these regions. These serve as highly specific markers for the presence of a tumour with little or no background signal.

Table 1 depicts regions selected for breast cancer screening.

TABLE 1

| Chromosome | Start (hg18) | End (hg18) | General Location | Tumour | Size |
|---|---|---|---|---|---|
| | | 2nd Generation | | | |
| chr1 | 167663259 | 167663533 | C1orf114 | P/B | 274 |
| chr7 | 49783577 | 49784309 | VWC2 | P/B/C | 732 |
| chr14 | 23873519 | 23873993 | ADCY4 | P/B/C | 474 |
| chr11 | 43559012 | 43559541 | MIR129-2 | B/C | 529 |
| | | 3rd Generation | | | |
| chr6 | 43319186 | 43319213 | TTBK1 | P/B | 27 |
| chr1 | 46723905 | 46724176 | DMBX1 | P/B/C | 271 |
| chr7 | 27171684 | 27172029 | HOXA9 | B | 345 |
| chr8 | 120720175 | 120720579 | ENPP2 | P/B | 404 |
| chr10 | 99521635 | 99521924 | SFRP5 | P/B | 289 |
| chr12 | 103376281 | 103376485 | CHST11 | P/B/C | 204 |
| chr19 | 51071603 | 51072234 | FOXA3 | P/B | 631 |

TABLE 1-continued

| Chromo-some | Start (hg18) | End (hg18) | General Location | Tumour | Size |
|---|---|---|---|---|---|
| | | 4th Generation | | | |
| chr1 | 47470535 | 47470713 | TAL1 | B | 178 |
| chr1 | 50658998 | 50659557 | DMRTA2 | B | 559 |
| chr1 | 66030610 | 66030634 | PDE4B | B | 24 |
| chr1 | 90967262 | 90967924 | BARHL2 | B | 662 |
| chr1 | 119331667 | 119332616 | TBX15 | B/C | 949 |
| chr1 | 153557070 | 153557585 | RUSC1, C1orf104 | B | 515 |
| chr1 | 233880632 | 233880962 | GNG4 | B | 330 |
| chr2 | 104836482 | 104837226 | POU3F3 | B | 744 |
| chr2 | 198359230 | 198359743 | BOLL | B/C | 513 |
| chr3 | 32834103 | 32834562 | TRIM71 | B/C | 459 |
| chr3 | 172228723 | 172228985 | SLC2A2 | B | 262 |
| chr4 | 5071985 | 5072137 | CYTL1 | B | 152 |
| chr4 | 42094549 | 42094615 | SHISA3 | B | 66 |
| chr4 | 46690266 | 46690578 | GABRA4 | B | 312 |
| chr5 | 38293273 | 38293312 | EGFLAM | B | 39 |
| chr5 | 43076195 | 43076642 | C5orf39 | B | 447 |
| chr5 | 115179918 | 115180393 | CDO1 | B | 475 |
| chr6 | 336189 | 337131 | IRF4 | B/C | 942 |
| chr6 | 19944994 | 19945298 | ID4 | B | 304 |
| chr6 | 28618285 | 28618318 | SCAND3 | B | 33 |
| chr6 | 31806197 | 31806205 | DDAH2 | B | 8 |
| chr6 | 33269254 | 33269355 | COL11A2 | B | 101 |
| chr6 | 86215822 | 86215929 | NT5E | B | 107 |
| chr6 | 101018889 | 101019751 | SIM1 | B | 862 |
| | | 5th Generation | | | |
| chr6 | 153493505 | 153494425 | RGS17 | B | 920 |
| chr7 | 121743738 | 121744126 | CAPDS2 | B | 388 |
| chr8 | 72918338 | 72918895 | MSC | B/C | 557 |
| chr10 | 22674438 | 22674584 | SPAG6 | B/C | 146 |
| chr10 | 105026601 | 105026737 | INA | B | 136 |
| chr11 | 128068895 | 128069316 | FLI1 | B/C | 421 |
| chr12 | 52357158 | 52357378 | ATP5G2 | B | 220 |
| chr12 | 94466892 | 94467095 | USP44 | B/C | 203 |
| chr13 | 78075521 | 78075764 | POU4F1 | B | 243 |
| chr14 | 55656275 | 55656325 | PELI2 | B | 50 |
| chr17 | 33176853 | 33178091 | HNF1B | B | 1238 |
| chr17 | 32368343 | 32368604 | LHX1 | B/C/L | 261 |
| chr17 | 44154844 | 44155027 | PRAC, C17orf93 | B/C | 183 |
| chr18 | 73090725 | 73091121 | GALR1 | B/C | 396 |
| chr19 | 12839383 | 12839805 | MAST1 | B | 422 |
| chr20 | 2729122 | 2729438 | CPXM1 | B/C | 316 |
| chr20 | 43952209 | 43952500 | CTSA, NEURL2 | B | 291 |

In Table 1, 'Start' and 'End' designate the coordinates of the target regions in the hg18 build of the human genome reference sequence. The 'General Location' field gives the name of one or more gene or ORF in the vicinity of the target region. Examination of these sequences relative to nearby genes indicates that they were found, e.g., in upstream, in 5' promoters, in 5' enhancers, in introns, in exons, in distal promoters, in coding regions, or in intergenic regions. The 'Tumour' field indicates whether a region is methylated in prostate (P), breast (B), colon (C), and/or lung (L) cancers. The 'Size' field indicates the size of the target region.

In the discussion here, it should be recognized that reference to genes such as CHST11, FOXA, and NT5 are not intended to be indicative of the genes in question per se, but rather to the associated methylated regions described in Table 1.

In total, 52 regions were found to be methylated in association with breast cancer, 17 were found to be methylated in association with prostate cancer, 9 were found to be methylated in association with prostate cancer, and 1 region was found to be methylated in association with lung cancer. Thus, some regions appear to be generally indicative of the various types of cancers assessed. Other regions methylated in subgroups of these, while others are specific for cancers. In the context of this assay and the types of cancers examined, regions may be described as being "specifically methylated in breast cancer". However, it is noted that the same approach may be used to identify regions methylated specifically in other cancers.

Assays may be developed for cancer generally, or to detect groups of cancers or specific cancers. A multi-tiered assay may be developed using "general" regions (methylated in multiple cancers) and "specific" regions (methylated in only specific cancers). A multi-tiered test of this sort may be run together in one multiplex reaction, or may have its tiers executed separately.

Probes for Breast Cancer

Over 150 different PCR primer pairs were developed to the 52 different regions in the genome shown to exhibit extensive methylation in multiple breast cancer samples from the TCGA database but with no or minimal methylation in multiple normal tissues and in blood cells (Peripheral Blood Mononuclear Cells and others).

As proof of concept, these were then used to amplify bisulphite converted DNA from breast cancer cell lines MCF-7 (ER+, PR+), T47-D (ER+, PR+), SK-BR-3 (HER2+), MDA-MD-231 (Triple Negative) and normal breast lines MCF-10A and 184-hTERT. Sequencing adapters were added and Next Generation Sequencing carried out on an Ion Torrent sequencer. The sequencing reads were then separated by region and the sequence reads were analyzed using the BiqAnalyzer HT program.

Results

Example results of methylation analysis will be discussed herein. CHST11 is an example of a region methylated in prostate, breast, and colon cancer. FOXA is a region methylated in breast and prostate cancer. NT5 is a region methylated specifically in breast cancer.

Figure 5:
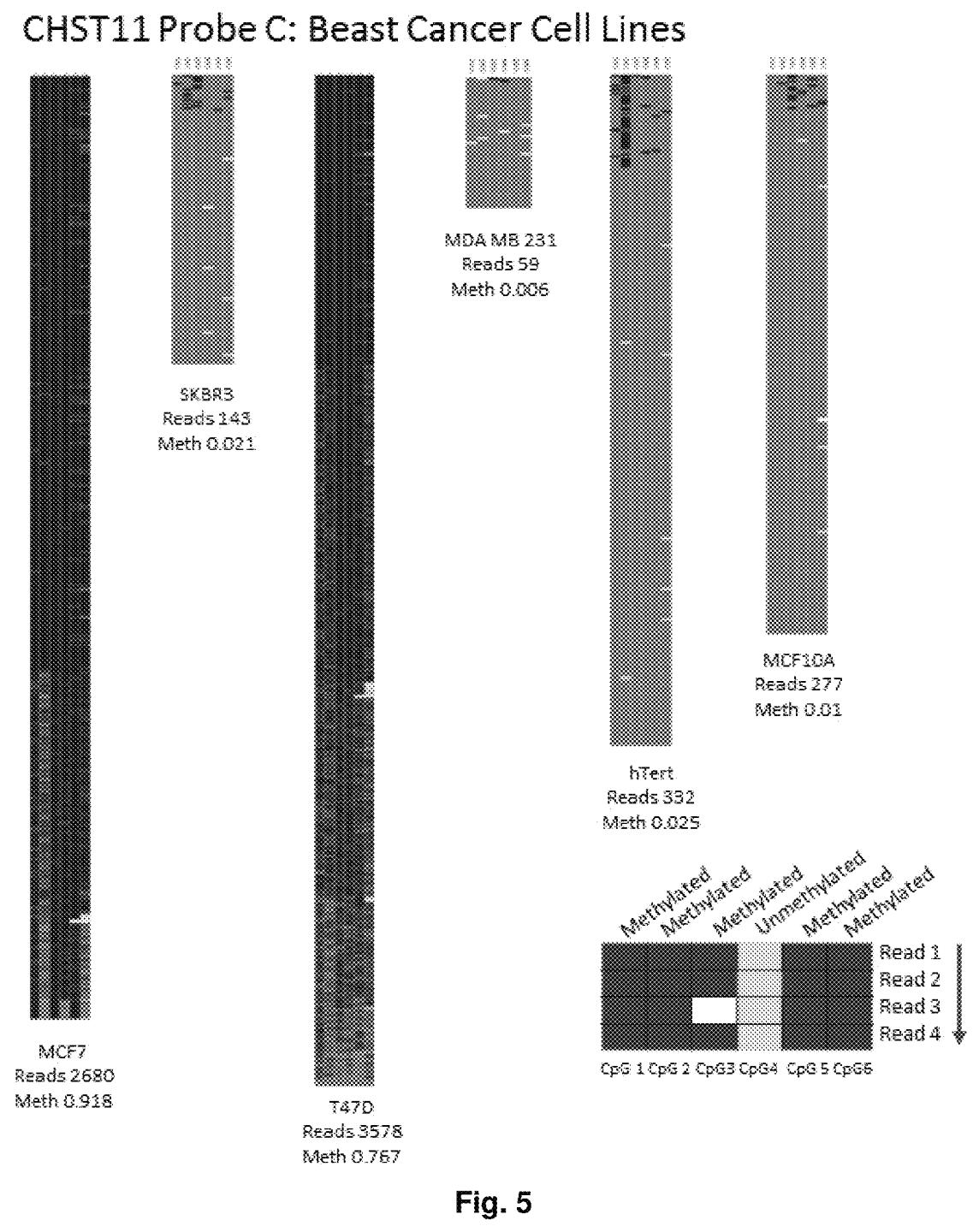

FIG. 5 depicts sequencing results from a region from near the CHST11 gene (Probe C) is shown. For each cell line the results of a single sequencing read is depicted as a horizontal bar with each box representing a single CpG residue from between the PCR primers (in this case there being 6 CpG residues, Illustration at bottom right). Methylated bases are shown in dark grey while un-methylated bases are shown in light grey. Where a CpG could not be identified by the alignment program it is shown as a white box. Multiple sequence reads are shown for each cell line, stacked on top of each other. The numbers at the bottom of each stack indicates the number of sequence reads (Reads) and the overall methylation level determined from these reads (Meth).

When sequenced, these probes produced strong concordant signals that consisted of multiple methylated CpGs (5 to 25) where there is a strong correlation between individual sites being methylated in tumours. This eliminates false positive results due to PCR and sequencing errors. These tumour specific multiple methylated sites can be detected against a high background of normal DNA, being limited only by the read depth of the sequencing. Based on bioinformatic analysis of TCGA tumours, this essentially eliminates false positive signals.

Figure 6:
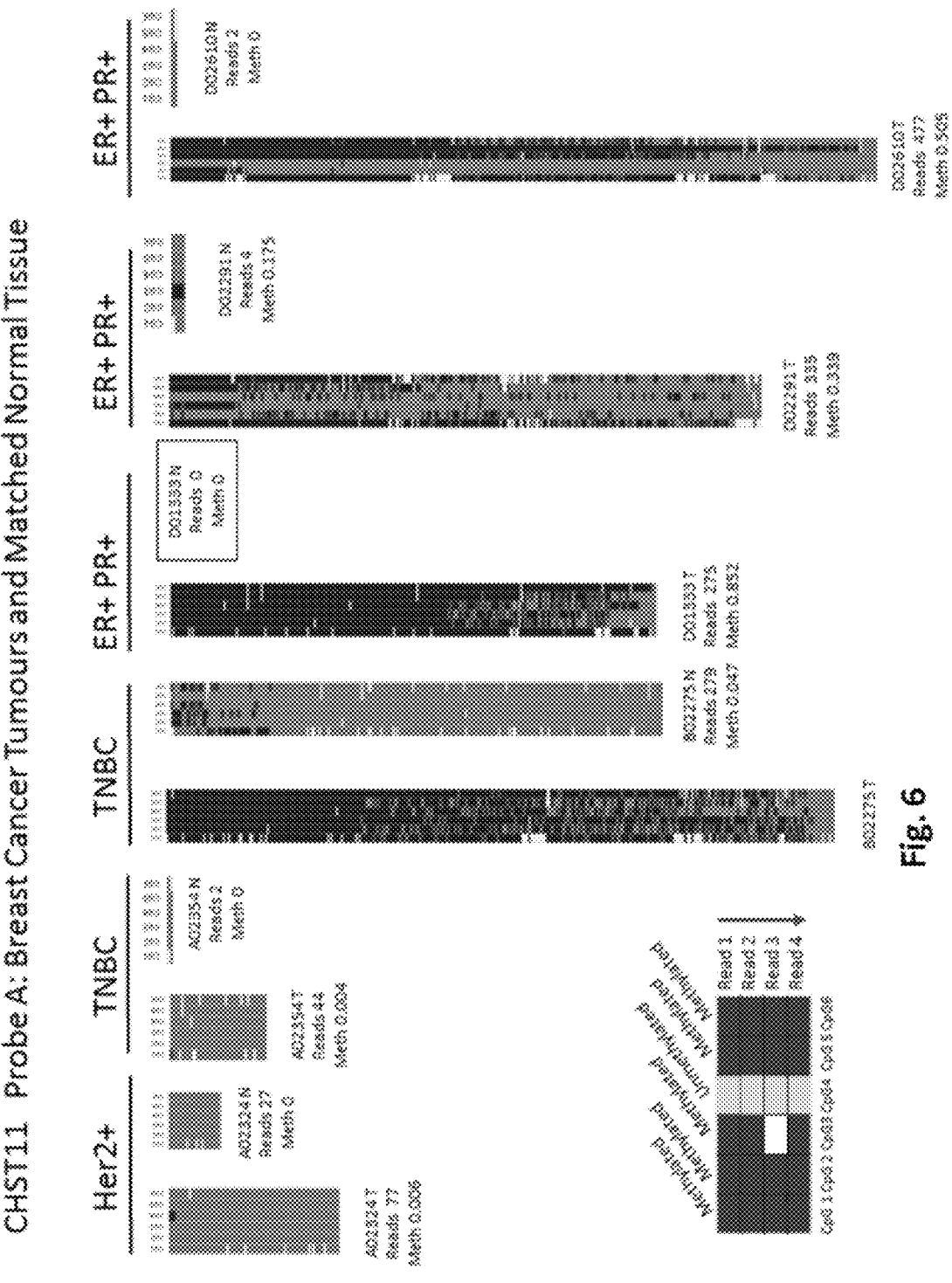
FIG. 6 depicts sequencing results to assess methylation status of CHST11 Probe A in breast cancer tumors and normal breast tissue.

FIG. 6 depicts results for CHST11 Probe A. Methylation in the region was characterized for a variety of breast cancer tumour samples (T) and in normal breast tissue samples (N) from the same patient. As in FIG. 5 the methylated bases are shown in dark grey while un-methylated bases are shown in light grey (illustration bottom left). Tumours of various subtypes were analysed including A02324 which is positive for HER2 amplification (HER2+), A02354 and B02275 which are Triple Negative Breast Cancer (TNBC), and D01333, D02291, D02610 which are all Estrogen and Progesterone Receptor positive tumours (ER+PR+). The values below each column refer to the number of sequence reads obtained by Next Generation Sequencing (Reads) and the overall level of methylation of all of the CpG residues (Meth) based on these reads. Where no sequence reads were obtained for a given sample and box is shown as for sample D01333 N (Normal).

Figure 7:
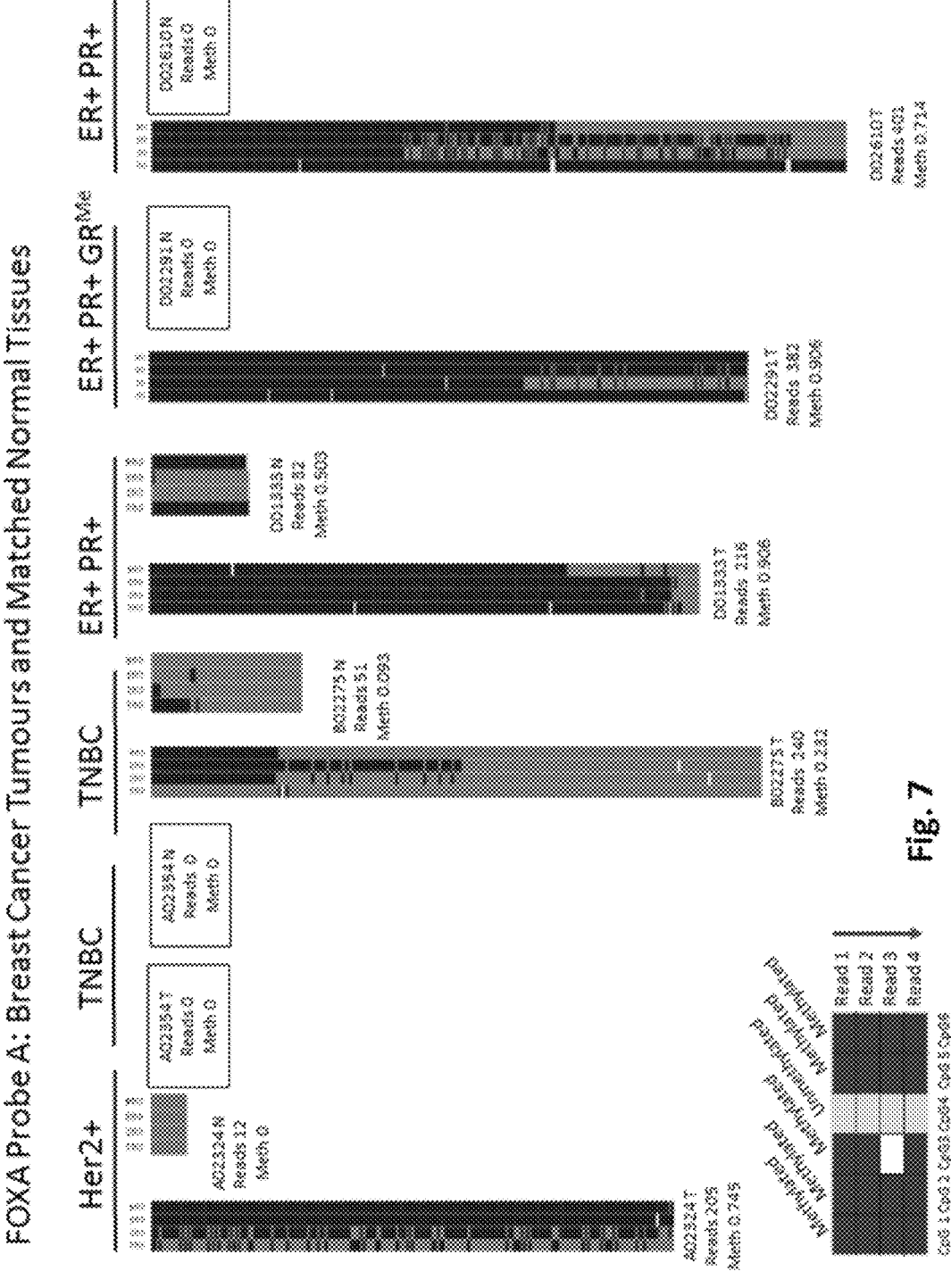
FIG. 7 depicts sequencing results to assess methylation status of FOXA Probe A in breast cancer cell lines.

FIG. 7 depicts results of similar analysis of FOXA Probe A in breast cancer cell lines.

Figure 15:
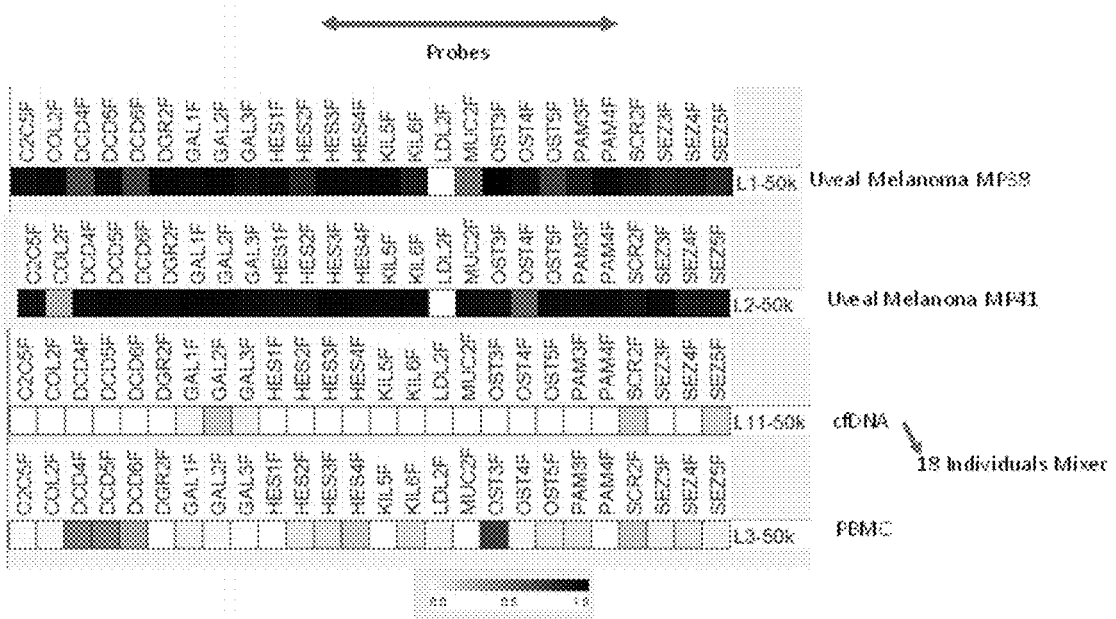
FIG. 15 is a diagram showing validation of various uveal melanoma (UM) probes in two cell lines MP38 (with loss of 3p) and MP41 (3p WT). Negative controls were cell free DNA (cfDNA) consisting of a pool of 18 individuals without cancer and peripheral mononuclear cells (PBMC). Probes for the indicated regions were PCR amplified individually and sequenced. Darker shading indicates higher level of methylation. OST3F was methylated in PBMCs while LDL3F was not methylated in tumours, with the majority showing strong methylation in the UM lines but not in the PBMCs or cfDNA.

FIG. 15 depicts a numerical summary generated methylation data for prostate cell lines. #Reads is indicative of the number of reads exported, and Mean Me is indicative of the mean methylation.

Figure 8:
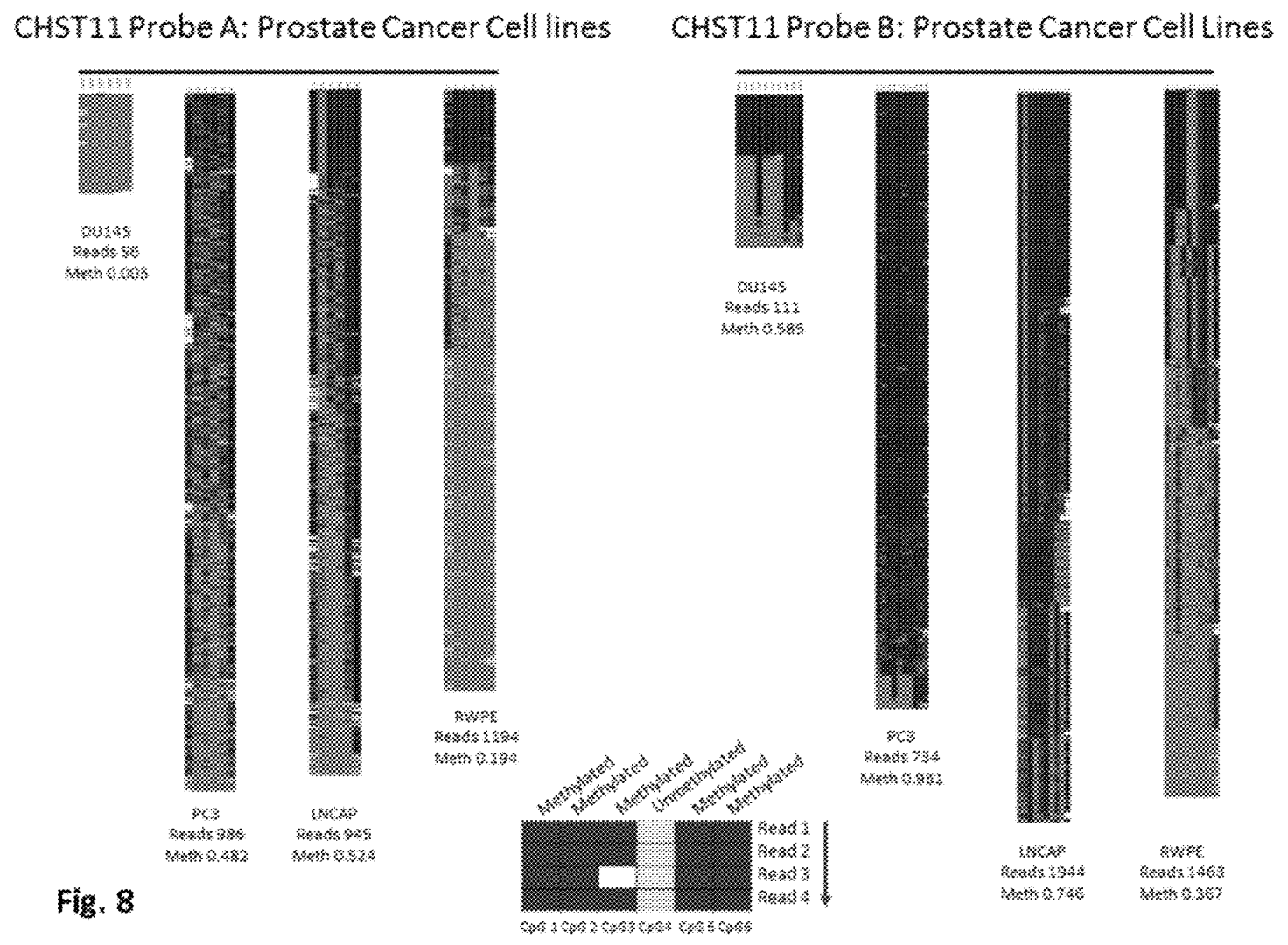

FIG. 8 depicts results of similar analysis of the CHST11 Probe A and CHST11 Probe B in prostate cancer cell lines. DU145 is an Androgen Receptor (AR–) negative cell line which is able to generate metastases in the mouse. PC3 is also AR– and also metastatic. LNCaP is an Androgen Receptor positive line (AR+) which does generate metastases in the mouse while RWPE cells are AR+ and non-metastatic.

Figure 9:
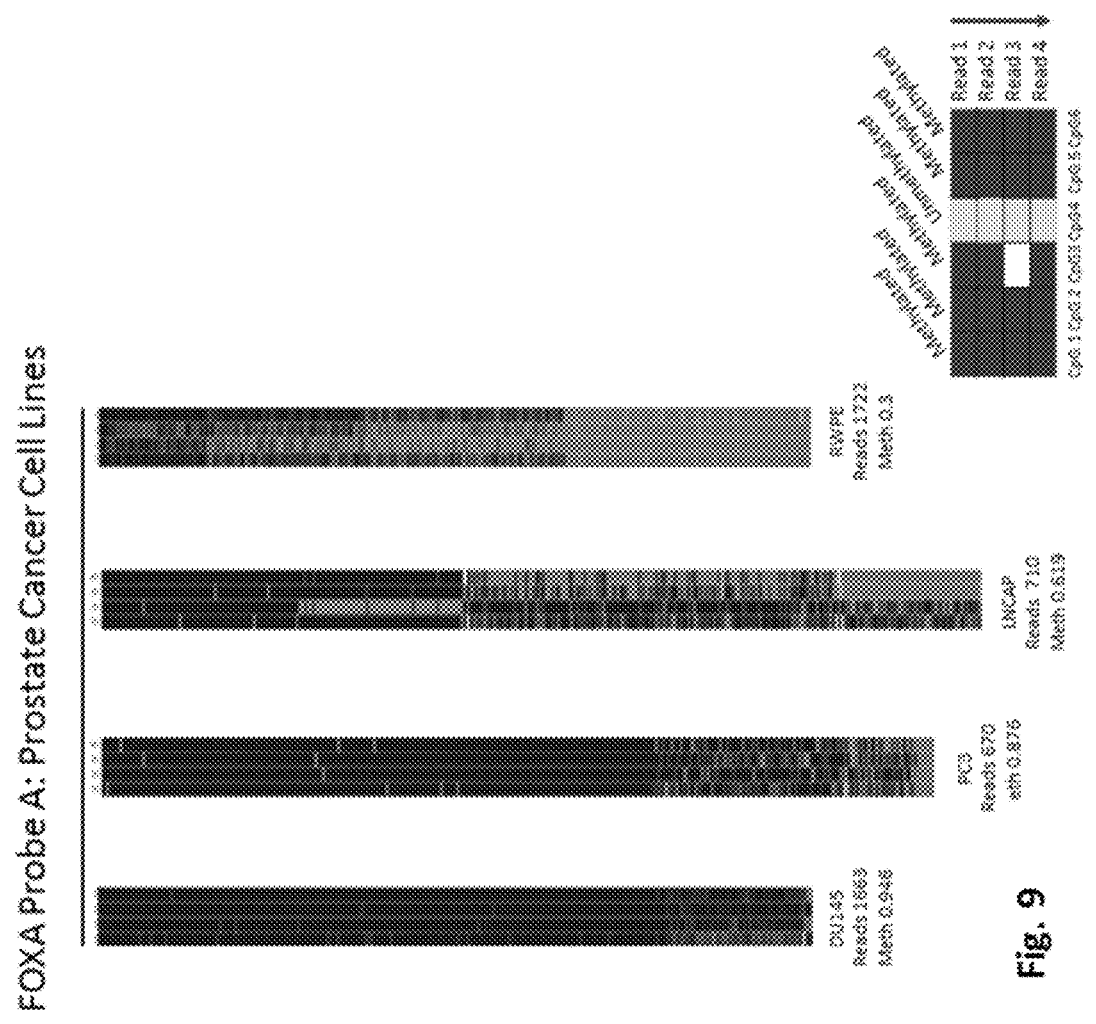

FIG. 9 depicts results of similar analysis of FOXA Probe A in prostate cell lines.

Figure 10:
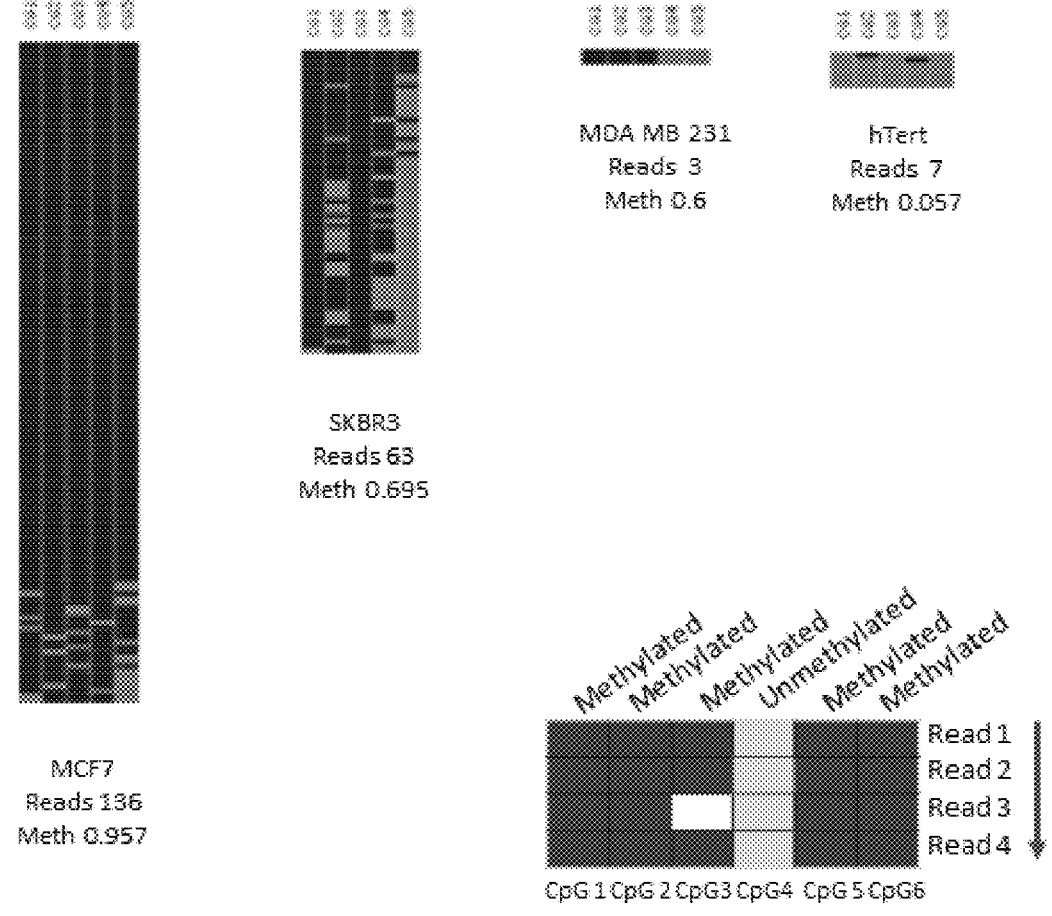
FIG. 10 depicts sequencing results to assess methylation status of NT5 Probe E in breast cancer cell lines.

FIG. 10 depicts sequencing results to assess methylation status NET5 Probe E in breast cancer cell lines.

These results exemplify probes of differing specificities that can be selected using the approach outlined herein.

Example 4

Probes for Uveal Cancer

Using the above-described methodologies, regions were selected for uveal cancer screening. Table 2 depicts these regions.

TABLE 2

| Chromo-some | Start | Stop | General Location | Descriptor | Size |
|---|---|---|---|---|---|
| chr10 | 89611399 | 89611920 | PTEN, KILLIN | Shore CGI | 521 |
| chr11 | 35503400 | 35504124 | PAMR1 | small CGI | 724 |
| chr11 | 1.18E+08 | 1.18E+08 | MPZL2 | Prox Prom | 599 |
| chr15 | 60146043 | 60147120 | C2CD4A | Shore CGI | 1077 |
| chr17 | 24370858 | 24371386 | SEZ6 | small CGI | 528 |
| chr19 | 11060476 | 11060965 | LDLR | Prox Prom | 489 |
| chr2 | 1.66E+08 | 1.66E+08 | GALNT3 | CGI | 1465 |
| chr2 | 2.23E+08 | 2.23E+08 | ccdc140/pax3 | Shore CGI | 4724 |
| chr6 | 21774638 | 21775386 | FLI22536/casc15 | small CGI | 748 |
| chr6 | 24465699 | 24466545 | KAAG1, DCDC2 | CGI | 846 |
| chr6 | 31031220 | 31031651 | MUC21 | CGI | 431 |
| chr6 | 70632889 | 70633262 | COL19A1 | Proc Prom | 373 |
| chr6 | 1.09E+08 | 1.09E+08 | NR2E1/OSTM1 | small CGI | 1001 |
| chr7 | 29996242 | 29996333 | SCRN1 | Shore CGI | 91 |
| chr1 | 2450725 | 2452224 | HES5 | CGI | 1499 |
| chr1 | 12601228 | 12601893 | DHRS3 | Shore CGI | 665 |

Example 5

Tests for Breast Cancer Subtypes

The screen that has been described above, which originally incorporated all breast tumours in the TCGA database, can also be done on subsets of the tumour database.

BRCA1 carriers were taken out of the dataset and analyzed individually to identify target methylated regions specific to this subgroup. Breast cancer can also be divided in other ways: e.g., into five subtypes, Basal, Luminal A., Luminal B, HER2 and Normal-like. Patients in each of these groups were identified and analyzed to identify target methylated regions for each subset.

The screen can also be changed to look at individual patients using the previously described criteria to see who are positive or negative. Target methylated regions can then be ranked based on how many individuals are positive. This can help to remove biasing due to amalgamation (averaging). Targets can then be selected, e.g., if they are present in greater than 75% of patients for each subtype, and then rationalize amongst these.

Test for BRCA Carriers

Current monitoring practices for women at high risk of developing breast cancer due to familial BRCA1 or 2 mutations involve yearly MRI, however the high false positive rates result in a large number of unnecessary biopsies. Using the methodology described herein, a test may be developed to serve as a secondary screen, e.g., to be employed after a positive MRI finding; or to be used for primary screening of high risk patients. The blood test is designed to detect all types of breast cancer but because ER+ breast cancer is the most frequent it is biased towards these cancers, though some of the constituent probes do recognize HER2+ and TNBC tumours. In order to provide optimal sensitivity for the monitoring of BRCA1 and 2 an assay optimized for these patients may be developed.

Both TNBC and BRCA1 and 2 patients were selected from the TOGA 450 k methylation database. Generally, most BRCA1 and 2 tumours will present as TNBC but many non-familial cancers are also TNBC. These patients were analyzed using the above-described tumour specific methylation region protocol on both the overall TNBC population and on the BRCA1 and 2 patients. 85 tumour specific regions were identified for TNBC, 67 for BRCA1 and 13 for BRCA2 populations. Of these 39 were present in any two populations and they constitute the starting point for the development of this assay. Appropriate regions for a BRCA1 specific test were identified and assessed in individual patients with known mutations. This population is surprisingly uniform and most patients are recognized by a large number of probes. AUCs for individual probes are for the most part very high. Based on these results, an assay can be developed to detect all three, i.e., TNBC, BRCA1 and 2. If additional detection sensitivity is required, then individual tests can be constructed. For high risk women who are BRCA1 or 2 mutation carriers, their mutation status should be known so that the appropriate test can be applied.

Test for BRCA1 Carriers

Probes have been developed for the detection of cancer in carriers of the BRCA1 mutation. Methylation data from the TCGA Breast cancer cohort were selected from patients known to be carriers of pathogenic BRCA1 mutations. This data was then analyzed as described to identify regions of the genome specifically methylated in this sub-set of breast cancers. Table 3 lists appropriate regions identified and their genomic locations.

TABLE 3

| | Target Region (hg18 reference) | | | |
|---|---|---|---|---|
| chr | Nearest Gene | Start (nt) | End (nt) | Size |
| chr1 | LOC105378683 | 43,023,840 | 43,023,487 | 353 |
| chr1 | NPHS2 | 177,811,942 | 177,811,671 | 271 |
| chr1 | NR5A2 | 198,278,599 | 198,278,409 | 190 |
| chr11 | PAX6 | 31,783,955 | 31,782,545 | 1,410 |
| chr11 | KCNE3 | 73,856,332 | 73,855,762 | 570 |

TABLE 3-continued

| Target Region (hg18 reference) | | | | |
|---|---|---|---|---|
| chr | Nearest Gene | Start (nt) | End (nt) | Size |
| chr12 | KCNA6 | 4,789,491 | 4,789,342 | 149 |
| chr12 | TMEM132C | 127,318,539 | 127,317,001 | 1,538 |
| chr13 | PDX1 | 27,390,265 | 27,389,540 | 725 |
| chr13 | EPSTI1 | 42,464,618 | 42,463,901 | 717 |
| chr16 | A2BP1 | 6,009,930 | 6,009,020 | 910 |
| chr16 | CRYM | 21,202,914 | 21,202,448 | 466 |
| chr16 | PRKCB | 23,755,504 | 23,754,826 | 678 |
| chr16 | IRF8 | 84,490,354 | 84,490,167 | 187 |
| chr18 | SALL3 | 74,842,145 | 74,839,705 | 2,440 |
| chr19 | LYPD5 | 49,016,848 | 49,016,696 | 152 |
| chr2: | DPP10 | 115,636,420 | 115,635,215 | 1,205 |
| chr20 | C20orf56 | 22,507,867 | 22,507,676 | 191 |
| chr3 | SOX2OT | 182,919,993 | 182,919,839 | 154 |
| chr4 | CDKL2 | 76,774,880 | 76,774,658 | 222 |
| chr5 | March 11 | 16,233,072 | 16,232,633 | 439 |
| chr5 | CCL28 | 43,433,329 | 43,432,559 | 770 |
| chr5 | AP3B1 | 77,304,644 | 77,304,208 | 436 |
| chr7 | CARD11 | 3,050,299 | 3,049,859 | 440 |
| chr7 | BLACE | 154,859,799 | 154,859,051 | 748 |
| chr7 | PTPRN2 | 157,176,806 | 157,176,096 | 710 |
| chr8 | RUNX1T1 | 93,183,481 | 93,183,326 | 155 |

52 different probes were then developed to various parts of these regions and the methylation pattern in tumor cell lines was characterized, including MDA-MB-436 and HCC1937 which are known to carry BRCA1 mutations. These probes will be combined with previously characterized probes to other regions which are also methylated in tumours from BRCA1 patients. This would provide for a highly sensitive assay able to detect cancer in these high risk women at the earliest possible stage.

Tests for Other Subtypes

A number of breast cell lines from women with known BRCA1 mutations have been isolated such as MDA-MB-436, HCC1937 and HCC1395 (all available from ATCC). These may be used to validate the assay as was done for the general blood test. For BRCA2 mutant lines there is only one ATCC cell line at present, HCC1937. There are several BRCA2 mutant ovarian cancer lines that have been identified and they may be used if the bioinformatic analysis confirms that these methylation markers are also found in ovarian cancer. The development of a single assay that detects both breast and ovarian cancer in BRCA2 carriers represents a distinct advantage as it would simultaneously monitor the two primary cancer risks in these patients.

The development of these assays follows the same course the above-described general assay proceeding from TCGA data to cells lines to patient samples. Tumour banks (some of which have mutation data) can be used for this, and analysis of these tumours provides an indication of their likely BRCA mutation. These samples can also be sequenced to confirm the prediction.

Example 6

Testing of Cell-Free Samples

Proof of concept testing was carried out using cell lines for ease of analysis. However, the assay can be applied to test for cell-free DNA, e.g., circulating cell-free tumour DNA in blood, and finds wide application in this context. A sample protocol for circulating tumour DNA is provided.

Sample Protocol: Test for Circulating Tumour DNA

DNA Preparation

The following example protocol may be used to detect circulating tumour DNA (tDNA).

Obtain DNA to be used for bisulfite conversion and downstream PCR amplification (i.e., cell line, tumour or normal DNA). Determine DNA purity on 0.8% agarose gel.

Determine genomic DNA (gDNA) for concentration in ug/uL by UV spectrophotometry.

Prepare a 1:100 dilution with TE buffer.

Remove RNA contaminates, if necessary, using the purification protocol for the GenElute Mammalian Genomic DNA Miniprep Kit, Sigma Aldrich, CAT #G1N350 (http://www.sigmaaldrich.com/technical-documents/protocols/biology/genelute-mammalian-genomic-dna-miniprep-kit.html). Follow purification protocol from steps A: 2a-3a, step 4-9.

OPTIONAL: For gDNA from a cell line, sonicate gDNA to approximately 90-120 bp (this represents general size of circulating tDNA). To do this, sonicate 5-10 ug of sample (50-100 ng/100 uL) using a sonicator. Use setting 4, and 15 pulses for 30 seconds with 30 seconds rest on ice in between. Determine sonicated DNA purity and bp size on 0.8% agarose gel.

Bisulfite convert DNA-EpiTect Fast Bisulfite Conversion Kit, QIAgen, CAT #59824 (https://www.qiagen.com/us/resources/resourcedetail?id=15863f2d-9d1c-4f12-b2e8-a0c6a82b2b1e&lang=en). Follow bisulfite conversion protocol on pages 1-18, 19-23. Refer to trouble shooting guide pages 30-32. Modifications to the protocol include: 1. Prepare reactions in 1.5 mL tubes, 2. High concentration samples at 2 ug, and low concentration samples at 500 ng-1 ug, 3. Perform the bisulfite conversion using 2 heat blocks set at 95° C. and 60° C., 4. Incubation at 60° C. extended to 20 minutes, to achieve complete bisulfite conversion, 5a Elute DNA in 10-20 uL of elution buffer for ~50-100 ng/uL final concentration, and 5b Dilute DNA to 10 ng/uL for use in PCR.

Perform nested PCR with Hot Star Taq Plus DNA Polymerase, Qiagen, CAT #203605 (https://www.qiagen-.com/ca/resources/resourcedetail?id=c505b538-7399-43b7-ad10-d27643013d10&lang=en).

Singleplex PCR Amplification

For singleplex PCR amplification of individual probes, carry out a primary PCR reaction with methylation-biased primers (MBP), (primer forward and reverse).

Table 4 recites reaction components.

TABLE 4

| Component | 1X (uL) |
|---|---|
| 10X PCR Buffer | 2.5 |
| 5 mM dNTP's | 1 |
| 5 U Hot Star Taq | 0.1 |
| 25 mM MgCl2 | 3 |
| PCR Grade H2O | 17 |
| [10 ng/uL] DNA | 1 |
| 10 pmol FWD Primer | 0.2 |
| 10 pmol REV Primer | 0.2 |
| Total | 25 |

Table 5 lists thermocycler conditions.

TABLE 5

| Thermocycler Conditions | | |
|---|---|---|
| Temp. | Time | |
| 95° C. | 15 min | |
| 95° C. | 30 sec | |
| 58° C. | 30 sec | X 40 |
| 72° C. | 30 sec | |
| 72° C. | 7 min | |
| 4° C. | ∞ | |

Carry out a secondary PCR reaction with universal primers CS1 (Barcode) and CS2 (P1 Adapter). To do this, remove an aliquot from the primary reaction, use as template DNA, this method serves as a two-step dilution PCR reaction Table 6 recites reaction components.

TABLE 6

| Component | 1X (uL) |
|---|---|
| 10X PCR Buffer | 5 |
| 5 mM dNTP's | 2 |
| 5 U Hot Star Taq | 0.2 |
| 25 mM MgCl2 | 6 |
| PCR Grade H2O | 34.4 |
| MBP PCR Template | 2 |
| 10 pmol CS1 Primer | 0.2 |
| 10 pmol CS2 Primer | 0.2 |
| Total | 50 |

Table 7 recites thermocycler conditions.

TABLE 7

| Thermocycler Conditions | | |
|---|---|---|
| Temp. | Time | |
| 95° C. | 15 min | |
| 95° C. | 30 sec | |
| 58° C. | 30 sec | X 3 |
| 72° C. | 30 sec | |
| 72° C. | 7 min | |
| 4° C. | ∞ | |

Determine PCR specificity on 2% agarose gel. Run the methylation-biased PCR product and the CS1 CS2 sequencing PCR product beside one another on the agarose to visualize the banding pattern and increase in bp size. PCR product should be between 200-300 bp For Singleplex PCR products, pool 5-10 uL of each PCR reaction (CS1 CS2 Secondary RXN) into a single tube for each sample type. Purify the pooled PCR with Agencourt AMPure XP beads at a 1.2:1 ratio (90 uL beads+75 uL sample), e.g., as below.

Agencourt Ampure XP Bead Purification

Use freshly prepared 70% ethanol. Allow the beads and pooled DNA to equilibrate to room temperature.

1. Add indicated volume of Agencourt AMPure XP beads to each sample: 90 uL beads+75 uL Pool (1.2:1)
2. Pipet up and down 5 times to thoroughly mix the bead suspension with the DNA. Incubate the suspension at RT for 5 minutes.
3. Place the tube on a magnet for 5 minutes or until the solution clears. Carefully remove the supernatant and store until purified library has been confirmed.

4. Remove the tube from the magnet; add 200 uL of freshly prepared 70% EtOH. Place the tube back on the magnet and incubate for 30 seconds; turn the tube around twice in the magnet to move the beads through the EtOH solution. After the solution clears, remove and discard the supernatant without disturbing the pellet.

5. Repeat step #4 for a second EtOH wash.

6. To remove residual EtOH, pulse-spin the tube. Place the tube back on the magnet, and carefully remove any remaining EtOH with a 20 uL Pipette, without disturbing the pellet.

7. Keeping the tube on the magnet, air-dry the beads at RT for ~5 minutes.

8. Remove the tube from the magnet; add 50 uL of TE directly to the pellet. Flick the tube to mix thoroughly. Incubate at RT for 5 minutes.

9. Pulse-spin and place the tube back on the magnet for ~2 minutes or until the solution clears. Transfer the supernatant containing the eluted DNA to a new 1.5 mL Eppendorf LoBind tube.

10. Remove the tube from the magnet; add 50 uL of TE directly to the pellet. Flick the tube to mix thoroughly. Store the beads, along with the supernatant, at 4° C. until purified library has been confirmed.

11. Visualize the sample pre- and post-purification on an 8% acrylamide gel (higher resolution). Pooled PCR product should be visualized as multiple bands (as each PCR product is a slightly different bp size). Purified sample should eliminate product beneath 150 bp.

Figure 11:
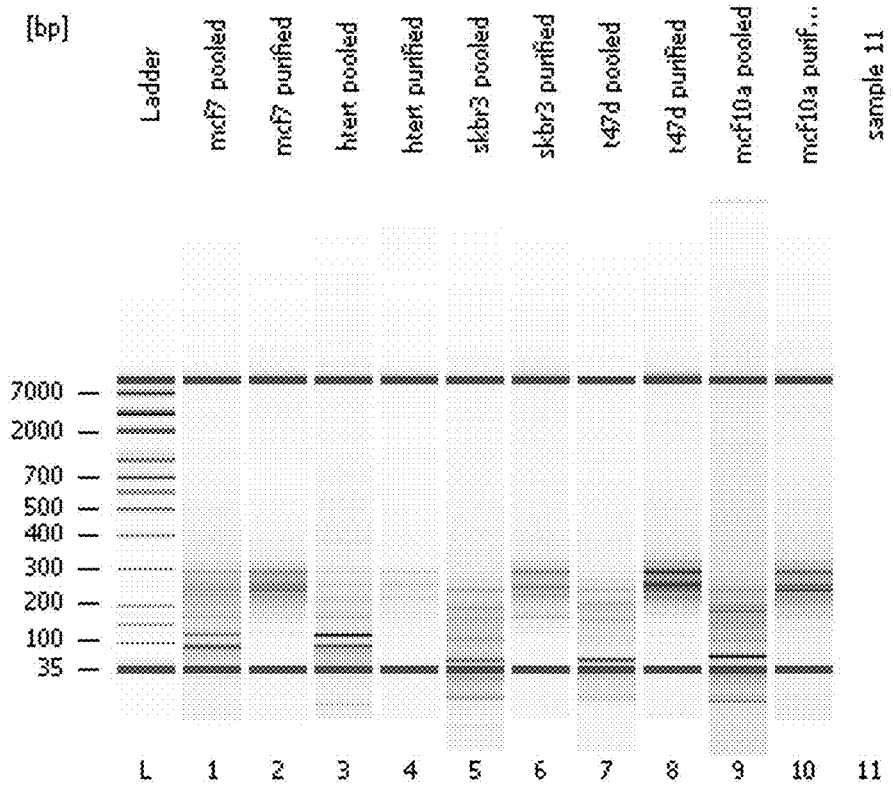
FIG. 11 depicts a summary of BioAnalyzer electrophoresis summary for amplification product generated from various cell lines.

FIG. 11 depicts a summary of BioAnalyzer electrophoresis summary for amplification product generated from various cell lines.

12. Perform nested PCR with Multiplex PCR Plus Kit, Qiagen, CAT #206152 (https://www.qiagen.com/ca/resources/resourcedetail?id=beb1f99e-0580-42c5-85d4-ea5f37573c07&lang=en), e.g., as below.

Multiplex PCR Amplification of Up to 50 Probes in a Single Reaction

Create multiplex primer mix by aliquot 1 uL of each forward and reverse primer at 10 pmol/uL into a single 1.5 mL tube. Calculate the final concentration of each primer by dividing the initial primer concentration by the final volume of primer mix in the tube, i.e., 15 probes to be multiplexed into a single reaction, would total 30 primers and at 1 uL each, 30 uL final volume. Thus ((10 pmol)(1 uL))/30 uL=0.333 pmol. Primer concentration requires optimization during PCR amplification, as the number of primers in a single reaction can influence the efficiency of the product, e.g.

15 primer sets ~2 pmol final [ ] in PCR 50 primer sets ~0.5 pmol final [ ] in PCR Carry out primary PCR reaction with methylation-biased primers.

Table 8 lists reaction components for multiple amplifications of 15 probes, and Table 9 lists reaction components for multiple amplifications of 50 probes. Table 10 list reaction conditions.

TABLE 8

| 15 primer pairs at 2 pmol | |
| --- | --- |
| Component | 1X (uL) |
| 2X Multiplex MM | 25 |
| PCR H2O | 18 |
| Primer Mix | 6 |
| [10 ng/uL] DNA | 1 |
| Total | 50 |

TABLE 9

| 50 primer pairs at 0.5 pmol | |
| --- | --- |
| Component | 1X (uL) |
| 2X Multiplex MM | 25 |
| PCR H2O | 19 |
| Primer Mix | 5 |
| [10 ng/uL] DNA | 1 |
| Total | 50 |

TABLE 10

| Thermocycling Conditions | | |
| --- | --- | --- |
| Temp. | Time | |
| 95° C. | 5 min | |
| 95° C. | 30 sec | |
| 58° C. | 90 sec | X 35 |
| 72° C. | 90 sec | |
| 68° C. | 10 in | |

Determine PCR specificity on 2% agarose gel. Multiplex products should be visualized with multiple banding pattern between 100-300 bp.

Pooling is not required for multiplex products, as the probes have already been combined and amplified into a single tube/reaction.

Purify the pooled PCR with Agencourt AMPure XP beads at a 1.2:1 ratio (60 uL beads+50 uL sample) (refer within document for purification protocol).

After PCR amplification, along with pooling and purifying, the samples can be quantified by qPCR, e.g., Ion Library Quantification Kit, TaqMan assay quantification of Ion Torrent libraries, Thermo Fisher Scientific, CAT #4468802 (https://tools.thermofisher.com/content/sfs/manuals/4468986_IonLibraryQuantitation-Kit_UG.pdf)

1. Create a standard curve of 6.8 pM, 0.68 pM, 0.068 pM, 0.0068 pM
2. Dilute samples 1:1000, and run in duplicate
3. Perform qPCR assay on the Step One Plus Real Time machine by Life Technologies
4. Sample libraries quantified ≥100 pM can proceed to be sequenced on the Life Technologies Ion Torrent Sequencing platform Life Technologies Ion Torrent PGM Sequencing Ion PGM Template OT2 200.

Perform template reaction with Ion PGM Template OT2 200 Kit, Thermo Fisher Scientific, CAT #4480974. Kit contents to be used on the One Touch 2 and Enrichment system (https://tools.thermofisher.com/content/sfs/manuals/MAN0007220_Ion_PGM_Template_OT2_2 00_Kit_UG.pdf Utilizing library quant. obtained from qPCR, dilute libraries appropriately to 100 pM. Follow Life Technologies guide on how to further dilute libraries for input into final template reaction.

Follow reference guide to complete template reaction
  Run the Ion One Touch 2 instrument
  Recover the template positive ISPs
  Enrich the template positive ISPs with the Ion One Touch ES Ion PGM Sequencing 200

Perform sequencing reaction with Ion PGM Sequencing 200 kit, Thermo Fisher Scientific, CAT #4482006. Kit contents to be used on the Ion PGM system (https://tools.thermofisher.com/content/sfs/manuals/MAN0007273_IonPGMSequenc_200 Kit_v2 UG.pdf).

Plan sequencing run
  Select chip capacity (314, 316 or 318)
  Determine sequencing flows and bp read length (i.e., 500 flows and 200 bp read length)

Follow reference guide to complete PGM sequencing
  Prepare enriched template positive ISPs
  Anneal the sequencing primer
  Chip check
  Bind sequencing polymerase to the ISPs
  Load the chip
  Select the planned run and perform sequencing analysis Sequencing Data Analysis and Work Flow
  Obtain run report generated by the PGM and Torrent Browser
  Run report includes the following information
    ISP Density and loading quality
    Total reads generated and ISP summary
    Read length distribution graph
    Barcoded samples: reads generated per sample and mean read length
  Obtain uBAM files generated by the PGM, available for download to an external hard drive
  Bioinformatics data analysis
    Upload uBAM files to a web based bioinformatics platform, Galaxy GenAp
      Perform quality control analysis (i.e., basic statistics and sequence quality check)
      Convert data files: BAM SAM FastQ
      Filter FastQ file: select bp size to trim (i.e., trim sequence <100 bp)
      Convert data files: FastQ FastA
      Download FastA file
    Upload FastA files to BiqAnalyzer software platform
      Create project
      Add sample
      Load reference sequence
      Set gap extension penalty and minimal sequence identity
      Link in FastA files to samples and reference sequences
      Analyze and collect data files (pattern maps and pearl necklace diagrams)

Example 7

Uveal Melanoma Test

The molecular biology of uveal melanoma (UM) is simpler than that of breast cancer, with minimal mutations and rearrangements, and only two major sub-types which correspond to the retention or loss of chromosome 3p. A test was developed for UM which is superior to current state of the art blood assays.

Analysis of 450 k methylation TCGA data for 80 UMs allowed for the identification of regions of tumour specific methylation in both 3p- and 3 pWT tumours using our algorithm. Table 11 shows 16 hypermethylated regions in both 3p- and 3 pWT tumours used for probe development and testing, according to one embodiment.

TABLE 11

| Gene | Chr | start | stop | Size | CGI | CpGs |
|---|---|---|---|---|---|---|
| PTEN, KILLIN | chr10 | 89611399 | 89611920 | 521 | Shore CGI | 171 |
| PAMR1 | chr11 | 35503400 | 35504124 | 724 | small CGI | 19 |
| MPZL2 | chr11 | 117640011 | 117640610 | 599 | Prox Prom | |
| C2CD4A | chr15 | 60146043 | 60147120 | 1077 | Shore CGI | 127 |
| SEZ6 | chr17 | 24370858 | 24371386 | 528 | small CGI | 34 |
| LDLR | chr19 | 11060476 | 11060965 | 489 | Prox Prom | |
| GALNT3 | chr2 | 166358156 | 166359621 | 1465 | CGI | 98 |
| ccdc140/pax3 | chr2 | 222881305 | 222886029 | 4724 | Shore CGI | 72 |
| FLI22536/casc15 | chr6 | 21774638 | 21775386 | 748 | small CG | 18 |
| KAAG1, DCDC2 | chr6 | 24465699 | 24466545 | 846 | CGI | 56 |
| MUC21 | chr6 | 31031220 | 31031651 | 431 | CGI | 46 |
| COL19A1 | chr6 | 70632889 | 70633262 | 373 | Proc Prom | |
| NR2E1/OSTM1 | chr6 | 108542808 | 108543809 | 1001 | small CG | 34 |
| SCRN1 | chr7 | 29996242 | 29996333 | 91 | Shore CGI | 133 |
| HES5 | chr1 | 2450725 | 2452224 | 1499 | CGI | 111 |
| DHRS3 | chr1 | 12601228 | 12601893 | 665 | Shore CGI | 133 |

The top 14 of these common regions were carried forward for probe development and a total of 26 different probes were characterized, with several regions having up to three probes targeting them. Each of these probes was then validated using six different UM cell lines to assess their methylation status. As negative controls, DNA from peripheral blood mononuclear cells (PBMCs), which are the main source of contaminating DNA in blood samples, as well as a pool of cell free DNA (cfDNA) from 16 individuals, were also tested (FIG. 15). These results indicated that the majority of the probes tested showed tumour specific methylation with little or no methylation in the negative controls. A total of 18 probes from 12 different regions were combined into a multiplex PCR reaction and used to analyze cell free DNA from plasma for a previously characterized cohort of metastatic UM patients.

The validated regions were C2CD4A, COL19A1, DCDC2, DHRS3, GALNT3, HES5, KILLIN, MUC21, NR2E1/OSTM1, PAMR1, SCRN1, and SEZ6. The validated probes were C2C5F, COL2F, DCD5F, DGR2F, GAL1F, GAL3F, HES1F, HES3F, HES4F, KIL5F, KIL6F, MUC2F, OST3F, OST4F, PAM4F, SCR2F, SEZ3F, and SEZ5F.

Figure 16:
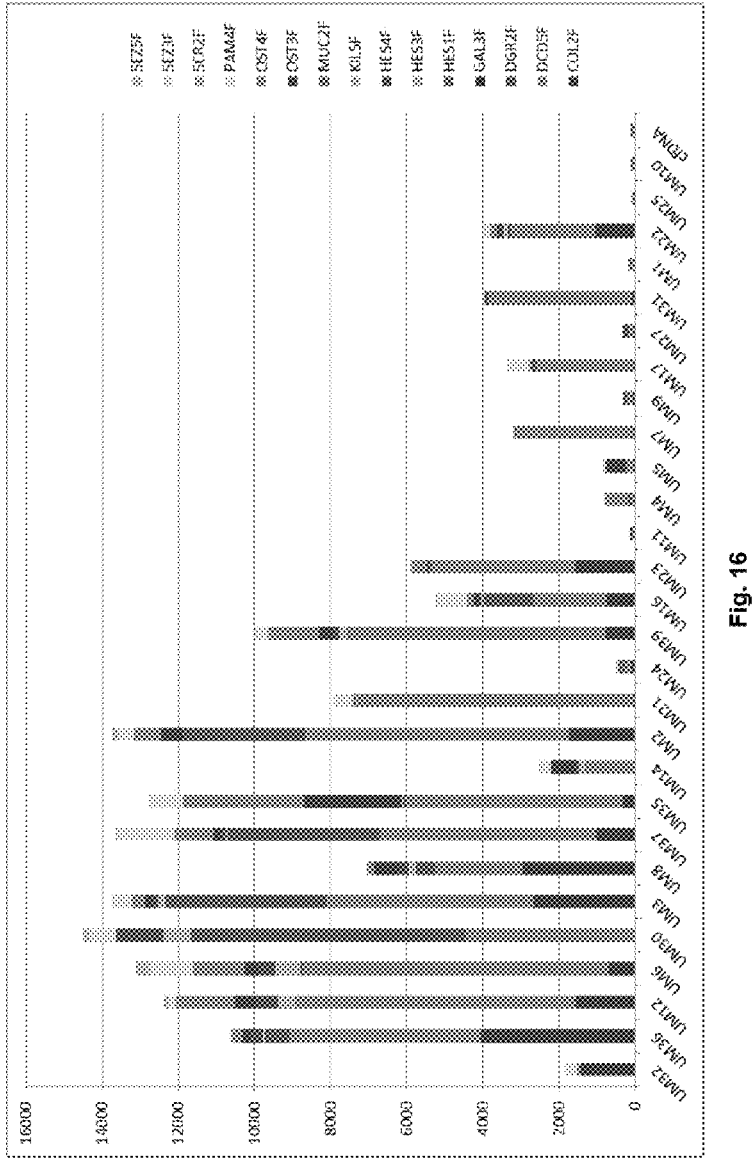
FIG. 16 is a diagram showing methylation of cfDNA from patients with metastatic uveal melanoma. Methylated reads for each probe were extracted and all reads were normalized for the total number of reads in the sample. Stacked columns represent the total reads from all of the individual probes with different probes identified by shading. The patients are sorted by PAP measurements with high values on the left and lower values on the right. cfDNA is a pool of cell free DNA from 18 normal donors.
Figure 17:
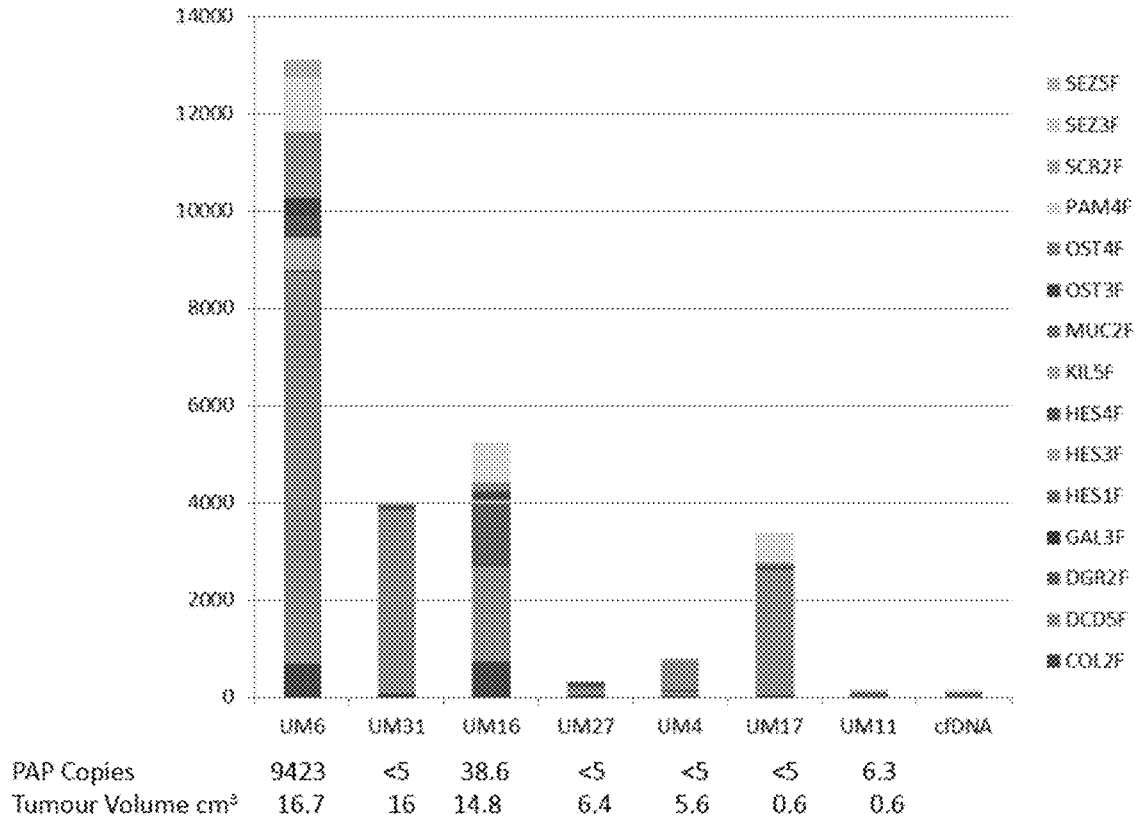
FIG. 17 is a diagram showing methylation of cfDNA from patients with metastatic uveal melanoma. Methylated reads for each probe were extracted and all reads were normalized for the total number of reads in the sample. Stacked columns represent the total reads from all of the individual probes with different probes identified by shading. The patients are sorted by tumour volume with larger volume on the left and lower volume on the right, and the volume indicated at the bottom. PAP values obtained from these patients is indicated. <5 refers to no detection of ctDNA in these samples. cfDNA is a pool of cell free DNA from 18 normal donors.
Figure 18A:
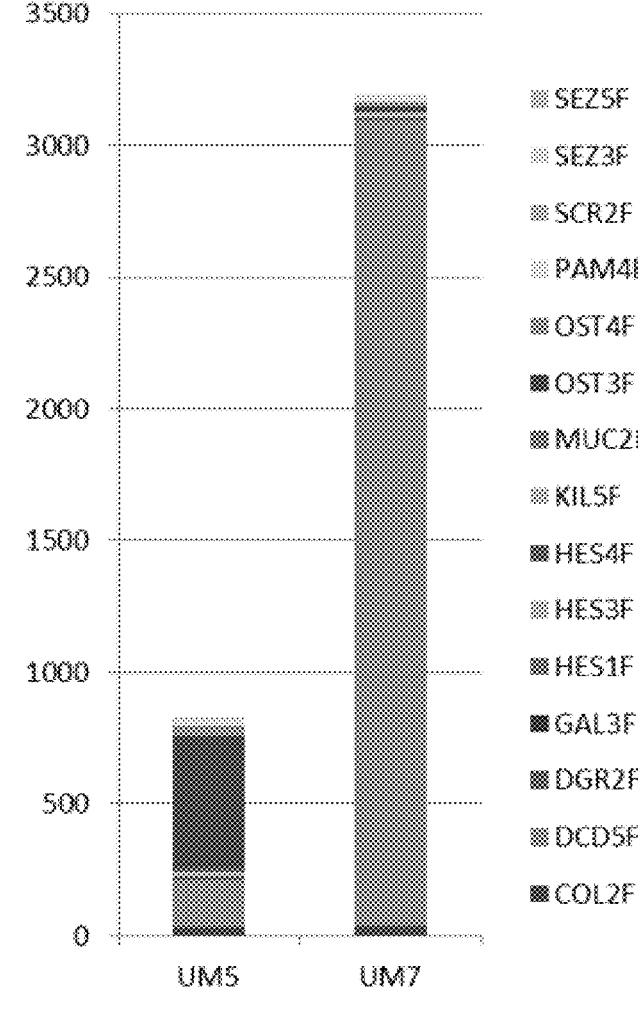
FIGS. 18A and 18B are diagrams showing methylation of cfDNA from sequential blood samples of two patients who were part of the patient groups shown in FIGS. 17 and 18.
Figure 18B:
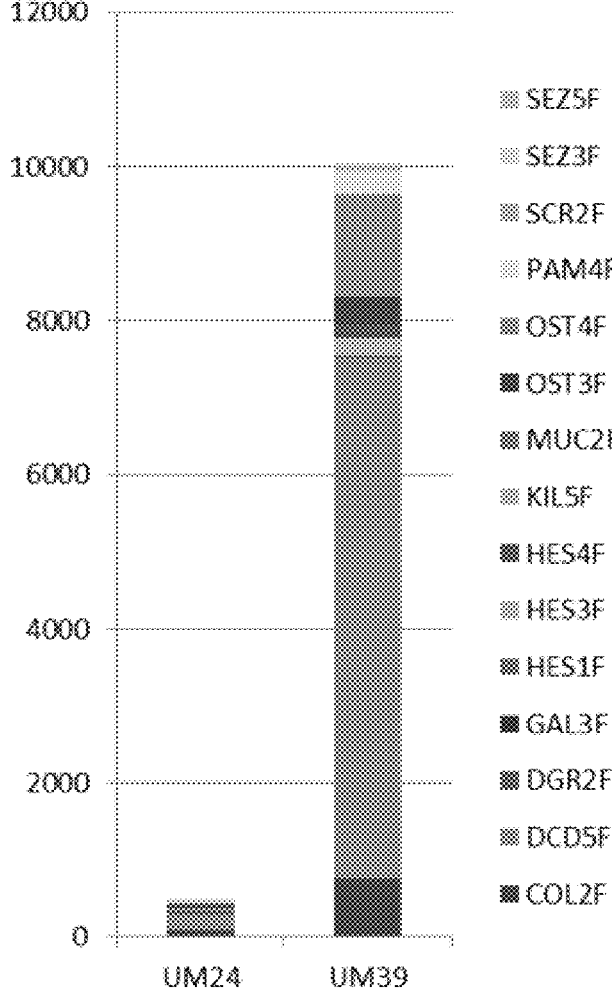
Figure 19:
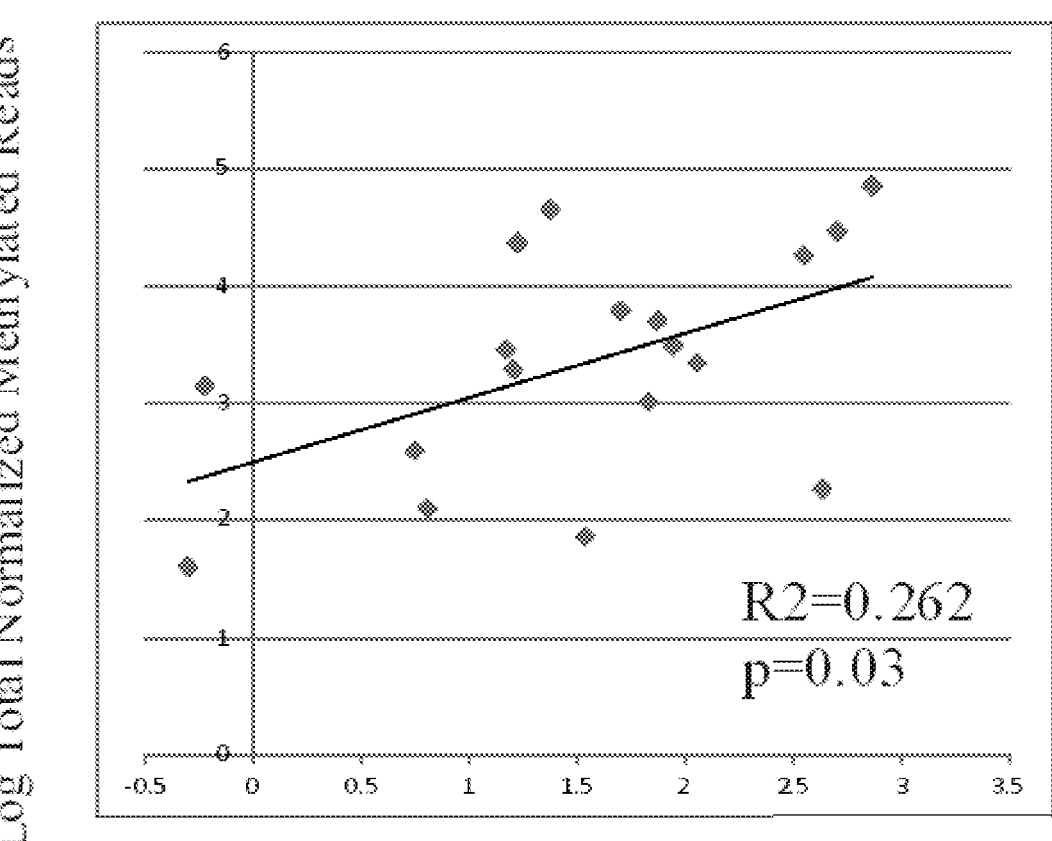
FIG. 19 is a log-log plot showing assay values (methylated reads) are correlated with tumour volume. The character of the metastatic tumour such as whether it is a solid mass or dispersed (miliary) was not taken into account.
Figure 20:
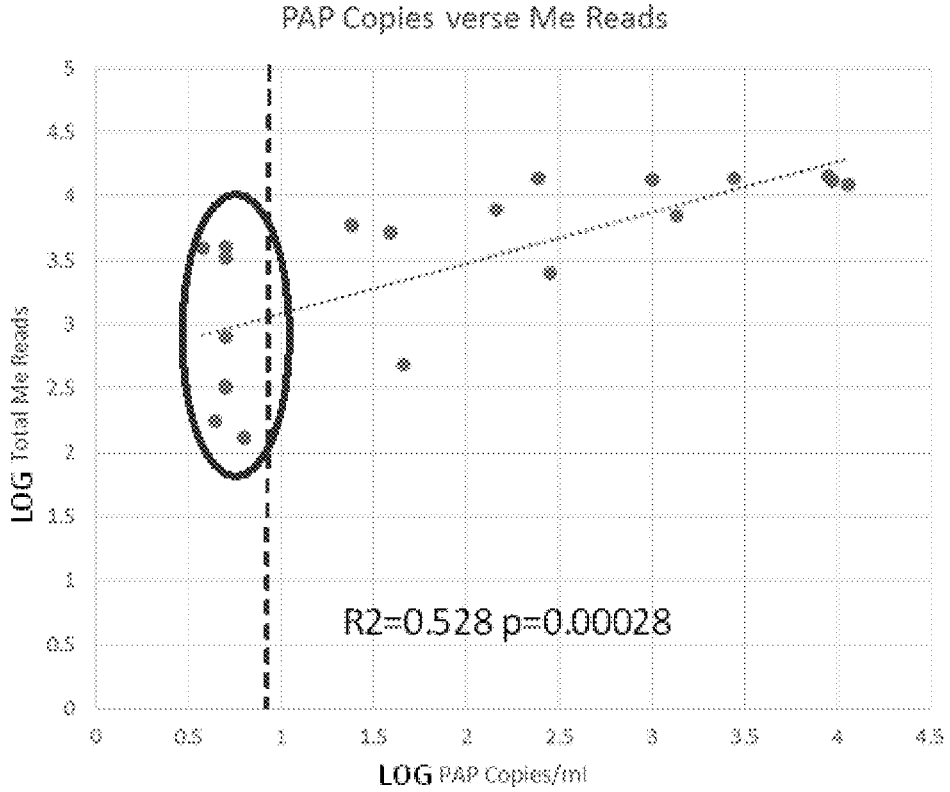
FIG. 20 is a log-log plot showing relationship between test results and PAP signal, where PAP and methylation signals were correlated at higher PAP levels (trend line), although below the detection threshold of PAP at 5 copies/ml (vertical dashed line) the PAP signals were not correlated (ellipse).

These patients were previously tested using the pyrophosphorolysis-activated polymerization (PAP) assay[26], which detects the frequent GNAQ or GNA11 mutations in UM27. In all cases the test detected cancer in these patients even when the PAP assay failed to register a signal (FIGS. 16 and 17). Most of the probes functioned like methylation specific PCR reactions, only giving product when there was tumour DNA present though with the additional validation that the specificity of each probe was guaranteed by the presence of multiple methylated CpG residues within each read. In two patients from which serial blood samples were obtained (FIGS. 18A and 18B) the test showed increased tumour levels over time even when the final tumour volume was 0.5 cm$^3$ (FIG. 18A). The test was also generally correlated with the volume of tumour, though the nature of the metastatic tumour as either a solid mass or dispersed has not yet been accounted for (FIG. 19). The levels detected by the test were generally in line with those of the PAP assay and notably gave a signal where PAP failed due to the lack of a mutation (FIG. 16, UM32). Where no or limited amounts of tumour DNA were detected by PAP, the test still gave significant signals (FIG. 20). Even greater sensitivity is expected when the total number of reads analyzed per patient is increased, as this run had less than optimal overall reads due to the presence of large amounts of primer dimer, an issue that has now been resolved. The specificity of the test was demonstrated by the extremely low levels of methylation seen in the pool of 16 cfDNA controls. Overall, the test has been validated in a patient population, and it has been shown to be superior to a state of the art mutation based assay.

Example 8

Prostate Cancer Test

An important aspect of any test is that it should be applicable to all patients. Based on our experience it is essential to consider specific subtypes of a given cancer to ensure that all patients are detected by the assay. The TCGA analysis of a large prostate cohort revealed sub-groups based on specific mutations and transcriptional profiles[28]. Four subtypes were identified based on the overall pattern of methylation found in these tumours. In this example the TCGA prostate cohort was divided into groups based on the methylation pattern and subjected to methylation analysis.

Table 12 lists 40 regions associated with all sub-types of prostate cancer.

TABLE 12

| | | | |
|---|---|---|---|
| HES5 | ANXA2 | HLA-F | HAAO |
| LOC376693 | RHCG | PON3 | RARB |
| CSRP1 | RARA | LRRC4 | ALDH1L1 |
| ALOX5 | PTRF | HLA-J | HIST1H3G |
| PPM1H | RND2 | PAH | ZSCAN12 |
| MON2 | TMP4 | EPSTI1 | HCG4P6 |
| KIAA0984 | HIF3A | ADCY4 | EYA4 |
| TXNRD1 | KLK5 | HAPLN3 | HOXA7 |
| CHST11 | AMOTL2 | AX747633 | HSF4 |
| EFS | SCGB3A1 | NBR1 | TMEM106A |

These regions common to all four methylation subtypes were identified and a total of 38 probes from 33 regions were selected and appropriate "biased" PCR probes were generated. These were characterized using four different prostate cancer lines. DU145 is an androgen receptor (AR−) negative cell line that is able to generate metastases in the mouse. PC3 is also AR− and also metastatic. LNCaP is an androgen receptor positive line (AR+) that is non-metastatic in the mouse while RWPE cells are AR+ and non-metastatic. DNA from PBMC was also tested as this represents the primary source of cell free DNA in the circulation.

Figure 21:
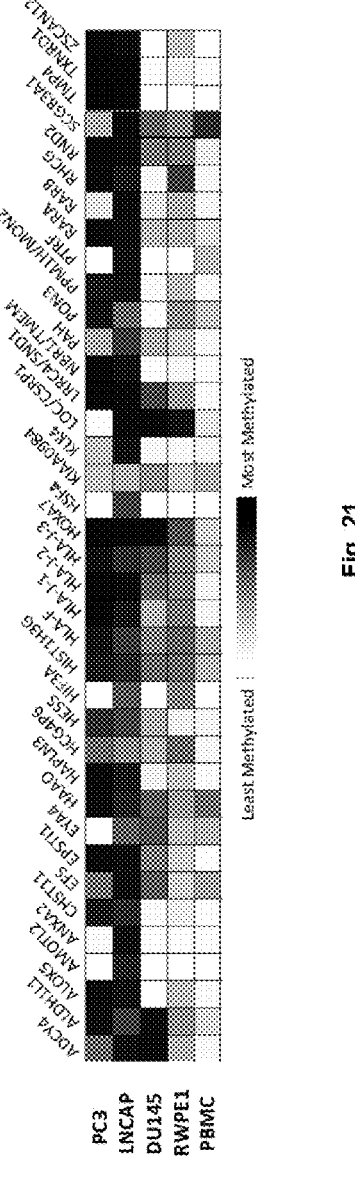
FIG. 21 is a heat map of gene methylation in indicated prostate cancer cell lines.

A total of 34 probes from 33 regions were validated in that they showed little or no methylation in PBMCs while showing large scale methylation in one or more of the tumour cell lines (FIG. 21).

The validated regions were ADCY4, ALDH1L1, ALOX5, AMOTL2, ANXA2, CHST11, EFS, EPSTI1, EYA4, HAAO, HAPLN3, HCG4P6, HES5, HIF3A, HLA-F, HLA-J, HOXA7, HSF4, KLK4, LOC376693, LRRC4, NBR1, PAH, PON3, PPM1H, PTRF, RARA, RARB, RHCG, RND2, TMP4, TXNRD1, and ZSCAN12.

The validated probes were ADCY4-F, ALDH1L1-F, ALOX5-F, AMOTL2-F, ANXA2-F, CHST11-F, EFS-F, EPSTI1-F, EYA4-F, HAAO-F, HAPLN3-F, HCG4P6-F, HES5-F, HIF3A-F, HLA-F-F, HLA-J-1-F, HLA-J-2-F, HOXA7-F, HSF4-F, KLK4-F, LOC376693-F, LRRC4-F, NBR1-F, PAH-F, PON3-F, PPM1H-F, PTRF-F, RARA-F, RARB-F, RHCG-F, RND2-F, TMP4-F, TXNRD1-F, and ZSCAN12-F.

To these 34 probes an additional 12 probes (from 7 regions) were added that had previously been characterized in breast cancer, which were also able to detect prostate cancer, for a total of 46 probes.

The added probes were C1Dtrim, C1Etrim, CHSAtrim, DMBCtrim, FOXAtrim, FOXEtrim, SFRAtrim, SFRCtrim, SFREtrim, TTBAtrim, VWCJtrim, and VWCKtrim.

These probes were multiplexed together and were then used to analyze plasma samples from five patients before they had initiated androgen deprivation therapy (ADT) and 12 months after starting treatment. These patients were part of a small cohort (~40 patients) being followed for depression and the plasma samples at 0.5 ml were much smaller than normally used for the assay (2 mls). All of the patients were MO with no sign of metastatic disease when placed on ADT.

Figure 22:
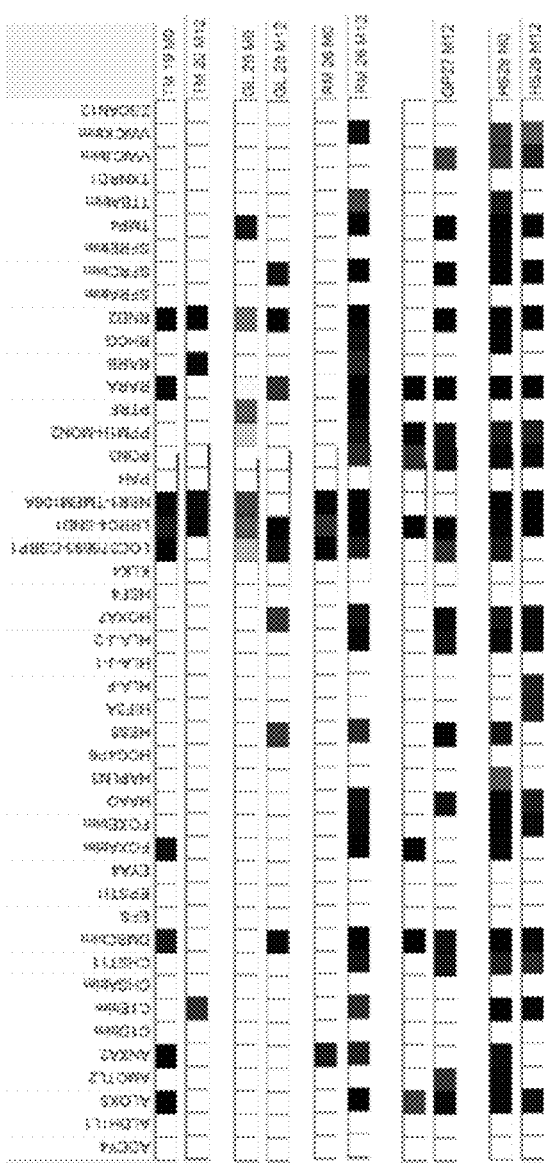
FIG. 22 is a heat map of multiplexed probes for each prostate cancer patient sample. Patient samples were taken before the initiation of ADT (START) and 12 months after (M12). A black square indicates that methylated reads having greater than 80% methylation per read were detected for that probe but does not take into consideration the number of reads for each.
Figure 23:
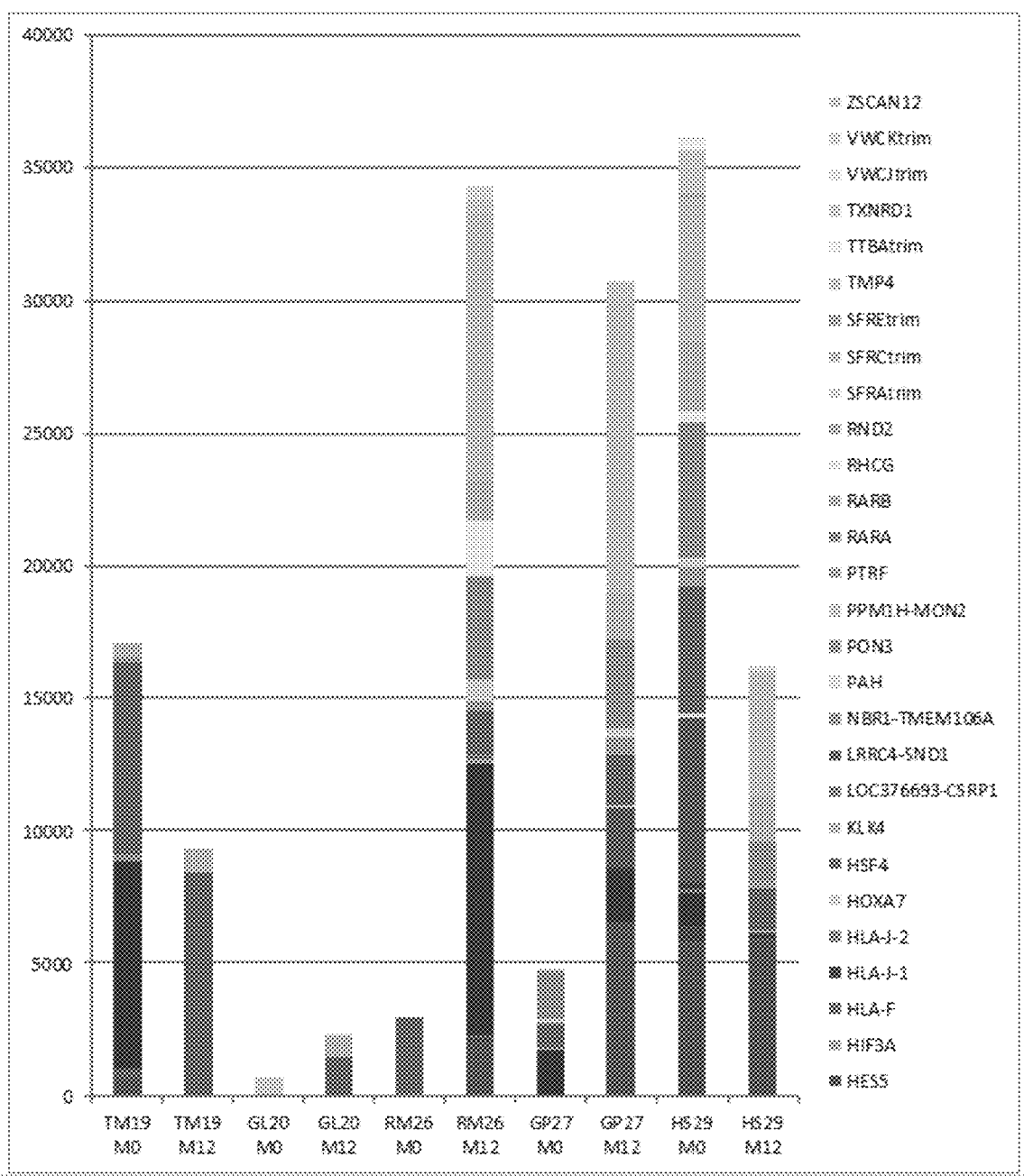
FIG. 23 is a diagram showing number of methylated reads per probe for each prostate cancer patient sample. Different probes are shown in different shading. The number of reads that were at least 80% methylated were determined for each sample and all probes are stacked per sample. Patient samples were taken before the initiation of ADT (START) and 12 months after (M12).
Figure 24:
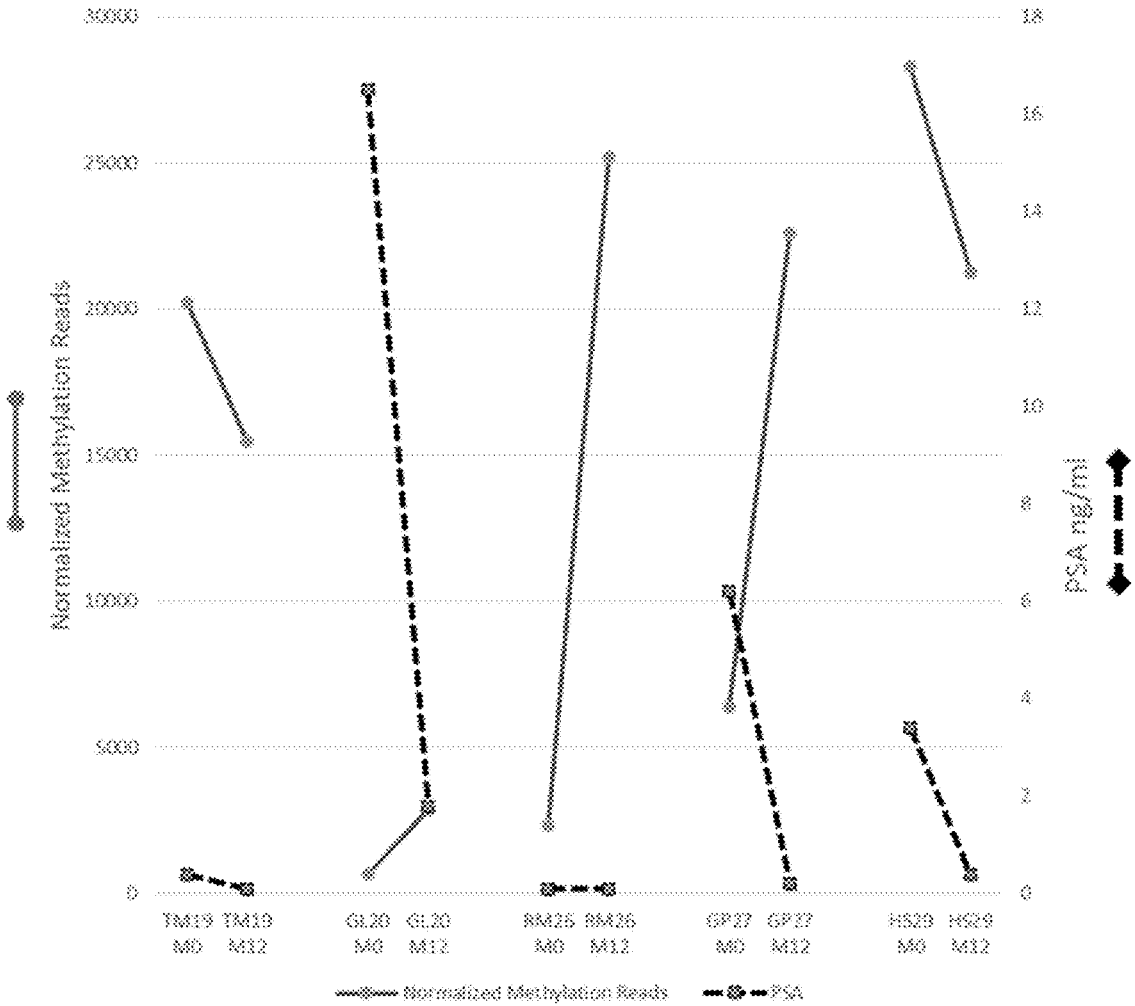
FIG. 24 is a plot showing normalized methylation reads per sample verses PSA levels for each patient. The totals of normalized methylated reads for all probes are plotted with solid lines. Patients initiated androgen deprivation therapy (START) and PSA levels measured at that time and after 12 months of treatment (M12) and are indicated with dashed lines. The methylation detection of circulating tumour DNA (mDETECT) test was performed on 0.5 ml of plasma from these same time points. The Gleason score for each patient at initial diagnosis is shown along with grading, as is the treatment applied as primary therapy (RRP, radical retropubic prostatectomy; BT, brachytherapy; EBR, external beam radiation; RT, radiotherapy).

A variety of probes were positive depending on the particular patient (FIG. 22). The total number of positive probes was in keeping with the total number of methylated reads, which were normalized for total reads for each sample (FIG. 23). In all cases significant ctDNA signals were observed with results that were notably different than PSA results (FIG. 24). Two of the patients, TM19 and RM26 were started on ADT due to their aggressive diseases (T3A and T3B) despite having low PSA levels. PSA levels for both remained low but methylation detection of circulating tumour DNA (mDETECT) either decreased slightly (TM19) or rose dramatically (RM26) suggesting their diseases did not express PSA but had stable or increasing disease. HS29 showed decreased PSA levels which mDETECT paralleled. Both GL20 and GP27 trended in opposite directions to PSA levels with mDETECT increasing even with dramatic drops in PSA levels. GL20 did develop a radiation induced secondary cancer which may be what is detected. Ongoing analysis of additional clinical data is expected to help explain these results.

Based on the literature, three of these regions appear to have prognostic significance as well. C1orf114 or CCDC1 has been shown to be correlated with biochemical relapse. HES5 is a transcription factor that is regulated by the Notch pathway and methylation of its promoter occurs early in prostate cancer development. KLK5 is part of the Kallikrein gene complex that includes KLK3 (the PSA gene). We can demonstrate that KLK5 expression is correlated with methylation and KLK5 expression has previously been shown to be increased in higher grade tumours. These results strongly suggest that the examination of a large number of methylation markers may yield significant insight into the specific processes involved in prostate cancer development and produce diagnostic and prognostic information that would be vital for management of the disease.

Example 9

Predictive Prostate Cancer Methylation Biomarkers

Figure 25:
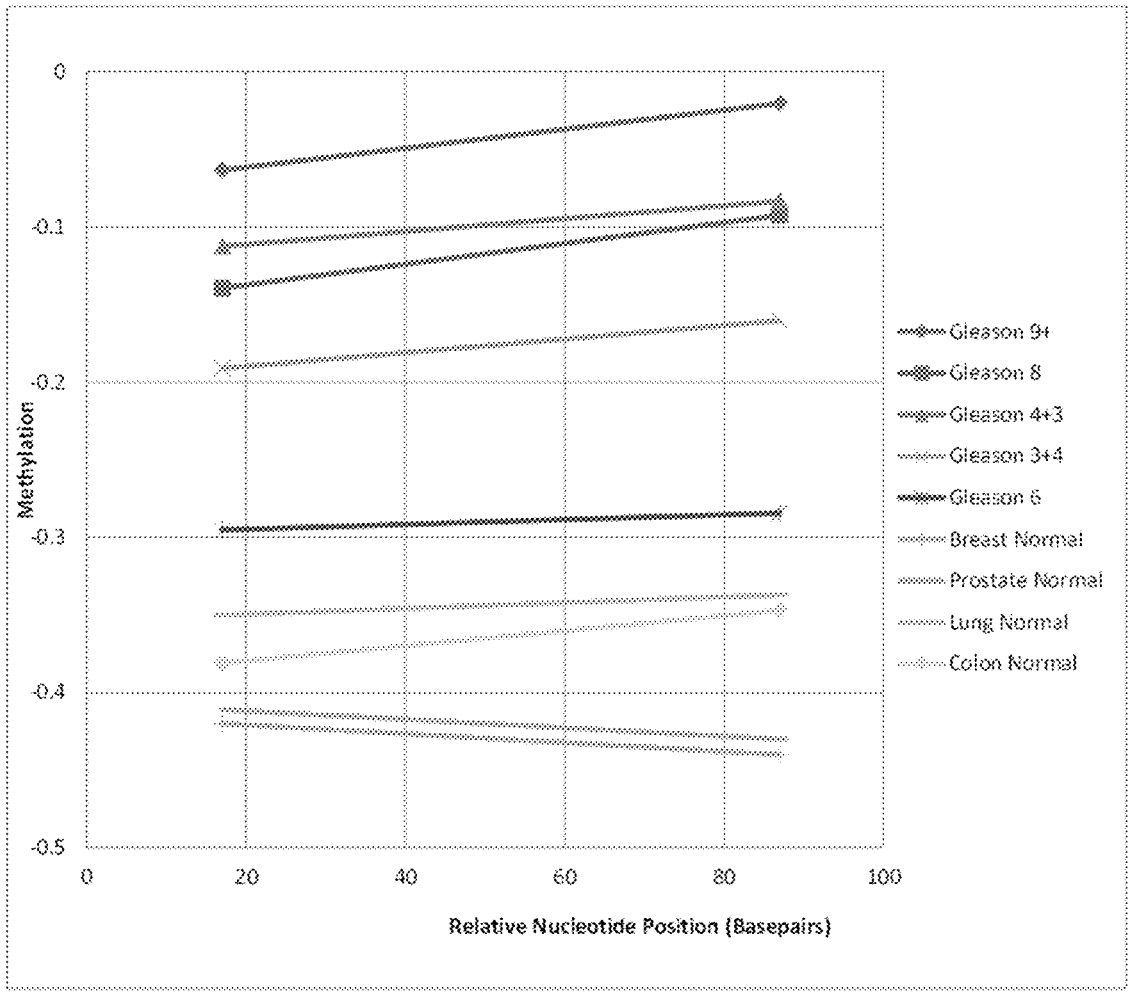
FIG. 25 is a plot of TCGA prostate cancer tumour data, showing the average methylation for each of various Gleason groups, as well as for normal tissue from breast, prostate, lung, and colon, verses position on the genome (in this case on chromosome 8 for the region upstream of the TCF24gene, a transcription factor of unknown function and PRSS3, a serine protease gene on chromosome 9).

The 50 region assay according to embodiments described herein is sufficiently sensitive to easily detect metastatic disease and to follow changes in tumour size over time and, as indicated, has predictive value in itself. As described above, at least three regions, KLK5, HER5, and C1orf114 have potential to predict progression. In order to develop additional probes that are able to predict outcome in this patient population, the prostate cancer TCGA data was reanalysed to divide the patients by Gleason score. An inter-cohort comparison was conducted to identify regions frequently methylated in higher score cancers. Initially, Gleason grades 6 and 9 were compared as these typically represent less and more aggressive tumours and both groups had sufficient numbers of patients to ensure significance of the results. Probe development was carried out under the same criteria as with the original probe sets so that they could be used with ctDNA. No single probe will be absolutely specific for a given grade but a number of the probes showed excellent division between Gleason scores with the proportion of the cohort positive for a given grade increasing with increasing grade (FIG. 25). One of these, PSS3, is a gene whose expression has previously been associated with prostate cancer and particularly metastasis. It should be noted that not all methylation is associated with gene repression. Forty-three new probes were developed based on selection criteria to target the 36 regions shown in Table 13, which are associated with aggressive prostate cancer.

TABLE 13

| | | | |
|---|---|---|---|
| ASAP1 | EMX1 | MIR1292 | SOX2OT |
| BC030768 | HFE | NBPF1 | TUBB2B |
| C18orf62 | HIST1H3G/1H2BI | NHLH2 | USP44 |
| C6orf141 | HMGCLL1 | NRN1 | Intergenic (Chr1) |
| CADPS2 | KCNK4 | PPM1H | Intergenic (Chr8) |
| CORO1C | KJ904227 | PPP2R5C | Intergenic (Chr2) |
| CYP27A1 | KRT78 | PRSS3 | Intergenic (Chr3) |
| CYTH4 | LINC240 | SFRP2 | Intergenic (Chr4) |
| DMRTA2 | Me3 | SLCO4C1 | Intergenic (Chr10) |

The probes were ASAP1/p, BC030768/p, C18orf62/p, C6orf141/p-1, C6orf141/p-2, CADPS2/p, CORO1C/p-1, CORO1C/p-2, CYP27A1/p, CYTH4/p, DMRTA2/p, EMX1/p, HFE/p-1, HFE/p-2, HIST1H3G/1H2BI/p, HMGCLL1/p, KCNK4/p, KJ904227/p, KRT78/p, LINC240/p-1, LINC240/p-2, Me3/p-1, Me3/p-2, MIR129, NBPF1/p, NHLH2/p, NRN1/p, PPM1H/p-1, PPM1H/p-2, PPP2R5C/p, PRSS3/p, SFRP2/p-1, SFRP2/p-2, SLCO4C1/p, SOX2OT/p, TUBB2B/p, USP44/p, Chr1/p-1, Chr2/p-1, Chr3/p-1, Chr4/p-1, Chr8/p-1, and Chr10/p-1.

It is expected that it will be an overall pattern of hyper-methylation, rather than a single probe, that will have the greatest predictive power.

Example 10

Breast Cancer Test

One approach described herein for identifying hyperm-ethylated regions in breast cancer focused on the most frequently methylated regions within the TCGA database. Due to the large number of LumA and LumB patients in this dataset there was a significant under-detection particularly of the Basal class of tumours.

Figure 27:
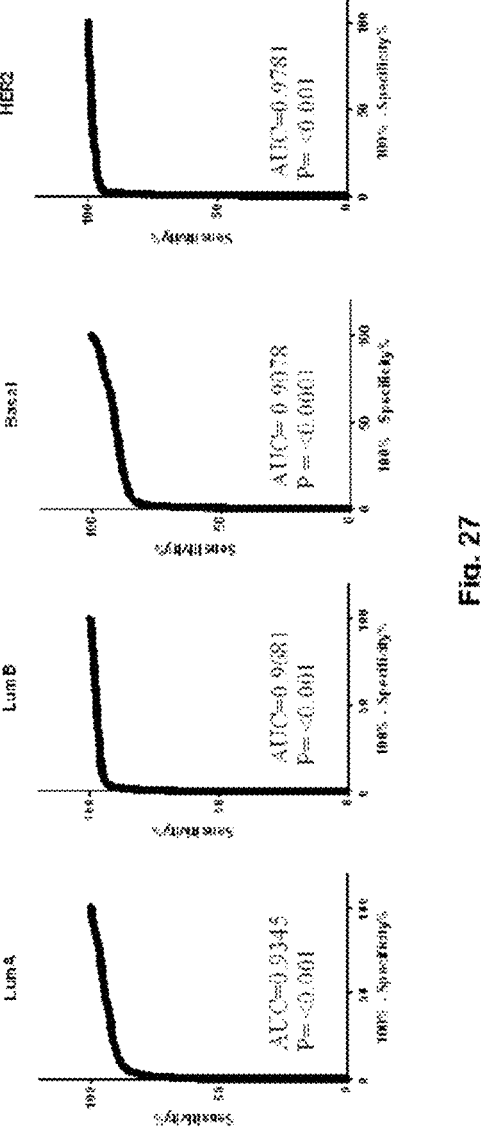
FIG. 27 shows theoretical area under the curve analyses of blood tests using the top 20 probes for each breast cancer subtype (LumA, LumB, Basal, HER2). These values were compared against normal tissue samples for the same probes.

Accordingly, the data were reanalyzed based on the four molecular subtypes LumA, LumB, Her2 and Basal. The Normal-like subtype is not very frequent in the dataset and as expected is very close to normal tissue, however a small number of regions recognizing this subtype were also included. Overall, methods and probes were developed and tested for over 230 different regions (some with multiple probes), and these have been validated using a variety of breast cancer cell lines and tumour samples. Some regions are subtype-specific but most recognize multiple subtypes. These have been assembled into a single test incorporating 167 different probes which recognize all subtypes (FIGS. 26A, 26B, and 26C), with all patients being recognized by a significant number of probes. By looking at just the top 20 probes for each subtype this test has an area under the curve (AUC) per subgroup from 0.9078 to 0.9781, indicating that high detection rates have been achieved for all types of tumours (FIG. 27). This also means that the test is able to identify the subtype of tumour based on the distribution of probe methylation.

Another test specific for the triple negative breast cancer (TNBC) subtype was developed from the larger set of general regions identified as described above. This test incorporates 86 probes from 71 regions, listed in Table 14.

Figure 28:
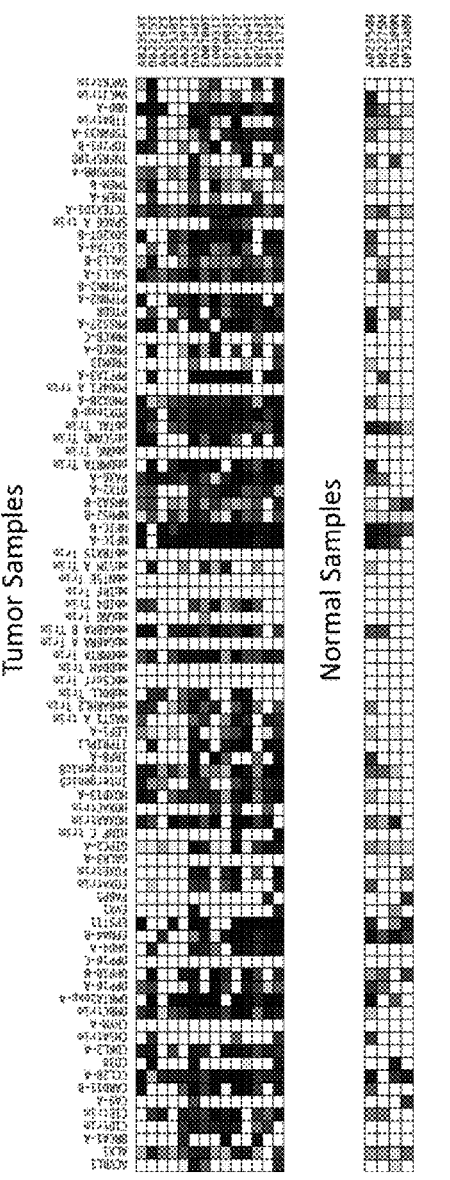
FIG. 28 is a heatmap of multiplexed probes for each TNBC tumour sample and selected normal samples. A black square indicates that methylated reads having greater than 80% methylation per read were detected for that probe but does not take into consideration the number of reads for each.

The ability of this test to detect TNBC was validated by the analysis of 14 TNBC primary tumours as well as matched normal tissue from four of these patients. Large scale methylation was observed for the majority of probes and was distinctly different from the normal samples (FIG. 28).

Example 11

Sensitivity of the Tests

Figure 29:
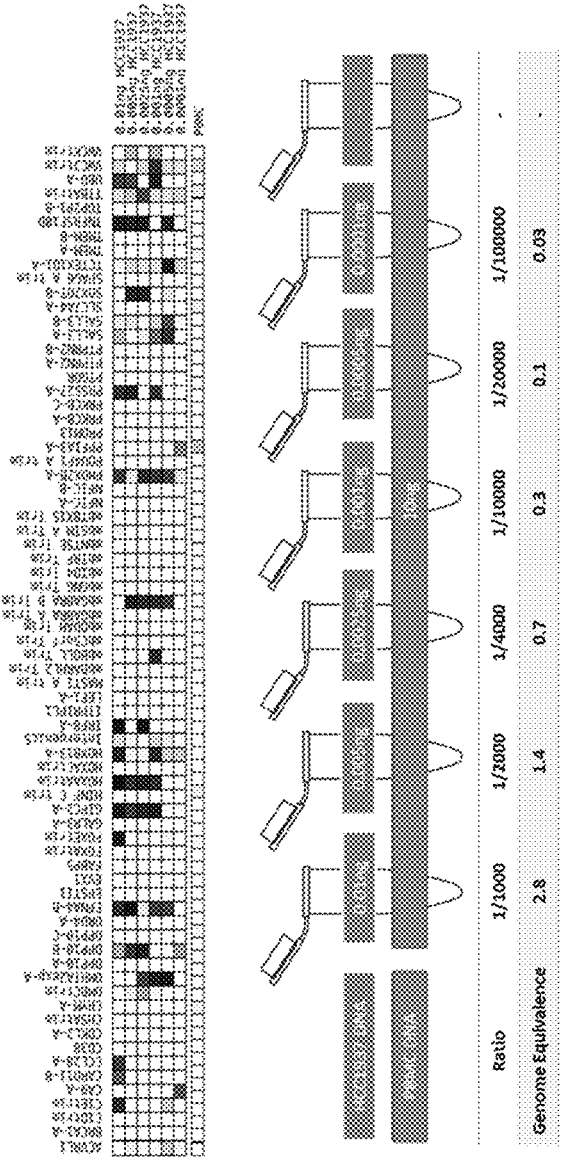
FIG. 29 is a diagram showing results of a sensitivity test for TNBC to detect low levels of tumour DNA, using HCC1937 DNA diluted into a fixed amount of PBMC DNA (10 ng). Shaded squares indicate a distinct methylation signature.

The tests described herein are designed to detect less than one genome's worth of DNA in a sample through the use of multiple regions where a single probe out of many can signal the presence of a tumour. The more regions and probes incorporated into a test the greater is the sensitivity. This is in contrast to mutation detection where the presence of a single mutation per genome equivalent means that random sampling effects rapidly limit sensitivity when the concentration of the tumour DNA falls below one genome equivalent per sample. The presence of large amounts of normal DNA in fluid samples also creates problems for the detection of mutations through the relatively high error rates for PCR and sequencing. To assess the limits of methods and tests described herein, a dilution experiment was performed wherein DNA from a TNBC cell line (HCC1937 DNA) was diluted into a constant amount of PBMC DNA (10 ng) from a normal patient (FIG. 29). These samples were then tested using the TNBC test. A conclusive signal was obtained from the test even when as little as 0.0001 ng of TNBC DNA was present in 10 ng of PBMC DNA. This represents a detection of 0.03 genome equivalents of tumour DNA against a background of 100,000 times more normal DNA.

TABLE 14

| CCL28 | PTPRN2 | UDB | IRF4 | HOXA9 | HINF1B | POU4F1 |
|---|---|---|---|---|---|---|
| PAX6 | BARHL2 | TMEM90B | SOX2OT | NT5E | TNFRSF10D | VWC2 |
| PPFIA3 | PRSS27 | C1orf114 | TSPAN33 | DPP10 | CD38 | BRCA1 |
| SPAG6 | DMRTA2 | ITPRIPL1 | CA9 | FOXA3 | CHST11 | HOXB13 |
| TMEM132C | NR5A2 | GIPC2 | IRF8 | C5orf39 | FABP5 | OTX2 |
| DMBX1 | BOLL | ERNA4 | CRYM | PTGDR | Intergenic5 | |
| TAL1 | SLC7A4 | MAST1 | GNG4 | SALL3 | EVX1 | |
| TOP2P1 | LEF1 | DRD4 | DDAH2 | ID4 | ACVRL1 | |
| PRDM13 | CARD11 | Intergenic 8 | EPSTI1 | GABRA4 | TBX15 | |
| GALR3 | NFIC | TCTEX1D1 | TTBK1 | PRKCB | ALX1 | |
| CDKL2 | PDX1 | PHOX2B | SCAND3 | NPHS2 | SIM1 | |

The probes were ALX1, AVCRL1, BRCA1-A, C1Dtrim, C1 Etrim, CA9-A, CARD11-B, CCL28-A, CD38, CDKL2-A, CHSAtrim, CRYM-A, DMBCtrim, DMRTA2exp-A, DPP10-A, DPP10-B, DPP10-C,DRD4-A, EFNA4-B, EPSTI1, EVX1, FABP5, FOXAtrim, FOXEtrim, GALR3-A, GIPC2-A, HINF C trim, HOXAAtrim, HOXACtrim, HOXB13-A, Int5, Int8, IRF8-A, ITRIPL1, LEF1-A, MAST1 A trim, mbBARHL2 Trim, mbBOLL Trim, mbC5orf Trim, mbDDAH Trim, mbDMRTA Trim, mbGA-BRA A Trim, mbGABRA B Trim, mbGNG Trim, mbID4 Trim, mbIRF Trim, mbNT5E Trim, mbSIM A Trim, mbTBX15 Trim, NFIC-B, NFIC-A, NPSH2-B, NR5A2-B, OTX2-A, PAX6-A, pbDMRTA Trim, pbGNG Trim, pbSCAND Trim, pbTAL Trim, PDX1exp-B, PHOX2B-A, POU4F1 A trim, PPFIA3-A, PRDM13, PRKCB-A, PRKCB-C, PRSS27-A, PTGDR, PTPRN2-A, PTPRN2-B, SALL3-A, SALL3-B, SLC7A4-A, SOX2OT-B, SPAG6 A trim, TCTEX1D1-A, TMEM-A, TMEM-B, TMEM90B-A, TNFRSF10D, TOP2P1-B, TSPAN33-A, TTBAtrim, UBD-A, VWCJtrim, and VWCKtrim.

Example 12

Discussion

The sensitivity of mutation based detection tests is limited by their detection of single unknown mutations in genes, such as p53 or ras. As only a single mutation is present per genome equivalent, this dramatically limits the sensitivity of these assays. Once the concentration of tumour DNA in the blood decreases to less than one genome equivalent per volume of blood analysed, the probability of detecting a mutation decreases dramatically as that particular segment of DNA may not be present in the blood sample. The assay described herein incorporates multiple probes for multiple regions from across the genome to dramatically increase sensitivity. For example, up to 100 or more probes may be incorporated into the assay, making it up to 100 or more times more sensitive than mutation based tests.

Circulating tumour DNA may be produced by the apop-totic or necrotic lysis of tumour cells. This produces very small DNA fragments in the blood. With this in mind, PCR primer pairs were designed to detect DNA in the range of 75 to 150 bp in length, which is optimal for the detection of circulating tumour DNA.

The use of DNA methylation offers one more advantage over mutation based approaches. Mutated genes are typically expressed in the cells (such as p53). They are thus in loosely compacted euchromatin, in comparison to methylated DNA which is in tightly compacted heterochromatin. This methylated and compacted DNA may be protected from apoptotic nucleases, increasing its concentration in the blood in comparison to these less compacted genes.

Extensive analysis of the genome wide methylation patterns in breast, colon, prostate and lung cancers and normal tissue in each of these organs based on TCGA data was carried out. 52 regions were identified for breast cancer which fulfill design criteria, which looks for an optimal difference in methylation between tumour and normal breast tissue, and where there is no methylation in any of the other normal tissues. As well, there should optimally be at least 2 CpG residues within 200 basepairs of each other. This ensured that regions of coordinated tumour specific methylation have been identified.

Within these 52 regions, 17 were found in common with colon cancer, and 9 in common with prostate cancer. Interestingly there were few appropriate regions identified in lung cancer, with only 1 overlapping with breast cancer. Most of these regions are associated with specific genes, though several are distantly intergenic, and almost all were found in CpG islands of various sizes. Probes were first developed for those regions with some commonality between cancers and designed PCR primers which recognize the methylated DNA sequence. This provides a bias in the amplification process for tumour DNA, enriching the tumour signal. These primer pairs amplify regions of 75 to 150 bp in accordance with our design criteria. Typically these regions contain from 3 to 12 CpG residues each, ensuring a robust positive signal when these regions are sequenced. Multiple non-overlapping probes were used as the CpG islands are generally larger than 150 bp, allowing for multiple probes for each appropriate region, providing more power to detect these regions and increasing the detection sensitivity of the assay.

Six different breast cancer lines were used in this validation analysis that have been shown to generally retain tumour specific methylation patterns[22]. MCF-7 and T47D lines are classic ER+ positive cell lines representing the most frequent class of breast cancer. SK-BR-3 cells are a HER2+ line and MDA-MB-231 cells represent a Triple Negative Breast cancer (TNBC), thus the 3 main categories of breast cancer are represented covering 95% of all tumours. Two "normal" lines were also used, the MCF10A line, though this line has been shown to contain some genomic anomalies, and the karyotypically normal 184-hTERT line. DNA was bisulphite converted, and the probes were amplified individually, barcoded then pooled according to cell line and subject to Next Generation Sequencing on an Ion Torrent sequencer. Not all PCR primer pairs produced a product due to the methylation-based nature of the primers, but in general, where a signal was detected, around 1000 reads were obtained per probe for each cell line. These reads were processed through our NGS pipeline using Galaxy and then loaded into the NGS methylation program BiqAnalyzer[23,24]. This program extracts probe specific reads, aligns them against the probe reference sequence, and calls methylated and unmethylated CpGs. It also carries out quality control measures related to bisulphite conversion and alignment criteria. In all of these probes there are several CpG residues within the primer sequence producing a bias towards amplifying methylated DNA. The analysis shown only includes CpGs outside of the primers which are solely representative of the methylation status of the sample being analysed.

FIGS. 5 and 6 depict results for the CHST11 gene, which is a good example where robust PCR primers are able to recognize tumour specific methylation. Four different primer pairs were assessed, three of which amplify probes that partially overlap. In all four cases these regions are completely methylated at all CpGs (not including CpGs in the primers) and are essentially completely unmethylated in the normal lines. CHST11 primers do not recognize the Her2 or TNBC lines, but other primers such as ADCY and MIRD do. The corresponding probes cover a small region of the CpG island and information about the status of the rest of the CpG island is limited due to the relatively coarse resolution of the 450K methylation data. Clearly the remaining part of the CpG island can be developed for additional probes that would increase the sensitivity of detection.

FIG. 7 shows that FOXA probe A had similar characteristics and recognized all but one TNBC tumour. This proves that the target and probe development pipeline moving from TCGA data to cell lines and then to patient normal and tumour tissue successfully identified primer pairs that are able to specifically recognize tumour DNA based on their methylation patterns.

Validation work continues to validate potential probe regions. A further 24 regions were characterized using 52 different probes in the cell lines as an initial screen for their suitability.

FIG. 4 shows the results of analysis of all of the potential CpGs identified in the TCGA cohort for individual patients indicates most patients are recognized by a large proportion of these probes.

FIG. 3 shows the results of ROC analysis[25] and indicates each of these probes has a very high AUC, suggesting excellent performance individually and presumably even better when combined.

It has been noted that there does appear to be a population of patients with relatively few positive probes. This is not subtype specific and other probes specific for this population have been identified. As appropriate, additional probes will be developed for all suitable regions and expanded to include other parts of the associated CpG islands. Overall it is expected that 100-150 separate probes in the assay will provide optimal sensitivity.

FIGS. 12A and 12B depict a numerical summary of validation data, wherein "#Reads" indicates the number of reads, and "Mean" Me indicates the mean methylation observed in results. Approximately half of the probes met the design criteria of having complete methylation of all CpG residues in the tumour samples and little or no methyation in the normal lines.

The next step in validating each of these probes was to examine their methylation patterns in actual patient tumour samples. A small cohort of patient samples was used to investigate GR methylation. From this group three ER+ tumours (one of which is positive for GR methylation), one HER2+ tumour and two TNBC tumours were chosen, as well as their corresponding normal controls. Taking the CHST11A probe as an example, FIG. 6 shows that all six of the normal breast tissue samples had either no reads due to the methylation biased amplification yielding no product or minimal methylation. In no case was there any concerted methylation signal where all CpGs were methylated. In contrast, in one TNBC and one ER+PR+ tumour a strong concordant methylation signal was seen at all six CpG sites. The other 2 ER+PR+ tumours also showed consistent methylation at four or five CpGs with their normal breast tissue controls having minimal reads with only one CpG showing any methylation.

FIGS. 13A and 13B depict a numerical summary of generated methylation data for tumour samples for all probes tested to date. #Reads is indicative of the number of reads exported, and Mean Me is indicative of the mean methylation.

Initial proof of concept work involved mixing experiments where non-methylated and methylated DNA was mixed in increasing ratios. This demonstrated that based in the presence of multiple CpG signatures methylated DNA could easily be detected in the presence of at least a 500 fold excess of unmethylated DNA. These probes were amplified with PCR primers that were not methylation specific or biased, and the probes developed to date do incorporate a bias towards methylated DNA, which further increases the detection sensitivity. However, they do amplify non-methylated DNA (in part because primers were designed with no preference as to the location of methylation sites within the primers). This was done intentionally as it provides for a potential quantitative aspect to this assay. Some of the circulating normal DNA in blood samples is likely from the lysis of nucleated blood cells, which is why serum is preferred over plasma as a source of DNA. However the ratio of tumour to normal DNA in blood may provide some quantitation of the actual concentration of tumour DNA present in the blood, which is thought to be correlated with tumour load. Since tumour can be distinguished from normal DNA reads, the ratio between them can be used as a proxy for the tumour DNA concentration. The number of tumour specific reads per volume of blood, regardless of the number of normal reads, may also prove to be closely linked to circulating tumour DNA levels.

Optimizing this test may include multiplexing to allow all of the probes the opportunity to amplify their targets in a given sample of DNA. Through the use of limited concentrations of primers and cycles, excellent amplification of all probes was obtained within a set of 17 primer pairs. Expanding this to include all of the optimized primers is not expected to be an issue.

The test may be implemented as a blood based breast cancer detection system in patient blood samples.

Based on development and validation work to date, the assay offers significant advantages other current and developing tests based on sensitivity, specificity, and detection sensitivity.

Some potential applications of the embodiments described herein are listed below by level of detection sensitivity:

Determining response to neo-adjuvant chemotherapy;
Monitoring tumour load in diagnosed patients;
Detecting residual disease post-surgery;
Detecting relapse;
Secondary screen after positive MRI in high risk patients;
Direct monitoring of high risk patients; and
Primary population screening.

The analysis of patients with active breast cancer offers the ability to assess a number of different aspects of this blood based test. Patients with locally advanced disease can be recruited preferentially, as these patients generally have larger tumours, receive neo-adjuvant therapy, are more likely to have residual disease and are at higher risk of relapse. By analysing blood samples from these patients upon diagnosis, after any neo-adjuvant treatments, pre-surgery, and at followup visits post-surgery it is possible to follow the relative tumour burden in these patients over the course of treatment. This will allow the tumour size and type to be correlated with the results of the test described herein.

Patients can be recruited in the clinic after a biopsy confirmed positive diagnosis. Blood can be drawn in conjunction with other routine blood work at diagnosis, after neo-adjuvant treatment, before surgery, within a month after surgery and every 3-6 months following that. Blood from 50 aged matched women without disease can also be collected from the community to provide control samples for the patient cohort. Relevant clinical data can be collected including radiological assessments and/or pathology reports. In particular, the receptor status of the tumours, the size of the tumour based on both radiological assessment and examination of the excised tumour, as well as treatments and response to therapy can be correlated with the circulating DNA analysis.

The assay described herein is expected to be quantitative at different levels. At very low levels of tumour DNA, the random presence of the tumour DNA in a sample will result in a subset of individual probes being positive, with the number of positive probes increasing with greater tumour DNA levels. At higher levels of tumour DNA the number of tumour specific reads will increase, either as an absolute number or in relation to the number of normal DNA reads. As a result methylation data can be treated in three ways:

(1) As a binary outcome where each probe will be considered to be positive if it has any tumour specific methylation pattern present;

(2) An individual threshold of methylation will be established for each probe based on the minimum number of reads required to call a tumour; or (3) Tumour specific reads per number of normal reads for each probe (or, e.g., per 100,000 total reads).

Each of these approaches may be used to carry out logistic regression on the patient and control sets. Receiver Operating Characteristic (ROC) analysis may be used to define thresholds for each probe that maximizes the sensitivity and sensitivity of the assay. The performance of the entire assay may be characterized using Area Under the Curve (AUC) analysis for overall sensitivity, specificity, classification accuracy and likelihood ratio. Pearson or Spearman correlations may be used to compare patient parameters with the test outcomes.

Changes in methylation may be important drivers of breast cancer development and that these occur very early during the process of transformation. This may explain why many of the observed methylations are common amongst different breast cancer sub-types, while some are even common to other cancers. This may mean that these changes predate the development of full malignancy and suggests that they could also have value in assessing the risk of a women developing breast cancer. It is envisaged that the assay described herein can be used to track the accumulation of risk in the form of increasing gene specific methylation levels and could be used to develop a risk assessment tool. This would be useful for the development and assessment of risk mitigation and prevention strategies.

TABLE 15

| Gene | Probe | SEQ ID NO. | 5' 3' Primer Sequence (Bisulfite) | Chr: Location | PCR Product Length |
|---|---|---|---|---|---|
| C1orf114/ CCDC181 | C1Df | 1 | TTGAGGTAAAGGAGATTT CGGT | chr1: 167663228 - 167663361 | 134 |
| | C1Dr | 2 | ACATACGCCTACGCAAAT TTTTA | | |
| | C1Ef | 3 | TTCGGTGTTTGCGAAGGG TTA | chr1: 167663398 - 167663508 | 111 |
| | + C1Er | 4 | TCACAACCAACACAACGA CACTT | | |
| | C1Er | 5 | ACAACCAACACAACGAC ACTT | | |
| | C1Ff | 6 | TCGGTATTTGTTTTCGCG GT | chr1: 167663245 - 167663356 | 112 |
| | C1Fr | 7 | CGCCTACGCAAATTTTTA TCGC | | |
| | C1Gf | 8 | CGAGAGCGATAAAAATTT GCGT | chr1: 167663330 - 167663417 | 88 |
| | C1Gr | 9 | ACCCTTCGCAAACACCGA AA | | |
| | C1 eAf | 10 | GGTAATAGCGTGTTTTTG C | chr1: 167663285- 167663366 | 82 |
| | C1 eAr | 11 | ATATTACATACGCCTACG CAAA | | |
| | C1 eBf | 12 | TTTGTGTAAAATGCGGCG GT | chr1: 167663149- 167663266 | 118 |
| | C1 eBr | 13 | CTACCGCGAAAACAAATA CCGA | | |
| | C1 eCf | 14 | ATTTCGGTGTTTGCGAAG GG | chr1: 167663395- 167663506 | 112 |
| | C1 eCr | 15 | ACAACCAACACAACGAC ACT | | |
| VWC2 | VWCJf | 16 | TTTCGGTTGTCGGGTTTG GA | | |
| | + VWCJf | 17 | TATTTCGGTTGTCGGGTTT GGA | chr7: 49783871 - 49784003 | 133 |
| | VWCJr | 18 | CCCTCAATCGCTCATCCT CC | | |
| | VWCKf | 19 | TCGTCGGTCGGTTTAGGA TG | chr7: 49784151 - 49784279 | 129 |
| | + VWCKr | 20 | AAAACCGACGCCAAACCT ACAT | | |
| | VWCKr | 21 | AACCGACGCCAAACCTAC AT | | |
| | VWCLf | 22 | CGGAGGATGAGCGATTG AGG | chr7: 49783983 - 49784100 | 118 |
| | VWCLr | 23 | TAACGCGCACACCGAACT AA | | |
| | VWCMf | 24 | CGAGTTGGGGTCGCGATT AT | chr7: 49784021 - 49784170 | 150 |
| | VWCMr | 25 | CATCCTAAACCGACCGAC GA | | |
| | VWCNf | 26 | CGACGCGTTACGGTTGTT TA | chr7: 49783849 - 49783973 | 125 |
| | VWCNr | 27 | CCGCTTCTCCGAAACCAA AC | | |
| | VWC2 eAf | 28 | TAAGGCGGGGTTTTTAGA GC | chr7: 49783687- 49783792 | 106 |
| | VWC2 eAr | 29 | TAAAAACTAACGCGCCCG | | |
| | VWC2 eBf | 30 | GGTTTCGGTGTTATTCGC | chr7: 49783797- 49783922 | 126 |
| | VWC2 eBr | 31 | CTCCTCTCCGCGAAAAAA T | | |
| | VWC2 eCf | 32 | CGGAGGATGAGCGATTG AGG | chr7: 49783983- 49784100 | 118 |
| | VWC2 eCr | 33 | TAACGCGCACACCGAACT AA | | |
| | VWC2 eDf | 34 | TCGTCGGTCGGTTTAGGA TG | chr7: 49784151- 49784277 | 127 |
| | VWC2 eDr | 35 | AACCGACGCCAAACCTAC AT | | |
| | VWC2 eEf | 36 | GTCGGACGCGTTTTAGTT GG | chr7: 49784315- 49784424 | 110 |
| | VWC2 eEr | 37 | TCCCTACCGACCTCAACA CT | | |

TABLE 15-continued lists the primers used herein for each probe.

| Gene | Probe | SEQ ID NO. | 5' 3' Primer Sequence (Bisulfite) | Chr: Location | PCR Product Length |
|---|---|---|---|---|---|
| MIR129-2 | MIRBf | 38 | TGGTTGGGGGATTTTGAG GG | chr11: 43559089 - 43559229 | 141 |
| | MIRBr | 39 | AAACCTCCCCGCCTACCT AT | | |
| | MIRCf | 40 | GCGGACGGTTTGGAGAA ATG | chr11: 43559343 - 43559424 | 82 |
| | MIRCr | 41 | CGCGACTCAATCTCACCA CT | | |
| | MIRDf | 42 | GGAGGTTGGGTTTCGGGA TT | chr11: 43559257 - 43559383 | 127 |
| | MIRDr | 43 | GCGCCCCTAAACTCGTAT CT | | |
| | MIREf | 44 | GCGGAGTGGTGAGATTG AGT | chr11: 43559401 - 43559513 | 113 |
| | MIREr | 45 | ACCGACTTCTTCGATTCG CC | | |
| | MIRFf | 46 | ATAGGTAGGCGGGGAGG TTT | chr11: 43559205 - 43559343 | 139 |
| | MIRFr | 47 | CGATCCCCCAACTCAACC C | | |
| | MIR eAf | 48 | TGAGTTGGCGGTTTCGTT TG | chr11: 43559004- 43559125 | 122 |
| | MIR eAr | 49 | CCCGAATCCCCTCTTATC CC | | |
| | MIR eBf | 50 | CGCGATTTTGTAGTCGGG GT | chr11: 43559156- 43559251 | 96 |
| | MIR eBr | 51 | TTTCCTATCGCCCCAACA CC | | |
| | MIR eCf | 52 | GGAGGTTGGGTTTCGGGA TT | chr11: 43559257- 43559383 | 127 |
| | MIR eCr | 53 | GCGCCCCTAAACTCGTAT CT | | |
| | MIR eDf | 54 | GATTGAGTCGCGATGGAA CG | chr11: 43559413- 43559494 | 81 |
| | MIR eDr | 55 | GCCGCCTTCAACCCAAAA TA | | |
| ADCY4 | ADCYFf | 56 | CGCGAGCGTATAGAGTAC GA | chr14: 23873573 23873735 | 163 |
| | ADCYFr | 57 | ACCCTAACCAACCCCGAA AC | | |
| | ADCYGf | 58 | TAGCGTCGCGAGCGTATA GA | chr14: 23873567 - 23873754 | 188 |
| | ADCYGr | 59 | AAAAATAACCCGACGCCC GA | | |
| | ADCYHf | 60 | GGTTTCGTAGAAGAGGTT TTC | chr14: 23873642 - 23873815 | 174 |
| | ADCYHr | 61 | CGCGAAATAATAACGACT TT | | |
| | ADCY4 eAf | 62 | AGAAGAGGTTTTCGTTGG GGG | chr14: 23873650- 23873729 | 80 |
| | ADCY4 eAr | 63 | ACCAACCCCGAAACTCGA AA | | |
| | ADCY4 eBf | 64 | TAGGATTTGGGGTTGGTG CG | chr14: 23873975- 23874115 | 141 |
| | ADCY4 eBr | 65 | AACGCAACGACGAACGT AAC | | |
| | ADCY4 eCf | 66 | TGGTAGTGGGGAGATCG AGG | chr14: 23874376- 23874474 | 99 |
| | ADCY4 eCr | 67 | AAACGCCCCCAACTCTAA CC | | |
| DMBX1 | DMBAf | 68 | GTTGCGGACGGCGTAGAT | chr1: 46723984 - 46724132 | 149 |
| | DMBAr | 69 | ACGCTCCCCGAAACAATA ACT | | |
| | DMBBf | 70 | TTGTTAGTTTTGTTAGCGC GG | chr1: 46723919 - 46723993 | 75 |
| | DMBBr | 71 | CGTCCGCAACGATTCATC ATC | | |
| | DMBCf | 72 | TGTTTAGGAGATGGTTCG TGGT | chr1: 46723889 - 46724003 | 115 |

TABLE 15-continued lists the primers used herein for each probe.

| Gene | Probe | SEQ ID NO. | 5' 3' Primer Sequence (Bisulfite) | Chr: Location | PCR Product Length |
|---|---|---|---|---|---|
| | + DMBCr | 73 | GCATCTACGCCGTCCGCA AC | | |
| | DMBCr | 74 | ATCTACGCCGTCCGCAAC | | |
| | DMBX1 eAf | 75 | TGTTTAGACGTGGGTTGG GG | chr1: 46723237-46723323 | 87 |
| | DMBX1 eAr | 76 | TCAACTCCACTCACCCCG TA | | |
| | DMBX1 eBf | 77 | GAGGAGGGTGGAGAGGG TAG | chr1: 46723478-46723610 | 133 |
| | DMBX1 eBr | 78 | ATACCGCACGTACTCCCA AC | | |
| | DMBX1 eCf | 79 | GGAGTGGAGTAGGTAGC GGT | chr1: 46723635-46723751 | 117 |
| | DMBX1 eCr | 80 | TTCCTAACCCTCTCCGAC CA | | |
| | DMBX1 eDf | 81 | TTTTTGAGCGGTGAAGGG GA | chr1: 46723764-46723888 | 125 |
| | DMBX1 eDr | 82 | AATTATTAACGCGACCGC CG | | |
| HOXA9 | HOXAAf | 83 | GTAATAATTTGGTGGTAT CGGGGG | chr7: 27171666 - 27171765 | 100 |
| | HOXAAr | 84 | TCTACTAAACGAACACGT AACGC | | |
| | HOXABf | 85 | ATAATTTGGTGGTATCGG GGG | chr7: 27171669 - 27171777 | 109 |
| | HOXABr | 86 | ACGCGTTATTATTCTACTA AACGAA | | |
| | HOXACf | 87 | TGGGGTTTGTTTTAATTGT GGTT | chr7: 27171878 - 27172029 | 152 |
| | + HOXACr | 88 | GCGAAACCCGCGCCTTCT TAAT | | |
| | HOXACr | 89 | GAAACCCGCGCCTTCTTA AT | | |
| | HOXADf | 90 | GGGGAAGTATAGTTATTT AATAAGTTG | chr7: 27171688 - 27171815 | 128 |
| | HOXADr | 91 | ACAAAACATCRAACCATT AATAA | | |
| | HOXA9 eAf | 92 | TTCGCGAAGGAGAGCGT ATC | chr7: 27171234-27171334 | 101 |
| | HOXA9 eAr | 93 | CCCTACGTACACCCCCAA AC | | |
| | HOXA9 eBf | 94 | CGTTTGGGGGTGTACGTA GG | chr7: 27171314-27171401 | 88 |
| | HOXA9 eBr | 95 | AAACCCAATACACGCGAC GA | | |
| | HOXA9 eCf | 96 | TTTGTCGGGGAGGTTGGT TT | chr7: 27171478-27171559 | 82 |
| | HOXA9 eCr | 97 | TTCCTACTAAACGCCGAC GC | | |
| | HOXA9 eDf | 98 | TAGCGTTTGGTTCGTTCG GT | chr7: 27171611-27171733 | 123 |
| | HOXA9 eDr | 99 | ATAAAAACGCGAACGCC GAC | | |
| SFRP5 | SFRAf | 100 | GCGGGCGTTTCGATTGAT TT | | |
| | + SFRAf | 101 | TTGCGGGCGTTTCGATTG ATTT | chr10: 99521730 - 99521860 | 131 |
| | SFRAr | 102 | TAAAAACCGCCCCCACTA CC | | |
| | SFRBf | 103 | TGTTCGGCGGTTTAGGTG TT | chr10: 99521628 - 99521751 | 124 |
| | SFRBr | 104 | AAATCAATCGAAACGCCC GC | | |
| | SFRCf | 105 | TAGTTCGGGTTTCGTCGT GC | chr10: 99521776 - 99521865 | 90 |
| | + SFRCr | 106 | AAAACTAAAAACCGCCCC CACT | | |
| | SFRCr | 107 | AACTAAAAACCGCCCCCA CT | | |
| | SFRDf | 108 | GTGGGTGGTAGTTTGCGT TG | chr10: 99521713 - 99521847 | 135 |

TABLE 15-continued lists the primers used herein for each probe.

| Gene | Probe | SEQ ID NO. | 5' 3' Primer Sequence (Bisulfite) | Chr: Location | PCR Product Length |
|---|---|---|---|---|---|
| | SFRDr | 109 | CACTACCTCCCCGCCTTA AA | | |
| | SFREf | 110 | GCGTGCGTTTTCGGTTTT GA | | |
| | + SFREf | 111 | CGGCGTGCGTTTTCGGTT TTGA | chr10: 99521649 - 99521731 | 83 |
| | SFREr | 112 | AACGCAAACTACCACCCA CC | | |
| | SFRP5 eAf | 113 | GGACGTTGGGTTGAGTTA GGA | chr10: 99520910- 99521018 | 109 |
| | SFRP5 eAr | 114 | ACGACCCTACAACTCCCC TA | | |
| | SFRP5 eBf | 115 | GGTGTTCGAATTGTACGG CG | chr10: 99521073- 99521179 | 107 |
| | SFRP5 eBr | 116 | CTACGCGCCGCTCATAAA AA | | |
| | SFRP5 eCf | 117 | GCGCGTACGGTTTCGTAT AG | chr10: 99521183- 99521257 | 75 |
| | SFRP5 eCr | 118 | ATACTCGCTCTTTACGCC CG | | |
| | SFRP5 eDf | 119 | TAGAGCGGTAGGTCGGTA GG | chr10: 99521393- 99521471 | 79 |
| | SFRP5 eDr | 120 | AACAAACCGAACCGCTAC AC | | |
| CHST11 | CHSAf | 121 | GCGGCGTGGGAATGAATT TT | | |
| | + CHSAf | 122 | GGGCGGCGTGGGAATGA ATTTT | chr12: 103376278 - 103376397 | 120 |
| | CHSAr | 123 | CTTTCCCTCGCACCCCTA AA | | |
| | CHSBf | 124 | TGCGAGGGAAAGTTTGG GTT | chr12: 103376386 - 103376508 | 123 |
| | CHSBr | 125 | CCGCGTTACCCGAAAAAC TT | | |
| | CHSCf | 126 | TTTTAGGGGTGCGAGGGA AA | chr12: 103376377 - 103376462 | 86 |
| | CHSCr | 127 | CGCAACCGAACTACTCAC CC | | |
| | CHSDf | 128 | GTGCGAGGGAAAGTTTG GGT | chr12: 103376385 - 103376510 | 126 |
| | CHSDr | 129 | ACCCGCGTTACCCGAAAA A | | |
| | CHST11 eAf | 130 | TTTTTTTGGTTGTCGGGTC | chr12: 103375901- 103376009 | 109 |
| | CHST11 eAr | 131 | CGAAACCCGAAACACGT A | | |
| | CHST11 eBf | 132 | AGAGTGGTCGGGTGTTTA GC | chr12: 103376031- 103376179 | 149 |
| | CHST11 eBr | 133 | ACGTAACCCAAAAACTCG AAA | | |
| | CHST11 eCf | 134 | GTCGTTTTTTAGGGGTGC | chr12: 103376371- 103376469 | 99 |
| | CHST11 eCr | 135 | TAAACTTCGCAACCGAAC TA | | |
| | CHST11 eDf | 136 | TATTAAGTTTGCGTTTGG GTC | chr12: 103376781- 103376889 | 109 |
| | CHST11 eDr | 137 | AAAACCGTCTATCCCTAC GC | | |
| FOXA3 | FOXAf | 138 | CGAGGTAGGAAGTTTTGC GG | chr19: 51071936 - 51072038 | 103 |
| | FOXAr | 139 | CGACTCCTCCCGCGAAAT AA | | |
| | FOXBf | 140 | CGGGGTGTTGTTGTAGGG TT | chr19: 51072158 - 51072250 | 93 |
| | FOXBr | 141 | AATCACACCTACCCACGC C | | |

TABLE 15-continued

<u>lists the primers used herein for each probe.</u>

| Gene | Probe | SEQ ID NO. | 5' 3' Primer Sequence (Bisulfite) | Chr: Location | PCR Product Length |
|---|---|---|---|---|---|
| | FOXCf | 142 | TAGGGCGGTTAGGTTTGG GG | chr19: 51072076 - 51072203 | 128 |
| | FOXCr | 143 | GACGAATAACCCCACCCT CC | | |
| | FOXDf | 144 | TTGTCGCGTTGGTTTTTCG T | chr19: 51071765 - 51071867 | 103 |
| | FOXDr | 145 | ACCTTTCTCTCGACCCCA AT | | |
| | FOXEf | 146 | CGTTTTGTCGGTTGCGTG TTA | chr19: 51071734 - 51071824 | 91 |
| | FOXEr | 147 | ATTCCCCGACCTACCCAA AAC | | |
| | FOXA3 eAf | 148 | GGTAGGTGATAACGTTAG TGGGTT | chr19: 51068615- 51068724 | 110 |
| | FOXA3 eAr | 149 | ACCTCCATCCCCTACCCA AC | | |
| | FOXA3 eBf | 150 | AGTAGGGGGAGGTGGTTT TG | chr19: 51069110- 51069244 | 135 |
| | FOXA3 eBr | 151 | TCCTCCTCCCCAACTTAA CC | | |
| | FOXA3 eCf | 152 | AGTTTGGGTGTGGCGGTT TA | chr19: 51070046- 51070156 | 111 |
| | FOXA3 eCr | 153 | ACCAACTTCGCCATATTA ACCA | | |
| TTBK1 | TTBAf | 154 | CGCGGTGTATTGTGGGTA GT | chr6: 43319189 - 43319287 | 99 |
| | TTBAr | 155 | CCTTCCGACCCGAATCAT CC | | |
| | TTBBf | 156 | GGTCGTCGGAACGTGATG T | chr6: 43319101 - 43319186 | 86 |
| | TTBBr | 157 | GCCAACATCAACACCAAC CC | | |
| | TTBCf | 158 | TCGTTTTGTCGTTGTCGTC G | chr6: 43319212 - 43319318 | 107 |
| | TTBCr | 159 | TTAAATAACCCGCTCCCT CCG | | |
| | TTBDf | 160 | GTCGTGATGTTAGAGCGG GC | chr6: 43319130 - 43319255 | 126 |
| | TTBDr | 161 | ACCCCGATCCTCCTTAAA CG | | |
| | TTBK1 eAf | 162 | TTAAGGAGGATCGGGGTC | chr6: 43319239- 43319329 | 91 |
| | TTBK1 eAr | 163 | TCAATACGACGTTAAATA ACCC | | |
| | TTBK1 eBf | 164 | TGGAGTTAAGCGGGTGGT AG | chr6: 43319008- 43319148 | 141 |
| | TTBK1 eBr | 165 | CCCGCTCTAACATCACGA CTC | | |
| TAL1 | pbTAL f | 166 | GTATTGTCGCGGGTTCGT TC | chr1: 47470631 - 47470738 | 129 |
| | pbTAL r | 167 | CTCAACCAATCCCCACTC CC | | |
| | mbTAL f | 168 | GTTTTAGGTTTCGTTAGTA TGGG | chr1: 47470570 - 47470698 | 129 |
| | + mbTAL r | 169 | CAAATTAAAATAAATCAT TTAACCCATAA | | |
| | mbTAL r | 170 | TTAAAATAAATCATTTAAC CCATAA | | |
| DMRTA2 | pbDMRTA f | 171 | CGAAGATTTCGTAGGCGG GT | chr1: 50659325 - 50659469 | 145 |
| | + pbDMRTA r | 172 | ACGACGCAAATAACGCTA CGCA | | |
| | pbDMRTA r | 173 | GACGCAAATAACGCTACG CA | | |
| | mbDMRTA f | 174 | TGTTTTAGAAGCGGGAGA AAG | | |
| | mbDMRTA r | 175 | AAATAAAACCCCCGTATC CAAT | | |
| | + mbDMRTA f | 176 | AATGTTTTAGAAGCGGGA GAAAG | chr1: 50659041 - 50659153 | 113 |
| | + | 177 | AAAAATAAAACCCCCGTA | | |

TABLE 15-continued lists the primers used herein for each probe.

| Gene | Probe | SEQ ID NO. | 5' 3' Primer Sequence (Bisulfite) | Chr: Location | PCR Product Length |
|---|---|---|---|---|---|
| | mbDMRTA r | | TCCAAT | | |
| | DMRTAexp Af | 178 | GCGGCGGTTAGCGTTAGT TTTTCGGTAG | chr1: 50659366 - 50659489 | 124 |
| | DMRTAexp Ar | 179 | CGAAACGCCAACGTATCA TAACGACGCA | | |
| PDE4B | pbPDE f | 180 | ACGTTTTAGGGACGGCGA AT | chr1: 66030622 - 66030698 | 77 |
| | pbPDE r | 181 | AATCCCAACGACCGTCTA CC | | |
| | mbPDE f | 182 | TTTCGTTTTGTATTTATGG TAGATGT | chr1: 66030580 - 66030694 | 115 |
| | mbPDE r | 183 | CCAACGACCGTCTACCAC TA | | |
| BARHL2 | pbBARHL f | 184 | CGTGGTATGGATTTCGGG GT | chr1: 90967266 - 90967376 | 111 |
| | pbBARHL r | 185 | ACTCCTAACCCTAAACGC GA | | |
| | mbBARHL f | 186 | GTTTTTTTCGGTTTTTGTT CGA | | |
| | mbBARHL r | 187 | TTTCTCCCAATTCCAATAT CCA | | |
| | + mbBARHL f | 188 | TGGTTTTTTTCGGTTTTTG TTCGA | chr1: 90967815 - 90967900 | 86 |
| | + mbBARHL r | 189 | ACTTTCTCCCAATTCCAAT ATCCA | | |
| TBX15 | pbTBX f | 190 | GCGATCGGCGATTGGTTT TT | chr1: 119331668 - 119331767 | 100 |
| | pbTBX r | 191 | GCGACGACACACGACCT AAA | | |
| | mbTBX f | 192 | TGAGGTTTTAGGTCGTGT GT | | |
| | + mbTBX f | 193 | GGTGAGGTTTTAGGTCGT GTGT | chr1: 119331740 - 119331881 | 142 |
| | mbTBX r | 194 | AAAACCTTAATCGACTCA AATAAAA | | |
| RUSC1, C1orf104 | pbRUSC f | 195 | GGGTGTAGTTGCGTAGCG TA | chr1: 153557280 - 153557421 | 142 |
| | pbRUSC r | 196 | CCGAACCCTCCTCACCAA AA | | |
| | mbRUSC f | 197 | TAGTTGCGTAGCGTAGGG TA | chr1: 153557285 - 153557410 | 126 |
| | mbRUSC r | 198 | TCACCAAAATCCTCCTAA AAC | | |
| GNG4 B | pbGNG f | 199 | ACGTAGTGTTGGTAAGAT TTGTAGA | chr1: 233880823 - 233880971 | 149 |
| | pbGNG r | 200 | ACAAAAACCGCTTATAAA CGACGA | | |
| | mbGNG f | 201 | GTAGGTTTTGCGTTGGA GATT | chr1: 233880677 - 233880817 | 141 |
| | mbGNG r | 202 | ATTTTCGTTACTTCTCTAT TCCCAAA | | |
| POU3F3 | pbPOU3F f | 203 | GGGGTTTCGCGTTTTGAG TT | chr2: 104836866 - 104836944 | 79 |
| | pbPOU3F r | 204 | AACACCAAAACCCCCGCT AA | | |
| | mbPOU3F f | 205 | AAAAGTAATTAATCGGAA CGGT | chr2: 104836837 - 104836970 | 134 |
| | mbPOU3F r | 206 | ACACTTTCCCAAATACAA AAAAA | | |
| BOLL B/C | pbBOLL f | 207 | TTTCGAGTCGGGGCGTTT TA | chr2: 198359264 - 198359401 | 138 |
| | pbBOLL r | 208 | TACCTAACCGCTCGCTCT CT | | |
| | mbBOLL f | 209 | GTTCGGTTTTGGGATTTTT | | |
| | mbBOLL r | 210 | AATCCCAAAAACCGACTC T | | |

TABLE 15-continued

| | | | lists the primers used herein for each probe. | | |
|---|---|---|---|---|---|
| Gene | Probe | SEQ ID NO. | 5' 3' Primer Sequence (Bisulfite) | Chr: Location | PCR Product Length |
| | + mbBOLL f | 211 | GAGGGTTCGGTTTTGGGA TTTTT | chr2: 198359331 - 198359461 | 131 |
| | + mbBOLL r | 212 | ACCAATCCCAAAAACCGA CTCT | | |
| TRIM71 | pbTRIM f | 213 | CGGAGGAATTTGTGTCGT CG | chr3: 32834331 - 32834440 | 110 |
| | pbTRIM r | 214 | CACCAAAACAACGCTACC CG | | |
| | mbTRIM Af | 215 | TTGGGAATTTTTTTCGTTT AT | chr3: 32834188 - 32834337 | 150 |
| | mbTRIM Ar | 216 | TCCTCCGAATAACTTAAA AACC | | |
| | mbTRIM Bf | 217 | TCGTTGGATAGTGGTATT TAATGT | chr3: 32834348 - 32834497 | 150 |
| | mbTRIM Br | 218 | AAAATCACCGACTCACTC AA | | |
| SLC2A2 | pbSLC f | 219 | CGGAGTACGGCGGTAGG AA | chr3: 172228914 - 172228993 | 80 |
| | + pbSLC r | 220 | AATACCCCGAAAACCCGC TAATA | | |
| | pbSLC r | 221 | ACCCCGAAAACCCGCTAA TA | | |
| | mbSLC f | 222 | ATGATATTTTGTAGGAAA GCGT | chr3: 172228748 - 172228850 | 103 |
| | mbSLC r | 223 | CAAATTCCGTTTCTAAAA AAAC | | |
| CYTL1 | pbCYTL f | 224 | GGGTTCGTATGCGGGAGT AG | chr4: 5071974 - 5072099 | 126 |
| | pbCYTL r | 225 | ACGAAACTACACCAACGC CT | | |
| | mbCYTL f | 226 | GGGGGTTTTCGTTAGGAG TAG | chr4: 5072020 - 5072142 | 123 |
| | mbCYTL r | 227 | AAACCGCCCTAAACCACC | | |
| SHISA3 | pbSHISA f | 228 | GAAGGGCGGTAGCGATA GTT | chr4: 42094543 - 42094650 | 108 |
| | + pbSHISA r | 229 | CTACGAATTCCGCAAACC GAAA | | |
| | pbSHISA r | 230 | ACGAATTCCGCAAACCGA AA | | |
| | mbSHISA f | 231 | ATTGTTTTTGTCGGCGTT | chr4: 42094569 - 42094654 | 86 |
| | mbSHISA r | 232 | TACACTACGAATTCCGCA A | | |
| GABRA4 | pbGAB f | 233 | GCGTGCGTATATTCGCGT TT | | |
| | + pbGAB f | 234 | CGGCGTGCGTATATTCGC GTTT | chr4: 46690291 - 46690385 | 95 |
| | pbGAB r | 235 | AAATTCCGCCTCCCCTAA CC | | |
| | mbGAB Af | 236 | TTTAGCGTTTAATGTGTAT GTAGA | chr4: 46690411 - 46690545 | 135 |
| | + mbGAB Ar | 237 | CGAAATTACAATCGAAAC AAACTTAC | | |
| | mbGAB Ar | 238 | AAATTACAATCGAAACAA ACTTAC | | |
| | mbGAB Bf | 239 | GTTTTGAGTAGGGTGCGA G | | |
| | mbGAB Br | 240 | AAAAAAACAAATTCCGCC T | | |
| | + mbGAB Bf | 241 | GATGTTTTGAGTAGGGTG CGAG | chr4: 46690248 - 46690398 | 151 |
| | + mbGAB Br | 242 | AAACGAAAAAAACAAATT CCGCCT | | |
| EGFLAM | pbEGF f | 243 | TGGTAGCGTTGTAAGGTG GG | chr5: 38293231 - 38293359 | 129 |
| | pbEGF r | 244 | AAAAACAAACGCGACCCT CG | | |

TABLE 15-continued lists the primers used herein for each probe.

| Gene | Probe | SEQ ID NO. | 5' 3' Primer Sequence (Bisulfite) | Chr: Location | PCR Product Length |
|------|-------|-----------|-----------------------------------|---------------|-------------------|
| | mbEGF f | 245 | TCGAGTTTTGGTAGCGTT GTAA | chr5: 38293223 - 38293306 | 84 |
| | + mbEGF r | 246 | AATACCCCGCAAAAAAAA TCTACA | | |
| | mbEGF r | 247 | CCCCGCAAAAAAAATCTA CA | | |
| C5orf39 | pbC5orf f | 248 | ACGAGAAATTGGCGCGTT GA | chr5: 43076304 - 43076404 | 101 |
| | pbC5orf r | 249 | AACAACACCCTTTACGAC GC | | |
| | mbC5orf f | 250 | TGTTTGTTAGGGTTTTGTT TTAA | | |
| | mbC5orf r | 251 | CGCCAAAACGAATATTTA TTTA | | |
| | + mbC5orf f | 252 | AATTGTTTGTTAGGGTTTT GTTTTAA | chr5: 43076267 - 43076390 | 124 |
| | + mbC5orf r | 253 | CGACGCCAAAACGAATAT TTATTTA | | |
| CDO1 B | pbCDO f | 254 | GGTAGCGTAGTGGATTCG GG | chr5: 115180192 - 115180333 | 142 |
| | pbCDO r | 255 | CTCGTCCTCCCTCCGAAA AC | | |
| | mbCDO f | 256 | GTTTGTTTTATTTCGTGGG GAG | chr5: 115179983 - 115180067 | 85 |
| | mbCDO r | 257 | CCAACTCCTTAACTCGCT CAA | | |
| IRF4 B/C | pbIRF f | 258 | TCGCGGGAAACGGTTTTA GT | | |
| | pbIRF r | 259 | GCCCTTAACGACCCTCCG | | |
| | + pbIRF f | 260 | TTTTCGCGGGAAACGGTT TTAGT | chr6: 336451 - 336550 | 100 |
| | + pbIRF r | 261 | GCGCCCTTAACGACCCTC CG | | |
| | mbIRF f | 262 | CGTTTTGTAAAGCGAAGT TT | | |
| | + mbIRF f | 263 | GTTATACGTTTTGTAAAG CGAAGTTT | chr6: 336298 - 336405 | 108 |
| | mbIRF r | 264 | AAACCAATCAATCACTAA ACTACA | | |
| ID4 B | pbID Af | 265 | GGTTTTTGGGCGTCGTGT TA | chr6: 19945064 - 19945170 | 107 |
| | pbID Ar | 266 | AAATTCACTCTCCACCGC CC | | |
| | pbID Bf | 267 | AGGCGAATAATGAAACG GAGGA | chr6: 19944950 - 19945083 | 134 |
| | pbID Br | 268 | TAACACGACGCCCAAAAA CC | | |
| | mbID f | 269 | ATTTTACGGATGGAGTGA TG | | |
| | + mbID f | 270 | GGAATTTTACGGATGGAG TGATG | chr6: 19945031 - 19945148 | 118 |
| | mbID r | 271 | CTTATCCCGACTAAACTA CTAAAAAA | | |
| SCAND3, GPX5 | pbSCAND f | 272 | AATTCGTTTCGCGACGTG AG | | |
| | + pbSCAND f | 273 | TTAATTCGTTTCGCGACG TGAG | chr6: 28618249 - 28618359 | 111 |
| | pbSCAND r | 274 | ACACGCCTTAAAACCTAC TCAT | | |
| | mbSCAND f | 275 | CGTGAGGGAGAATTTAGG AG | chr6: 28618265 - 28618368 | 104 |
| | mbSCAND r | 276 | TAAAAAAACACACGCCTT AAAACCTA | | |
| DDAH2 | pbDDAH f | 277 | TCGTTTAGCGAGCGTTGT TT | chr6: 31806112 - 31806210 | 99 |
| | pbDDAH r | 278 | GATCCGCCGTTACGCTAT TC | | |

TABLE 15-continued

| | | | | PCR |
|---|---|---|---|---|
| | | SEQ | | |
| | | ID | 5' 3' Primer Sequence | Product |
| Gene | Probe | NO. | (Bisulfite) | Chr: Location | Length |
|---|---|---|---|---|---|
| | mbDDAH f | 279 | TGTTAGAAATCGGTATCG TTTA | | |
| | mbDDAH r | 280 | TCTACGAAACGTTTACAA CC | | |
| | + mbDDAH f | 281 | TTTTTTGTTAGAAATCGGT ATCGTTTA | chr6: 31806097 - 31806189 | 97 |
| | + mbDDAH r | 282 | AAAATCTACGAAACGTTT ACAACC | | |
| COL11A2 | pbCOL f | 283 | TTTAGGGATCGCGTTCGG AG | chr6: 33269259 - 33269402 | 144 |
| | pbCOL r | 284 | AAACTCCTTTCCCCTCTC ATAC | | |
| | mbCOL f | 285 | CGGAGTTTTTAATCGGAT AT | chr6: 33269274 - 33269415 | 142 |
| | mbCOL r | 286 | TCCCTTCTCTTTAAAACTC CT | | |
| NT5E B | mbNT5E f | 287 | GTCGGATTTTATTTTAATC GTG | | |
| | mbNT5E r | 288 | AAACAAAAAAATCTCAAA AACTAAAA | | |
| | + mbNT5E f | 289 | GTTGTCGGATTTTATTTTA ATCGTG | chr6: 86215769 - 86215912 | 144 |
| | + mbNT5E r | 290 | CTTAAACAAAAAAATCTC AAAAACTAAAA | | |
| SIM1 B | pbSIM Af | 291 | GTTAGGGGCGAGGCGTTT AT | chr6: 101019614 - 101019695 | 82 |
| | pbSIM Ar | 292 | CGAAACCTAAACGCGCG AAA | | |
| | pbSIM Bf | 293 | AGGTTAATAGGTGGCGCG TT | chr6: 101019077 - 101019171 | 95 |
| | pbSIM Br | 294 | CCCGCAACTCCGCGATAA TA | | |
| | pbSIM Cf | 295 | AGTCGTTTTTCGCGCGTTT A | | |
| | + pbSIM Cf | 296 | CGAGTCGTTTTTCGCGCG TTTA | chr6: 101019667 - 101019756 | 90 |
| | pbSIM Cr | 297 | GACCCGACACCCTAAACT CAT | | |
| | mbSIM Af | 298 | AGGCGTTTATTGGTTAAT AGGG | chr6: 101019624 - 101019757 | 134 |
| | + mbSIM Ar | 299 | CGACCCGACACCCTAAAC TCAT | | |
| | mbSIM Ar | 300 | ACCCGACACCCTAAACTC AT | | |
| | mbSIM Bf | 301 | TTTAATTTGGGTTTTAAGT TGAGG | chr6: 101018944 - 101019075 | 132 |
| | mbSIM Br | 302 | ACGCTACTAAACCCCGCT TAT | | |
| RGS17 | RGS17 Af | 303 | GCGTTTAGGTAGCGACGC | chr6: 153493700 - 153493820 | 121 |
| | RGS17 Ar | 304 | ATACCCCGACGAAAACG AC | | |
| | RGS17 Bf | 305 | TTTGGGATTTGGTCGAGC | chr6: 153493620 - 153493730 | 111 |
| | RGS17 Br | 306 | AAAATTAAATCCCGCGTC G | | |
| CAPDS2 | CAPDS Af | 307 | CGTTTAGGTTTGTGGACG C | chr7: 121743823 - 121743951 | 129 |
| | CAPDS Ar | 308 | AAAAACGAAATCGCTAAT ACGC | | |
| MSC | MSC Af | 309 | TTTTTCGAATTTTTGCGC | | |
| | MSC Ar | 310 | AACACGCTCCGACTAACT TC | | |
| | + MSC Af | 311 | GGTTGTTTTTTTCGAATTTT TGCGC | chr8: 72918397 - 72918531 | 135 |
| | + MSC Ar | 312 | TAAACACGCTCCGACTAA CTTC | | |
| | MSC Bf | 313 | CGTTCGCGTTATTATTTGC | | |

TABLE 15-continued lists the primers used herein for each probe.

| Gene | Probe | SEQ ID NO. | 5' 3' Primer Sequence (Bisulfite) | Chr: Location | PCR Product Length |
|---|---|---|---|---|---|
| | MSC Br | 314 | CGCCCAATAACAACTCGT | | |
| | + MSC Bf | 315 | ATTATCGTTCGCGTTATTA TTTGC | chr8: 72918698 - 72918852 | 155 |
| | + MSC Br | 316 | CCTCGCCCAATAACAACT CGT | | |
| SPAG6 | SPAG6 Af | 317 | GTCGAGTCGTCGTTACGA TC | chr10: 22674453 - 22674529 | 77 |
| | SPAG6 Ar | 318 | CTACCCTCCTCGAACTCT ACG | | |
| INA | INA Af | 319 | GTTTTCGGATGGGAAATT TTAG | | |
| | INA Ar | 320 | AAACCATCTACATCGAAA TCGC | | |
| | + INA Af | 321 | GTGGTTTTCGGATGGGAA ATTTTAG | chr10: 105026593 - 105026715 | 123 |
| | + INA Ar | 322 | AACAAAACCATCTACATC GAAATCGC | | |
| FLI | FLI Af | 323 | TTTTTAGGAGTAAGTATTT TGTGTG | chr11: 128068870 - 128068981 | 112 |
| | FLI Ar | 324 | CCCTCTTCCTCCCCTACT AAT | | |
| ATP5G2 | ATP5G2 Af | 325 | TAGGTATATTTCGGTCGG C | chr12: 52357363 - 52357478 | 116 |
| | ATP5G2 Ar | 326 | AACTCGAAACCTCATCCG | | |
| USP44 | USP44 Af | 327 | ACGGGAGGGTAAATTTAG C | chr12: 94466977 - 94467090 | 114 |
| | USP44 Ar | 328 | TACCAAACAATTCGACGT TA | | |
| POU4F1 | POU4F1 Af | 329 | GCGTACGTCGGTTTATTC | | |
| | POU4F1 Ar | 330 | ACGCTCTACGCGATCAAA | | |
| | + POU4F1 Af | 331 | AAGTGCGTACGTCGGTTT ATTC | chr13: 78075512 - 78075652 | 141 |
| | + POU4F1 Ar | 332 | GCGACGCTCTACGCGATC AAA | | |
| LHX1 | LHX Af | 333 | CGAGCGATTGTGGGGTTA GA | chr17: 32368543 - 32368624 | 82 |
| | LHX Ar | 334 | CAACTCGCGACCGCCTAA A | | |
| HINF1B | HINF Af | 335 | TTCGGGCGTTTATAGAGT TC | chr17: 33176898 - 33177017 | 120 |
| | HINF Ar | 336 | AAAATCAAAACGCGAAC G | | |
| | HINF Bf | 337 | TAGCGTCGCGTTAGAAAG C | | |
| | HINF Br | 338 | ATCGCTCAAAACCTAACG AA | | |
| | + HINF Bf | 339 | TTTTAGCGTCGCGTTAGA AAGC | chr17: 33177225 - 33177341 | 117 |
| | + HINF Br | 340 | AAAAATCGCTCAAAACCT AACGAA | | |
| | HINF Cf | 341 | AGGTTTAGTTTCGAAATC GC | | |
| | HINF Cr | 342 | AACCGAACGATTCCCTAA | | |
| | + HINF Cf | 343 | GTTAAGGTTTAGTTTCGA AATCGC | chr17: 33177654 - 33177773 | 120 |
| | + HINF Cr | 344 | CTAAAAAACCGAACGATT CCCTAA | | |
| GALR1 | GALR1 Af | 345 | GAATTTTTGGAAAAGTCG GGA | | |
| | GALR1 Ar | 346 | CTCCTACAAAAAAAACTC CC | | |
| | + GALR1 Af | 347 | TTCGGAATTTTTGGAAAA GTCGGGA | chr18: 73090886 - 73090989 | 104 |

TABLE 15-continued lists the primers used herein for each probe.

| Gene | Probe | SEQ ID NO. | 5' 3' Primer Sequence (Bisulfite) | Chr: Location | PCR Product Length |
|------|-------|------------|-----------------------------------|---------------|---------------------|
| | + GALR1 Ar | 348 | CGACTCCTACAAAAAAAA CTCCC | | |
| MAST1 | MAST1 Af | 349 | AGAAGGTGGTCGGTAAG C | | |
| | MAST1 Ar | 350 | ACGTAATTATAAAAAACA CGCC | | |
| | + MAST1 Af | 351 | GGAGAAGGTGGTCGGTA AGC | chr19: 12839386 - 12839533 | 148 |
| | + MAST1 Ar | 352 | AAAACGTAATTATAAAAA ACACGCC | | |
| | MAST1 Bf | 353 | TAGTTTTTTGGAGGGAGA GG | chr19: 12839568 - 12839670 | 103 |
| | MAST1 Br | 354 | ATCCTCGTCCTCTTAAAA AAC | | |
| CPXM1 | CPXM1 Af | 355 | GTCGAGTTTGGGATTTTG GT | | |
| | CPXM1 Ar | 356 | AAACTCCTACTCGCCCTA ACC | | |
| | + CPXM1 Af | 357 | GGGGTCGAGTTTGGGATT TTGGT | chr20: 2729097 - 2729214 | 118 |
| | + CPXM1 Ar | 358 | AAAAACTCCTACTCGCCC TAACC | | |
| NEURL2 | NEURL2 Af | 359 | TCGAGTTGGATAAGGCGT AC | chr20: 43952304 - 43952445 | 142 |
| | NEURL2 Ar | 360 | CCGATAACACGACCGAC ATA | | |
| | NEURL2 Bf | 361 | TGTATGTCGGTCGTGTTA TC | chr20: 43952424 - 43952505 | 82 |
| | NEURL2 Br | 362 | TAAACGTACTACCTCCGA CC | | |
| ACVRL1 | ACVRL 1f | 363 | GGATGTGGGAGGTTCGGT TCGGGTG | chr12: 50587308- 50587443 | 136 |
| | ACVRL1r | 364 | CCGCTCGCCCCTCGCTAA AACTACA | | |
| AFF3 | AFF3f | 365 | GGCGCGAGGTAGTTTTAG TACGTAGTTTTT | chr2: 99542180- 99542257 | 78 |
| | AFF3r | 366 | ATAACAACGTCGTCCTTT CCGCAAAACG | | |
| AKR1B1 | AKR1B1f | 367 | GGGGATTTTGTAAGTTCG CGCGTGGTTT | chr7: 133794143- 133794250 | 108 |
| | AKR1B1r | 368 | ACACTCTCCGCGCGACCT ATATTAACGA | | |
| | AKR1B1R_f | 369 | GGAGACGGTTTGTTATGG TTGTTGCGTT | chr15: 43266838- 43266959 | 122 |
| | AKR1B1R_r | 370 | ACGCCCTTTCTACCGACC TCACGAACTA | | |
| ALDOC | ALDOCf | 371 | TTTTTCGGGGCGTGGTT TGTATGTTT | chr17: 23928071- 23928193 | 123 |
| | ALDOCr | 372 | TACCTAACGAAACGCTCA CTCCACCTCG | | |
| ALOX5 | ALOX5f | 373 | TTTTGCGGTTAGGTGAAG GCGTAGAGGT | chr10: 45234654- 45234759 | 106 |
| | ALOX5r | 374 | GACCGAATACCCCGCTTT CTCTCTCGAC | | |
| | ALOX5R_f | 375 | GAGGTCGAGAGAGAAAG CGGGGTATTCG | chr10: 45234729- 45234838 | 110 |
| | ALOX5R_r | 376 | AACGCTCTCAACCCAACC CCTAAACTCA | | |
| ALX1 | ALX1f | 377 | AGGATAGTAGCGGTGAGT CGTTAGCGTT | chr12: 84198385- 84198501 | 117 |
| | ALX1r | 378 | CGCTCCCACTTTTCTCCTT TCTCCCTCC | | |
| ALX4 | ALX4f | 379 | TTTTGATAAAGTGGGGAG GGCGTAGGGG | chr11: 44289270- 44289375 | 106 |

TABLE 15-continued lists the primers used herein for each probe.

| Gene | Probe | SEQ ID NO. | 5' 3' Primer Sequence (Bisulfite) | Chr: Location | PCR Product Length |
|------|-------|------------|-----------------------------------|---------------|--------------------|
| | ALX4r | 380 | ACACTCTCAAATACCCGT CGCGCTCTAT | | |
| C1orf230 | C1orf230f | 381 | TTTTGATAAAGTGGGGAG GGCGTAGGGG | chr1: 149960830- 149960921 | 92 |
| | C1orf230r | 382 | ACACTCTCAAATACCCGT CGCGCTCTAT | | |
| | C1orf230R_ f | 383 | AGCGTAGCGTAGTTGGAG TAGTTGCGAA | chr1: 149960685- 149960805 | 121 |
| | C1orf230R_ r | 384 | CGACGACTCTCTTCCCAA TCTAAAACCCCA | | |
| C6orf186 | C6orf186f | 385 | CGGAGTTTAGAAGGGCGT TCGGTTACGG | chr6: 110785585- 110785700 | 116 |
| | C6orf186r | 386 | CTCCACGAATCGCATCTT TCAATACCCA | | |
| C17orf64 | C17orf64f | 387 | AAAGGTGGTTCGAGTGAG GAAATTGCGG | chr17: 55853711- 55853789 | 79 |
| | C17orf64r | 388 | GCGTCCCTAAACGACACA CGACGAAATC | | |
| | C17orf64R_ f | 389 | GTCGACGGCGGTTTTATC GTATTGTCGC | chr17: 55853578- 55853689 | 112 |
| | C17orf64R_ r | 390 | CCTTCTCCCGAACCTTCC TTCGTATCCT | | |
| C19orf41 | C19orf41f | 391 | TTAGAGGTATGGCGGGGT TTTTGTGACG | chr19: 55358254- 55358348 | 95 |
| | C19orf41r | 392 | AATACTCCCTAAACCTCC TAACCGCGCC | | |
| CCDC67 | CCDC67f | 393 | GAGGTTTAATTGTTTCGTT GGTCGC | chr11: 92703424- 92703546 | 123 |
| | CCDC67r | 394 | ACGCAAAACCGCGTATAT CACCT | | |
| CCDC8 | CCDC8f | 395 | GGTTTTAGGGACGCGGTT GGAATTTGGG | chr19: 51608460- 51608548 | 89 |
| | CCDC8r | 396 | CCCAACGCCTCGACCATA TTAAATAACTT | | |
| CD38 | CD38f | 397 | GCGATTAAGGCGTATCGG TGGGTATTGC | chr4: 15389377- 15389501 | 125 |
| | CD38r | 398 | AACACCACCCGACGAACT CTCGACTAAC | | |
| CD8A | CD8Af | 399 | TAGGACGTTGTTTGGTTC GAAGTTCGGG | chr2: 86871471- 86871569 | 99 |
| | CD8Ar | 400 | CTCCGAACCGACCGAAA AACGCAACTTT | | |
| CDH23 | CDH23f | 401 | GGCGGGGTATTGTTTTGT TTC | chr10: 72826313- 72826423 | 111 |
| | CDH23r | 402 | TCTACCGATATCATAACA CCGACT | | |
| CDK5R2 | CDK5R2f | 403 | AAAGGTAGAGGGAAGGA GAGTTGTTTTT | chr2: 219532251- 219532354 | 104 |
| | CDK5R2r | 404 | ACTCCTACCTCCTCCGAA TCCTAAAACCT | | |
| CHST2 | CHST2f | 405 | CGGAATGAAGGTGTTTCG TAGGAAGGCG | chr3: 144322486- 144322636 | 151 |
| | CHST2r | 406 | GCTACGACACCCAACGA CCCATCGAAA | | |
| CLCN1 | CLCN1f | 407 | AATGATTTTGTTGGGTTC GGTGGAGCGG | chr7: 142752740- 142752852 | 113 |
| | CLCN1r | 408 | CCGACAACTTCCGCGCCA TCTCTTAAAC | | |
| | CLCN1R_ f | 409 | TTGTGTTTTGAGCGTAGG TTGCGCGTAG | chr7: 142752798- 142752874 | 77 |
| | CLCN1R_ r | 410 | GCCTTCCCGTCGTAAAC AACTCCGACA | | |

TABLE 15-continued lists the primers used herein for each probe.

| Gene | Probe | SEQ ID NO. | 5' 3' Primer Sequence (Bisulfite) | Chr: Location | PCR Product Length |
|------|-------|-----------|-----------------------------------|---------------|--------------------|
| COL16A1 | COL16A1f | 411 | GTTTTAGGGGGTTGGGGG TTTGTTAGGGA | chr1: 31942237- 31942382 | 146 |
|  | COL16A1r | 412 | AACCCGAAACGAAACTAT ACACCCCGCA |  |  |
| CPNE8 | CPNE8f | 413 | TCGATGTTCGTAGTGTTG TTGTAGCGGT | chr12: 37585569- 37585689 | 121 |
|  | CPNE8r | 414 | CCATCCCCGCCTAACGAA AACTAACCCT |  |  |
| DIO3 | DIO3f | 415 | CGTTTCGAGAAGAAGTTT CGCGGTTGGT | chr14: 101095917- 101096005 | 89 |
|  | DIO3r | 416 | ATCTAAACCCAAATCGAA AACCGCCGCC |  |  |
| DNM3 | DNM3f | 417 | TTGGAGTTGTCGTAGATC GTCGTGGTGG | chr1: 170077504- 170077626 | 123 |
|  | DNM3r | 418 | AAATCGCCCCACTACCGC ATCCTTACTC |  |  |
|  | DNM3R_f | 419 | GCGGTTAGGTGTGGTAAA GTAGTTGGCG | chr1: 170077283- 170077405 | 123 |
|  | DNM3R_r | 420 | GCGCACAACCAACCTATA AACTCCGACG |  |  |
| DUOX1 | DUOX1f | 421 | GGGATTTGTGAAGGCGG ATTTG | chr15: 43209229- 43209307 | 79 |
|  | DUOX1r | 422 | AATATTCCGTCGATACCG AAAACCCGA |  |  |
| EMX1 | EMX1f | 423 | CGGTTGGAGCGCGTTTTC GAGAAGAAT | chr2: 73005041- 73005163 | 123 |
|  | EMX1r | 424 | AACGCAAAACAAACCGC GACCGAAAATA |  |  |
| EMX2OS | EMX2OSf | 425 | AGGAGAAGTCGTAGCGG GCGTC | chr10: 119291932- 119292032 | 101 |
|  | EMX2OSr | 426 | GACTAAACCTTCTACCGC CCACCG |  |  |
| ESPN | ESPNf | 427 | TAGTTGCGATGGGGTGGG AAGTTACGTT | chr1: 6430246- 6430357 | 112 |
|  | ESPNr | 428 | AAAACCATCGCCATCCAC GAAAACGACA |  |  |
| EVX1 | EVX1f | 429 | AGGAGGATGATAGTTTAG AAAGAAGAGGGT | chr7: 27248900- 27249019 | 120 |
|  | EVX1r | 430 | CGCGACCGCGACGATAA CGATAAAAACT |  |  |
| FABP5 | FABP5f | 431 | GAAACGTGTAGGCGTCG GCGTTTATGAG | chr8: 82355078- 82355157 | 80 |
|  | FABP5r | 432 | CGACCTCTCGAACGCCTC CTACAAACAA |  |  |
| FBRSL1 | FBRSL1f | 433 | GTGGAGGAGGAAGTTCG TTTC | chr12: 131575948- 131576052 | 105 |
|  | FBRSL1r | 434 | AACTACTACCAAACACGA AACGCA |  |  |
| FLI41350 | FLIf | 435 | GGTTAGAGTCGGTTGCGT AGTTT | chr10: 102979731- 102979855 | 125 |
|  | FLIr | 436 | TTTTTGTTAGGCGAAGTAT AGAGAGCG |  |  |
| FOXG1 | FOXG1f | 437 | TTTTTCGATTGGTCGACG GCGAGAGAG | chr14: 28305617- 28305740 | 124 |
|  | FOXG1r | 438 | TTTCCGAACTACAAACGC ACACTAAAAC |  |  |
| FOXL2 | FOXL2f | 439 | GATTCGTATGGGTTTTATC GAGTTTC | chr3: 140148670- 140148764 | 95 |
|  | FOXL2r | 440 | ACTTAAAAATAAACTCGC CCGTACG |  |  |

TABLE 15-continued lists the primers used herein for each probe.

| Gene | Probe | SEQ ID NO. | 5' 3' Primer Sequence (Bisulfite) | Chr: Location | PCR Product Length |
|------|-------|------------|-----------------------------------|---------------|--------------------|
| FZD2 | FZD2f | 441 | TCGTTGGTGAAGGTGTAG TGTTCGTTCG | chr17: 39990814-39990938 | 125 |
|  | FZD2r | 442 | TAACGCGCGCGCTCACAA ATAAAACGAC |  |  |
|  | FZD2R_f | 443 | TTTTTAGTGGTTCGAGCG TTTGCGTTGC | chr17: 39990969-39991059 | 91 |
|  | FZD2R_r | 444 | TCCGTCCTCGAAATAATT CTAACCGACGC |  |  |
| HIF3A | HIF3Af | 445 | CGTGGTATAGTTAATCGC GCGGCGT | chr19: 51492066-51492190 | 125 |
|  | HIF3Ar | 446 | TACAACCCCAACGCCATA ACTCGCCAAT |  |  |
| HIVEP3 | HIVEP3f | 447 | TGTCGTCGTCGTCGGGGT TTTGTTATTT | chr1: 41901039-41901114 | 76 |
|  | HIVEP3r | 448 | ACGACGATAAACTCCCGC TAAACCCGAA |  |  |
|  | HIVEP3R_f | 449 | GAACGAGGATTTGCGTTT TTGGATCGC | chr1: 41901096-41901175 | 80 |
|  | HIVEP3R_r | 450 | CCTAAACTCCTCTACATA TTCCTCTACCT |  |  |
| HLA-F | HLA-Ff | 451 | GAATGGTTGCGATATGGG GTTCGACGG | chr6: 946778-946902 | 125 |
|  | HLA-Fr | 452 | CCACGATATCCGCCGCGA TCCAAAAAC |  |  |
| HOTAIR | HOTAIRf | 453 | TAAGGGTCGGTTGTTGTT TTTTTTC | chr12: 52645919-52646034 | 116 |
|  | HOTAIRr | 454 | ACCGACGCCTTCCTTATA AAATACG |  |  |
| HOXA10 | HOXA10f | 455 | TGTGGGATAATTTGGCGA AGGGAGTAGA | chr7: 27180403-27180526 | 124 |
|  | HOXA10r | 456 | AACTCGAAATTAACTACG AACGCCCGCC |  |  |
| HOXD11 | HOXD11f | 457 | GGCGGGGGTAGTTTTTGT ATTAAGGCGA | chr2: 176680987-176681111 | 125 |
|  | HOXD11r | 458 | CCTACGCTACTACTCTTCT CGACCCCCG |  |  |
| HOXD8 | HOXD8f | 459 | CGTTTCGTTCGTCGGTCG TAGCGATTG | chr2: 176702636-176702749 | 114 |
|  | HOXD8r | 460 | CCGACGAAACATTTTCGC ACCACAACAC |  |  |
|  | HOXD8R_f | 461 | CGCGGTTTCGGGGTATAC GGAGTTTTTG | chr2: 176702549-176702668 | 120 |
|  | HOXD8R_r | 462 | GCAATTCAATCGCTACGA CCGACGAACG |  |  |
| HSPA12B | HSPA12Bf | 463 | CGTCGTAGCGGGTACGGT TAACGAGTTG | chr20: 3661361-3661485 | 125 |
|  | HSPA12Br | 464 | TTTCTCCACTCGAAACGC CCGACAACC |  |  |
| ISL1 | ISL 1f | 465 | CGGGGGAGAACGGTTTG AGTTTCGAGTA | chr5: 50714776-50714885 | 110 |
|  | ISL1r | 466 | TCATATTTCAACCTCGCC GCCGCTAAAC |  |  |
| Intergenic1 | Int1f | 467 | AGTAGGGATGGTCGTTCG TTGTTCGGTG | chr11: 68379573-68379679 | 107 |
|  | Int1r | 468 | GACAAACGACCGAAAAT ACTCGCGCAAC |  |  |
|  | Int1R_f | 469 | TTTTACGGTCGGGGCGAT AGTTGAAGGT | chr11: 68379395-68379493 | 99 |
|  | Int1R_r | 470 | TCACGCCAATACCCGCTA ATCCCTCCTA |  |  |
| Intergenic2 | Int2f | 471 | GGGGATGGATAATTTTTA GGCGTTAAC | chr17: 69460223-69460339 | 117 |

TABLE 15-continued

| Gene | Probe | SEQ ID NO. | 5' 3' Primer Sequence (Bisulfite) | Chr: Location | PCR Product Length |
|------|-------|-----|-----------------------------|---------------|---------|
| | Int2r | 472 | TAACCTCGTCTTTATCCCC GCG | | |
| Intergenic3 | Int3f | 473 | AGTGTGTAGTCGTTTGTG GGTGAGGAGTT | chr8: 95315865- 95315994 | 130 |
| | Int3r | 474 | CACCGCGAAAAACGCCC ACAATCTTACC | | |
| | Int3R_f | 475 | CGCGGGGGAGTTTATTTT TGAGGATTCGG | chr8: 95315775- 95315892 | 118 |
| | Int3R_r | 476 | ACTCCTCACCCACAAACG ACTACACACT | | |
| Intergenic4 | Int4f | 477 | TAGTATTTGTACGGAGTTT TTCGGCGGTC | chr5: 43054172- 43054263 | 92 |
| | Int4r | 478 | TACGACGCAACCAACGAT ACTATCACCAA | | |
| Intergenic5 | Int5f | 479 | TAGTGATTGGTTATTTGG GCGCGGGGC | chr10: 43138416- 43138530 | 115 |
| | Int5r | 480 | AAACGACATCCATCATCT CCCTCGACCC | | |
| Intergenic6 | Int6f | 481 | AGGTCGCGTTTTGGTCGT GC | chr3: 14827613- 14827688 | 76 |
| | Int6r | 482 | ACTTAAAAATAAACTCGC CCGTACG | | |
| Intergenic7 | Int7f | 483 | ATTTTACGTAGGGTGGGG TTGAGGGCGT | chr12: 52897799- 52897910 | 112 |
| | Int7r | 484 | ATCCTAACCGTCCCGCCT CAAAACCGTA | | |
| Intergenic8 | Int8f | 485 | CGTCGTAGTATTTGGCGG CGCGTTTC | chr2: 236737778- 236737883 | 106 |
| | Int8r | 486 | AACGTACCTAATCCCCAA ACCCACTCCT | | |
| Intergenic9 | Int9f | 487 | TCGTTGTGCGCGTTTCGT TTGTTGGATTA | chr6: 778755- 778846 | 92 |
| | Int9r | 488 | TCGATAATATCTCCGTCG CCTCCGCAAA | | |
| Intergenic10 | Int10f | 489 | GCGCGTTTAATCGTGGGA TTTTTGGGAG | chr2: 174899379- 174899494 | 116 |
| | Int10r | 490 | CAAATTCGCGACACCCTA CCCCAACAC | | |
| | Int10R_f | 491 | GGGTGTCGCGAATTTGGG GTA | chr2: 174899479- 174899602 | 124 |
| | Int10R_r | 492 | CTAAACCTCTCCCCTCCC AAATTTACCT | | |
| Intergenic12 | Int12f | 493 | ATCGAGTTTTTAGCGGTTT TTGGGGCGG | chr1: 119344866- 119344974 | 109 |
| | Int12r | 494 | ACTAACATCGCGCACTTA AATCTTTCCG | | |
| Intergenic13 | Int13f | 495 | GGTAGCGGCGGGTAAAA AGTC | chr7: 64675119- 64675225 | 107 |
| | Int13r | 496 | TACAACTTTTTACCTCCGC CGC | | |
| Intergenic14 | Int14f | 497 | CGTCGATTTGCGGAATTT CGTCGTCGTT | chr1: 238227938- 238228045 | 108 |
| | Int14r | 498 | ACATCCGCGTAAACTCGC CCTTTAACAC | | |
| | Int14R_f | 499 | TTTCGGGATTAGGGTTTC GGAGGGTGTC | chr1: 238227822- 238227913 | 92 |
| | Int14R_r | 500 | CGTATCGATCCGTCCCTC CCGCTTAAAA | | |
| Intergenic15 | Int15f | 501 | CGGTTTTGGTGGTAGTTTT GGTAATC | chr19: 48895723- 48895802 | 80 |
| | Int15r | 502 | AAAACCTCCCGAACGAC GAAATAATCCA | | |

TABLE 15-continued lists the primers used herein for each probe.

| Gene | Probe | SEQ ID NO. | 5' 3' Primer Sequence (Bisulfite) | Chr: Location | PCR Product Length |
|------|-------|-----------|-----------------------------------|---------------|--------------------|
| | Int15R_f | 503 | GTAGGCGGTCGGAACGT GAAC | chr19: 48895536-48895660 | 125 |
| | Int15R_r | 504 | CGATAAAAACTACAATAA CTCGACAACCA | | |
| Intergenic16 | Int16f | 505 | GTTGTGAGGGTTTTCGGC GGTATC | chr1: 54713046-54713165 | 120 |
| | Int16r | 506 | CATAACAACGCGCGACC CCTA | | |
| Intergenic17 | Int17f | 507 | TGATTATAAATTAGGGGG TTTGGTCGTCG | chr12: 61311832-61311945 | 114 |
| | Int17r | 508 | AAACCCTCCACCCTCGCA ATACTACTCC | | |
| Intergenic18 | Int18f | 509 | TGTAGGAGATAATGGGAG TGAAGAGGGA | chr6: 4971256-4971338 | 83 |
| | Int18r | 510 | TTCCACGAAACGCGCGAC TTCCTAACTA | | |
| | Int18R_f | 511 | GTTGAGTTAGGAGAGGTC GATAGC | chr6: 4971467-4971570 | 104 |
| | Int18R_r | 512 | CCCGAAAACAACGACTAT CGAAATCCAA | | |
| Intergenic19 | Int19f | 513 | ATAAGGTTTGGTGGAAGC GTAGGAGCGT | chr6: 3177175-3177289 | 115 |
| | Int19r | 514 | ACGCCGAATAAAAATCCC GCAACCACAA | | |
| Intergenic20 | Int20f | 515 | GGAGGGGAGGAGATAGC GTTATTTAGGG | chr10: 118912740-118912842 | 103 |
| | Int20r | 516 | AAACAAAACCCGAAACC CCACCTACACC | | |
| Intergenic21 | Int21f | 517 | GCGTGGTAGTTGAGGATG TAGACGTGGT | chr16: 45381613-45381736 | 124 |
| | Int21r | 518 | TCCGAACTACTTAAAAAT CCCCGCCGCC | | |
| Intergenic22 | Int22f | 519 | TCGTTGGTTGTGATTTTTA TGCGGGCGT | chr8: 68037259-68037357 | 99 |
| | Int22r | 520 | ACCTCTCCGATAAACCAA ATCCTCCGCC | | |
| | Int22R_f | 521 | CGGGTGAGGTTTGTGGTT AATTTCGCGT | chr8: 68037556-68037675 | 120 |
| | Int22R_r | 522 | CTCAACCAAACTACAACG TTCCCGCCTC | | |
| Intergenic23 | Int23f | 523 | AATGGAGGCGTAGATTAA CGAGCGGTGT | chr5: 42987147-42987254 | 108 |
| | Int23r | 524 | ATCCTTAACAACCCCGCC GACTAACGTC | | |
| | Int23R_f | 525 | ACGGGTACGGAGAAACG TCGGATTTAGT | chr5: 42987852-42987946 | 95 |
| | Int23R_r | 526 | TCCCCGCGACACTCTACC TATAACGTCC | | |
| KCNH8 | KCNH8f | 527 | CGTTTGGCGGGTATTGTT GTTC | chr3: 19164879-19164971 | 93 |
| | KCNH8r | 528 | CCCGACGCAAACTCCCTC TC | | |
| KCNJ2 | KCNJ2f | 529 | GAAGTTGTTTTTTAGGGG TTTGCGC | chr17: 65676355-65676440 | 86 |
| | KCNJ2r | 530 | ACTCAAATCTACCCTCGC TTCAACG | | |
| KCKN4 | KCNK4f | 531 | GCGCGGGGGTATTTTGGA GGGTTAGTTA | chr11: 63816449-63816549 | 101 |
| | KCNK4r | 532 | TCCCTACTCGCCCGCTAC GACTATAACA | | |
| KCNK17 | KCNK17f | 533 | CGGATTTTGTTTTCGGGA GTCGTTCGGG | chr6: 39390031-39390150 | 120 |

TABLE 15-continued lists the primers used herein for each probe.

| Gene | Probe | SEQ ID NO. | 5' 3' Primer Sequence (Bisulfite) | Chr: Location | PCR Product Length |
|------|-------|-----------|-----------------------------------|---------------|--------------------|
|  | KCNK17r | 534 | AACTAAACGCCTAACCCT TCCCTCCCAC |  |  |
| KIAA1751 | KIAAf | 535 | TTCGTTTTGTTTTTCGGTT GGAGCGGGT | chr1: 1925171- 1925288 | 118 |
|  | KIAAr | 536 | TATAACCTAACCCTTCAA CCGCGCCTCG |  |  |
|  | KIAA1751R_ f | 537 | AGGCGGCGGTTTTTGGCG ATTGTTTTTC | chr1: 1925065- 1925140 | 76 |
|  | KIAA1751R_ r | 538 | TTCCGTTACCATAAAACT ACCCGCCCC |  |  |
| LASS1 | LASS1f | 539 | GATTTCGCGTATCGTCGT GTC | chr19: 18868171- 18868273 | 103 |
|  | LASS1r | 540 | TAATATCCCCCGTACCCC CCG |  |  |
| LOC255167 | LOCf | 541 | TTTCGATAATAGCGTTTTT GCGGCGTGG | chr5: 6636474- 6636619 | 146 |
|  | LOCr | 542 | CAAAAACACGCGACCTAC GCCCTCCTAA |  |  |
| LRRC4 | LRRC4f | 543 | CGAGTCGGAGTGAGCGTT AAGTGAGGGG | chr7: 127459680- 127459780 | 101 |
|  | LRRC4r | 544 | CCTATCAACGACCACCCA ACTACTCCCT |  |  |
| MIR155HG | MIR155HGf | 545 | TCGGGTTTAGCGTCGTTT GTAGTTTCGG | chr21: 25856335- 25856430 | 96 |
|  | MIR155HGr | 546 | AAAAACGTCTCCTTAATT CCCCGCGCTT |  |  |
| NEXN | NEXNf | 547 | GCGGTTGGAGTAGAAGT GTTAGCGGTTAGA | chr1: 78126913- 78127036 | 124 |
|  | NEXNr | 548 | TCACCCTACAAAAACCGA TAACCGACGA |  |  |
| NKX2-1 | NKX2-1f | 549 | AGTTGGTTATAGGCGGCG AATTGGGTTT | chr14: 36057307- 36057397 | 91 |
|  | NKX2-1r | 550 | TCAACACCCCCTCTCCTA ACCTCTCCAA |  |  |
| NKX6-2 | NXX6-2f | 551 | CGGGGAAGAGTTTCGGTT CGCGTTTTAG | chr10: 134449988- 134450110 | 123 |
|  | NXX6-2r | 552 | CCCTCCTATAACCCCGAC CTACCCGAAA |  |  |
|  | NKX6-2R_f | 553 | GCGCGGTAGGTGTTTTTC GGGTTGTAAA | chr10: 134449796- 134449892 | 97 |
|  | NKX6-2R_r | 554 | ACCTTTACCTAACTACAC TCCCATCCAA |  |  |
| NOTUM | NOTUMf | 555 | AGAGTAGGTCGTGGGGG ATTC | chr17: 77512836- 77512922 | 87 |
|  | NOTUMr | 556 | CGCGCTAACCGCGATAAA AAC |  |  |
| NRN1 | NRN1f | 557 | AGGAGCGGGAGAGGGAA AAATAGTTAAG | chr6: 5952635- 5952759 | 125 |
|  | NRN1r | 558 | ACTACGCCCAAAACTCAA CTACTAAAT |  |  |
| PLTP | PLTPf | 559 | TGGGAACGGGATAGGGA CGCGTTTTAAT | chr20: 43974093- 43974184 | 92 |
|  | PLTPr | 560 | GAATCCCCTAAACTACCC GCCATCCCAC |  |  |
|  | PLTPR_f | 561 | TGTACGCGTATTTTTGGA GGGTGGTTTGC | chr20: 43973871- 43973950 | 80 |
|  | PLTPR_r | 562 | CGATCTAATCGACCACCT CCTCTCCTCC |  |  |
| PRDM13 | PRDM13f | 563 | AAGTTTCGTCGAGTTGGG GTCGTTGGTT | chr6: 100168753- 100168844 | 92 |
|  | PRDM13r | 564 | GACCCTTCCCGACAACCA TCTCGAACA |  |  |

TABLE 15-continued

| | | | lists the primers used herein for each probe. | | |
|---|---|---|---|---|---|
| Gene | Probe | SEQ ID NO. | 5' 3' Primer Sequence (Bisulfite) | Chr: Location | PCR Product Length |
| PRDM15 | PRDM15f | 565 | GAAAATTGCGCGGTTGGG TTAGTAGGGG | chr21: 42110148- 42110259 | 112 |
| | PRDM15r | 566 | ACCTACAAATACCGTCCC CACCCGAAAC | | |
| PTGDR | TGDRf | 567 | AAGAGGGGTGTGATTCGC GAGTTTAGAT | chr14: 51804089- 51804198 | 110 |
| | TGDRr | 568 | CCGCGCGCGACTCGAAC GAAAAA | | |
| RECK | RECKf | 569 | AAGGGTGCGATGTTTTCG TTTAGGATCG | chr9: 36027398- 36027485 | 88 |
| | RECKr | 570 | TAACTAACTAAAACCGCG ATAAAACGACT | | |
| RTN4RL1 | RTN4f | 571 | TGGTAATCGCGTAGGTGT GTGATAGGGC | chr17: 1827825- 1827931 | 107 |
| | RTN4r | 572 | AAAATACAAAATACGCCC CCGACCCCGA | | |
| | RTN4RL1R_ f | 573 | TGAGGAGAGATTCGGAGT AGTTAGTAGA | chr17: 1827743- 1827851 | 109 |
| | RTN4RL1R_ r | 574 | CCCTATCACACACCTACG CGATTACCAA | | |
| SFRP5 | SFRP5f | 575 | TTTCGAAAAGTTGGTAGT CGGCGGTTGG | chr4: 154929548- 154929670 | 123 |
| | SFRP5r | 576 | CATTCTACTCCCCCGAAT CGAAACCCCC | | |
| | SFRP5R_f | 577 | AAGAGGAAGAGTTCGCG CGTCGAGTTTA | chr4: 154929355- 154929454 | 100 |
| | SFRP5R_r | 578 | GAAATCGCGCGCCCACG ATACTACAAA | | |
| SHF | SHFf | 579 | TTATTAGTAGGCGGCGTC GGGGGTT | chr15: 43266978- 43267127 | 150 |
| | SHFr | 580 | CGAAAACCCCTACTCCGA AAAATCGTCCG | | |
| | SHFR_f | 581 | GTTGAGATATCGAGGGGT TCGGGTTAGG | chr15: 43266838- 43266959 | 122 |
| | SHFR_r | 582 | CGCCAACAACGATAAAATAAATACCGCGCC | | |
| SHOX2 | SHOX2f | 583 | CGTTTGTTCGATCGGGGT CGTACGAGTAT | chr3: 159304063- 159304162 | 100 |
| | SHOX2r | 584 | TTTCCGCCTCCTACCTTCT AACCCGACT | | |
| SNCA | SNCAf | 585 | GGTTGGGGGAGTGGGAG GTAAATTCGTT | chr4: 90977105- 90977221 | 117 |
| | SNCAr | 586 | CTAAACGCTCCCTCACGC CTTACCTTCA | | |
| SNX32 | SNX32f | 587 | TTGAGGGAAACGCGGTG GGAATCGTTTT | chr11: 65357939- 65358057 | 119 |
| | SNX32r | 588 | CCGTAACTCGCCCGAAAA ACTAACCGAA | | |
| SP9 | SP9f | 589 | TGATTGGTTGCGGGGTAG TTTC | chr2: 174907826- 174907911 | 86 |
| | SP9r | 590 | ACACCCGCTTTAAAATAC CGCTAA | | |
| STK33 | STK33f | 591 | GCGTTTCGGGTCGTTCGT TTTATTTCGC | chr11: 8572140- 8572262 | 123 |
| | STK33r | 592 | CGACAACCTACGCCGAAT ATACGCACCT | | |
| SYNGR3 | SYNGR3f | 593 | GAAGGGATGAGGTTGAG GTTGGAGGTCG | chr16: 1981075- 1981195 | 121 |
| | SYNGR3r | 594 | ACCTCCTACCCACCAATT CCGAAAAACAA | | |
| T | Tf | 595 | TTACGGAGTTTTAGGCGG CGTTAC | chr6: 166501979- 166502099 | 121 |

TABLE 15-continued

| | | | | | |
|---|---|---|---|---|---|
| | | | lists the primers used herein for each probe. | | |
| Gene | Probe | SEQ ID NO. | 5' 3' Primer Sequence (Bisulfite) | Chr: Location | PCR Product Length |
| | Tr | 596 | CATTTCCCTCTCTACGCG CGAAC | | |
| THBS2 | THBS2f | 597 | CGTAGGTTTTGTTGGAGC GAGAGATCGG | chr6: 169395805-169395898 | 94 |
| | THBS2r | 598 | ACATATAAAACCGCGCTA CCCGAAAACCG | | |
| TLX1NB | TLX1NBf | 599 | TGAAAGGGGAGAGGGGA ATGTTATTGTT | chr10: 102871413-102871518 | 106 |
| | TLX1NBr | 600 | AATATTCTCGCAAACCCA CCGCCAAACC | | |
| TMEM22 | TMEM22f | 601 | AAAGAGATTCGTGTTGCG GCGGATGAAG | chr3: 138021575-138021691 | 117 |
| | TMEM22r | 602 | GATCAACACTCGAACCCG AACTTTCCGC | | |
| TNFRSF10D | TNFRSf | 603 | AAGGGAGGAGGGTGGAT CGAAAGCGTTA | chr8: 23077397-23077475 | 79 |
| | TNFRSr | 604 | CGAAAACCTTTACACGCG CACAAACTACG | | |
| TXNRD1 | TXNDR1f | 605 | TATGGGTTGCGTCGAGGG TAAGGTAGTG | chr12: 103133710-103133788 | 79 |
| | TXNDR1r | 606 | ACCATCGCCGTTCTTACC TTTCGTCTACA | | |
| VSTM2B | VSTM2Bf | 607 | TTTTTAATTCGGTTCGGCG TTGATTTGT | chr19: 34711435-34711559 | 125 |
| | VSTM2Br | 608 | ACAACCGCGCGCTCCCG ATAC | | |
| ZFPM2 | ZFPM2f | 609 | TAGCGCGGAAGTIGTGAG TTTAAGGCG | chr8: 106401146-106401241 | 96 |
| | ZFPM2r | 610 | TCCTCTAAACACCATCGA AACCCCCGAAC | | |
| ZNF280B | ZNF280Bf | 611 | AGTGGCGTTCGTTGAGAT TAGGGAAGGG | chr22: 21192757-21192877 | 121 |
| | ZNF280Br | 612 | ACCGTACGCTACCGAAAC GACCTTTACA | | |
| LOC105378683 | LOC105 Af | 613 | GTTTGTAATTGGTATGAG CGGC | chr1: 43023566-43023673 | 108 |
| | LOC105 Ar | 614 | ATAACGAAACGACGCCTC | | |
| | LOC105 Bf | 615 | GTAATTGGTATGAGCGGC GT | chr1: 43023570-43023660 | 91 |
| | LOC105 Br | 616 | GCCTCCGCGAAATAAAAC CAT | | |
| | LOC105 Cf | 617 | AGTTAGAGTGGGTTAGGG GAT | chr1: 43023464 43023613 | 150 |
| | LOC105 Cr | 618 | ACGCGTAACACAAACAC GAC | | |
| NPHS2 | NPHS2 Af | 619 | GGGGGATTTTAAAGATCG TC | chr1: 177811721-177811842 | 122 |
| | NPHS2 Ar | 620 | GACGAACGCAATCCACA A | | |
| | NPHS2 Bf | 621 | TGGTGGAGTTGTGGATTG CG | chr1: 177811817-177811891 | 75 |
| | NPHS2 Br | 622 | TCCCACCCAAACCTCTCT CT | | |
| NR5A2 | NR5A2 Af | 623 | GGTGCGTTTACGGGTTTC | chr1: 198278389-198278538 | 150 |
| | NR5A2 Ar | 624 | ACCTAATCCGATATTTCC CGA | | |
| | NR5A2 Bf | 625 | GGTAGGGTTTCGGTTGCG TA | chr1: 198278432-198278527 | 139 |
| | + NR5A2 Br | 626 | TATTTCCCGAAAACTCCA CATCCA | | |
| | NR5A2 Br | 627 | TCCCGAAAACTCCACATC CA | | |

TABLE 15-continued lists the primers used herein for each probe.

| Gene | Probe | SEQ ID NO. | 5' 3' Primer Sequence (Bisulfite) | Chr: Location | PCR Product Length |
|---|---|---|---|---|---|
| PAX6 | PAX6 Af | 628 | ATTTGGATGTTTCGCGTTT C | | |
| | PAX6 Ar | 629 | TATCGCTACGACCCGACT AA | | |
| | + PAX6 Af | 630 | GTTAATTTGGATGTTTCGC GTTTC | chr11: 31783206- 31783322 | 117 |
| | + PAX6 Ar | 631 | GTTTATCGCTACGACCCG ACTAA | | |
| | PAX6 Bf | 632 | AGGGGAGTCGCGTTTTTA GG | chr11: 31782520- 31782652 | 133 |
| | PAX6 Br | 633 | TCCCGACCGAAACCCAAA TC | | |
| KCNE3 | KCNE3 Af | 634 | GAATAACGGCGTAAGTTT TTAC | chr11: 73855818- 73855915 | 98 |
| | KCNE3 Ar | 635 | ATCCTCCCGAACGCAATA | | |
| | KCNE3 Bf | 636 | TTGTACGTTTGTGGGTGT GGA | chr11: 73855765- 73855914 | 150 |
| | KCNE3 Br | 637 | TCCTCCCGAACGCAATAA TCG | | |
| KCNA6 | KCNA6 Af | 638 | TTAACGGTTAGGTTAGAT CGC | chr12: 4789322- 4789421 | 100 |
| | KCNA6 Ar | 639 | CAATCTCTAAAACGCGAC AC | | |
| | KCNA6 Bf | 640 | CGGGTGTCGCGTTTTAGA GAT | chr12: 4789399- 4789482 | 84 |
| | KCNA6 Br | 641 | TTCTCCGATCTCATACCC CCT | | |
| TMEM132C | TMEM Af | 642 | GAGAAAAGTTGTTTCGGT C | | |
| | TMEM Ar | 643 | GCTACGTCTCTACTATCC GA | | |
| | + TMEM Af | 644 | CGGGAGAAAAGTTGTTTC GGTC | chr12: 127317663- 127317786 | 124 |
| | + TMEM Ar | 645 | CCGCTACGTCTCTACTAT CCGA | | |
| | TMEM Bf | 646 | TTCGGGGTGAGGGTAGTC | | |
| | TMEM Br | 647 | CCGACGCCCAACTAAAAA | | |
| | + TMEM Bf | 648 | GAGTTCGGGGTGAGGGT AGTC | chr12: 127318043- 127318179 | 137 |
| | + TMEM Br | 649 | GAATCCCGACGCCCAACT AAAAA | | |
| | TMEM Cf | 650 | TTTTCGGGTTACGGGTCG TT | chr12: 127317330- 127317424 | 95 |
| | TMEM Cr | 651 | ACGACTCCTCCGAAAATC CG | | |
| PDX1 | PDX1 Af | 652 | GTCGATTTTTGTTTTGAGC | chr13: 27390195- 27390280 | 86 |
| | PDX1 Ar | 653 | TAAAAATAATCTACCGAA TCGC | | |
| | PDX1 Bf | 654 | GGCGTTAGCGGGGATTTA GA | chr13: 27389563- 27389694 | 132 |
| | PDX1 Br | 655 | CGCATCAAACGAAACCCT CC | | |
| | PDX1exp Af | 656 | CGGGAAGGTGTTCGTTTA ATGGTTCGGT | chr13: 27389489- 27389590 | 102 |
| | PDX1exp Ar | 657 | GTTTCCGCTCTAAATCCC CGCTAACGCC | | |
| | PDX1exp Bf | 658 | GGAAAAAGGAGGAGGAT AAGAAGCGCGG | chr13: 27396588- 27396685 | 98 |
| | PDX1exp Br | 659 | CTCGCCGAAAATCACGAC GCAATCCTAC | | |
| EPSTI1 | EPSTI1 Af | 660 | TAGGGGAGGCGTCGAGT TC | chr13: 42464253- 42464369 | 117 |
| | EPSTI1 Ar | 661 | ACTCGCTAAACGTCCCAA CC | | |
| A2BP1 | A2BP1 Af | 662 | GAGTTTAGGGGTCGCGTC | chr16: 6009425- 6009564 | 140 |

TABLE 15-continued lists the primers used herein for each probe.

| Gene | Probe | SEQ ID NO. | 5' 3' Primer Sequence (Bisulfite) | Chr: Location | PCR Product Length |
|------|-------|-----------|-----------------------------------|---------------|--------------------|
|  | A2BP1 Ar | 663 | CAATACCGCCGCCTCTAC TA |  |  |
|  | A2BP1 Bf | 664 | GAGAGAGTAGGAGCGGA TCG | chr16: 6009706-6009842 | 137 |
|  | A2BP1 Br | 665 | ACAAATCAACCCCGCCCT AA |  |  |
| CRYM | CRYM Af | 666 | AGTGAGTGTTCGGGAGTT TC |  |  |
|  | CRYM Ar | 667 | TCATTTATTAAAAACGCG CG |  |  |
|  | + CRYM Af | 668 | GCAGTGAGTGCTCGGGA GCCCC | chr16: 21202786-21202934 | 149 |
|  | + CRYM Ar | 669 | GGTTTTCATTTGTTAGAG GCGCGCG |  |  |
|  | CRYM Bf | 670 | CGGGTTCGCGTAGGATTA GG | chr16: 21202650-21202732 | 83 |
|  | CRYM Br | 671 | ACTCCTCATCCCAACACC CT |  |  |
| PRKCB | PRKCB Af | 672 | GTTCGTAGTTCGCGGTTT C |  |  |
|  | PRKCB Ar | 673 | CGATACTCTCCTCGCCCT |  |  |
|  | + PRKCB Af | 674 | TCGGTTCGTAGTTCGCGG TTTC | chr16: 23754928-23755052 | 125 |
|  | + PRKCB Ar | 675 | GCACGATACTCTCCTCGC CCT |  |  |
|  | PRKCB Bf | 676 | TTGGGCGAGTGATAGTTT C | chr16: 23754821-23754909 | 89 |
|  | PRKCB Br | 677 | GACCGCTACTACACCCGA |  |  |
|  | PRKCB Cf | 678 | CGGTAGAAGAACGTGTAT GAGGT | chr16: 23755076-23755216 | 141 |
|  | PRKCB Cr | 679 | GCTACCCTCGAAAACCCG AA |  |  |
| IRF8 | IRF8 Af | 680 | GATTTTTTTTAAGGTCGCG C | chr16: 84490230-84490341 | 112 |
|  | + IRF8 Af | 681 | TTACGATTTTTTTTAAGGT CGCGC |  |  |
|  | IRF8 Ar | 682 | ACTATACCTACCTACCGC CGTC |  |  |
|  | IRF8 Bf | 683 | ATTTCGAAGAAGGCGGGT CG | chr16: 84490149-84490276 | 128 |
|  | IRF8 Br | 684 | CTCCAAACGATACGCCAA CG |  |  |
| SALL3 | SALL3 Af | 685 | TTTTGCGGGTAAGCGTTC |  |  |
|  | SALL3 Ar | 686 | CCACAACTCTCTCGACGA C |  |  |
|  | + SALL3 Af | 687 | TGTTTTTTGCGGGTAAGC GTTC | chr18: 74841456-74841551 | 96 |
|  | + SALL3 Ar | 688 | GCCCACAACTCTCTCGAC GAC |  |  |
|  | SALL3 Bf | 689 | ATTTCGGGAAAGGGTGG GTC | chr18: 74840051-74840163 | 113 |
|  | SALL3 Br | 690 | ACCCTAATCCCCCTTCAC CA |  |  |
|  | SALL3 Cf | 691 | TTTCGTTTCGTTTCGGTCG C | chr18: 74840452-74840573 | 122 |
|  | SALL3 Cr | 692 | AACCCGCCCGAACTCAAA TA |  |  |
| LYPD5 | LYPD5 Af | 693 | ATTAGGAGCGTACGTTTA TTC | chr19: 49016646-49016788 | 143 |
|  | LYPD5 Ar | 694 | TACGCACTCGAAACACAA |  |  |
|  | LYPD5 Bf | 695 | CGGCGCGTTTTAAGGGTT TT | chr19: 49016738-49016863 | 126 |
|  | LYPD5 Br | 696 | ATTACTCTCACCTCCGCA CG |  |  |
| DPP10 | DPP10 Af | 697 | GATTGCGGGAAGAAGGT AC |  |  |
|  | DPP10 Ar | 698 | AAACGAAACCAAACGAC AA |  |  |

TABLE 15-continued lists the primers used herein for each probe.

| Gene | Probe | SEQ ID NO. | 5' 3' Primer Sequence (Bisulfite) | Chr: Location | PCR Product Length |
|---|---|---|---|---|---|
| | + DPP10 Af | 699 | CGGATTGCGGGAAGAAG GTAC | chr2: 115635638-115635739 | 102 |
| | + DPP10 Ar | 700 | GACGAAACGAAACCAAA CGACAA | | |
| | DPP10 Bf | 701 | TTTTCGAGTTTGAAGCGTT C | | |
| | DPP10 Br | 702 | CGACTCTCACCTAATCCG C | | |
| | + DPP10 Bf | 703 | CGGTTTTCGAGTTTGAAG CGTTC | chr2: 115635947-115636088 | 142 |
| | + DPP10 Br | 704 | TACCGACTCTCACCTAAT CCGC | | |
| | DPP10 Cf | 705 | TTACGACGGGGAGTTCGT TC | chr2: 115635821-115635943 | 123 |
| | + DPP10 Cr | 706 | CTTAACAACGTTCGCAAA TCACGA | | |
| | DPP10 Cr | 707 | ACAACGTTCGCAAATCAC GA | | |
| C20orf56 | C20orf Af | 708 | GTTCGTTATTTCGGAATTC | chr20: 22507658-22507804 | 147 |
| | C20orf Ar | 709 | CCGACCGATAAAATATAA TTC | | |
| | C20orf Bf | 710 | GGGAGGGATTTAAGCGG GAG | chr20: 22507684-22507819 | 136 |
| | C20orf Br | 711 | CCCCCTTCACTAATCCCG AC | | |
| SOX2OT | SOX2OT Af | 712 | AGTGTTGAGAGTCGACGC | chr3: 182919951-182920042 | 92 |
| | SOX2OT Ar | 713 | AATAAAATAACCCGAACC GC | | |
| | SOX2OT Bf | 714 | GGGTTACGGTTTCGGGTT GT | chr3: 182919884-182919969 | 86 |
| | SOX2OT Br | 715 | CGCGTCGACTCTCAACAC TA | | |
| CDKL2 | CDKL2 Af | 716 | GGTCGAGTCGAGTCGTTA C | | |
| | CDKL2 Ar | 717 | AAAACGCCTCCTAACGAA | | |
| | + CDKL2 Af | 718 | ATTGGTCGAGTCGAGTCG TTAC | chr4: 76774785-76774935 | 151 |
| | + CDKL2 Ar | 719 | ACAAAAAAACGCCTCCTA ACGAA | | |
| | CDKL2 Bf | 720 | TATTTTTGGGCGAAGGCG TTG | chr4: 76774698-76774806 | 109 |
| | CDKL2 Br | 721 | GTAACGACTCGACTCGAC CA | | |
| MARCH11 | MARCH11 Af | 722 | TCGGCGTTTTCGTTTTTC | chr5: 16232623-16232697 | 75 |
| | MARCH11 Ar | 723 | CGACGACACAACCATAAA CTTT | | |
| | MARCH11 Bf | 724 | AAGGTTTTGTAGTTGCGG CG | chr5: 16232839-16232935 | 97 |
| | MARCH11 Br | 725 | TCTCACGCGCAACCGAAT | | |
| CCL28 | CCL28 Af | 726 | GTGGAGTTTTAGGTAGCG C | | |
| | CCL28 Ar | 727 | ACCCGCGATAAACTAAAC C | | |
| | + CCL28 Af | 728 | AGGGTGGAGTTTTAGGTA GCGC | chr5: 43433001-43433128 | 128 |
| | + CCL28 Ar | 729 | AACAACCCGCGATAAACT AAACC | | |
| | CCL28 Bf | 730 | TGTAGTCGTGGTTGTCGT GG | chr5: 43432695-43432834 | 140 |
| | CCL28 Br | 731 | CCAAATAAACGACGTCCC GC | | |
| AP3B1 | AP3B1 Af | 732 | ATTTTATAGTCGCGTTAAA AGC | chr5: 77304383-77304519 | 137 |

TABLE 15-continued lists the primers used herein for each probe.

| Gene | Probe | SEQ ID NO. | 5' 3' Primer Sequence (Bisulfite) | Chr: Location | PCR Product Length |
|------|-------|-----------|-----------------------------------|---------------|--------------------|
| | AP3B1 Ar | 733 | ACTTTTATTACTCGCGATC C | | |
| | AP3B1 Bf | 734 | GGTAGGGTGAGTTTGGTC GG | chr5: 77304339-77304484 | 146 |
| | AP3B1 Br | 735 | CGCCGAACCACGTAAAA ACT | | |
| CARD11 | CARD11 Af | 736 | ATTTGGGGCGTTTATGTTT C | chr7: 3049825-3049944 | 120 |
| | CARD11 Ar | 737 | CCCTCGAAAAACGACTCC | | |
| | CARD11 Bf | 738 | AGGGGTTGTAGGGTCGG G | | |
| | + CARD11 Bf | 739 | TTTAGGGGTTGTAGGGTC GGG | chr7: 3049955-3050087 | 133 |
| | CARD11Br | 740 | ATTTTACATTTCCCTCCCC CGC | | |
| BLACE | BLACE Af | 741 | AGAATAAAAGTAGGCGG C | chr7: 154859246-154859384 | 139 |
| | BLACE Ar | 742 | TCTCGAAACCAAAATAAA CG | | |
| | BLACE Bf | 743 | AGTAGGCGGCGGATTTGT AG | chr7: 154859254-154859357 | 104 |
| | BLACE Br | 744 | CCGAAAATACGCGAAATC AACC | | |
| PTPRN2 | PTPRN2 Af | 745 | GAGGAGATAAAGGTGTC GC | | |
| | PTPRN2 Ar | 746 | AACGTACCTAACCCGAAA AC | | |
| | + PTPRN2 Af | 747 | TCGGAGGAGATAAAGGT GTCGC | chr7: 157176188-157176342 | 155 |
| | + PTPRN2 Ar | 748 | CCAACGTACCTAACCCGA AAAC | | |
| | PTPRN2 Bf | 749 | GACGGTTTCGGTAGGGTC | | |
| | PTPRN2 Br | 750 | CCGAACCGAATATAAAAC GA | | |
| | + PTPRN2 Bf | 751 | CGGACGGTTTCGGTAGG GTC | chr7: 157176379-157176463 | 85 |
| | + PTPRN2 Br | 752 | GCGCCGAACCGAATATAA AACGA | | |
| RUNX1T1 | RUNX1T1 Af | 753 | TTAGGTTCGTAAAGAGGG C | chr8: 93183286-93183401 | 116 |
| | RUNX1T1 Ar | 754 | TTAAAACCACGTCCGAAT A | | |
| | RUNX1T1 Bf | 755 | TTTCGGGCGGGAGTTATA GG | chr8: 93183412-93183529 | 118 |
| | RUNX1T1 Br | 756 | ACGCGCTCTAAACTCAAC CG | | |
| L1TD1 | L1TD1 Af | 757 | GCGCGTGGGGTTCGTAG CGTTTTAAG | chr1: 62433357-62433465 | 109 |
| | L1TD1 Ar | 758 | TTACCCGAAACACCCCGC GCCCTTC | | |
| PPFIA3 | PPFIA3 Af | 759 | AGATACGGAGATTTAGCG CGAGATCGGT | chr19: 54337953-54338094 | 143 |
| | PPFIA3 Ar | 760 | AAATTAACCGCCGAACAC TCACAATACG | | |
| FILIP1L | FILIP1L Af | 761 | TTGTAGTGTCGCGTTGCG AGTCGATTGT | chr3: 101077651-101077753 | 103 |
| | FILIP1L Ar | 762 | ACAATAACGTAACGCCCA TAAACCGAACG | | |
| NUDT16P | NUDT Af | 763 | GAGGACGGGTTGAATCGT GGTTTGTTGG | chr3: 132563775-132563858 | 84 |
| | NUDT Ar | 764 | ACTACGATAATCAAAACG CTCCACGCGA | | |
| TOP2P1 | TOP Af | 765 | GTGCGCGTTTTAGTAGGG CGAGAATGG | chr6: 28283268-28283417 | 150 |

TABLE 15-continued

| Gene | Probe | SEQ ID NO. | 5' 3' Primer Sequence (Bisulfite) | Chr: Location | PCR Product Length |
|---|---|---|---|---|---|
| | TOP Ar | 766 | CGAAAACCAAATCCGAAC CACCGTCTCC | | |
| | TOP Bf | 767 | TGATTTGGGTGGATGTAG AGGTTGTGGT | chr6: 28283447- 28283568 | 122 |
| | TOP Br | 768 | TTTCGAATAACGCTACTC CGAACCGCGA | | |
| UNKWN1 | UNKWN1 Af | 769 | TTGAGAGTAGGGATTGTG GTGCGTCGTC | chr5: 72634694- 72634838 | 145 |
| | UNKWN1 Ar | 770 | CTAACTCCCGAACGCTAC ATTCGCTCCA | | |
| GALR3 | GALR3 Af | 771 | GGTTGTGGTGAGTTTGGT TTACGGGCG | chr22: 36550907- 36551049 | 143 |
| | GALR3 Ar | 772 | CGTAAAACGCGACCACC GCCAACATA | | |
| PRSS27 | PRSS Af | 773 | GGGAGGTTATTCGTAGGA TTTGGCGCGG | chr16: 2705610- 2705748 | 139 |
| | PRSS Ar | 774 | ATCCTAACGACTACGCAC TACTTCCGCA | | |
| SLC7A4 | SLC Af | 775 | GAGTTCGTTTAGTTCGTC GGCGTC | chr22: 19716858- 19717005 | 148 |
| | SLC Ar | 776 | AACCCCGATAAACTCCGA TAACGACCT | | |
| LEF1 | LEF1 Af | 777 | AGAGTTGGGGGGGGTAT AGTTAGGGTGT | chr4: 109307444- 109307547 | 104 |
| | LEF1 Ar | 778 | TTCAATCCCTACGACCCC AACGCCTAAA | | |
| NFIC | NFIC Af | 779 | CGTGGATACGAGTTTTGG CGGCGATTAT | chr19: 3386117- 3386219 | 103 |
| | NFIC Ar | 780 | GCCACCAACCCTACCTCC TTCCATATCC | | |
| | NFIC Bf | 781 | TTTTTCGGTTTGAGTTATC GTGGCGGGA | chr19: 3386234- 3386379 | 146 |
| | NFIC Br | 782 | CGAACCGTACTTCCAACC AAACGCAACT | | |
| TMEM90B | TMEM90 Af | 783 | TAGGAAGGGGTCGATGTT GGTTTGGGTT | chr20: 24398648- 24398747 | 100 |
| | TMEM90 Ar | 784 | TCTCACCAACTCCCATCG AATTCGCACA | | |
| | TMEM90 Bf | 785 | GTTTTGGTTTCGTTTCGGA GCGCGTAGA | chr20: 24398510- 24398642 | 133 |
| | TMEM90 Br | 786 | TTTCTCTACCGACTCAACT CCCCCTCCC | | |
| UBD | UBD Af | 787 | TCGGTTGCGTAAATCGCG TTTTTGGTTG | chr6: 29629437- 29629564 | 128 |
| | UBD Ar | 788 | TTCTCGATAATATCTCCGT CGCCTCCGC | | |
| GIPC2 | GIPC Af | 789 | GTTTAGGGGTGGAGGTCG GGGTTTTGA | chr1: 78284199- 78284289 | 91 |
| | GIPC Ar | 790 | CCGAACCCCGCGCAAAT AAAAACAACCT | | |
| EFNA4 ERNA4 | ERNA Af | 791 | GGGGCGCGTTTTTATGGA AAGTTAGGGT | chr1: 153310423- 153310549 | 127 |
| | ERNA Ar | 792 | CTACGCCCTAAAACACGC CTCGACTTCT | | |
| | ERNA Bf | 793 | TGTGCGAAAGAGACGCG GGGTTTAGTTA | chr1: 153310139- 153310288 | 150 |
| | ERNA Br | 794 | CCCGTAATCGCTAAAACA TCCGCCCTTA | | |
| DRD4 | DRD4 Af | 795 | CGTCGGGCGATGTTGGTT TGTTCGTG | chr11: 627035- 627175 | 141 |
| | DRD4 Ar | 796 | GCGACGCTCCACCGTAAA CCCAATATTTA | | |

TABLE 15-continued lists the primers used herein for each probe.

| Gene | Probe | SEQ ID NO. | 5' 3' Primer Sequence (Bisulfite) | Chr: Location | PCR Product Length |
|------|-------|------------|-----------------------------------|---------------|--------------------|
| TCTEX1D1 | TCTEX Af | 797 | CGGGGAGGGTCGAGGGT TTTGTTTGAG | chr1: 66990668-66990782 | 101 |
| | TCTEX Ar | 798 | GCGTCCCAAACTTCATTC AACCGACGAC | | |
| PHOX2B | PHOX Af | 799 | GCGGACGTAGTAATGGAT TAAACGGGGA | chr4: 41447111-41447255 | 145 |
| | PHOX Ar | 800 | AAATCCGACTCCCTACAC TCCCGACTTT | | |
| TSPAN33 | TSPAN Af | 801 | GGGGGTTGTGTTAGTTGT TTGTTTAGCGA | chr7: 128596487-128596593 | 107 |
| | TSPAN Ar | 802 | CGAAACTATTTCCCGCCA AACCGAACCC | | |
| CA9 | CA9 Af | 803 | TTTCGGGCGGGAGTATCG GGTTTTGTAG | chr9: 35666101-35666239 | 139 |
| | CA9 Ar | 804 | GCTCCTTTACCCCTTCTC GACCAACTCC | | |
| UNKWN2 | UNKWN2 Af | 805 | TTACGGATTTTATTTGTAT TCGGAATCGTA | chr10: 102409232-102409335 | 104 |
| | UNKWN2 Ar | 806 | ACGCATCAAACTCGACAC AAAATTTCATC | | |
| WT1 | WT1 Af | 807 | GGTGTTTTCGTAAGACGG GGTAGTGGGT | chr11: 32406776-32406869 | 94 |
| | WT1 Ar | 808 | TTCTCCTCCGCTAAAAAT CCGAATACGA | | |
| OTX2 | OTX2 Af | 809 | AGGGATTGTATTTCGAGG TGGTCGAGGT | chr14: 56331673-56331781 | 109 |
| | OTX2 Ar | 810 | CCGACAAATCGAAACCTT CGCCCGAAAC | | |
| HOXB13 | HOXB13 Af | 811 | TCGCGGGTTATAAATATT TGGTTGCGGC | chr17: 44157793-44157885 | 93 |
| | HOXB13 Ar | 812 | GACCGCCACTACCTCGAA AACATTTCCC | | |
| BRCA1 | BRCA1 Af | 813 | GGTAACGGAAAAGCGCG GGAATTATAGA | chr17: 38530874-38530968 | 95 |
| | BRCA1 Ar | 814 | CCCACAACCTATCCCCCG TCCAAAAA | | |
| ITPRIPL1 | ITPRIPL 1f | 815 | TTTTGTACGTTGGGTTAC GGGGGTTTGG | chr2: 96354715-96354857 | 143 |
| | ITPRIPL1r | 816 | TAAACGCGATAAACCCCT ACGACCCCCA | | |
| HES5 | HES5-F | 817 | TATCGGTTTTCGTAGTTGC GGGAGGAGG | Chr1: 2451323-2451386 | 118 |
| | HES5-R | 818 | CCGAATAAATACCAAACT CGCCCGACGC | | |
| CSRP1/ LOC376693 | CSRP1/ LOC376693-F | 819 | CGGGTAGAGGGGAGGTA GGAATTGGAGA | Chr1: 199775889-199775914 | 80 |
| | CSRP1/ LOC376693-R | 820 | CCGAATAAACGTCACCCC TACACACCGC | | |
| ALOX5 | ALOX5-F | 821 | TTTTGCGGTTAGGTGAAG GCGTAGAGGT | Chr10: 45234681-45234732 | 106 |
| | ALOX5-R | 822 | GACCGAATACCCCGCTTT CTCTCTCGAC | | |
| PPM1H/ MON2 | PPM1H/ MON2-F | 823 | AGGAGTAGTATTGCGAGG GTGGAGGGT | Chr12: 61311943-61312001 | 112 |
| | PPM1H/ MON2-R | 824 | TAAACCCGAAAAACAACG CCAATCCCGC | | |
| KIAA0984 | KIAA0984-F | 825 | GGGGATTGTTGTAGAGT CGTAGGAGAA | Chr12: 63515983-63516043 | 62 |
| | KIAA0984-R | 826 | CCGCATCCCACCCTTTAA AACTCTA | | |

TABLE 15-continued

<u>lists the primers used herein for each probe.</u>

| Gene | Probe | SEQ ID NO. | 5' 3' Primer Sequence (Bisulfite) | Chr: Location | PCR Product Length |
|------|-------|------------|-----------------------------------|---------------|--------------------|
| TXNRD1 | TXNRD1-F | 827 | TATGGGTTGCGTCGAGGG TAAGGTAGTG | Chr12: 103133737-103133768 | 86 |
| | TXNRD1-R | 828 | TACGACGACCATCGCCGT TCTTACCTTT | | |
| CHST11 | CHST11-F | 829 | AAATTTGGATTGGGGGAG GGACGAGGTT | Chr12: 103376469-103376538 | 124 |
| | CHST11-R | 830 | CTTCGCAACCGAACTACT CACCCCCGAC | | |
| EFS | EFS-F | 831 | GGTCGTTGGAGTGGTCGT TTCGGTTTAG | Chr14: 22904743-22904785 | 98 |
| | EFS-R | 832 | CCTCAAACCCCCGAACGC GCTAAATAAA | | |
| ANXA2 | ANXA2-F | 833 | GTTCGGGGAGGGAGGGA GATTCGTTTTG | Chr15: 58478046-58478098 | 107 |
| | ANXA2-R | 834 | AACTCCCGACTTTAACCT CCCAACCCAA | | |
| RHCG | RHCG-F | 835 | GTTGTAGGGGTGTTTGGT CGGGTTGGTA | Chr15: 87840807-87840869 | 118 |
| | RHCG-R | 836 | ATCAACTACTCCGTACCC CACGTAACCG | | |
| RARA | RARA-F | 837 | AGTCGGGGTTGGTTGGTG GAAGAGG | Chr17: 35718896-35718981 | 137 |
| | RARA-R | 838 | CCCTCTCAACTCGATTCA AAATTCCCCC | | |
| PTRF | PTRF-F | 839 | AAAGTAATAAGTGGTTTC GGGCGGAGTC | Chr17: 37827277-37827326 | 104 |
| | PTRF-R | 840 | ACCCCGCATACCTACGAA AACGAAAACC | | |
| RND2 | RND2-F | 841 | CGGGATTATGGAGGGGT AGAGCGGTCG | Chr17: 38430910-38430955 | 99 |
| | RND2-R | 842 | ACGTCCTTAACGAACACC TACAACAACG | | |
| TMP4 | TMP4-F | 843 | AGGTTTTGTAGTAGTAGG CGGACGAGGC | Chr19: 16048446-16048512 | 121 |
| | TMP4-R | 844 | ACGAATACGAAACCCGA AACCGAAACGC | | |
| HIF3A | HIF3A-F | 845 | CGTGGTATAGTTAATCGC GCGGCGT | Chr19: 51492259-51492376 | 118 |
| | HIF3A-R | 846 | TACAACCCCAACGCCATA ACTCGCCAAT | | |
| KLK5 | KLK4-F | 847 | TAGCGGGGATTTATTAGG GGAGAGGTGG | Chr19: 56107959-56108027 | 123 |
| | KLK4-R | 848 | ATCACCTACGAACACTAT CCCTCACCCG | | |
| AMOTL2 | AMOTL2-F | 849 | GCGGAATAGTTCGCGGTT TTGGAATGTT | Chr3: 135565786-135565856 | 125 |
| | AMOTL2-R | 850 | AAACGTTTCCGCTCCCCG AAAAACGAAT | | |
| SCGB3A1 | SCGB3A1-F | 851 | GGAGATAGTTTTGAGAGG GGGAGGTCGC | Chr5: 179950858-179950923 | 120 |
| | SCGB3A1-R | 852 | CGCTACCTACGCCGATCG TAAATCCCAA | | |
| HLA-F | HLA-F-F | 853 | GAATGGTTGCGATATGGG GTTCGACGGA | Chr6: 29799978-29800035 | 112 |
| | HLA-F-R | 854 | CGCGATCCAAAAACGCA AATCCTCGTTC | | |
| HLA-J-1 | HLA-J, NCRNA00171-1-F | 855 | GGTTTTGGTCGAGATTTG GGCGGGTGAG | Chr6: 30082430-30082476 | 101 |

TABLE 15-continued

<u>lists the primers used herein for each probe.</u>

| Gene | Probe | SEQ ID NO. | 5' 3' Primer Sequence (Bisulfite) | Chr: Location | PCR Product Length |
|------|-------|-----|-----------------------------|--------------|--------|
| | HLA-J, NCRNA00171-1-R | 856 | CCCGAATCCTACGCCCCA ACCAAATAAA | | |
| HLA-J-3 HLA-J | HLA-J, NCRNA00171-2-F | 857 | TGAGTGATTTCGGTTCGG GGCGTAGATT | Chr6: 30083115-30083168 | 125 |
| | HLA-J, NCRNA00171-2-R | 858 | CGAAAATCTCTACAAATC CCGCAACCTCG | | |
| PON3 | PON3-F | 859 | ATGGTTTCGGGGTGTTTA GCGGCGATTG | Chr7: 94863624-94863674 | 105 |
| | PON3-R | 860 | AACGAAACCGAACGAAC CCCAATCCGTA | | |
| LRRC4/ SND1 | LRRC4-F | 861 | GAGTCGGAGTGAGCGTTA AGTGAGGGG | Chr7: 127459707-127459730 | 77 |
| | LRRC4-R | 862 | TCCCTCCGACCGACCCAA AATAACTACG | | |
| PAH | PAH-F | 863 | TTCGTTGTTCGTTTTGGGT AAAGGGAAG | Chr12: 101835348-101835409 | 116 |
| | PAH-R | 864 | AAACTCGCTTCCCAAACT TCTAAAAATC | | |
| EPSTI1 | EPSTI1-F | 865 | GGGGAGGCGTCGAGTTC GGAGTTTATTA | Chr13: 42464282-42464345 | 117 |
| | EPSTI1-R | 866 | AAAACTCGCTAAACGTCC CAACCGCATC | | |
| ADCY4 | ADCY4-F | 867 | CGGGTATTGTTGGTTTAG GTTGTAGTAGGT | Chr14: 23873644-23873710 | 123 |
| | ADCY4-R | 868 | CGACCCTAACCAACCCCG AAACTCGAAA | | |
| HAPLN3 | HAPLN3-F | 869 | AGGGTAGAAAGGAAGCG GTAGTAGAAAA | Chr15: 87239811-87239872 | 116 |
| | HAPLN3-R | 870 | ACAACAACTCCTCCCTTC GAACCCAACC | | |
| HSF4 | HSF4-F | 871 | TGTGGGAGGGAAGGGAA ATCGAGATTGG | Chr16: 65762053-65762164 | 113 |
| | HSF4-R | 872 | ACGACAAAACGAAACCC ACAATCCTACCC | | |
| NBR1/ TMEM106A | NBR1/ TMEM106A-F | 873 | ATTCGGATTGGTTAGTTTT TGCGGAAGT | Chr17: 38719260-38719296 | 91 |
| | NBR1/ TMEM106A-R | 874 | TTCGCCACGCAACAACCT AAAACGCTAC | | |
| HAAO | HAAO-F | 875 | GGTTGCGGCGTTTATTTA GCGGGAAGTC | Chr2: 42873761-42873822 | 114 |
| | HAAO-R | 876 | CTCGCCGAACCCGCGAC GAAATCTAC | | |
| RARB | RARB-F | 877 | TAGAGGAATTTAAAGTGT GGGTTGGGGG | Chr3: 25444371-25444441 | 125 |
| | RARB-R | 878 | ACCAACTTCTCTCCCTTTA CGCCTTTTT | | |
| ALDH1L1 | ALDH1L1-F | 879 | TGGGTTAAGTATTTGTTAT GTGTTACGGA | Chr3: 127382511-127382580 | 121 |
| | ALDH1L1-R | 880 | CGCTATCCACCCGAATAC GCAACT | | |
| HIST1H3G | HIST1H3G-F | 881 | GCGCGGCGTTTTGTTATC GGTGGATT | Chr6: 26379588-26379647 | 60 |
| | HIST1H3G-R | 882 | TCTAAAATAACCCGCACC AAACAAACTACA | | |
| ZSCAN12 | ZSCAN12-F | 883 | TTATAAAGGTCGGAAGCG GTTACGGGGG | Chr6: 28475534-28475572 | 93 |

TABLE 15-continued lists the primers used herein for each probe.

| Gene | Probe | SEQ ID NO. | 5' 3' Primer Sequence (Bisulfite) | Chr: Location | PCR Product Length |
|------|-------|-----------|-----------------------------------|---------------|--------------------|
| | ZSCAN12-R | 884 | AACCCCTTTCGCTCCCTT CCTAAAACGA | | |
| HCG4P6 | HCG4P6-F | 885 | GTATGGTTGCGATTTGGG GTTGGAAGGG | Chr6: 30002983-30003042 | 114 |
| | HCG4P6-R | 886 | GCCGCGATCCAAAAACG CAAATCCTAAT | | |
| HLA-J-3 | HLA-J, NCRNA00171-3-F | 887 | TAGGGAATGTTTGGTTGC GATTTGGGG | Chr6: 30083115-30083168 | 80 |
| | HLA-J, NCRNA00171-3-R | 888 | TCCTTACCGTCGTAAACA TACTACTCAT | | |
| EYA4 | EYA4-F | 889 | GCGTAAGTGCGAGGTTGT CGGTAGC | Chr6: 133604154-133604229 | 125 |
| | EYA4-R | 890 | TTTCCCGCAACTCTTTCCC CCTCTCT | | |
| HOXA7 | HOXA7-F | 891 | TGCGGTTAAAGAATTCGT TCGCGTTCGG | Chr7: 27162955-27162982 | 82 |
| | HOXA7-R | 892 | CTAAACGCTCCCGCGAAA CCTCCAAATC | | |
| USP44 | USP44/p-F | 893 | TTCGGGTATTTTGAGGTT GTCGTCGGGA | Chr12: 94466379-94466481 | 103 |
| | USP44/p-R | 894 | GACGACGACGCGTCCGA CGAATTTTA | | |
| CYP27A1 | CYP27A1/p-F | 895 | GTTTTGGTCGGGGCGTCG TGGATATTTT | Chr2: 219354932-219355042 | 111 |
| | CYP27A1/p-R | 896 | AAAAACCAACTAAACCCC TTCCCGCTCG | | |
| PRSS3 | PRSS3/p-F | 897 | GTGTGGAAAGGGTTTGGC GGTTGTTAGG | Chr9: 33740574-33740686 | 113 |
| | PRSS3/p-R | 898 | CTCGCCAAATACGTCCAC CCAAAAACGA | | |
| C18orf62 | C18orf62/p-F | 899 | TAGGAGGGGACGTAGAG TTTACGGCGAA | Chr18: 71296729-71296833 | 105 |
| | C18orf62/p-R | 900 | GAATACCCGACCCGACC CATCCATCAC | | |
| SFRP2 | SFRP2/p-1-F | 901 | TGCGTTTGTAGGAGAAGT CGGGTTGGTT | Chr4: 154929326-154929408 | 83 |
| | SFRP2/p-1-R | 902 | ACTCTTCCTCGCCTCGCA CTACTACCTA | | |
| | SFRP2/p-2-F | 903 | GTGCGATTCGGGGTTTCG AAAAGTTGGT | Chr4: 154929535-154929641 | 107 |
| | SFRP2/p-2-R | 904 | GAAACTACGCGCGAACTT ACAACGCCTC | | |
| SLCO4C1 | SLCO4C1/p-F | 905 | GAGCGTAGAGCGTTGAG CGGGG | Chr5: 101660047-101660169 | 123 |
| | SLCO4C1/p-R | 906 | CGCCGCCGAATAACACG CCCAC | | |
| CORO1C | CORO1C/p-1-F | 907 | AGCGGGGATTTTCGGAGT TGGAGAGTTT | Chr12: 107686622-107686733 | 112 |
| | CORO1C/p-1-R | 908 | CTCCATCCGCCCGACCTA ACCCTAAAAA | | |
| | CORO1C/p-2-F | 909 | GGGAAGTGGCGTAGTGG GCGTTTGTATC | Chr12: 107686752-107686848 | 97 |
| | CORO1C/p-2-R | 910 | TACCTCCAACGACCACGC CCACAAAATA | | |
| KJ904227 | KJ904227/p-F | 911 | TGGAGCGTTGAGTCGAAG TTTTGATTTT | Chr3: 127489474-127489582 | 109 |
| | KJ904227/p-R | 912 | TCTTACCCGAACTTTAAC CCCAACCGCT | | |

TABLE 15-continued lists the primers used herein for each probe.

| Gene | Probe | SEQ ID NO. | 5' 3' Primer Sequence (Bisulfite) | Chr: Location | PCR Product Length |
|---|---|---|---|---|---|
| C6orf141 | C6orf141/p-1-F | 913 | GGTTGGGAGTTCGGAGTT GTAGTAGAGG | Chr6: 49626357-49626455 | 99 |
| | C6orf141/p-1-R | 914 | CTTTAACCGATTCAAACA ACAAACGCCT | | |
| | C6orf141/p-2-F | 915 | GTAGGGCGCGGGGTTTC GTTAGTTTC | Chr6: 49626570-49626668 | 99 |
| | C6orf141/p-2-R | 916 | ATCTACCGTTCTATCCTC GTAACCGCCG | | |
| BC030768 | BC030768/p-F | 917 | TCGTTTGGGAGGGATCGT TTTTGGGAGA | Chr1: 26424688-26424767 | 80 |
| | BC030768/p-R | 918 | AACCCGAATACTATCCAA CTACCGCCGC | | |
| DMRTA2 | DMRTA2/p-F | 919 | CGAGCGTGGGTATTAAGT CGGTAGTGGA | Chr1: 50657067-50657169 | 103 |
| | DMRTA2/p-R | 920 | GACCTCAACCCCCTACGC CTAACCTACT | | |
| HFE | HFE/p-1-F | 921 | GTAGATCGCGGTTTTGTA GGGGCGTTTG | Chr6: 26195692-26195783 | 92 |
| | HFE/p-1-R | 922 | CTAATTTCGATTTTTCCAC CCCCGCCGC | | |
| | HFE/p-2-F | 923 | GAGTGTTTGTCGAGAAGG TTGAGTAAAT | Chr6: 26196140-26196221 | 82 |
| | HFE/p-2-R | 924 | CACCGCCCAACGCATTCG TTCTAAAATA | | |
| CADPS2 | CADPS2/p-F | 925 | ATAAAAGTGGGGTGGGT GGCGGAGGG | Chr7: 121744063-121744166 | 104 |
| | CADPS2/p-R | 926 | GCGCCGAAATAACAACC CAACCTACCAA | | |
| CYTH4 | CYTH4/p-F | 927 | TTTATCGGGGAAGTTTTC GAGGGTGGGC | Chr22: 36050993-36051112 | 120 |
| | CYTH4/p-R | 928 | TCCCAACTACCTCCTACG CACGAACGAT | | |
| Intergenic (Chr4) | Chr4/p-1-F | 929 | ATGAAATGTGGTTCGTGG AAGGTGTTTGT | Chr4: 186174475-186174549 | 75 |
| | Chr4/p-1-R | 930 | ACGACCCGAACGTTAATC CTCTTACTAC | | |
| NHLH2 | NHLH2/p-F | 931 | ACGTAGTTTTCGAGTTAG TGTCGTTAGAA | Chr1: 116172677-116172793 | 117 |
| | NHLH2/p-R | 932 | GACAAACGCCTCAAACCC GACCG | | |
| NRN1 | NRN1/p-F | 933 | AGGAGCGGGAGAGGGAA AAATAGTTAAG | Chr6: 5952635-5952767 | 133 |
| | NRN1/p-R | 934 | CGCTCCAAACTACGCCCA AAACTCAA | | |
| HMGCLL1 | HMGCLL1/p-F | 935 | ATTAGAGTTGTTTTGCGTA TTGCGGCGG | Chr6: 55551934-55552030 | 97 |
| | HMGCLL1/p-R | 936 | CAAATACCCCGTACACCC GCTACCCCAA | | |
| Me3 | Me3/p-1-F | 937 | GGGAGTTGAGGTTTACGC GGTTTCGTTG | Chr11: 86061026-86061124 | 99 |
| | Me3/p-1-R | 938 | GACCGCCAACGCGATCC ACCCATTAAC | | |
| | Me3/p-2-F | 939 | AGTTTTGGAAGTAGATTC GGTGCGGGTG | Chr11: 86060867-86060948 | 82 |
| | Me3/p-2-R | 940 | GCCGCGCAATCGCCTCTT TTTCAC | | |
| Intergenic (Chr3) | Chr3/p-1-F | 941 | AGACGATAGATGGCGGG TAGGAAGGGAG | Chr3: 135608250-135608374 | 125 |
| | Chr3/p-1-R | 942 | GCCGCCTACAACCGACG AACTACAAATC | | |
| Intergenic (Chr8) | Chr8/p-1-F | 943 | TCGCGGGTGAGGTTTGTG GTTAATTTCG | Chr8: 68037553-68037676 | 124 |

TABLE 15-continued

| | | | | | |
|---|---|---|---|---|---|
| Gene | Probe | SEQ ID NO. | 5' 3' Primer Sequence (Bisulfite) | Chr: Location | PCR Product Length |
| | Chr8/p-1-R | 944 | GCTCAACCAAACTACAAC GTTCCCGCCT | | |
| NBPF1 | NBPF1/p-F | 945 | TGAGAGGCGTATTTTGTT GGTTACGGTT | Chr1: 146219493- 146219574 | 82 |
| | NBPF1/p-R | 946 | CGAAAACCATTCCGCTAC CCTTCCAACT | | |
| Intergenic (Chr10) | Chr10/p-1-F | 947 | GGGGCGTTGGGTTATGGA GATTACGTTTT | Chr10: 42748953- 42749053 | 101 |
| | Chr10/p-1-R | 948 | GTCCCGCGCTTAACGAAT TCTACGAACG | | |
| ASAP1 | ASAP1/p-F | 949 | GTTCGGGTAGGGGTCGG GGGTC | Chr8: 131524437- 131524546 | 110 |
| | ASAP1/p-R | 950 | CCCGAAACGACGTACTTA ACGACCCGAA | | |
| Intergenic (Chr1) | Chr1/p-1-F | 951 | GGGAGGTTTGAGCGTCG AAGTTTTCGTT | Chr1: 119352428- 119352549 | 122 |
| | Chr1/p-1-R | 952 | GCCCACTACCCCGCGAA ACCTTATCAAC | | |
| PPP2R5C | PPP2R5C/p- F | 953 | AGTCGTTAGGTTGTTAAG GCGCGTTGTG | Chr14: 101317476- 101317534 | 59 |
| | PPP2R5C/p- R | 954 | ACAAAAATAAAATCGAAC CTAACCCCACG | | |
| Intergenic (Chr2) | Chr2/p-1-F | 955 | CGTATTAAGGGTTAAGCG GCGCGGT | Chr22: 44883312- 44883404 | 93 |
| | Chr2/p-1-R | 956 | AACTTTCTCGAACGACTC GATAAACCTAA | | |
| KRT78 | KRT78/p-F | 957 | AGGTTTTGGGAATTTGGA AGTTCGCGGG | Chr12: 51554274- 51554370 | 97 |
| | KRT78/p-R | 958 | AAAAACGCTCGAACCCAA CCAATCGACG | | |
| LINC240 | LINC240/p- 1-F | 959 | AAAGGAAGATCGTGGGT AGTTCGTGCG | Chr6: 27167780- 27167859 | 80 |
| | LINC240/p- 1-R | 960 | ACTACAACTCACGTTTCC CCTCCAACAC | | |
| | LINC240/p- 2-F | 961 | AGGTTTATTTGACGTTTTA GGTCGATAGT | Chr6: 27172709- 27172830 | 122 |
| | LINC240/p- 2-R | 962 | CGATCTCTCCCTTTCTTCC GCTTCCTAA | | |
| Intergenic (Chr16) | Chr16/p-1-F | 963 | GGCGTCGGTTGCGGTTTT AGAT | Chr16: 53648145- 53648269 | 125 |
| | Chr16/p-1-R | 964 | ACGCGAAAATCTACCTTT TAATTACGAACC | | |
| HIST1H3G/ 1H2BI | HIST1H3G/ 1H2BI/p-F | 965 | TCGTCGGTGGTCGGCGC GTTTTT | Chr6: 26379488- 26379589 | 102 |
| | HIST1H3G/ 1H2BI/p-R | 966 | AACCCGCACCAAACAAA CTACACGCAAA | | |
| PPM1H | PPM1H/p-1- F | 967 | GAATGGTAGCGAGAGGTT GCGGGTTAGG | Chr12: 61312222- 61312310 | 89 |
| | PPM1H/p-1- R | 968 | CTCTACCCTCAAAATCGC GACGCAAACG | | |
| | PPM1H/p-2- F | 969 | AGGAGTAGTATTGCGAGG GTGGAGGGTT | Chr12: 61311917- 61312012 | 96 |
| | PPM1H/p-2- R | 970 | CGCCAATCCCGCTCCGAC ACTATAACAA | | |
| TUBB2B | TUBB2B/p- F | 971 | ATAAGGTTTGGTGGAAGC GTAGGAGCGT | Chr12: 3177175- 3177262 | 88 |
| | TUBB2B/p- R | 972 | ACGATATTCTAACCTCCG CCGCGAAACT | | |
| C2CD4A | C2C5F | 973 | GGTAGAGGGATAGGGAA GAGTTTGGCGT | Chr15: 60146378- 60146528 | 150 |

TABLE 15-continued lists the primers used herein for each probe.

| Gene | Probe | SEQ ID NO. | 5' 3' Primer Sequence (Bisulfite) | Chr: Location | PCR Product Length |
|------|-------|-----------|-----------------------------------|---------------|--------------------|
| | C2C5R | 974 | ATTCAAAACGCGCGCGAC GAAATTCAAC | | |
| COL19A1 | COL2F | 975 | GCGGAGTGGGAGGGTTA TATTGGGAGAG | Chr6: 70633134-70633240 | 106 |
| | COL2R | 976 | CCGAACAAAACTACGACA CCGCCGAAAA | | |
| DCDC2 | DCD5F | 977 | ACGACGGGTTGAGATAG GTGGTTGGATT | Chr6: 24465938-24466027 | 90 |
| | DCD5R | 978 | CCCGACGCGAAACAACG AACTAAAACGA | | |
| DHRS3 | DGR2F | 979 | TTTTTGTACGTTTTCGGGG TCGGAGGAG | Chr1: 12601840-12601942 | 102 |
| | DHR2R | 980 | AATCGCCGTCTAAACAAA TCGCGAACTA | | |
| GALNT3 | GAL1F | 981 | CGGCGGTCGCGGTTTGTA GTTTAGAATTG | Chr2: 166358281-166358431 | 150 |
| | GAL1R | 982 | ACGCGCTTCCACTCCGAC TAACAAATTA | | |
| | GAL3F | 983 | GGCGTCGTTCGGGTTAAG TTTGGTTGT | Chr2: 166359152-166359230 | 78 |
| | GAL3R | 984 | CACAACTTACGCGAAACA ACAACCTCGC | | |
| HES5 | HES1F | 985 | TGGGTTGGTGTCGCGCGA ATTTTTGTTT | Chr1: 2451234-2451350 | 116 |
| | HES1R | 986 | CCTCCTCCCGCAACTACG AAAACCGATA | | |
| | HES3F | 987 | GTTGGGGGTTATGTTTGG CGCGGAATAG | Chr1: 2451478-2451622 | 144 |
| | HES3R | 988 | CGCCTATATAAAACGTCG ACGCGCGAAA | | |
| | HES4F | 989 | GTTCGGGCGTCGCGGTC GTTTTTATATT | Chr1: 2453144-2453266 | 122 |
| | HES4R | 990 | AAAACGCCCATTATACCC GCGCCAATTC | | |
| KILLIN | KIL5F | 991 | TAAGAATCGGCGGTAGTT AGTAGGCGGG | Chr10: 89611638-89611783 | 145 |
| | KIL5R | 992 | TCCTACGCCGCGACGAAA ACAAAAACTC | | |
| | KIL6F | 993 | AGGTGGGGCGCGTTTATT AGTTTAGGGG | Chr10: 89611428-89611578 | 150 |
| | KIL6R | 994 | ACCTCTCCATCGCTAATA CCCTACCGCT | | |
| MUC21 | MUC2F | 995 | GAGTGTTTCGAGGGTAGG AGGTTGTCGG | Chr6: 31031426-31031559 | 133 |
| | MUC2R | 996 | CAAAAACCGCCCGCAAA ACGAAACCTAA | | |
| NR2E1/ OSTM1 | OST3F | 997 | ACGGATCGATCGCGGTTT TGGTAAGGAT | Chr6: 108542828-108542915 | 87 |
| | OST3R | 998 | CGCAAAAACGAAAAACTA CGTACGCGCT | | |
| | OST4F | 999 | GTTGTTTGAGGACGGGTC GTTTAGCGG | Chr6: 108543090-108543189 | 99 |
| | OST4R | 1000 | ACCCCTATCCTACAACCC TACGAACGCA | | |
| PAMR1 | PAM4F | 1001 | TTTCGGGAGGTGTGGTTA CGTTTGGAGA | Chr11: 35503958-35504077 | 119 |
| | PAM4R | 1002 | CCCCTCCTCCCAACACCC AACACTAAAA | | |
| SCRN1 | SCR2F | 1003 | GGTTGTGGTTTTTAAAAG GGAAAATTCGGG | Chr7: 29996282-29996388 | 106 |
| | SCR2R | 1004 | TAAACGCCGAAACCCGA ACGTAACAACC | | |

TABLE 15-continued lists the primers used herein for each probe.

| Gene | Probe | SEQ ID NO. | 5' 3' Primer Sequence (Bisulfite) | Chr: Location | PCR Product Length |
|------|-------|------------|-----------------------------------|---------------|--------------------|
| SEZ6 | SEZ3F | 1005 | AGGTGATTAGAAGGGAG AGGGGGAGGTT | Chr17: 24371083- 24371180 | 97 |
| | SEZ3R | 1006 | TCATTATACACGACGCGC CCCTCCAAAT | | |
| | SEZ5F | 1007 | TACGTGGGTGTAGGTTAG GTCGGGTTGA | Chr17: 24371224- 24371345 | 121 |
| | SEZ5R | 1008 | ACCACGCGACTACCGTAT AAACAACCGAA | | |

EQUIVALENTS

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

1. How K A, Nielsen H M, Tost J. DNA methylation based biomarkers: practical considerations and applications. Biochimie 2012; 94: 2314-37.
2. Mikeska T, Craig J M. DNA methylation biomarkers: cancer and beyond. Genes (Basel) 2014; 5: 821-64.
3. Noehammer C, Pulverer W, Hassler M R, Hofner M, Wielscher M, Vierlinger K, et al. Strategies for validation and testing of DNA methylation biomarkers. Epigenomics. 2014; 6: 603-22.
4. Warton K, Samimi G. Methylation of cell-free circulating DNA in the diagnosis of cancer. Front Mol. Biosci. 2015; 2: 13.
5. Wittenberger T, Sleigh S, Reisel D, Zikan M, Wahl B, Alunni-Fabbroni M, et al. DNA methylation markers for early detection of women's cancer: promise and challenges. Epigenomics. 2014; 6: 311-27.
6. Usadel H, Brabender J, Danenberg K D, Jeronimo C, Harden S, Engles J, et al. Quantitative adenomatous polyposis coli promoter methylation analysis in tumour tissue, serum, and plasma DNA of patients with lung cancer. Cancer Res. 2002; 62: 371-5.
7. Esteller M, Sanchez-Cespedes M, Rosell R, Sidransky D, Baylin S B, Herman J G. Detection of aberrant promoter hypermethylation of tumour suppressor genes in serum DNA from non-small cell lung cancer patients. Cancer Res. 1999; 59: 67-70.
8. Mazurek A, Pierzyna M, Giglok M, Dworzecka U, Suwinski R, Ma U E. Quantification of concentration and assessment of EGFR mutation in circulating DNA. Cancer Biomark. 2015; 15: 515-24.
9. Ostrow K L, Hoque M O, Loyo M, Brait M, Greenberg A, Siegfried J M, et al. Molecular analysis of plasma DNA for the early detection of lung cancer by quantitative methylation-specific PCR. Clin. Cancer Res. 2010; 16: 3463-72.
10. Powrozek T, Krawczyk P, Kucharczyk T, Milanowski J. Septin 9 promoter region methylation in free circulating DNA-potential role in noninvasive diagnosis of lung cancer: preliminary report. Med. Oncol. 2014; 31: 917.
11. Lin P C, Lin J K, Lin C H, Lin H H, Yang S H, Jiang J K, et al. Clinical Relevance of Plasma DNA Methylation in Colorectal Cancer Patients Identified by Using a Genome-Wide High-Resolution Array. Ann. Surg. Oncol. 2014.
12. Philipp A B, Nagel D, Stieber P, Lamerz R, Thalhammer I, Herbst A, et al. Circulating cell-free methylated DNA and lactate dehydrogenase release in colorectal cancer. BMC. Cancer 2014; 14: 245.
13. Chimonidou M, Strati A, Malamos N, Georgoulias V, Lianidou E S. SOX17 promoter methylation in circulating tumour cells and matched cell-free DNA isolated from plasma of patients with breast cancer. Clin. Chem. 2013; 59: 270-9.
14. Chimonidou M, Tzitzira A, Strati A, Sotiropoulou G, Sfikas C, Malamos N, et al. CST6 promoter methylation in circulating cell-free DNA of breast cancer patients. Clin. Biochem. 2013; 46: 235-40.
15. Martinez-Galan J, Torres-Torres B, Nunez M I, Lopez-Penalver J, Del M R, Ruiz De Almodovar J M, et al. ESR1 gene promoter region methylation in free circulating DNA and its correlation with estrogen receptor protein expression in tumour tissue in breast cancer patients. BMC. Cancer 2014; 14: 59.
16. Matuschek C, Bolke E, Lammering G, Gerber P A, Peiper M, Budach W, et al. Methylated APC and GSTP1 genes in serum DNA correlate with the presence of circulating blood tumour cells and are associated with a more aggressive and advanced breast cancer disease. Eur. J. Med. Res. 2010; 15: 277-86.
17. Fackler M J, Lopez B Z, Umbricht C, Teo W W, Cho S, Zhang Z, et al. Novel methylated biomarkers and a robust assay to detect circulating tumour DNA in metastatic breast cancer. Cancer Res. 2014; 74: 2160-70.
18. Avraham A, Uhlmann R, Shperber A, Birnbaum M, Sandbank J, Sella A, et al. Serum DNA methylation for monitoring response to neoadjuvant chemotherapy in breast cancer patients. Int. J. Cancer 2012; 131: E1166-E1172.
19. Sharma G, Mirza S, Parshad R, Gupta S D, Ralhan R. DNA methylation of circulating DNA: a marker for monitoring efficacy of neoadjuvant chemotherapy in breast cancer patients. Tumour. Biol. 2012; 33: 1837-43.
20. Legendre C, Gooden G C, Johnson K, Martinez R A, Liang W S, Salhia B. Whole-genome bisulfite sequencing of cell-free DNA identifies signature associated with metastatic breast cancer. Clin. Epigenetics. 2015; 7: 100.
21. Jones P A. Functions of DNA methylation: islands, start sites, gene bodies and beyond. Nat. Rev. Genet. 2012; 13: 484-92.

22. Cope L M, Fackler M J, Lopez-Bujanda Z, Wolff A C, Visvanathan K, Gray J W, et al. Do breast cancer cell lines provide a relevant model of the patient tumour methylome? PLOS. One. 2014; 9: e105545.

23. Becker D, Lutsik P, Ebert P, Bock C, Lengauer T, Walter J. BiQ Analyzer HiMod: an interactive software tool for high-throughput locus-specific analysis of 5-methylcytosine and its oxidized derivatives. Nucleic Acids Res. 2014; 42: W501-W507

24. Lutsik P, Feuerbach L, Arand J, Lengauer T, Walter J, Bock C. BiQ Analyzer HT: locus-specific analysis of DNA methylation by high-throughput bisulfite sequencing. Nucleic Acids Res. 2011; 39: W551-W556.

25. Soreide K. Receiver-operating characteristic curve analysis in diagnostic, prognostic and predictive biomarker research. J. Clin. Pathol. 2009; 62: 1-5.

26. Madic, J. et al. Pyrophosphorolysis-activated polymerization detects circulating tumor DNA in metastatic uveal melanoma. Clinical Cancer Research: an official journal of the American Association for Cancer Research. 2012; 18: 3934-3941.

27. Bidard, F. C. et al. Detection rate and prognostic value of circulating tumor cells and circulating tumor DNA in metastatic uveal melanoma. International Journal of Cancer 2014; 134: 1207-1213.

28 The Molecular Taxonomy of Primary Prostate Cancer. Cell. 2015; 163(4): 1011-25.

All references referred to herein are expressly incorporated by reference in their entireties.

---

The invention claimed is:

1. A method of detecting methylated DNA in a tumour of a human subject having breast cancer, comprising:

amplifying multiple regions of tumour DNA extracted from a cell-free sample obtained from a human subject with a plurality of PCR primer pairs;

wherein the multiple regions are either (I) the regions amplified by a primer pair from each of (1) to (19) below:

(1) SEQ ID NOs: 166 and 167, SEQ ID NOs: 168 and 169, or SEQ ID NOs: 168 and 170, (2) SEQ ID NOs: 171 and 172, SEQ ID NOs: 171 and 173, SEQ ID NOs: 174 and 175, SEQ ID NOs: 174 and 177, SEQ ID NOs: 176 and 177, SEQ ID NOs: 176 and 175, SEQ ID NOs: 178 and 179, or SEQ ID NOs: 919 and 920, (3) SEQ ID NOs: 184 and 185, SEQ ID NOs: 186 and 187, SEQ ID NOs: 186 and 189, SEQ ID NOs: 188 and 189, or SEQ ID NOs: 188 and 187, (4) SEQ ID NOs: 199 and 200, or SEQ ID NOs: 201 and 202, (5) SEQ ID NOs: 213 and 214, SEQ ID NOs: 215 and 216, or SEQ ID NOs: 217 and 218, (6) SEQ ID NOs: 233 and 235, SEQ ID NOs: 234 and 235, SEQ ID NOs: 236 and 237, SEQ ID NOs: 236 and 238, SEQ ID NOs: 239 and 240, SEQ ID NOs: 239 and 242, SEQ ID NOs: 241 and 242, or SEQ ID NOs: 241 and 240, (7) SEQ ID NOs: 243 and 244, SEQ ID NOs: 245 and 246, or SEQ ID NOs: 245 and 247, (8) SEQ ID NOs: 254 and 255, or SEQ ID NOs: 256 and 257, (9) SEQ ID NOs: 317 and 318,

(10) SEQ ID NOs: 652 and 653, SEQ ID NOs: 654 and 655, SEQ ID NOs: 656 and 657, or SEQ ID NOs: 658 and 659,

(11) SEQ ID NOs: 712 and 713, or SEQ ID NOs: 714 and 715,

(12) SEQ ID NOs: 736 and 737, SEQ ID NOs: 738 and 740, or SEQ ID NOs: 739 and 740,

(13) SEQ ID NOs: 787 and 788,

(14) SEQ ID NOs: 803 and 804,

(15) SEQ ID NOs: 789 and 190,

(16) SEQ ID NOs: 567 and 568,

(17) SEQ ID NOs: 429 and 430,

(18) SEQ ID NOs: 779 and 780, or SEQ ID NOs: 781 and 782, and

(19) SEQ ID NOs: 797 and 798, or (II) the regions amplified by a primer pair from a plurality of (20) to (124) below:

(20) SEQ ID NOs: 1 and 2, SEQ ID NOs: 3 and 4, SEQ ID NOs: 3 and 5, SEQ ID NOs: 6 and 7, SEQ ID NOs: 8 and 9, SEQ ID NOs: 10 and 11, SEQ ID NOs: 12 and 13, or SEQ ID NOs: 14 and 15,

(21) SEQ ID NOs: 16 and 18, SEQ ID NOs: 17 and 18, SEQ ID NOs: 19 and 20, SEQ ID NOs: 19 and 21, SEQ ID NOs: 22 and 23, SEQ ID NOs: 24 and 25, SEQ ID NOs: 26 and 27, SEQ ID NOs: 28 and 29, SEQ ID NOs: 30 and 31, SEQ ID NOs: 32 and 33, SEQ ID NOs: 34 and 35, or SEQ ID NOs: 36 and 37,

(22) SEQ ID NOs: 56 and 57, SEQ ID NOs: 58 and 59, SEQ ID NOs: 60 and 61, SEQ ID NOs: 62 and 63, SEQ ID NOs: 64 and 65, or SEQ ID NOs: 66 and 67,

(23) SEQ ID NOs: 38 and 39, SEQ ID NOs: 40 and 41, SEQ ID NOs: 42 and 43, SEQ ID NOs: 44 and 45, SEQ ID NOs: 46 and 47, SEQ ID NOs: 48 and 49, SEQ ID NOs: 50 and 51, SEQ ID NOs: 52 and 53, or SEQ ID NOs: 54 and 55,

(24) SEQ ID NOs: 154 and 155, SEQ ID NOs: 156 and 157, SEQ ID NOs: 158 and 159, SEQ ID NOs: 160 and 161, SEQ ID NOs: 162 and 163, or SEQ ID NOs: 164 and 165,

(25) SEQ ID NOs: 68 and 69, SEQ ID NOs: 70 and 71, SEQ ID NOs: 72 and 73, SEQ ID NOs: 72 and 74, SEQ ID NOs: 75 and 76, SEQ ID NOs: 77 and 78, SEQ ID NOs: 79 and 80, or SEQ ID NOs: 81 and 82,

(26) 83 and 84, SEQ ID NOs: 85 and 86, SEQ ID NOs: 87 and 88, SEQ ID NOs: 87 and 89, SEQ ID NOs: 90 and 91, SEQ ID NOs: 92 and 93, SEQ ID NOs: 94 and 95, SEQ ID NOs: 96 and 97, or SEQ ID NOs: 98 and 99,

(27) 100 and 102, SEQ ID NOs: 101 and 102, SEQ ID NOs: 103 and 104, SEQ ID NOs: 105 and 106, SEQ ID NOs: 105 and 107, SEQ ID NOs: 108 and 109, SEQ ID NOs: 110 and 112, SEQ ID NOs: 111 and 112, SEQ ID NOs: 113 and 114, SEQ ID NOs: 115 and 116, SEQ ID NOs: 117 and 118, SEQ ID NOs: 119 and 120, SEQ ID NOs: 575 and 576, or SEQ ID NOs: 577 and 578,

(28) SEQ ID NOs: 121 and 123, SEQ ID NOs: 122 and 123, SEQ ID NOs: 124 and 125, SEQ ID NOs: 126 and 127, SEQ ID NOs: 128 and 129, SEQ ID NOs: 130 and 131, SEQ ID NOs: 132 and 133, SEQ ID NOs: 134 and 135, SEQ ID NOs: 136 and 137, or SEQ ID NOs: 829 and 830,

(29) SEQ ID NOs: 138 and 139, SEQ ID NOs: 140 and 141, SEQ ID NOs: 142 and 143, SEQ ID NOs: 144 and 145, SEQ ID NOs: 146 and 147, SEQ ID NOs: 148 and 149, SEQ ID NOs: 150 and 151, or SEQ ID NOs: 152 and 153,

(30) SEQ ID NOs: 166 and 167, SEQ ID NOs: 168 and 169, or SEQ ID NOs: 168 and 170,

(31) SEQ ID NOs: 171 and 172, SEQ ID NOs: 171 and 173, SEQ ID NOs: 174 and 175, SEQ ID NOs: 174 and 177, SEQ ID NOs: 176 and 177, SEQ ID NOs: 176 and 175, SEQ ID NOs: 178 and 179, or SEQ ID NOs: 919 and 920,

(32) SEQ ID NOs: 180 and 181, or SEQ ID NOs: 182 and 183,

(33) SEQ ID NOs: 184 and 185, SEQ ID NOs: 186 and 187, SEQ ID NOs: 186 and 189, SEQ ID NOs: 188 and 189, or SEQ ID NOs: 188 and 187,

(34) SEQ ID NOs: 190 and 191, SEQ ID NOs: 192 and 194, or SEQ ID NOs: 193 and 194,

(35) SEQ ID NOs: 195 and 196, or SEQ ID NOs: 197 and 198,

(36) SEQ ID NOs: 199 and 200, or SEQ ID NOs: 201 and 202,

(37) SEQ ID NOs: 203 and 204, or SEQ ID NOs: 205 and 206,

(38) SEQ ID NOs: 207 and 208, SEQ ID NOs: 209 and 210, SEQ ID NOs: 209 and 211, SEQ ID NOs: 211 and 212, or SEQ ID NOs: 211 and 210,

(39) SEQ ID NOs: 213 and 214, SEQ ID NOs: 215 and 216, or SEQ ID NOs: 217 and 218,

(40) SEQ ID NOs: 219 and 220, SEQ ID NOs: 219 and 221, or SEQ ID NOs: 222 and 223,

(41) SEQ ID NOs: 224 and 225, or SEQ ID NOs: 226 and 227,

(42) SEQ ID NOs: 228 and 229, SEQ ID NOs: 228 and 230, or SEQ ID NOs: 231 and 232,

(43) SEQ ID NOs: 233 and 235, SEQ ID NOs: 234 and 235, SEQ ID NOs: 236 and 237, SEQ ID NOs: 236 and 238, SEQ ID NOs: 239 and 240, SEQ ID NOs: 239 and 242, SEQ ID NOs: 241 and 242, or SEQ ID NOs: 241 and 240,

(44) SEQ ID NOs: 243 and 244, SEQ ID NOs: 245 and 246, or SEQ ID NOs: 245 and 247,

(45) SEQ ID NOs: 248 and 249, SEQ ID NOs: 250 and 251, SEQ ID NOs: 250 and 253, SEQ ID NOs: 252 and 253, or SEQ ID NOs: 252 and 251,

(46) SEQ ID NOs: 254 and 255, or SEQ ID NOs: 256 and 257,

(47) SEQ ID NOs: 258 and 259, SEQ ID NOs: 258 and 261, SEQ ID NOs: 260 and 261, SEQ ID NOs: 260 and 259, SEQ ID NOs: 262 and 264, or SEQ ID NOs: 263 and 264,

(48) SEQ ID NOs: 265 and 266, SEQ ID NOs: 267 and 268, SEQ ID NOs: 269 and 271, or SEQ ID NOs: 270 and 271,

(49) SEQ ID NOs: 272 and 274, SEQ ID NOs: 273 and 274, or SEQ ID NOs: 275 and 276,

(50) SEQ ID NOs: 277 and 278, SEQ ID NOs: 279 and 280, SEQ ID NOs: 279 and 281, SEQ ID NOs: 281 and 282, or SEQ ID NOs: 281 and 280,

(51) SEQ ID NOs: 283 and 284, or 285 and 286,

(52) SEQ ID NOs: 287 and 288, SEQ ID NOs: 287 and 290, SEQ ID NOs: 289 and 291, or SEQ ID NOs: 289 and 288,

(53) SEQ ID NOs: 291 and 292, SEQ ID NOs: 293 and 294, SEQ ID NOs: 295 and 297, SEQ ID NOs: 296 and 297, SEQ ID NOs: 298 and 299, SEQ ID NOs: 298 and 300, or SEQ ID NOs: 301 and 302,

(54) SEQ ID NOs: 303 and 304, or SEQ ID NOs: 305 and 306,

(55) SEQ ID NOs: 307 and 308,

(56) SEQ ID NOs: 309 and 310, SEQ ID NOs: 309 and 312, SEQ ID NOs: 311 and 312, SEQ ID NOs: 311 and 310, SEQ ID NOs: 313 and 314, SEQ ID NOs: 313 and 316, SEQ ID NOs: 315 and 316, or SEQ ID NOs: 315 and 314,

(57) SEQ ID NOs: 317 and 318,

(58) SEQ ID NOs: 319 and 320, SEQ ID NOs: 319 and 322, SEQ ID NOs: 321 and 322, or SEQ ID NOs: 321 and 320,

(59) SEQ ID NOs: 323 and 324,

(60) SEQ ID NOs: 325 and 326,

(61) SEQ ID NOs: 327 and 328, or SEQ ID NOs: 893 and 894,

(62) SEQ ID NOs: 329 and 330, SEQ ID NOs: 329 and 322, SEQ ID NOs: 331 and 332, or SEQ ID NOs: 331 and 330,

(63) SEQ ID NOs: 335 and 336, SEQ ID NOs: 337 and 338, SEQ ID NOs: 337 and 340, SEQ ID NOs: 339 and 340, SEQ ID NOs: 340 and 339, SEQ ID NOs: 341 and 342, SEQ ID NOs: 341 and 344, SEQ ID NOs: 343 and 344, or SEQ ID NOs: 343 and 342,

(64) SEQ ID NOs: 333 and 334,

(65) SEQ ID NOs: 345 and 346, SEQ ID NOs: 345 and 348, SEQ ID NOs: 347 and 348, or SEQ ID NOs: 347 and 346,

(66) SEQ ID NOs: 349 and 350, SEQ ID NOs: 349 and 352, SEQ ID NOs: 351 and 352, SEQ ID NOs: 351 and 350, or SEQ ID NOs: 353 and 354,

(67) SEQ ID NOs: 355 and 356, SEQ ID NOs: 355 and 358, SEQ ID NOs: 357 and 358, or SEQ ID NOs: 357 and 356,

(68) SEQ ID NOs: 359 and 360, or SEQ ID NOs: 361 and 362,

(69) SEQ ID NOs: 613 and 614, SEQ ID NOs: 615 and 616, or SEQ ID NOs: 617 and 618,

(70) SEQ ID NOs: 619 and 620, or 621 and 622,

(71) SEQ ID NOs: 623 and 624, SEQ ID NOs: 625 and 626, or SEQ ID NOs: 625 and 627,

(72) SEQ ID NOs: 628 and 629, SEQ ID NOs: 628 and 631, SEQ ID NOs: 630 and 631, SEQ ID NOs: 630 and 629, or SEQ ID NOs: 632 and 633,

(73) SEQ ID NOs: 634 and 635, or SEQ ID NOs: 636 and 637,

(74) SEQ ID NOs: 638 and 639, or SEQ ID NOs: 640 and 641,

(75) SEQ ID NOs: 642 and 643, SEQ ID NOs: 642 and 645, SEQ ID NOs: 644 and 645, SEQ ID NOs: 644 and 643, SEQ ID NOs: 646 and 647, SEQ ID NOs: 646 and 649, SEQ ID NOs: 648 and 649, or SEQ ID NOs: 650 and 651,

(76) SEQ ID NOs: 652 and 653, SEQ ID NOs: 654 and 655, SEQ ID NOs: 656 and 657, or SEQ ID NOs: 658 and 659,

(77) SEQ ID NOs: 660 and 661, or SEQ ID NOs: 865 and 866,

(78) SEQ ID NOs: 662 and 663, or SEQ ID NOs: 664 and 665,

(79) SEQ ID NOs: 666 and 667, SEQ ID NOs: 666 and 669, SEQ ID NOs: 668 and 669, SEQ ID NOs: 668 and 667, or SEQ ID NOs: 670 and 671, SEQ ID NOs: 672 and 673, SEQ ID NOs: 672 and 675, SEQ ID NOs: 674 and (80) 675, SEQ ID NOs: 674 and 673, SEQ ID NOs: 676 and 677, or SEQ ID NOs: 678 and 679,

(81) SEQ ID NOs: 680 and 682, SEQ ID NOs: 681 and 682, or SEQ ID NOs: 683 and 684,

(82) SEQ ID NOs: 685 and 686, SEQ ID NOs: 685 and 688, SEQ ID NOs: 687 and 688, SEQ ID NOs: 687 and 686, SEQ ID NOs: 689 and 690, or SEQ ID NOs: 691 and 692,

(83) SEQ ID NOs: 694 and 694, or SEQ ID NOs: 695 and 696,

(84) SEQ ID NOs: 697 and 698, SEQ ID NOs: 697 and 700, SEQ ID NOs: 699 and 700, SEQ ID NOs: 699 and 698, SEQ ID NOs: 701 and 702, SEQ ID NOs: 701 and 704, SEQ ID NOs: 703 and 704, SEQ ID NOs: 703 and 702, SEQ ID NOs: 705 and 706, or SEQ ID NOs: 705 and 707,

(85) SEQ ID NOs: 708 and 709, or SEQ ID NOs: 710 and 711,

(86) SEQ ID NOs: 712 and 713, or SEQ ID NOs: 714 and 715,

(87) SEQ ID NOs: 716 and 717, SEQ ID NOs: 716 and 719, SEQ ID NOs: 718 and 719, SEQ ID NOs: 718 and 717, or SEQ ID NOs: 720 and 721,

(88) SEQ ID NOs: 722 and 723, or SEQ ID NOs: 724 and 725,

(89) SEQ ID NOs: 726 and 727, SEQ ID NOs: 726 and 729, SEQ ID NOs: 728 and 729, SEQ ID NOs: 728 and 727, or SEQ ID NOs: 730 and 731,

(90) SEQ ID NOs: 732 and 733, or SEQ ID NOs: 734 and 735,

(91) SEQ ID NOs: 736 and 737, SEQ ID NOs: 738 and 740, or SEQ ID NOs: 739 and 740,

(92) SEQ ID NOs: 741 and 742, or SEQ ID NOs: 743 and 744,

(93) SEQ ID NOs: 745 and 746, SEQ ID NOs: 745 and 748, SEQ ID NOs: 747 and 748, SEQ ID NOs: 747 and 746, SEQ ID NOs: 749 and 750, SEQ ID NOs: 749 and 752, SEQ ID NOs: 751 and 752, or SEQ ID NOs: 751 and 750,

(94) SEQ ID NOs: 753 and 754, or SEQ ID NOs: 755 and 756,

(95) SEQ ID NOs: 787 and 788,

(96) SEQ ID NOs: 335 and 336, SEQ ID NOs: 337 and 338, SEQ ID NOs: 337 and 340, SEQ ID NOs: 339 and 340, SEQ ID NOs: 339 and 338, SEQ ID NOs: 341 and 342, SEQ ID NOs: 341 and 344, SEQ ID NOs: 343 and 344, or SEQ ID NOs: 343 and 342,

(97) SEQ ID NOs: 783 and 784, or SEQ ID NOs: 785 and 786,

(98) SEQ ID NOs: 602 and 604,

(99) SEQ ID NOs: 759 and 760, (100) SEQ ID NOs: 773 and 774, (101) SEQ ID NOs: 801 and 802, (102) SEQ ID NOs: 397 and 398, (103) SEQ ID NOs: 813 and 814, (104) SEQ ID NOs: 815 and 816, (105) SEQ ID NOs: 803 and 804, (106) SEQ ID NOs: 811 and 812, (107) SEQ ID NOs: 789 and 190, (108) SEQ ID NOs: 431 and 432

(109) SEQ ID NOs: 809 and 810, (110) SEQ ID NOs: 791 and 792, or SEQ ID NOs: 793 and 794, (111) SEQ ID NOs: 567 and 568, (112) SEQ ID NOs: 479 and 480, (113) SEQ ID NOs: 775 and 776, (114) SEQ ID NOs: 429 and 430, (115) SEQ ID NOs: 765 and 766, or SEQ ID NOs: 767 and 768, (116) SEQ ID NOs: 777 and 778, (117) SEQ ID NOs: 795 and 796, (118) SEQ ID NOs: 363 and 364, (119) SEQ ID NOs: 563 and 564, (120) SEQ ID NOs: 486 and 486, (121) SEQ ID NOs: 779 and 780, or SEQ ID NOs: 781 and 782, (122) SEQ ID NOs: 797 and 798, (123) SEQ ID NOs: 378 and 379, and (124) SEQ ID NOs: 799 and 800, wherein individual primer pairs of the plurality of PCR primer pairs are modified to include non-native DNA sequences corresponding to methylation specific versions of the multiple regions by selecting C residues to be replaced with T residues according to their methylation status within individual regions of the multiple selected regions;

generating sequencing reads from each of the amplified regions;

aligning the sequencing reads with a reference sequence for each region, wherein the reference sequence is obtained from a cell-free sample obtained from a healthy human subject and the aligning is performed by a computer; and detecting with a computer a level of methylation of CpG residues within the two or more selected regions in the DNA extracted from the cell-free sample.

2. The method according to claim 1, wherein the cell-free sample is a blood sample.

3. A kit for detecting breast cancer in tumour DNA extracted from a cell-free sample obtained from a human subject, comprising:

reagents for carrying out a method of detecting breast cancer, the reagents comprising either:

(I) primer pairs from each of (1) to (19) below:

(1) SEQ ID NOs: 166 and 167, SEQ ID NOs: 168 and 169, or SEQ ID NOs: 168 and 170, (2) SEQ ID NOs: 171 and 172, SEQ ID NOs: 171 and 173, SEQ ID NOs: 174 and 175, SEQ ID NOs: 174 and 177, SEQ ID NOs: 176 and 177, SEQ ID NOs: 176 and 175, SEQ ID NOs: 178 and 179, or SEQ ID NOs: 919 and 920, (3) SEQ ID NOs: 184 and 185, SEQ ID NOs: 186 and 187, SEQ ID NOs: 186 and 189, SEQ ID NOs: 188 and 189, or SEQ ID NOs: 188 and 187, (4) SEQ ID NOs: 199 and 200, or SEQ ID NOs: 201 and 202, (5) SEQ ID NOs: 213 and 214, SEQ ID NOs: 215 and 216, or SEQ ID NOs: 217 and 218, (6) SEQ ID NOs: 233 and 235, SEQ ID NOs: 234 and 235, SEQ ID NOs: 236 and 237, SEQ ID NOs: 236 and 238, SEQ ID NOs: 239 and 240, SEQ ID NOs: 239 and 242, SEQ ID NOs: 241 and 242, or SEQ ID NOs: 241 and 240, (7) SEQ ID NOs: 243 and 244, SEQ ID NOs: 245 and 246, or SEQ ID NOs: 245 and 247, (8) SEQ ID NOs: 254 and 255, or SEQ ID NOs: 256 and 257, (9) SEQ ID NOs: 317 and 318,

(10) SEQ ID NOs: 652 and 653, SEQ ID NOs: 654 and 655, SEQ ID NOs: 656 and 657, or SEQ ID NOs: 658 and 659,

(11) SEQ ID NOs: 712 and 713, or SEQ ID NOs: 714 and 715,

(12) SEQ ID NOs: 736 and 737, SEQ ID NOs: 738 and 740, or SEQ ID NOs: 739 and 740,

(13) SEQ ID NOs: 787 and 788,

(14) SEQ ID NOs: 803 and 804,

(15) SEQ ID NOs: 789 and 190,

(16) SEQ ID NOs: 567 and 568,

(17) SEQ ID NOs: 429 and 430,

(18) SEQ ID NOs: 779 and 780, or SEQ ID NOs: 781 and 782, and

(19) SEQ ID NOs: 797 and 798, or (II) the primer pairs of a plurality of (20) to (124) below:

(20) SEQ ID NOs: 1 and 2, SEQ ID NOs: 3 and 4, SEQ ID NOs: 3 and 5, SEQ ID NOs: 6 and 7, SEQ ID NOs: 8 and 9, SEQ ID NOs: 10 and 11, SEQ ID NOs: 12 and 13, or SEQ ID NOs: 14 and 15,

(21) SEQ ID NOs: 16 and 18, SEQ ID NOs: 17 and 18, SEQ ID NOs: 19 and 20, SEQ ID NOs: 19 and 21, SEQ ID NOs: 22 and 23, SEQ ID NOs: 24 and 25, SEQ ID NOs: 26 and 27, SEQ ID NOs: 28 and 29, SEQ ID NOs: 30 and 31, SEQ ID NOs: 32 and 33, SEQ ID NOs: 34 and 35, or SEQ ID NOs: 36 and 37,

(22) SEQ ID NOs: 56 and 57, SEQ ID NOs: 58 and 59, SEQ ID NOs: 60 and 61, SEQ ID NOs: 62 and 63, SEQ ID NOs: 64 and 65, or SEQ ID NOs: 66 and 67,

(23) SEQ ID NOs: 38 and 39, SEQ ID NOs: 40 and 41, SEQ ID NOs: 42 and 43, SEQ ID NOs: 44 and 45, SEQ ID NOs: 46 and 47, SEQ ID NOs: 48 and 49, SEQ ID NOs: 50 and 51, SEQ ID NOs: 52 and 53, or SEQ ID NOs: 54 and 55,

(24) SEQ ID NOs: 154 and 155, SEQ ID NOs: 156 and 157, SEQ ID NOs: 158 and 159, SEQ ID NOs: 160 and 161, SEQ ID NOs: 162 and 163, or SEQ ID NOs: 164 and 165,

(25) SEQ ID NOs: 68 and 69, SEQ ID NOs: 70 and 71, SEQ ID NOs: 72 and 73, SEQ ID NOs: 72 and 74, SEQ ID NOs: 75 and 76, SEQ ID NOs: 77 and 78, SEQ ID NOs: 79 and 80, or SEQ ID NOs: 81 and 82,

(26) 83 and 84, SEQ ID NOs: 85 and 86, SEQ ID NOs: 87 and 88, SEQ ID NOs: 87 and 89, SEQ ID NOs: 90 and 91, SEQ ID NOs: 92 and 93, SEQ ID NOs: 94 and 95, SEQ ID NOs: 96 and 97, or SEQ ID NOs: 98 and 99,

(27) 100 and 102, SEQ ID NOs: 101 and 102, SEQ ID NOs: 103 and 104, SEQ ID NOs: 105 and 106, SEQ ID NOs: 105 and 107, SEQ ID NOs: 108 and 109, SEQ ID NOs: 110 and 112, SEQ ID NOs: 111 and 112, SEQ ID NOs: 113 and 114, SEQ ID NOs: 115 and 116, SEQ ID NOs: 117 and 118, SEQ ID NOs: 119 and 120, SEQ ID NOs: 575 and 576, or SEQ ID NOs: 577 and 578,

(28) SEQ ID NOs: 121 and 123, SEQ ID NOs: 122 and 123, SEQ ID NOs: 124 and 125, SEQ ID NOs: 126 and 127, SEQ ID NOs: 128 and 129, SEQ ID NOs: 130 and 131, SEQ ID NOs: 132 and 133, SEQ ID NOs: 134 and 135, SEQ ID NOs: 136 and 137, or SEQ ID NOs: 829 and 830,

(29) SEQ ID NOs: 138 and 139, SEQ ID NOs: 140 and 141, SEQ ID NOs: 142 and 143, SEQ ID NOs: 144 and 145, SEQ ID NOs: 146 and 147, SEQ ID NOs: 148 and 149, SEQ ID NOs: 150 and 151, or SEQ ID NOs: 152 and 153,

(30) SEQ ID NOs: 166 and 167, SEQ ID NOs: 168 and 169, or SEQ ID NOs: 168 and 170,

(31) SEQ ID NOs: 171 and 172, SEQ ID NOs: 171 and 173, SEQ ID NOs: 174 and 175, SEQ ID NOs: 174 and 177, SEQ ID NOs: 176 and 177, SEQ ID NOs: 176 and 175, SEQ ID NOs: 178 and 179, or SEQ ID NOs: 919 and 920,

(32) SEQ ID NOs: 180 and 181, or SEQ ID NOs: 182 and 183,

(33) SEQ ID NOs: 184 and 185, SEQ ID NOs: 186 and 187, SEQ ID NOs: 186 and 189, SEQ ID NOs: 188 and 189, or SEQ ID NOs: 188 and 187,

(34) SEQ ID NOs: 190 and 191, SEQ ID NOs: 192 and 194, or SEQ ID NOs: 193 and 194,

(35) SEQ ID NOs: 195 and 196, or SEQ ID NOs: 197 and 198,

(36) SEQ ID NOs: 199 and 200, or SEQ ID NOs: 201 and 202,

(37) SEQ ID NOs: 203 and 204, or SEQ ID NOs: 205 and 206,

(38) SEQ ID NOs: 207 and 208, SEQ ID NOs: 209 and 210, SEQ ID NOs: 209 and 211, SEQ ID NOs: 211 and 212, or SEQ ID NOs: 211 and 210,

(39) SEQ ID NOs: 213 and 214, SEQ ID NOs: 215 and 216, or SEQ ID NOs: 217 and 218,

(40) SEQ ID NOs: 219 and 220, SEQ ID NOs: 219 and 221, or SEQ ID NOs: 222 and 223,

(41) SEQ ID NOs: 224 and 225, or SEQ ID NOs: 226 and 227,

(42) SEQ ID NOs: 228 and 229, SEQ ID NOs: 228 and 230, or SEQ ID NOs: 231 and 232,

(43) SEQ ID NOs: 233 and 235, SEQ ID NOs: 234 and 235, SEQ ID NOs: 236 and 237, SEQ ID NOs: 236 and 238, SEQ ID NOs: 239 and 240, SEQ ID NOs: 239 and 242, SEQ ID NOs: 241 and 242, or SEQ ID NOs: 241 and 240,

(44) SEQ ID NOs: 243 and 244, SEQ ID NOs: 245 and 246, or SEQ ID NOs: 245 and 247,

(45) SEQ ID NOs: 248 and 249, SEQ ID NOs: 250 and 251, SEQ ID NOs: 250 and 253, SEQ ID NOs: 252 and 253, or SEQ ID NOs: 252 and 251,

(46) SEQ ID NOs: 254 and 255, or SEQ ID NOs: 256 and 257,

(47) SEQ ID NOs: 258 and 259, SEQ ID NOs: 258 and 261, SEQ ID NOs: 260 and 261, SEQ ID NOs: 260 and 259, SEQ ID NOs: 262 and 264, or SEQ ID NOs: 263 and 264,

(48) SEQ ID NOs: 265 and 266, SEQ ID NOs: 267 and 268, SEQ ID NOs: 269 and 271, or SEQ ID NOs: 270 and 271,

(49) SEQ ID NOs: 272 and 274, SEQ ID NOs: 273 and 274, or SEQ ID NOs: 275 and 276,

(50) SEQ ID NOs: 277 and 278, SEQ ID NOs: 279 and 280, SEQ ID NOs: 279 and 281, SEQ ID NOs: 281 and 282, or SEQ ID NOs: 281 and 280,

(51) SEQ ID NOs: 283 and 284, or 285 and 286,

(52) SEQ ID NOs: 287 and 288, SEQ ID NOs: 287 and 290, SEQ ID NOs: 289 and 291, or SEQ ID NOs: 289 and 288,

(53) SEQ ID NOs: 291 and 292, SEQ ID NOs: 293 and 294, SEQ ID NOs: 295 and 297, SEQ ID NOs: 296 and 297, SEQ ID NOs: 298 and 299, SEQ ID NOs: 298 and 300, or SEQ ID NOs: 301 and 302,

(54) SEQ ID NOs: 303 and 304, or SEQ ID NOs: 305 and 306,

(55) SEQ ID NOs: 307 and 308,

(56) SEQ ID NOs: 309 and 310, SEQ ID NOs: 309 and 312, SEQ ID NOs: 311 and 312, SEQ ID NOs: 311 and 310, SEQ ID NOs: 313 and 314, SEQ ID NOs: 313 and 316, SEQ ID NOs: 315 and 316, or SEQ ID NOs: 315 and 314,

(57) SEQ ID NOs: 317 and 318,

(58) SEQ ID NOs: 319 and 320, SEQ ID NOs: 319 and 322, SEQ ID NOs: 321 and 322, or SEQ ID NOs: 321 and 320,

(59) SEQ ID NOs: 323 and 324,

(60) SEQ ID NOs: 325 and 326,

(61) SEQ ID NOs: 327 and 328, or SEQ ID NOs: 893 and 894,

(62) SEQ ID NOs: 329 and 330, SEQ ID NOs: 329 and 322, SEQ ID NOs: 331 and 332, or SEQ ID NOs: 331 and 330,

(63) SEQ ID NOs: 335 and 336, SEQ ID NOs: 337 and 338, SEQ ID NOs: 337 and 340, SEQ ID NOs: 339 and 340, SEQ ID NOs: 340 and 339, SEQ ID NOs: 341 and 342, SEQ ID NOs: 341 and 344, SEQ ID NOs: 343 and 344, or SEQ ID NOs: 343 and 342,

(64) SEQ ID NOs: 333 and 334,

(65) SEQ ID NOs: 345 and 346, SEQ ID NOs: 345 and 348, SEQ ID NOs: 347 and 348, or SEQ ID NOs: 347 and 346,

(66) SEQ ID NOs: 349 and 350, SEQ ID NOs: 349 and 352, SEQ ID NOs: 351 and 352, SEQ ID NOs: 351 and 350, or SEQ ID NOs: 353 and 354,

(67) SEQ ID NOs: 355 and 356, SEQ ID NOs: 355 and 358, SEQ ID NOs: 357 and 358, or SEQ ID NOs: 357 and 356,

(68) SEQ ID NOs: 359 and 360, or SEQ ID NOs: 361 and 362,

(69) SEQ ID NOs: 613 and 614, SEQ ID NOs: 615 and 616, or SEQ ID NOs: 617 and 618,

(70) SEQ ID NOs: 619 and 620, or 621 and 622,

(71) SEQ ID NOs: 623 and 624, SEQ ID NOs: 625 and 626, or SEQ ID NOs: 625 and 627,

(72) SEQ ID NOs: 628 and 629, SEQ ID NOs: 628 and 631, SEQ ID NOs: 630 and 631, SEQ ID NOs: 630 and 629, or SEQ ID NOs: 632 and 633,

(73) SEQ ID NOs: 634 and 635, or SEQ ID NOs: 636 and 637,

(74) SEQ ID NOs: 638 and 639, or SEQ ID NOs: 640 and 641,

(75) SEQ ID NOs: 642 and 643, SEQ ID NOs: 642 and 645, SEQ ID NOs: 644 and 645, SEQ ID NOs: 644 and 643, SEQ ID NOs: 646 and 647, SEQ ID NOs: 646 and 649, SEQ ID NOs: 648 and 649, or SEQ ID NOs: 650 and 651,

(76) SEQ ID NOs: 652 and 653, SEQ ID NOs: 654 and 655, SEQ ID NOs: 656 and 657, or SEQ ID NOs: 658 and 659,

(77) SEQ ID NOs: 660 and 661, or SEQ ID NOs: 865 and 866,

(78) SEQ ID NOs: 662 and 663, or SEQ ID NOs: 664 and 665,

(79) SEQ ID NOs: 666 and 667, SEQ ID NOs: 666 and 669, SEQ ID NOs: 668 and 669, SEQ ID NOs: 668 and 667, or SEQ ID NOs: 670 and 671,

(80) SEQ ID NOs: 672 and 673, SEQ ID NOs: 672 and 675, SEQ ID NOs: 674 and 675, SEQ ID NOs: 674 and 673, SEQ ID NOs: 676 and 677, or SEQ ID NOs: 678 and 679,

(81) SEQ ID NOs: 680 and 682, SEQ ID NOs: 681 and 682, or SEQ ID NOs: 683 and 684,

(82) SEQ ID NOs: 685 and 686, SEQ ID NOs: 685 and 688, SEQ ID NOs: 687 and 688, SEQ ID NOs: 687 and 686, SEQ ID NOs: 689 and 690, or SEQ ID NOs: 691 and 692,

(83) SEQ ID NOs: 694 and 694, or SEQ ID NOs: 695 and 696,

(84) SEQ ID NOs: 697 and 698, SEQ ID NOs: 697 and 700, SEQ ID NOs: 699 and 700, SEQ ID NOs: 699 and 698, SEQ ID NOs: 701 and 702, SEQ ID NOs: 701 and 704, SEQ ID NOs: 703 and 704, SEQ ID NOs: 703 and 702, SEQ ID NOs: 705 and 706, or SEQ ID NOs: 705 and 707,

(85) SEQ ID NOs: 708 and 709, or SEQ ID NOs: 710 and 711,

(86) SEQ ID NOs: 712 and 713, or SEQ ID NOs: 714 and 715,

(87) SEQ ID NOs: 716 and 717, SEQ ID NOs: 716 and 719, SEQ ID NOs: 718 and 719, SEQ ID NOs: 718 and 717, or SEQ ID NOs: 720 and 721,

(88) SEQ ID NOs: 722 and 723, or SEQ ID NOs: 724 and 725,

(89) SEQ ID NOs: 726 and 727, SEQ ID NOs: 726 and 729, SEQ ID NOs: 728 and 729, SEQ ID NOs: 728 and 727, or SEQ ID NOs: 730 and 731,

(90) SEQ ID NOs: 732 and 733, or SEQ ID NOs: 734 and 735,

(91) SEQ ID NOs: 736 and 737, SEQ ID NOs: 738 and 740, or SEQ ID NOs: 739 and 740,

(92) SEQ ID NOs: 741 and 742, or SEQ ID NOs: 743 and 744,

(93) SEQ ID NOs: 745 and 746, SEQ ID NOs: 745 and 748, SEQ ID NOs: 747 and 748, SEQ ID NOs: 747 and 746, SEQ ID NOs: 749 and 750, SEQ ID NOs: 749 and 752, SEQ ID NOs: 751 and 752, or SEQ ID NOs: 751 and 750,

(94) SEQ ID NOs: 753 and 754, or SEQ ID NOs: 755 and 756,

(95) SEQ ID NOs: 787 and 788,

(96) SEQ ID NOs: 335 and 336, SEQ ID NOs: 337 and 338, SEQ ID NOs: 337 and 340, SEQ ID NOs: 339 and 340, SEQ ID NOs: 339 and 338, SEQ ID NOs: 341 and 342, SEQ ID NOs: 341 and 344, SEQ ID NOs: 343 and 344, or SEQ ID NOs: 343 and 342,

(97) SEQ ID NOs: 783 and 784, or SEQ ID NOs: 785 and 786,

(98) SEQ ID NOs: 602 and 604,

(99) SEQ ID NOs: 759 and 760, (100) SEQ ID NOs: 773 and 774, (101) SEQ ID NOs: 801 and 802, (102) SEQ ID NOs: 397 and 398, (103) SEQ ID NOs: 813 and 814, (104) SEQ ID NOs: 815 and 816, (105) SEQ ID NOs: 803 and 804, (106) SEQ ID NOs: 811 and 812, (107) SEQ ID NOs: 789 and 190, (108) SEQ ID NOs: 431 and 432

(109) SEQ ID NOs: 809 and 810, (110) SEQ ID NOs: 791 and 792, or SEQ ID NOs: 793
    and 794,
(111) SEQ ID NOs: 567 and 568,
(112) SEQ ID NOs: 479 and 480,
(113) SEQ ID NOs: 775 and 776,
(114) SEQ ID NOs: 429 and 430,
(115) SEQ ID NOs: 765 and 766, or SEQ ID NOs: 767
    and 768,
(116) SEQ ID NOs: 777 and 778,
(117) SEQ ID NOs: 795 and 796,
(118) SEQ ID NOs: 363 and 364,
(119) SEQ ID NOs: 563 and 564,
(120) SEQ ID NOs: 486 and 486,
(121) SEQ ID NOs: 779 and 780, or SEQ ID NOs: 781
    and 782,
(122) SEQ ID NOs: 797 and 798,
(123) SEQ ID NOs: 378 and 379, and
(124) SEQ ID NOs: 799 and 800,
wherein the primers are modified to include non-native
    DNA sequences corresponding to methylation spe-
    cific versions of the multiple regions by selecting C
    residues to be replaced with T residues according to
    their methylation status such that the primers anneal
    to a methylated sequence.

*    *    *    *    *

SEQUENCE LISTING

```
Sequence total quantity: 1008
SEQ ID NO: 1              moltype = DNA  length = 22
FEATURE                  Location/Qualifiers
source                   1..22
                         mol_type = unassigned DNA
                         organism = Homo sapiens
SEQUENCE: 1
ttgaggtaaa ggagatttcg gt                                          22

SEQ ID NO: 2              moltype = DNA  length = 23
FEATURE                  Location/Qualifiers
source                   1..23
                         mol_type = unassigned DNA
                         organism = Homo sapiens
SEQUENCE: 2
acatacgcct acgcaaattt tta                                         23

SEQ ID NO: 3              moltype = DNA  length = 21
FEATURE                  Location/Qualifiers
source                   1..21
                         mol_type = unassigned DNA
                         organism = Homo sapiens
SEQUENCE: 3
ttcggtgttt gcgaagggtt a                                           21

SEQ ID NO: 4              moltype = DNA  length = 23
FEATURE                  Location/Qualifiers
source                   1..23
                         mol_type = unassigned DNA
                         organism = Homo sapiens
SEQUENCE: 4
tcacaaccaa cacaacgaca ctt                                         23

SEQ ID NO: 5              moltype = DNA  length = 21
FEATURE                  Location/Qualifiers
source                   1..21
                         mol_type = unassigned DNA
                         organism = Homo sapiens
SEQUENCE: 5
acaaccaaca caacgacact t                                           21

SEQ ID NO: 6              moltype = DNA  length = 20
FEATURE                  Location/Qualifiers
source                   1..20
                         mol_type = unassigned DNA
                         organism = Homo sapiens
SEQUENCE: 6
tcggtatttg ttttcgcggt                                             20

SEQ ID NO: 7              moltype = DNA  length = 22
FEATURE                  Location/Qualifiers
source                   1..22
                         mol_type = unassigned DNA
                         organism = Homo sapiens
SEQUENCE: 7
cgcctacgca aatttttatc gc                                          22
```

-continued

```
SEQ ID NO: 8          moltype = DNA  length = 22
FEATURE               Location/Qualifiers
source                1..22
                      mol_type = unassigned DNA
                      organism = Homo sapiens
SEQUENCE: 8
cgagagcgat aaaaatttgc gt                                              22

SEQ ID NO: 9          moltype = DNA  length = 20
FEATURE               Location/Qualifiers
source                1..20
                      mol_type = unassigned DNA
                      organism = Homo sapiens
SEQUENCE: 9
acccttcgca aacaccgaaa                                                 20

SEQ ID NO: 10         moltype = DNA  length = 19
FEATURE               Location/Qualifiers
source                1..19
                      mol_type = unassigned DNA
                      organism = Homo sapiens
SEQUENCE: 10
ggtaatagcg tgtttttgc                                                  19

SEQ ID NO: 11         moltype = DNA  length = 22
FEATURE               Location/Qualifiers
source                1..22
                      mol_type = unassigned DNA
                      organism = Homo sapiens
SEQUENCE: 11
atattacata cgcctacgca aa                                              22

SEQ ID NO: 12         moltype = DNA  length = 20
FEATURE               Location/Qualifiers
source                1..20
                      mol_type = unassigned DNA
                      organism = Homo sapiens
SEQUENCE: 12
tttgtgtaaa atgcggcggt                                                 20

SEQ ID NO: 13         moltype = DNA  length = 22
FEATURE               Location/Qualifiers
source                1..22
                      mol_type = unassigned DNA
                      organism = Homo sapiens
SEQUENCE: 13
ctaccgcgaa aacaaatacc ga                                              22

SEQ ID NO: 14         moltype = DNA  length = 20
FEATURE               Location/Qualifiers
source                1..20
                      mol_type = unassigned DNA
                      organism = Homo sapiens
SEQUENCE: 14
atttcggtgt ttgcgaaggg                                                 20

SEQ ID NO: 15         moltype = DNA  length = 20
FEATURE               Location/Qualifiers
source                1..20
                      mol_type = unassigned DNA
                      organism = Homo sapiens
SEQUENCE: 15
acaaccaaca caacgacact                                                 20

SEQ ID NO: 16         moltype = DNA  length = 20
FEATURE               Location/Qualifiers
source                1..20
                      mol_type = unassigned DNA
                      organism = Homo sapiens
SEQUENCE: 16
tttcggttgt cgggtttgga                                                 20

SEQ ID NO: 17         moltype = DNA  length = 22
FEATURE               Location/Qualifiers
source                1..22
                      mol_type = unassigned DNA
                      organism = Homo sapiens
SEQUENCE: 17
tatttcggtt gtcgggtttg ga                                              22
```

```
SEQ ID NO: 18          moltype = DNA   length = 20
FEATURE                Location/Qualifiers
source                 1..20
                       mol_type = unassigned DNA
                       organism = Homo sapiens
SEQUENCE: 18
ccctcaatcg ctcatcctcc                                              20

SEQ ID NO: 19          moltype = DNA   length = 20
FEATURE                Location/Qualifiers
source                 1..20
                       mol_type = unassigned DNA
                       organism = Homo sapiens
SEQUENCE: 19
tcgtcggtcg gtttaggatg                                              20

SEQ ID NO: 20          moltype = DNA   length = 22
FEATURE                Location/Qualifiers
source                 1..22
                       mol_type = unassigned DNA
                       organism = Homo sapiens
SEQUENCE: 20
aaaaccgacg ccaaacctac at                                           22

SEQ ID NO: 21          moltype = DNA   length = 20
FEATURE                Location/Qualifiers
source                 1..20
                       mol_type = unassigned DNA
                       organism = Homo sapiens
SEQUENCE: 21
aaccgacgcc aaacctacat                                              20

SEQ ID NO: 22          moltype = DNA   length = 20
FEATURE                Location/Qualifiers
source                 1..20
                       mol_type = unassigned DNA
                       organism = Homo sapiens
SEQUENCE: 22
cggaggatga gcgattgagg                                              20

SEQ ID NO: 23          moltype = DNA   length = 20
FEATURE                Location/Qualifiers
source                 1..20
                       mol_type = unassigned DNA
                       organism = Homo sapiens
SEQUENCE: 23
taacgcgcac accgaactaa                                              20

SEQ ID NO: 24          moltype = DNA   length = 20
FEATURE                Location/Qualifiers
source                 1..20
                       mol_type = unassigned DNA
                       organism = Homo sapiens
SEQUENCE: 24
cgagttgggg tcgcgattat                                              20

SEQ ID NO: 25          moltype = DNA   length = 20
FEATURE                Location/Qualifiers
source                 1..20
                       mol_type = unassigned DNA
                       organism = Homo sapiens
SEQUENCE: 25
catcctaaac cgaccgacga                                              20

SEQ ID NO: 26          moltype = DNA   length = 20
FEATURE                Location/Qualifiers
source                 1..20
                       mol_type = unassigned DNA
                       organism = Homo sapiens
SEQUENCE: 26
cgacgcgtta cggttgttta                                              20

SEQ ID NO: 27          moltype = DNA   length = 20
FEATURE                Location/Qualifiers
source                 1..20
                       mol_type = unassigned DNA
                       organism = Homo sapiens
SEQUENCE: 27
```

-continued

```
ccgcttctcc gaaaccaaac                                                       20

SEQ ID NO: 28          moltype = DNA   length = 20
FEATURE                Location/Qualifiers
source                 1..20
                       mol_type = unassigned DNA
                       organism = Homo sapiens
SEQUENCE: 28
taaggcgggg tttttagagc                                                       20

SEQ ID NO: 29          moltype = DNA   length = 18
FEATURE                Location/Qualifiers
source                 1..18
                       mol_type = unassigned DNA
                       organism = Homo sapiens
SEQUENCE: 29
taaaaactaa cgcgcccg                                                         18

SEQ ID NO: 30          moltype = DNA   length = 18
FEATURE                Location/Qualifiers
source                 1..18
                       mol_type = unassigned DNA
                       organism = Homo sapiens
SEQUENCE: 30
ggtttcggtg ttattcgc                                                         18

SEQ ID NO: 31          moltype = DNA   length = 19
FEATURE                Location/Qualifiers
source                 1..19
                       mol_type = unassigned DNA
                       organism = Homo sapiens
SEQUENCE: 31
ctcctctccg cgaaaaat                                                         19

SEQ ID NO: 32          moltype = DNA   length = 20
FEATURE                Location/Qualifiers
source                 1..20
                       mol_type = unassigned DNA
                       organism = Homo sapiens
SEQUENCE: 32
cggaggatga gcgattgagg                                                       20

SEQ ID NO: 33          moltype = DNA   length = 20
FEATURE                Location/Qualifiers
source                 1..20
                       mol_type = unassigned DNA
                       organism = Homo sapiens
SEQUENCE: 33
taacgcgcac accgaactaa                                                       20

SEQ ID NO: 34          moltype = DNA   length = 20
FEATURE                Location/Qualifiers
source                 1..20
                       mol_type = unassigned DNA
                       organism = Homo sapiens
SEQUENCE: 34
tcgtcggtcg gtttaggatg                                                       20

SEQ ID NO: 35          moltype = DNA   length = 20
FEATURE                Location/Qualifiers
source                 1..20
                       mol_type = unassigned DNA
                       organism = Homo sapiens
SEQUENCE: 35
aaccgacgcc aaacctacat                                                       20

SEQ ID NO: 36          moltype = DNA   length = 20
FEATURE                Location/Qualifiers
source                 1..20
                       mol_type = unassigned DNA
                       organism = Homo sapiens
SEQUENCE: 36
gtcggacgcg ttttagttgg                                                       20

SEQ ID NO: 37          moltype = DNA   length = 20
FEATURE                Location/Qualifiers
source                 1..20
                       mol_type = unassigned DNA
                       organism = Homo sapiens
```

```
SEQUENCE: 37
tccctaccga cctcaacact                                                    20

SEQ ID NO: 38          moltype = DNA   length = 20
FEATURE                Location/Qualifiers
source                 1..20
                       mol_type = unassigned DNA
                       organism = Homo sapiens
SEQUENCE: 38
tggttggggg attttgaggg                                                    20

SEQ ID NO: 39          moltype = DNA   length = 20
FEATURE                Location/Qualifiers
source                 1..20
                       mol_type = unassigned DNA
                       organism = Homo sapiens
SEQUENCE: 39
aaacctcccc gcctacctat                                                    20

SEQ ID NO: 40          moltype = DNA   length = 20
FEATURE                Location/Qualifiers
source                 1..20
                       mol_type = unassigned DNA
                       organism = Homo sapiens
SEQUENCE: 40
gcggacggtt tggagaaatg                                                    20

SEQ ID NO: 41          moltype = DNA   length = 20
FEATURE                Location/Qualifiers
source                 1..20
                       mol_type = unassigned DNA
                       organism = Homo sapiens
SEQUENCE: 41
cgcgactcaa tctcaccact                                                    20

SEQ ID NO: 42          moltype = DNA   length = 20
FEATURE                Location/Qualifiers
source                 1..20
                       mol_type = unassigned DNA
                       organism = Homo sapiens
SEQUENCE: 42
ggaggttggg tttcgggatt                                                    20

SEQ ID NO: 43          moltype = DNA   length = 20
FEATURE                Location/Qualifiers
source                 1..20
                       mol_type = unassigned DNA
                       organism = Homo sapiens
SEQUENCE: 43
gcgcccctaa actcgtatct                                                    20

SEQ ID NO: 44          moltype = DNA   length = 20
FEATURE                Location/Qualifiers
source                 1..20
                       mol_type = unassigned DNA
                       organism = Homo sapiens
SEQUENCE: 44
gcggagtggt gagattgagt                                                    20

SEQ ID NO: 45          moltype = DNA   length = 20
FEATURE                Location/Qualifiers
source                 1..20
                       mol_type = unassigned DNA
                       organism = Homo sapiens
SEQUENCE: 45
accgacttct tcgattcgcc                                                    20

SEQ ID NO: 46          moltype = DNA   length = 20
FEATURE                Location/Qualifiers
source                 1..20
                       mol_type = unassigned DNA
                       organism = Homo sapiens
SEQUENCE: 46
ataggtaggc ggggaggttt                                                    20

SEQ ID NO: 47          moltype = DNA   length = 19
FEATURE                Location/Qualifiers
source                 1..19
                       mol_type = unassigned DNA
```

```
                        organism = Homo sapiens
SEQUENCE: 47
cgatccccca actcaaccc                                                               19

SEQ ID NO: 48          moltype = DNA  length = 20
FEATURE                Location/Qualifiers
source                 1..20
                       mol_type = unassigned DNA
                       organism = Homo sapiens
SEQUENCE: 48
tgagttggcg gtttcgtttg                                                              20

SEQ ID NO: 49          moltype = DNA  length = 20
FEATURE                Location/Qualifiers
source                 1..20
                       mol_type = unassigned DNA
                       organism = Homo sapiens
SEQUENCE: 49
cccgaatccc ctcttatccc                                                              20

SEQ ID NO: 50          moltype = DNA  length = 20
FEATURE                Location/Qualifiers
source                 1..20
                       mol_type = unassigned DNA
                       organism = Homo sapiens
SEQUENCE: 50
cgcgattttg tagtcggggt                                                              20

SEQ ID NO: 51          moltype = DNA  length = 20
FEATURE                Location/Qualifiers
source                 1..20
                       mol_type = unassigned DNA
                       organism = Homo sapiens
SEQUENCE: 51
tttcctatcg ccccaacacc                                                              20

SEQ ID NO: 52          moltype = DNA  length = 20
FEATURE                Location/Qualifiers
source                 1..20
                       mol_type = unassigned DNA
                       organism = Homo sapiens
SEQUENCE: 52
ggaggttggg tttcgggatt                                                              20

SEQ ID NO: 53          moltype = DNA  length = 20
FEATURE                Location/Qualifiers
source                 1..20
                       mol_type = unassigned DNA
                       organism = Homo sapiens
SEQUENCE: 53
gcgcccctaa actcgtatct                                                              20

SEQ ID NO: 54          moltype = DNA  length = 20
FEATURE                Location/Qualifiers
source                 1..20
                       mol_type = unassigned DNA
                       organism = Homo sapiens
SEQUENCE: 54
gattgagtcg cgatggaacg                                                              20

SEQ ID NO: 55          moltype = DNA  length = 20
FEATURE                Location/Qualifiers
source                 1..20
                       mol_type = unassigned DNA
                       organism = Homo sapiens
SEQUENCE: 55
gccgccttca acccaaaata                                                              20

SEQ ID NO: 56          moltype = DNA  length = 20
FEATURE                Location/Qualifiers
source                 1..20
                       mol_type = unassigned DNA
                       organism = Homo sapiens
SEQUENCE: 56
cgcgagcgta tagagtacga                                                              20

SEQ ID NO: 57          moltype = DNA  length = 20
FEATURE                Location/Qualifiers
source                 1..20
```

-continued

```
                        mol_type = unassigned DNA
                        organism = Homo sapiens
SEQUENCE: 57
accctaacca accccgaaac                                            20

SEQ ID NO: 58          moltype = DNA   length = 20
FEATURE                Location/Qualifiers
source                 1..20
                        mol_type = unassigned DNA
                        organism = Homo sapiens
SEQUENCE: 58
tagcgtcgcg agcgtataga                                            20

SEQ ID NO: 59          moltype = DNA   length = 20
FEATURE                Location/Qualifiers
source                 1..20
                        mol_type = unassigned DNA
                        organism = Homo sapiens
SEQUENCE: 59
aaaaataacc cgacgcccga                                            20

SEQ ID NO: 60          moltype = DNA   length = 21
FEATURE                Location/Qualifiers
source                 1..21
                        mol_type = unassigned DNA
                        organism = Homo sapiens
SEQUENCE: 60
ggtttcgtag aagaggtttt c                                          21

SEQ ID NO: 61          moltype = DNA   length = 20
FEATURE                Location/Qualifiers
source                 1..20
                        mol_type = unassigned DNA
                        organism = Homo sapiens
SEQUENCE: 61
cgcgaaataa taacgacttt                                            20

SEQ ID NO: 62          moltype = DNA   length = 21
FEATURE                Location/Qualifiers
source                 1..21
                        mol_type = unassigned DNA
                        organism = Homo sapiens
SEQUENCE: 62
agaagaggtt ttcgttgggg g                                          21

SEQ ID NO: 63          moltype = DNA   length = 20
FEATURE                Location/Qualifiers
source                 1..20
                        mol_type = unassigned DNA
                        organism = Homo sapiens
SEQUENCE: 63
accaaccccg aaactcgaaa                                            20

SEQ ID NO: 64          moltype = DNA   length = 20
FEATURE                Location/Qualifiers
source                 1..20
                        mol_type = unassigned DNA
                        organism = Homo sapiens
SEQUENCE: 64
taggatttgg ggttggtgcg                                            20

SEQ ID NO: 65          moltype = DNA   length = 20
FEATURE                Location/Qualifiers
source                 1..20
                        mol_type = unassigned DNA
                        organism = Homo sapiens
SEQUENCE: 65
aacgcaacga cgaacgtaac                                            20

SEQ ID NO: 66          moltype = DNA   length = 20
FEATURE                Location/Qualifiers
source                 1..20
                        mol_type = unassigned DNA
                        organism = Homo sapiens
SEQUENCE: 66
tggtagtggg gagatcgagg                                            20

SEQ ID NO: 67          moltype = DNA   length = 20
FEATURE                Location/Qualifiers
```

-continued

```
source                  1..20
                        mol_type = unassigned DNA
                        organism = Homo sapiens
SEQUENCE: 67
aaacgccccc aactctaacc                                                    20

SEQ ID NO: 68           moltype = DNA   length = 18
FEATURE                 Location/Qualifiers
source                  1..18
                        mol_type = unassigned DNA
                        organism = Homo sapiens
SEQUENCE: 68
gttgcggacg gcgtagat                                                      18

SEQ ID NO: 69           moltype = DNA   length = 21
FEATURE                 Location/Qualifiers
source                  1..21
                        mol_type = unassigned DNA
                        organism = Homo sapiens
SEQUENCE: 69
acgctccccg aaacaataac t                                                  21

SEQ ID NO: 70           moltype = DNA   length = 21
FEATURE                 Location/Qualifiers
source                  1..21
                        mol_type = unassigned DNA
                        organism = Homo sapiens
SEQUENCE: 70
ttgttagttt tgttagcgcg g                                                  21

SEQ ID NO: 71           moltype = DNA   length = 21
FEATURE                 Location/Qualifiers
source                  1..21
                        mol_type = unassigned DNA
                        organism = Homo sapiens
SEQUENCE: 71
cgtccgcaac gattcatcat c                                                  21

SEQ ID NO: 72           moltype = DNA   length = 22
FEATURE                 Location/Qualifiers
source                  1..22
                        mol_type = unassigned DNA
                        organism = Homo sapiens
SEQUENCE: 72
tgtttaggag atggttcgtg gt                                                 22

SEQ ID NO: 73           moltype = DNA   length = 20
FEATURE                 Location/Qualifiers
source                  1..20
                        mol_type = unassigned DNA
                        organism = Homo sapiens
SEQUENCE: 73
gcatctacgc cgtccgcaac                                                    20

SEQ ID NO: 74           moltype = DNA   length = 18
FEATURE                 Location/Qualifiers
source                  1..18
                        mol_type = unassigned DNA
                        organism = Homo sapiens
SEQUENCE: 74
atctacgccg tccgcaac                                                      18

SEQ ID NO: 75           moltype = DNA   length = 20
FEATURE                 Location/Qualifiers
source                  1..20
                        mol_type = unassigned DNA
                        organism = Homo sapiens
SEQUENCE: 75
tgtttagacg tgggttgggg                                                    20

SEQ ID NO: 76           moltype = DNA   length = 20
FEATURE                 Location/Qualifiers
source                  1..20
                        mol_type = unassigned DNA
                        organism = Homo sapiens
SEQUENCE: 76
tcaactccac tcaccccgta                                                    20

SEQ ID NO: 77           moltype = DNA   length = 20
```

-continued

```
FEATURE                 Location/Qualifiers
source                  1..20
                        mol_type = unassigned DNA
                        organism = Homo sapiens
SEQUENCE: 77
gaggagggtg gagagggtag                                                          20

SEQ ID NO: 78          moltype = DNA   length = 20
FEATURE                 Location/Qualifiers
source                  1..20
                        mol_type = unassigned DNA
                        organism = Homo sapiens
SEQUENCE: 78
ataccgcacg tactcccaac                                                          20

SEQ ID NO: 79          moltype = DNA   length = 20
FEATURE                 Location/Qualifiers
source                  1..20
                        mol_type = unassigned DNA
                        organism = Homo sapiens
SEQUENCE: 79
ggagtggagt aggtagcggt                                                          20

SEQ ID NO: 80          moltype = DNA   length = 20
FEATURE                 Location/Qualifiers
source                  1..20
                        mol_type = unassigned DNA
                        organism = Homo sapiens
SEQUENCE: 80
ttcctaaccc tctccgacca                                                          20

SEQ ID NO: 81          moltype = DNA   length = 20
FEATURE                 Location/Qualifiers
source                  1..20
                        mol_type = unassigned DNA
                        organism = Homo sapiens
SEQUENCE: 81
tttttgagcg gtgaagggga                                                          20

SEQ ID NO: 82          moltype = DNA   length = 20
FEATURE                 Location/Qualifiers
source                  1..20
                        mol_type = unassigned DNA
                        organism = Homo sapiens
SEQUENCE: 82
aattattaac gcgaccgccg                                                          20

SEQ ID NO: 83          moltype = DNA   length = 24
FEATURE                 Location/Qualifiers
source                  1..24
                        mol_type = unassigned DNA
                        organism = Homo sapiens
SEQUENCE: 83
gtaataattt ggtggtatcg gggg                                                     24

SEQ ID NO: 84          moltype = DNA   length = 23
FEATURE                 Location/Qualifiers
source                  1..23
                        mol_type = unassigned DNA
                        organism = Homo sapiens
SEQUENCE: 84
tctactaaac gaacacgtaa cgc                                                      23

SEQ ID NO: 85          moltype = DNA   length = 21
FEATURE                 Location/Qualifiers
source                  1..21
                        mol_type = unassigned DNA
                        organism = Homo sapiens
SEQUENCE: 85
ataatttggt ggtatcgggg g                                                        21

SEQ ID NO: 86          moltype = DNA   length = 25
FEATURE                 Location/Qualifiers
source                  1..25
                        mol_type = unassigned DNA
                        organism = Homo sapiens
SEQUENCE: 86
acgcgttatt attctactaa acgaa                                                    25
```

-continued

```
SEQ ID NO: 87          moltype = DNA   length = 23
FEATURE                Location/Qualifiers
source                 1..23
                       mol_type = unassigned DNA
                       organism = Homo sapiens
SEQUENCE: 87
tggggtttgt tttaattgtg gtt                                        23

SEQ ID NO: 88          moltype = DNA   length = 22
FEATURE                Location/Qualifiers
source                 1..22
                       mol_type = unassigned DNA
                       organism = Homo sapiens
SEQUENCE: 88
gcgaaacccg cgccttctta at                                         22

SEQ ID NO: 89          moltype = DNA   length = 20
FEATURE                Location/Qualifiers
source                 1..20
                       mol_type = unassigned DNA
                       organism = Homo sapiens
SEQUENCE: 89
gaaacccgcg ccttcttaat                                            20

SEQ ID NO: 90          moltype = DNA   length = 27
FEATURE                Location/Qualifiers
source                 1..27
                       mol_type = unassigned DNA
                       organism = Homo sapiens
SEQUENCE: 90
ggggaagtat agttatttaa taagttg                                    27

SEQ ID NO: 91          moltype = DNA   length = 23
FEATURE                Location/Qualifiers
source                 1..23
                       mol_type = unassigned DNA
                       organism = Homo sapiens
SEQUENCE: 91
acaaaacatc raaccattaa taa                                        23

SEQ ID NO: 92          moltype = DNA   length = 20
FEATURE                Location/Qualifiers
source                 1..20
                       mol_type = unassigned DNA
                       organism = Homo sapiens
SEQUENCE: 92
ttcgcgaagg agagcgtatc                                            20

SEQ ID NO: 93          moltype = DNA   length = 20
FEATURE                Location/Qualifiers
source                 1..20
                       mol_type = unassigned DNA
                       organism = Homo sapiens
SEQUENCE: 93
ccctacgtac acccccaaac                                            20

SEQ ID NO: 94          moltype = DNA   length = 20
FEATURE                Location/Qualifiers
source                 1..20
                       mol_type = unassigned DNA
                       organism = Homo sapiens
SEQUENCE: 94
cgtttggggg tgtacgtagg                                            20

SEQ ID NO: 95          moltype = DNA   length = 20
FEATURE                Location/Qualifiers
source                 1..20
                       mol_type = unassigned DNA
                       organism = Homo sapiens
SEQUENCE: 95
aaacccaata cacgcgacga                                            20

SEQ ID NO: 96          moltype = DNA   length = 20
FEATURE                Location/Qualifiers
source                 1..20
                       mol_type = unassigned DNA
                       organism = Homo sapiens
SEQUENCE: 96
tttgtcgggg aggttggttt                                            20
```

-continued

```
SEQ ID NO: 97           moltype = DNA   length = 20
FEATURE                 Location/Qualifiers
source                  1..20
                        mol_type = unassigned DNA
                        organism = Homo sapiens
SEQUENCE: 97
ttcctactaa acgccgacgc                                             20

SEQ ID NO: 98           moltype = DNA   length = 20
FEATURE                 Location/Qualifiers
source                  1..20
                        mol_type = unassigned DNA
                        organism = Homo sapiens
SEQUENCE: 98
tagcgtttgg ttcgttcggt                                             20

SEQ ID NO: 99           moltype = DNA   length = 20
FEATURE                 Location/Qualifiers
source                  1..20
                        mol_type = unassigned DNA
                        organism = Homo sapiens
SEQUENCE: 99
ataaaaacgc gaacgccgac                                             20

SEQ ID NO: 100          moltype = DNA   length = 20
FEATURE                 Location/Qualifiers
source                  1..20
                        mol_type = unassigned DNA
                        organism = Homo sapiens
SEQUENCE: 100
gcgggcgttt cgattgattt                                             20

SEQ ID NO: 101          moltype = DNA   length = 22
FEATURE                 Location/Qualifiers
source                  1..22
                        mol_type = unassigned DNA
                        organism = Homo sapiens
SEQUENCE: 101
ttgcgggcgt ttcgattgat tt                                          22

SEQ ID NO: 102          moltype = DNA   length = 20
FEATURE                 Location/Qualifiers
source                  1..20
                        mol_type = unassigned DNA
                        organism = Homo sapiens
SEQUENCE: 102
taaaaaccgc ccccactacc                                             20

SEQ ID NO: 103          moltype = DNA   length = 20
FEATURE                 Location/Qualifiers
source                  1..20
                        mol_type = unassigned DNA
                        organism = Homo sapiens
SEQUENCE: 103
tgttcggcgg tttaggtgtt                                             20

SEQ ID NO: 104          moltype = DNA   length = 20
FEATURE                 Location/Qualifiers
source                  1..20
                        mol_type = unassigned DNA
                        organism = Homo sapiens
SEQUENCE: 104
aaatcaatcg aaacgcccgc                                             20

SEQ ID NO: 105          moltype = DNA   length = 20
FEATURE                 Location/Qualifiers
source                  1..20
                        mol_type = unassigned DNA
                        organism = Homo sapiens
SEQUENCE: 105
tagttcgggt ttcgtcgtgc                                             20

SEQ ID NO: 106          moltype = DNA   length = 22
FEATURE                 Location/Qualifiers
source                  1..22
                        mol_type = unassigned DNA
                        organism = Homo sapiens
SEQUENCE: 106
```

-continued

```
aaaactaaaa accgcccca ct                                                22

SEQ ID NO: 107            moltype = DNA   length = 20
FEATURE                   Location/Qualifiers
source                    1..20
                          mol_type = unassigned DNA
                          organism = Homo sapiens
SEQUENCE: 107
aactaaaaac cgcccccact                                                  20

SEQ ID NO: 108            moltype = DNA   length = 20
FEATURE                   Location/Qualifiers
source                    1..20
                          mol_type = unassigned DNA
                          organism = Homo sapiens
SEQUENCE: 108
gtgggtggta gtttgcgttg                                                  20

SEQ ID NO: 109            moltype = DNA   length = 20
FEATURE                   Location/Qualifiers
source                    1..20
                          mol_type = unassigned DNA
                          organism = Homo sapiens
SEQUENCE: 109
cactacctcc ccgccttaaa                                                  20

SEQ ID NO: 110            moltype = DNA   length = 20
FEATURE                   Location/Qualifiers
source                    1..20
                          mol_type = unassigned DNA
                          organism = Homo sapiens
SEQUENCE: 110
gcgtgcgttt tcggttttga                                                  20

SEQ ID NO: 111            moltype = DNA   length = 22
FEATURE                   Location/Qualifiers
source                    1..22
                          mol_type = unassigned DNA
                          organism = Homo sapiens
SEQUENCE: 111
cggcgtgcgt tttcggtttt ga                                               22

SEQ ID NO: 112            moltype = DNA   length = 20
FEATURE                   Location/Qualifiers
source                    1..20
                          mol_type = unassigned DNA
                          organism = Homo sapiens
SEQUENCE: 112
aacgcaaact accacccacc                                                  20

SEQ ID NO: 113            moltype = DNA   length = 21
FEATURE                   Location/Qualifiers
source                    1..21
                          mol_type = unassigned DNA
                          organism = Homo sapiens
SEQUENCE: 113
ggacgttggg ttgagttagg a                                                21

SEQ ID NO: 114            moltype = DNA   length = 20
FEATURE                   Location/Qualifiers
source                    1..20
                          mol_type = unassigned DNA
                          organism = Homo sapiens
SEQUENCE: 114
acgaccctac aactcccta                                                   20

SEQ ID NO: 115            moltype = DNA   length = 20
FEATURE                   Location/Qualifiers
source                    1..20
                          mol_type = unassigned DNA
                          organism = Homo sapiens
SEQUENCE: 115
ggtgttcgaa ttgtacggcg                                                  20

SEQ ID NO: 116            moltype = DNA   length = 20
FEATURE                   Location/Qualifiers
source                    1..20
                          mol_type = unassigned DNA
                          organism = Homo sapiens
```

-continued

```
SEQUENCE: 116
ctacgcgccg ctcataaaaa                                                                              20

SEQ ID NO: 117            moltype = DNA   length = 20
FEATURE                   Location/Qualifiers
source                    1..20
                          mol_type = unassigned DNA
                          organism = Homo sapiens
SEQUENCE: 117
gcgcgtacgg tttcgtatag                                                                              20

SEQ ID NO: 118            moltype = DNA   length = 20
FEATURE                   Location/Qualifiers
source                    1..20
                          mol_type = unassigned DNA
                          organism = Homo sapiens
SEQUENCE: 118
atactcgctc tttacgcccg                                                                              20

SEQ ID NO: 119            moltype = DNA   length = 20
FEATURE                   Location/Qualifiers
source                    1..20
                          mol_type = unassigned DNA
                          organism = Homo sapiens
SEQUENCE: 119
tagagcggta ggtcggtagg                                                                              20

SEQ ID NO: 120            moltype = DNA   length = 20
FEATURE                   Location/Qualifiers
source                    1..20
                          mol_type = unassigned DNA
                          organism = Homo sapiens
SEQUENCE: 120
aacaaaccga accgctacac                                                                              20

SEQ ID NO: 121            moltype = DNA   length = 20
FEATURE                   Location/Qualifiers
source                    1..20
                          mol_type = unassigned DNA
                          organism = Homo sapiens
SEQUENCE: 121
gcggcgtggg aatgaatttt                                                                              20

SEQ ID NO: 122            moltype = DNA   length = 22
FEATURE                   Location/Qualifiers
source                    1..22
                          mol_type = unassigned DNA
                          organism = Homo sapiens
SEQUENCE: 122
gggcggcgtg ggaatgaatt tt                                                                           22

SEQ ID NO: 123            moltype = DNA   length = 20
FEATURE                   Location/Qualifiers
source                    1..20
                          mol_type = unassigned DNA
                          organism = Homo sapiens
SEQUENCE: 123
ctttccctcg cacccctaaa                                                                              20

SEQ ID NO: 124            moltype = DNA   length = 20
FEATURE                   Location/Qualifiers
source                    1..20
                          mol_type = unassigned DNA
                          organism = Homo sapiens
SEQUENCE: 124
tgcgagggaa agtttgggtt                                                                              20

SEQ ID NO: 125            moltype = DNA   length = 20
FEATURE                   Location/Qualifiers
source                    1..20
                          mol_type = unassigned DNA
                          organism = Homo sapiens
SEQUENCE: 125
ccgcgttacc cgaaaaactt                                                                              20

SEQ ID NO: 126            moltype = DNA   length = 20
FEATURE                   Location/Qualifiers
source                    1..20
                          mol_type = unassigned DNA
```

-continued

```
                        organism = Homo sapiens
SEQUENCE: 126
ttttaggggt gcgagggaaa                                                  20

SEQ ID NO: 127          moltype = DNA   length = 20
FEATURE                 Location/Qualifiers
source                  1..20
                        mol_type = unassigned DNA
                        organism = Homo sapiens
SEQUENCE: 127
cgcaaccgaa ctactcaccc                                                  20

SEQ ID NO: 128          moltype = DNA   length = 20
FEATURE                 Location/Qualifiers
source                  1..20
                        mol_type = unassigned DNA
                        organism = Homo sapiens
SEQUENCE: 128
gtgcgaggga aagtttgggt                                                  20

SEQ ID NO: 129          moltype = DNA   length = 19
FEATURE                 Location/Qualifiers
source                  1..19
                        mol_type = unassigned DNA
                        organism = Homo sapiens
SEQUENCE: 129
acccgcgtta cccgaaaaa                                                   19

SEQ ID NO: 130          moltype = DNA   length = 19
FEATURE                 Location/Qualifiers
source                  1..19
                        mol_type = unassigned DNA
                        organism = Homo sapiens
SEQUENCE: 130
ttttttttggt tgtcgggtc                                                  19

SEQ ID NO: 131          moltype = DNA   length = 18
FEATURE                 Location/Qualifiers
source                  1..18
                        mol_type = unassigned DNA
                        organism = Homo sapiens
SEQUENCE: 131
cgaaacccga aacacgta                                                    18

SEQ ID NO: 132          moltype = DNA   length = 20
FEATURE                 Location/Qualifiers
source                  1..20
                        mol_type = unassigned DNA
                        organism = Homo sapiens
SEQUENCE: 132
agagtggtcg ggtgtttagc                                                  20

SEQ ID NO: 133          moltype = DNA   length = 21
FEATURE                 Location/Qualifiers
source                  1..21
                        mol_type = unassigned DNA
                        organism = Homo sapiens
SEQUENCE: 133
acgtaaccca aaaactcgaa a                                                21

SEQ ID NO: 134          moltype = DNA   length = 18
FEATURE                 Location/Qualifiers
source                  1..18
                        mol_type = unassigned DNA
                        organism = Homo sapiens
SEQUENCE: 134
gtcgtttttt aggggtgc                                                    18

SEQ ID NO: 135          moltype = DNA   length = 20
FEATURE                 Location/Qualifiers
source                  1..20
                        mol_type = unassigned DNA
                        organism = Homo sapiens
SEQUENCE: 135
taaacttcgc aaccgaacta                                                  20

SEQ ID NO: 136          moltype = DNA   length = 21
FEATURE                 Location/Qualifiers
source                  1..21
```

-continued

```
                        mol_type = unassigned DNA
                        organism = Homo sapiens
SEQUENCE: 136
tattaagttt gcgtttgggt c                                         21

SEQ ID NO: 137         moltype = DNA   length = 20
FEATURE                Location/Qualifiers
source                 1..20
                       mol_type = unassigned DNA
                       organism = Homo sapiens
SEQUENCE: 137
aaaaccgtct atccctacgc                                          20

SEQ ID NO: 138         moltype = DNA   length = 20
FEATURE                Location/Qualifiers
source                 1..20
                       mol_type = unassigned DNA
                       organism = Homo sapiens
SEQUENCE: 138
cgaggtagga agttttgcgg                                          20

SEQ ID NO: 139         moltype = DNA   length = 20
FEATURE                Location/Qualifiers
source                 1..20
                       mol_type = unassigned DNA
                       organism = Homo sapiens
SEQUENCE: 139
cgactcctcc cgcgaaataa                                          20

SEQ ID NO: 140         moltype = DNA   length = 20
FEATURE                Location/Qualifiers
source                 1..20
                       mol_type = unassigned DNA
                       organism = Homo sapiens
SEQUENCE: 140
cggggtgttg ttgtagggtt                                          20

SEQ ID NO: 141         moltype = DNA   length = 19
FEATURE                Location/Qualifiers
source                 1..19
                       mol_type = unassigned DNA
                       organism = Homo sapiens
SEQUENCE: 141
aatcacacct acccacgcc                                           19

SEQ ID NO: 142         moltype = DNA   length = 20
FEATURE                Location/Qualifiers
source                 1..20
                       mol_type = unassigned DNA
                       organism = Homo sapiens
SEQUENCE: 142
tagggcggtt aggtttgggg                                          20

SEQ ID NO: 143         moltype = DNA   length = 20
FEATURE                Location/Qualifiers
source                 1..20
                       mol_type = unassigned DNA
                       organism = Homo sapiens
SEQUENCE: 143
gacgaataac cccaccctcc                                          20

SEQ ID NO: 144         moltype = DNA   length = 20
FEATURE                Location/Qualifiers
source                 1..20
                       mol_type = unassigned DNA
                       organism = Homo sapiens
SEQUENCE: 144
ttgtcgcgtt ggtttttcgt                                          20

SEQ ID NO: 145         moltype = DNA   length = 20
FEATURE                Location/Qualifiers
source                 1..20
                       mol_type = unassigned DNA
                       organism = Homo sapiens
SEQUENCE: 145
acctttctct cgaccccaat                                          20

SEQ ID NO: 146         moltype = DNA   length = 21
FEATURE                Location/Qualifiers
```

```
source                    1..21
                          mol_type = unassigned DNA
                          organism = Homo sapiens
SEQUENCE: 146
cgttttgtcg gttgcgtgtt a                                           21

SEQ ID NO: 147            moltype = DNA   length = 21
FEATURE                   Location/Qualifiers
source                    1..21
                          mol_type = unassigned DNA
                          organism = Homo sapiens
SEQUENCE: 147
attccccgac ctacccaaaa c                                           21

SEQ ID NO: 148            moltype = DNA   length = 24
FEATURE                   Location/Qualifiers
source                    1..24
                          mol_type = unassigned DNA
                          organism = Homo sapiens
SEQUENCE: 148
ggtaggtgat aacgttagtg ggtt                                        24

SEQ ID NO: 149            moltype = DNA   length = 20
FEATURE                   Location/Qualifiers
source                    1..20
                          mol_type = unassigned DNA
                          organism = Homo sapiens
SEQUENCE: 149
acctccatcc cctacccaac                                             20

SEQ ID NO: 150            moltype = DNA   length = 20
FEATURE                   Location/Qualifiers
source                    1..20
                          mol_type = unassigned DNA
                          organism = Homo sapiens
SEQUENCE: 150
agtaggggga ggtggttttg                                             20

SEQ ID NO: 151            moltype = DNA   length = 20
FEATURE                   Location/Qualifiers
source                    1..20
                          mol_type = unassigned DNA
                          organism = Homo sapiens
SEQUENCE: 151
tcctcctccc caacttaacc                                             20

SEQ ID NO: 152            moltype = DNA   length = 20
FEATURE                   Location/Qualifiers
source                    1..20
                          mol_type = unassigned DNA
                          organism = Homo sapiens
SEQUENCE: 152
agtttgggtg tggcggttta                                             20

SEQ ID NO: 153            moltype = DNA   length = 22
FEATURE                   Location/Qualifiers
source                    1..22
                          mol_type = unassigned DNA
                          organism = Homo sapiens
SEQUENCE: 153
accaacttcg ccatattaac ca                                          22

SEQ ID NO: 154            moltype = DNA   length = 20
FEATURE                   Location/Qualifiers
source                    1..20
                          mol_type = unassigned DNA
                          organism = Homo sapiens
SEQUENCE: 154
cgcggtgtat tgtgggtagt                                             20

SEQ ID NO: 155            moltype = DNA   length = 20
FEATURE                   Location/Qualifiers
source                    1..20
                          mol_type = unassigned DNA
                          organism = Homo sapiens
SEQUENCE: 155
ccttccgacc cgaatcatcc                                             20

SEQ ID NO: 156            moltype = DNA   length = 19
```

-continued

```
FEATURE               Location/Qualifiers
source                1..19
                      mol_type = unassigned DNA
                      organism = Homo sapiens
SEQUENCE: 156
ggtcgtcgga acgtgatgt                                          19

SEQ ID NO: 157        moltype = DNA  length = 20
FEATURE               Location/Qualifiers
source                1..20
                      mol_type = unassigned DNA
                      organism = Homo sapiens
SEQUENCE: 157
gccaacatca acaccaaccc                                         20

SEQ ID NO: 158        moltype = DNA  length = 20
FEATURE               Location/Qualifiers
source                1..20
                      mol_type = unassigned DNA
                      organism = Homo sapiens
SEQUENCE: 158
tcgttttgtc gttgtcgtcg                                         20

SEQ ID NO: 159        moltype = DNA  length = 21
FEATURE               Location/Qualifiers
source                1..21
                      mol_type = unassigned DNA
                      organism = Homo sapiens
SEQUENCE: 159
ttaaataacc cgctccctcc g                                       21

SEQ ID NO: 160        moltype = DNA  length = 20
FEATURE               Location/Qualifiers
source                1..20
                      mol_type = unassigned DNA
                      organism = Homo sapiens
SEQUENCE: 160
gtcgtgatgt tagagcgggc                                         20

SEQ ID NO: 161        moltype = DNA  length = 20
FEATURE               Location/Qualifiers
source                1..20
                      mol_type = unassigned DNA
                      organism = Homo sapiens
SEQUENCE: 161
accccgatcc tccttaaacg                                         20

SEQ ID NO: 162        moltype = DNA  length = 18
FEATURE               Location/Qualifiers
source                1..18
                      mol_type = unassigned DNA
                      organism = Homo sapiens
SEQUENCE: 162
ttaaggagga tcggggtc                                           18

SEQ ID NO: 163        moltype = DNA  length = 22
FEATURE               Location/Qualifiers
source                1..22
                      mol_type = unassigned DNA
                      organism = Homo sapiens
SEQUENCE: 163
tcaatacgac gttaaataac cc                                      22

SEQ ID NO: 164        moltype = DNA  length = 20
FEATURE               Location/Qualifiers
source                1..20
                      mol_type = unassigned DNA
                      organism = Homo sapiens
SEQUENCE: 164
tggagttaag cgggtggtag                                         20

SEQ ID NO: 165        moltype = DNA  length = 21
FEATURE               Location/Qualifiers
source                1..21
                      mol_type = unassigned DNA
                      organism = Homo sapiens
SEQUENCE: 165
cccgctctaa catcacgact c                                       21
```

-continued

```
SEQ ID NO: 166          moltype = DNA   length = 20
FEATURE                 Location/Qualifiers
source                  1..20
                        mol_type = unassigned DNA
                        organism = Homo sapiens
SEQUENCE: 166
gtattgtcgc gggttcgttc                                              20

SEQ ID NO: 167          moltype = DNA   length = 20
FEATURE                 Location/Qualifiers
source                  1..20
                        mol_type = unassigned DNA
                        organism = Homo sapiens
SEQUENCE: 167
ctcaaccaat ccccactccc                                              20

SEQ ID NO: 168          moltype = DNA   length = 23
FEATURE                 Location/Qualifiers
source                  1..23
                        mol_type = unassigned DNA
                        organism = Homo sapiens
SEQUENCE: 168
gttttaggtt tcgttagtat ggg                                          23

SEQ ID NO: 169          moltype = DNA   length = 29
FEATURE                 Location/Qualifiers
source                  1..29
                        mol_type = unassigned DNA
                        organism = Homo sapiens
SEQUENCE: 169
caaattaaaa taaatcattt aacccataa                                    29

SEQ ID NO: 170          moltype = DNA   length = 25
FEATURE                 Location/Qualifiers
source                  1..25
                        mol_type = unassigned DNA
                        organism = Homo sapiens
SEQUENCE: 170
ttaaaataaa tcatttaacc cataa                                        25

SEQ ID NO: 171          moltype = DNA   length = 20
FEATURE                 Location/Qualifiers
source                  1..20
                        mol_type = unassigned DNA
                        organism = Homo sapiens
SEQUENCE: 171
cgaagatttc gtaggcgggt                                              20

SEQ ID NO: 172          moltype = DNA   length = 22
FEATURE                 Location/Qualifiers
source                  1..22
                        mol_type = unassigned DNA
                        organism = Homo sapiens
SEQUENCE: 172
acgacgcaaa taacgctacg ca                                           22

SEQ ID NO: 173          moltype = DNA   length = 20
FEATURE                 Location/Qualifiers
source                  1..20
                        mol_type = unassigned DNA
                        organism = Homo sapiens
SEQUENCE: 173
gacgcaaata acgctacgca                                              20

SEQ ID NO: 174          moltype = DNA   length = 21
FEATURE                 Location/Qualifiers
source                  1..21
                        mol_type = unassigned DNA
                        organism = Homo sapiens
SEQUENCE: 174
tgttttagaa gcgggagaaa g                                            21

SEQ ID NO: 175          moltype = DNA   length = 22
FEATURE                 Location/Qualifiers
source                  1..22
                        mol_type = unassigned DNA
                        organism = Homo sapiens
SEQUENCE: 175
aaataaaacc cccgtatcca at                                           22
```

-continued

```
SEQ ID NO: 176          moltype = DNA  length = 23
FEATURE                 Location/Qualifiers
source                  1..23
                        mol_type = unassigned DNA
                        organism = Homo sapiens
SEQUENCE: 176
aatgtttttag aagcgggaga aag                                          23

SEQ ID NO: 177          moltype = DNA  length = 24
FEATURE                 Location/Qualifiers
source                  1..24
                        mol_type = unassigned DNA
                        organism = Homo sapiens
SEQUENCE: 177
aaaaataaaa cccccgtatc caat                                          24

SEQ ID NO: 178          moltype = DNA  length = 28
FEATURE                 Location/Qualifiers
source                  1..28
                        mol_type = unassigned DNA
                        organism = Homo sapiens
SEQUENCE: 178
gcggcggtta gcgttagttt ttcggtag                                      28

SEQ ID NO: 179          moltype = DNA  length = 28
FEATURE                 Location/Qualifiers
source                  1..28
                        mol_type = unassigned DNA
                        organism = Homo sapiens
SEQUENCE: 179
cgaaacgcca acgtatcata acgacgca                                      28

SEQ ID NO: 180          moltype = DNA  length = 20
FEATURE                 Location/Qualifiers
source                  1..20
                        mol_type = unassigned DNA
                        organism = Homo sapiens
SEQUENCE: 180
acgtttttagg gacggcgaat                                              20

SEQ ID NO: 181          moltype = DNA  length = 20
FEATURE                 Location/Qualifiers
source                  1..20
                        mol_type = unassigned DNA
                        organism = Homo sapiens
SEQUENCE: 181
aatcccaacg accgtctacc                                               20

SEQ ID NO: 182          moltype = DNA  length = 26
FEATURE                 Location/Qualifiers
source                  1..26
                        mol_type = unassigned DNA
                        organism = Homo sapiens
SEQUENCE: 182
tttcgttttg tatttatggt agatgt                                        26

SEQ ID NO: 183          moltype = DNA  length = 20
FEATURE                 Location/Qualifiers
source                  1..20
                        mol_type = unassigned DNA
                        organism = Homo sapiens
SEQUENCE: 183
ccaacgaccg tctaccacta                                               20

SEQ ID NO: 184          moltype = DNA  length = 20
FEATURE                 Location/Qualifiers
source                  1..20
                        mol_type = unassigned DNA
                        organism = Homo sapiens
SEQUENCE: 184
cgtggtatgg atttcggggt                                               20

SEQ ID NO: 185          moltype = DNA  length = 20
FEATURE                 Location/Qualifiers
source                  1..20
                        mol_type = unassigned DNA
                        organism = Homo sapiens
SEQUENCE: 185
```

-continued

```
actcctaacc ctaaacgcga                                          20

SEQ ID NO: 186          moltype = DNA   length = 22
FEATURE                 Location/Qualifiers
source                  1..22
                        mol_type = unassigned DNA
                        organism = Homo sapiens
SEQUENCE: 186
gtttttttcg gttttttgttc ga                                      22

SEQ ID NO: 187          moltype = DNA   length = 22
FEATURE                 Location/Qualifiers
source                  1..22
                        mol_type = unassigned DNA
                        organism = Homo sapiens
SEQUENCE: 187
tttctcccaa ttccaatatc ca                                       22

SEQ ID NO: 188          moltype = DNA   length = 24
FEATURE                 Location/Qualifiers
source                  1..24
                        mol_type = unassigned DNA
                        organism = Homo sapiens
SEQUENCE: 188
tggttttttt cggtttttgt tcga                                     24

SEQ ID NO: 189          moltype = DNA   length = 24
FEATURE                 Location/Qualifiers
source                  1..24
                        mol_type = unassigned DNA
                        organism = Homo sapiens
SEQUENCE: 189
actttctccc aattccaata tcca                                     24

SEQ ID NO: 190          moltype = DNA   length = 20
FEATURE                 Location/Qualifiers
source                  1..20
                        mol_type = unassigned DNA
                        organism = Homo sapiens
SEQUENCE: 190
gcgatcggcg attggttttt                                          20

SEQ ID NO: 191          moltype = DNA   length = 20
FEATURE                 Location/Qualifiers
source                  1..20
                        mol_type = unassigned DNA
                        organism = Homo sapiens
SEQUENCE: 191
gcgacgacac acgacctaaa                                          20

SEQ ID NO: 192          moltype = DNA   length = 20
FEATURE                 Location/Qualifiers
source                  1..20
                        mol_type = unassigned DNA
                        organism = Homo sapiens
SEQUENCE: 192
tgaggtttta ggtcgtgtgt                                          20

SEQ ID NO: 193          moltype = DNA   length = 22
FEATURE                 Location/Qualifiers
source                  1..22
                        mol_type = unassigned DNA
                        organism = Homo sapiens
SEQUENCE: 193
ggtgaggttt taggtcgtgt gt                                       22

SEQ ID NO: 194          moltype = DNA   length = 25
FEATURE                 Location/Qualifiers
source                  1..25
                        mol_type = unassigned DNA
                        organism = Homo sapiens
SEQUENCE: 194
aaaaccttaa tcgactcaaa taaaa                                    25

SEQ ID NO: 195          moltype = DNA   length = 20
FEATURE                 Location/Qualifiers
source                  1..20
                        mol_type = unassigned DNA
                        organism = Homo sapiens
```

-continued

```
SEQUENCE: 195
gggtgtagtt gcgtagcgta                                                            20

SEQ ID NO: 196          moltype = DNA   length = 20
FEATURE                 Location/Qualifiers
source                  1..20
                        mol_type = unassigned DNA
                        organism = Homo sapiens
SEQUENCE: 196
ccgaaccctc ctcaccaaaa                                                            20

SEQ ID NO: 197          moltype = DNA   length = 20
FEATURE                 Location/Qualifiers
source                  1..20
                        mol_type = unassigned DNA
                        organism = Homo sapiens
SEQUENCE: 197
tagttgcgta gcgtagggta                                                            20

SEQ ID NO: 198          moltype = DNA   length = 21
FEATURE                 Location/Qualifiers
source                  1..21
                        mol_type = unassigned DNA
                        organism = Homo sapiens
SEQUENCE: 198
tcaccaaaat cctcctaaaa c                                                          21

SEQ ID NO: 199          moltype = DNA   length = 25
FEATURE                 Location/Qualifiers
source                  1..25
                        mol_type = unassigned DNA
                        organism = Homo sapiens
SEQUENCE: 199
acgtagtgtt ggtaagattt gtaga                                                      25

SEQ ID NO: 200          moltype = DNA   length = 24
FEATURE                 Location/Qualifiers
source                  1..24
                        mol_type = unassigned DNA
                        organism = Homo sapiens
SEQUENCE: 200
acaaaaaccg cttataaacg acga                                                       24

SEQ ID NO: 201          moltype = DNA   length = 22
FEATURE                 Location/Qualifiers
source                  1..22
                        mol_type = unassigned DNA
                        organism = Homo sapiens
SEQUENCE: 201
gtaggttttt gcgttggaga tt                                                         22

SEQ ID NO: 202          moltype = DNA   length = 26
FEATURE                 Location/Qualifiers
source                  1..26
                        mol_type = unassigned DNA
                        organism = Homo sapiens
SEQUENCE: 202
attttcgtta cttctctatt cccaaa                                                     26

SEQ ID NO: 203          moltype = DNA   length = 20
FEATURE                 Location/Qualifiers
source                  1..20
                        mol_type = unassigned DNA
                        organism = Homo sapiens
SEQUENCE: 203
ggggtttcgc gttttgagtt                                                            20

SEQ ID NO: 204          moltype = DNA   length = 20
FEATURE                 Location/Qualifiers
source                  1..20
                        mol_type = unassigned DNA
                        organism = Homo sapiens
SEQUENCE: 204
aacaccaaaa cccccgctaa                                                            20

SEQ ID NO: 205          moltype = DNA   length = 22
FEATURE                 Location/Qualifiers
source                  1..22
                        mol_type = unassigned DNA
```

-continued

```
                          organism = Homo sapiens
SEQUENCE: 205
aaaagtaatt aatcggaacg gt                                              22

SEQ ID NO: 206          moltype = DNA  length = 23
FEATURE                 Location/Qualifiers
source                  1..23
                        mol_type = unassigned DNA
                        organism = Homo sapiens
SEQUENCE: 206
acactttccc aaatacaaaa aaa                                             23

SEQ ID NO: 207          moltype = DNA  length = 20
FEATURE                 Location/Qualifiers
source                  1..20
                        mol_type = unassigned DNA
                        organism = Homo sapiens
SEQUENCE: 207
tttcgagtcg gggcgtttta                                                 20

SEQ ID NO: 208          moltype = DNA  length = 20
FEATURE                 Location/Qualifiers
source                  1..20
                        mol_type = unassigned DNA
                        organism = Homo sapiens
SEQUENCE: 208
tacctaaccg ctcgctctct                                                 20

SEQ ID NO: 209          moltype = DNA  length = 19
FEATURE                 Location/Qualifiers
source                  1..19
                        mol_type = unassigned DNA
                        organism = Homo sapiens
SEQUENCE: 209
gttcggtttt gggattttt                                                  19

SEQ ID NO: 210          moltype = DNA  length = 19
FEATURE                 Location/Qualifiers
source                  1..19
                        mol_type = unassigned DNA
                        organism = Homo sapiens
SEQUENCE: 210
aatcccaaaa accgactct                                                  19

SEQ ID NO: 211          moltype = DNA  length = 23
FEATURE                 Location/Qualifiers
source                  1..23
                        mol_type = unassigned DNA
                        organism = Homo sapiens
SEQUENCE: 211
gagggttcgg ttttgggatt ttt                                             23

SEQ ID NO: 212          moltype = DNA  length = 22
FEATURE                 Location/Qualifiers
source                  1..22
                        mol_type = unassigned DNA
                        organism = Homo sapiens
SEQUENCE: 212
accaatccca aaaccgact ct                                               22

SEQ ID NO: 213          moltype = DNA  length = 20
FEATURE                 Location/Qualifiers
source                  1..20
                        mol_type = unassigned DNA
                        organism = Homo sapiens
SEQUENCE: 213
cggaggaatt tgtgtcgtcg                                                 20

SEQ ID NO: 214          moltype = DNA  length = 20
FEATURE                 Location/Qualifiers
source                  1..20
                        mol_type = unassigned DNA
                        organism = Homo sapiens
SEQUENCE: 214
caccaaaaca acgctacccg                                                 20

SEQ ID NO: 215          moltype = DNA  length = 21
FEATURE                 Location/Qualifiers
source                  1..21
```

-continued

```
                            mol_type = unassigned DNA
                            organism = Homo sapiens
SEQUENCE: 215
ttgggaattt ttttcgttta t                                              21

SEQ ID NO: 216          moltype = DNA   length = 22
FEATURE                 Location/Qualifiers
source                  1..22
                            mol_type = unassigned DNA
                            organism = Homo sapiens
SEQUENCE: 216
tcctccgaat aacttaaaaa cc                                             22

SEQ ID NO: 217          moltype = DNA   length = 24
FEATURE                 Location/Qualifiers
source                  1..24
                            mol_type = unassigned DNA
                            organism = Homo sapiens
SEQUENCE: 217
tcgttggata gtggtattta atgt                                           24

SEQ ID NO: 218          moltype = DNA   length = 20
FEATURE                 Location/Qualifiers
source                  1..20
                            mol_type = unassigned DNA
                            organism = Homo sapiens
SEQUENCE: 218
aaaatcaccg actcactcaa                                                20

SEQ ID NO: 219          moltype = DNA   length = 19
FEATURE                 Location/Qualifiers
source                  1..19
                            mol_type = unassigned DNA
                            organism = Homo sapiens
SEQUENCE: 219
cggagtacgg cggtaggaa                                                 19

SEQ ID NO: 220          moltype = DNA   length = 23
FEATURE                 Location/Qualifiers
source                  1..23
                            mol_type = unassigned DNA
                            organism = Homo sapiens
SEQUENCE: 220
aataccccga aaacccgcta ata                                            23

SEQ ID NO: 221          moltype = DNA   length = 20
FEATURE                 Location/Qualifiers
source                  1..20
                            mol_type = unassigned DNA
                            organism = Homo sapiens
SEQUENCE: 221
accccgaaaa cccgctaata                                                20

SEQ ID NO: 222          moltype = DNA   length = 22
FEATURE                 Location/Qualifiers
source                  1..22
                            mol_type = unassigned DNA
                            organism = Homo sapiens
SEQUENCE: 222
atgatatttt gtaggaaagc gt                                             22

SEQ ID NO: 223          moltype = DNA   length = 22
FEATURE                 Location/Qualifiers
source                  1..22
                            mol_type = unassigned DNA
                            organism = Homo sapiens
SEQUENCE: 223
caaattccgt ttctaaaaaa ac                                             22

SEQ ID NO: 224          moltype = DNA   length = 20
FEATURE                 Location/Qualifiers
source                  1..20
                            mol_type = unassigned DNA
                            organism = Homo sapiens
SEQUENCE: 224
gggttcgtat gcgggagtag                                                20

SEQ ID NO: 225          moltype = DNA   length = 20
FEATURE                 Location/Qualifiers
```

```
source                     1..20
                           mol_type = unassigned DNA
                           organism = Homo sapiens
SEQUENCE: 225
acgaaactac accaacgcct                                                          20

SEQ ID NO: 226             moltype = DNA   length = 21
FEATURE                    Location/Qualifiers
source                     1..21
                           mol_type = unassigned DNA
                           organism = Homo sapiens
SEQUENCE: 226
gggggttttc gttaggagta g                                                        21

SEQ ID NO: 227             moltype = DNA   length = 18
FEATURE                    Location/Qualifiers
source                     1..18
                           mol_type = unassigned DNA
                           organism = Homo sapiens
SEQUENCE: 227
aaaccgccct aaaccacc                                                            18

SEQ ID NO: 228             moltype = DNA   length = 20
FEATURE                    Location/Qualifiers
source                     1..20
                           mol_type = unassigned DNA
                           organism = Homo sapiens
SEQUENCE: 228
gaagggcggt agcgatagtt                                                          20

SEQ ID NO: 229             moltype = DNA   length = 22
FEATURE                    Location/Qualifiers
source                     1..22
                           mol_type = unassigned DNA
                           organism = Homo sapiens
SEQUENCE: 229
ctacgaattc cgcaaaccga aa                                                       22

SEQ ID NO: 230             moltype = DNA   length = 20
FEATURE                    Location/Qualifiers
source                     1..20
                           mol_type = unassigned DNA
                           organism = Homo sapiens
SEQUENCE: 230
acgaattccg caaaccgaaa                                                          20

SEQ ID NO: 231             moltype = DNA   length = 18
FEATURE                    Location/Qualifiers
source                     1..18
                           mol_type = unassigned DNA
                           organism = Homo sapiens
SEQUENCE: 231
attgtttttg tcggcgtt                                                            18

SEQ ID NO: 232             moltype = DNA   length = 19
FEATURE                    Location/Qualifiers
source                     1..19
                           mol_type = unassigned DNA
                           organism = Homo sapiens
SEQUENCE: 232
tacactacga attccgcaa                                                           19

SEQ ID NO: 233             moltype = DNA   length = 20
FEATURE                    Location/Qualifiers
source                     1..20
                           mol_type = unassigned DNA
                           organism = Homo sapiens
SEQUENCE: 233
gcgtgcgtat attcgcgttt                                                          20

SEQ ID NO: 234             moltype = DNA   length = 22
FEATURE                    Location/Qualifiers
source                     1..22
                           mol_type = unassigned DNA
                           organism = Homo sapiens
SEQUENCE: 234
cggcgtgcgt atattcgcgt tt                                                       22

SEQ ID NO: 235             moltype = DNA   length = 20
```

-continued

```
FEATURE              Location/Qualifiers
source               1..20
                     mol_type = unassigned DNA
                     organism = Homo sapiens
SEQUENCE: 235
aaattccgcc tcccctaacc                                                    20

SEQ ID NO: 236       moltype = DNA   length = 24
FEATURE              Location/Qualifiers
source               1..24
                     mol_type = unassigned DNA
                     organism = Homo sapiens
SEQUENCE: 236
tttagcgttt aatgtgtatg taga                                               24

SEQ ID NO: 237       moltype = DNA   length = 26
FEATURE              Location/Qualifiers
source               1..26
                     mol_type = unassigned DNA
                     organism = Homo sapiens
SEQUENCE: 237
cgaaattaca atcgaaacaa acttac                                             26

SEQ ID NO: 238       moltype = DNA   length = 24
FEATURE              Location/Qualifiers
source               1..24
                     mol_type = unassigned DNA
                     organism = Homo sapiens
SEQUENCE: 238
aaattacaat cgaaacaaac ttac                                               24

SEQ ID NO: 239       moltype = DNA   length = 19
FEATURE              Location/Qualifiers
source               1..19
                     mol_type = unassigned DNA
                     organism = Homo sapiens
SEQUENCE: 239
gttttgagta gggtgcgag                                                     19

SEQ ID NO: 240       moltype = DNA   length = 19
FEATURE              Location/Qualifiers
source               1..19
                     mol_type = unassigned DNA
                     organism = Homo sapiens
SEQUENCE: 240
aaaaaaacaa attccgcct                                                     19

SEQ ID NO: 241       moltype = DNA   length = 22
FEATURE              Location/Qualifiers
source               1..22
                     mol_type = unassigned DNA
                     organism = Homo sapiens
SEQUENCE: 241
gatgttttga gtagggtgcg ag                                                 22

SEQ ID NO: 242       moltype = DNA   length = 24
FEATURE              Location/Qualifiers
source               1..24
                     mol_type = unassigned DNA
                     organism = Homo sapiens
SEQUENCE: 242
aaacgaaaaa aacaaattcc gcct                                               24

SEQ ID NO: 243       moltype = DNA   length = 20
FEATURE              Location/Qualifiers
source               1..20
                     mol_type = unassigned DNA
                     organism = Homo sapiens
SEQUENCE: 243
tggtagcgtt gtaaggtggg                                                    20

SEQ ID NO: 244       moltype = DNA   length = 20
FEATURE              Location/Qualifiers
source               1..20
                     mol_type = unassigned DNA
                     organism = Homo sapiens
SEQUENCE: 244
aaaaacaaac gcgaccctcg                                                    20
```

-continued

```
SEQ ID NO: 245        moltype = DNA   length = 22
FEATURE               Location/Qualifiers
source                1..22
                      mol_type = unassigned DNA
                      organism = Homo sapiens
SEQUENCE: 245
tcgagttttg gtagcgttgt aa                                              22

SEQ ID NO: 246        moltype = DNA   length = 24
FEATURE               Location/Qualifiers
source                1..24
                      mol_type = unassigned DNA
                      organism = Homo sapiens
SEQUENCE: 246
aataccccgc aaaaaaaatc taca                                            24

SEQ ID NO: 247        moltype = DNA   length = 20
FEATURE               Location/Qualifiers
source                1..20
                      mol_type = unassigned DNA
                      organism = Homo sapiens
SEQUENCE: 247
ccccgcaaaa aaaatctaca                                                 20

SEQ ID NO: 248        moltype = DNA   length = 20
FEATURE               Location/Qualifiers
source                1..20
                      mol_type = unassigned DNA
                      organism = Homo sapiens
SEQUENCE: 248
acgagaaatt ggcgcgttga                                                 20

SEQ ID NO: 249        moltype = DNA   length = 20
FEATURE               Location/Qualifiers
source                1..20
                      mol_type = unassigned DNA
                      organism = Homo sapiens
SEQUENCE: 249
aacaacaccc tttacgacgc                                                 20

SEQ ID NO: 250        moltype = DNA   length = 23
FEATURE               Location/Qualifiers
source                1..23
                      mol_type = unassigned DNA
                      organism = Homo sapiens
SEQUENCE: 250
tgtttgttag ggttttgttt taa                                             23

SEQ ID NO: 251        moltype = DNA   length = 22
FEATURE               Location/Qualifiers
source                1..22
                      mol_type = unassigned DNA
                      organism = Homo sapiens
SEQUENCE: 251
cgccaaaacg aatatttatt ta                                              22

SEQ ID NO: 252        moltype = DNA   length = 26
FEATURE               Location/Qualifiers
source                1..26
                      mol_type = unassigned DNA
                      organism = Homo sapiens
SEQUENCE: 252
aattgtttgt tagggttttg ttttaa                                          26

SEQ ID NO: 253        moltype = DNA   length = 25
FEATURE               Location/Qualifiers
source                1..25
                      mol_type = unassigned DNA
                      organism = Homo sapiens
SEQUENCE: 253
cgacgccaaa acgaatattt attta                                           25

SEQ ID NO: 254        moltype = DNA   length = 20
FEATURE               Location/Qualifiers
source                1..20
                      mol_type = unassigned DNA
                      organism = Homo sapiens
SEQUENCE: 254
ggtagcgtag tggattcggg                                                 20
```

```
SEQ ID NO: 255            moltype = DNA   length = 20
FEATURE                   Location/Qualifiers
source                    1..20
                          mol_type = unassigned DNA
                          organism = Homo sapiens
SEQUENCE: 255
ctcgtcctcc ctccgaaaac                                              20

SEQ ID NO: 256            moltype = DNA   length = 22
FEATURE                   Location/Qualifiers
source                    1..22
                          mol_type = unassigned DNA
                          organism = Homo sapiens
SEQUENCE: 256
gtttgtttta tttcgtgggg ag                                           22

SEQ ID NO: 257            moltype = DNA   length = 21
FEATURE                   Location/Qualifiers
source                    1..21
                          mol_type = unassigned DNA
                          organism = Homo sapiens
SEQUENCE: 257
ccaactcctt aactcgctca a                                            21

SEQ ID NO: 258            moltype = DNA   length = 20
FEATURE                   Location/Qualifiers
source                    1..20
                          mol_type = unassigned DNA
                          organism = Homo sapiens
SEQUENCE: 258
tcgcgggaaa cggttttagt                                              20

SEQ ID NO: 259            moltype = DNA   length = 18
FEATURE                   Location/Qualifiers
source                    1..18
                          mol_type = unassigned DNA
                          organism = Homo sapiens
SEQUENCE: 259
gcccttaacg accctccg                                                18

SEQ ID NO: 260            moltype = DNA   length = 23
FEATURE                   Location/Qualifiers
source                    1..23
                          mol_type = unassigned DNA
                          organism = Homo sapiens
SEQUENCE: 260
ttttcgcggg aaacggtttt agt                                          23

SEQ ID NO: 261            moltype = DNA   length = 20
FEATURE                   Location/Qualifiers
source                    1..20
                          mol_type = unassigned DNA
                          organism = Homo sapiens
SEQUENCE: 261
gcgcccttaa cgaccctccg                                              20

SEQ ID NO: 262            moltype = DNA   length = 20
FEATURE                   Location/Qualifiers
source                    1..20
                          mol_type = unassigned DNA
                          organism = Homo sapiens
SEQUENCE: 262
cgttttgtaa agcgaagttt                                              20

SEQ ID NO: 263            moltype = DNA   length = 26
FEATURE                   Location/Qualifiers
source                    1..26
                          mol_type = unassigned DNA
                          organism = Homo sapiens
SEQUENCE: 263
gttatacgtt ttgtaaagcg aagttt                                       26

SEQ ID NO: 264            moltype = DNA   length = 24
FEATURE                   Location/Qualifiers
source                    1..24
                          mol_type = unassigned DNA
                          organism = Homo sapiens
SEQUENCE: 264
```

-continued

```
aaaccaatca atcactaaac taca                                              24

SEQ ID NO: 265              moltype = DNA   length = 20
FEATURE                     Location/Qualifiers
source                      1..20
                            mol_type = unassigned DNA
                            organism = Homo sapiens
SEQUENCE: 265
ggtttttggg cgtcgtgtta                                                   20

SEQ ID NO: 266              moltype = DNA   length = 20
FEATURE                     Location/Qualifiers
source                      1..20
                            mol_type = unassigned DNA
                            organism = Homo sapiens
SEQUENCE: 266
aaattcactc tccaccgccc                                                   20

SEQ ID NO: 267              moltype = DNA   length = 22
FEATURE                     Location/Qualifiers
source                      1..22
                            mol_type = unassigned DNA
                            organism = Homo sapiens
SEQUENCE: 267
aggcgaataa tgaaacggag ga                                                22

SEQ ID NO: 268              moltype = DNA   length = 20
FEATURE                     Location/Qualifiers
source                      1..20
                            mol_type = unassigned DNA
                            organism = Homo sapiens
SEQUENCE: 268
taacacgacg cccaaaaacc                                                   20

SEQ ID NO: 269              moltype = DNA   length = 20
FEATURE                     Location/Qualifiers
source                      1..20
                            mol_type = unassigned DNA
                            organism = Homo sapiens
SEQUENCE: 269
attttacgga tggagtgatg                                                   20

SEQ ID NO: 270              moltype = DNA   length = 23
FEATURE                     Location/Qualifiers
source                      1..23
                            mol_type = unassigned DNA
                            organism = Homo sapiens
SEQUENCE: 270
ggaattttac ggatggagtg atg                                               23

SEQ ID NO: 271              moltype = DNA   length = 26
FEATURE                     Location/Qualifiers
source                      1..26
                            mol_type = unassigned DNA
                            organism = Homo sapiens
SEQUENCE: 271
cttatcccga ctaaactact aaaaaa                                            26

SEQ ID NO: 272              moltype = DNA   length = 20
FEATURE                     Location/Qualifiers
source                      1..20
                            mol_type = unassigned DNA
                            organism = Homo sapiens
SEQUENCE: 272
aattcgtttc gcgacgtgag                                                   20

SEQ ID NO: 273              moltype = DNA   length = 22
FEATURE                     Location/Qualifiers
source                      1..22
                            mol_type = unassigned DNA
                            organism = Homo sapiens
SEQUENCE: 273
ttaattcgtt tcgcgacgtg ag                                                22

SEQ ID NO: 274              moltype = DNA   length = 22
FEATURE                     Location/Qualifiers
source                      1..22
                            mol_type = unassigned DNA
                            organism = Homo sapiens
```

-continued

```
SEQUENCE: 274
acacgcctta aaacctactc at                                              22

SEQ ID NO: 275          moltype = DNA   length = 20
FEATURE                 Location/Qualifiers
source                  1..20
                        mol_type = unassigned DNA
                        organism = Homo sapiens
SEQUENCE: 275
cgtgagggag aatttaggag                                                 20

SEQ ID NO: 276          moltype = DNA   length = 26
FEATURE                 Location/Qualifiers
source                  1..26
                        mol_type = unassigned DNA
                        organism = Homo sapiens
SEQUENCE: 276
taaaaaaaca cacgccttaa aaccta                                          26

SEQ ID NO: 277          moltype = DNA   length = 20
FEATURE                 Location/Qualifiers
source                  1..20
                        mol_type = unassigned DNA
                        organism = Homo sapiens
SEQUENCE: 277
tcgtttagcg agcgttgttt                                                 20

SEQ ID NO: 278          moltype = DNA   length = 20
FEATURE                 Location/Qualifiers
source                  1..20
                        mol_type = unassigned DNA
                        organism = Homo sapiens
SEQUENCE: 278
gatccgccgt tacgctattc                                                 20

SEQ ID NO: 279          moltype = DNA   length = 22
FEATURE                 Location/Qualifiers
source                  1..22
                        mol_type = unassigned DNA
                        organism = Homo sapiens
SEQUENCE: 279
tgttagaaat cggtatcgtt ta                                              22

SEQ ID NO: 280          moltype = DNA   length = 20
FEATURE                 Location/Qualifiers
source                  1..20
                        mol_type = unassigned DNA
                        organism = Homo sapiens
SEQUENCE: 280
tctacgaaac gtttacaacc                                                 20

SEQ ID NO: 281          moltype = DNA   length = 27
FEATURE                 Location/Qualifiers
source                  1..27
                        mol_type = unassigned DNA
                        organism = Homo sapiens
SEQUENCE: 281
tttttttgtta gaaatcggta tcgttta                                        27

SEQ ID NO: 282          moltype = DNA   length = 24
FEATURE                 Location/Qualifiers
source                  1..24
                        mol_type = unassigned DNA
                        organism = Homo sapiens
SEQUENCE: 282
aaaatctacg aaacgtttac aacc                                            24

SEQ ID NO: 283          moltype = DNA   length = 20
FEATURE                 Location/Qualifiers
source                  1..20
                        mol_type = unassigned DNA
                        organism = Homo sapiens
SEQUENCE: 283
tttagggatc gcgttcggag                                                 20

SEQ ID NO: 284          moltype = DNA   length = 22
FEATURE                 Location/Qualifiers
source                  1..22
                        mol_type = unassigned DNA
```

-continued

```
                        organism = Homo sapiens
SEQUENCE: 284
aaactccttt cccctctcat ac                                    22

SEQ ID NO: 285          moltype = DNA   length = 20
FEATURE                 Location/Qualifiers
source                  1..20
                        mol_type = unassigned DNA
                        organism = Homo sapiens
SEQUENCE: 285
cggagttttt aatcggatat                                       20

SEQ ID NO: 286          moltype = DNA   length = 21
FEATURE                 Location/Qualifiers
source                  1..21
                        mol_type = unassigned DNA
                        organism = Homo sapiens
SEQUENCE: 286
tcccttctct ttaaaactcc t                                     21

SEQ ID NO: 287          moltype = DNA   length = 22
FEATURE                 Location/Qualifiers
source                  1..22
                        mol_type = unassigned DNA
                        organism = Homo sapiens
SEQUENCE: 287
gtcggatttt attttaatcg tg                                    22

SEQ ID NO: 288          moltype = DNA   length = 26
FEATURE                 Location/Qualifiers
source                  1..26
                        mol_type = unassigned DNA
                        organism = Homo sapiens
SEQUENCE: 288
aaacaaaaaa atctcaaaaa ctaaaa                                26

SEQ ID NO: 289          moltype = DNA   length = 25
FEATURE                 Location/Qualifiers
source                  1..25
                        mol_type = unassigned DNA
                        organism = Homo sapiens
SEQUENCE: 289
gttgtcggat tttattttaa tcgtg                                 25

SEQ ID NO: 290          moltype = DNA   length = 29
FEATURE                 Location/Qualifiers
source                  1..29
                        mol_type = unassigned DNA
                        organism = Homo sapiens
SEQUENCE: 290
cttaaacaaa aaaatctcaa aaactaaaa                             29

SEQ ID NO: 291          moltype = DNA   length = 20
FEATURE                 Location/Qualifiers
source                  1..20
                        mol_type = unassigned DNA
                        organism = Homo sapiens
SEQUENCE: 291
gttaggggcg aggcgtttat                                       20

SEQ ID NO: 292          moltype = DNA   length = 20
FEATURE                 Location/Qualifiers
source                  1..20
                        mol_type = unassigned DNA
                        organism = Homo sapiens
SEQUENCE: 292
cgaaacctaa acgcgcgaaa                                       20

SEQ ID NO: 293          moltype = DNA   length = 20
FEATURE                 Location/Qualifiers
source                  1..20
                        mol_type = unassigned DNA
                        organism = Homo sapiens
SEQUENCE: 293
aggttaatag gtggcgcgtt                                       20

SEQ ID NO: 294          moltype = DNA   length = 20
FEATURE                 Location/Qualifiers
source                  1..20
```

```
                              mol_type = unassigned DNA
                              organism = Homo sapiens
SEQUENCE: 294
cccgcaactc cgcgataata                                            20

SEQ ID NO: 295        moltype = DNA   length = 20
FEATURE               Location/Qualifiers
source                1..20
                      mol_type = unassigned DNA
                      organism = Homo sapiens
SEQUENCE: 295
agtcgttttt cgcgcgttta                                            20

SEQ ID NO: 296        moltype = DNA   length = 22
FEATURE               Location/Qualifiers
source                1..22
                      mol_type = unassigned DNA
                      organism = Homo sapiens
SEQUENCE: 296
cgagtcgttt ttcgcgcgtt ta                                         22

SEQ ID NO: 297        moltype = DNA   length = 21
FEATURE               Location/Qualifiers
source                1..21
                      mol_type = unassigned DNA
                      organism = Homo sapiens
SEQUENCE: 297
gacccgacac cctaaactca t                                          21

SEQ ID NO: 298        moltype = DNA   length = 22
FEATURE               Location/Qualifiers
source                1..22
                      mol_type = unassigned DNA
                      organism = Homo sapiens
SEQUENCE: 298
aggcgtttat tggttaatag gg                                         22

SEQ ID NO: 299        moltype = DNA   length = 22
FEATURE               Location/Qualifiers
source                1..22
                      mol_type = unassigned DNA
                      organism = Homo sapiens
SEQUENCE: 299
cgacccgaca ccctaaactc at                                         22

SEQ ID NO: 300        moltype = DNA   length = 20
FEATURE               Location/Qualifiers
source                1..20
                      mol_type = unassigned DNA
                      organism = Homo sapiens
SEQUENCE: 300
acccgacacc ctaaactcat                                            20

SEQ ID NO: 301        moltype = DNA   length = 25
FEATURE               Location/Qualifiers
source                1..25
                      mol_type = unassigned DNA
                      organism = Homo sapiens
SEQUENCE: 301
tttaatttgg gttttaagtt tgagg                                      25

SEQ ID NO: 302        moltype = DNA   length = 21
FEATURE               Location/Qualifiers
source                1..21
                      mol_type = unassigned DNA
                      organism = Homo sapiens
SEQUENCE: 302
acgctactaa accccgctta t                                          21

SEQ ID NO: 303        moltype = DNA   length = 18
FEATURE               Location/Qualifiers
source                1..18
                      mol_type = unassigned DNA
                      organism = Homo sapiens
SEQUENCE: 303
gcgtttaggt agcgacgc                                              18

SEQ ID NO: 304        moltype = DNA   length = 19
FEATURE               Location/Qualifiers
```

-continued

```
source                  1..19
                        mol_type = unassigned DNA
                        organism = Homo sapiens
SEQUENCE: 304
atacccgac gaaaacgac                                                      19

SEQ ID NO: 305          moltype = DNA   length = 18
FEATURE                 Location/Qualifiers
source                  1..18
                        mol_type = unassigned DNA
                        organism = Homo sapiens
SEQUENCE: 305
tttgggattt ggtcgagc                                                      18

SEQ ID NO: 306          moltype = DNA   length = 19
FEATURE                 Location/Qualifiers
source                  1..19
                        mol_type = unassigned DNA
                        organism = Homo sapiens
SEQUENCE: 306
aaaattaaat cccgcgtcg                                                     19

SEQ ID NO: 307          moltype = DNA   length = 19
FEATURE                 Location/Qualifiers
source                  1..19
                        mol_type = unassigned DNA
                        organism = Homo sapiens
SEQUENCE: 307
cgtttaggtt tgtggacgc                                                     19

SEQ ID NO: 308          moltype = DNA   length = 22
FEATURE                 Location/Qualifiers
source                  1..22
                        mol_type = unassigned DNA
                        organism = Homo sapiens
SEQUENCE: 308
aaaaacgaaa tcgctaatac gc                                                 22

SEQ ID NO: 309          moltype = DNA   length = 18
FEATURE                 Location/Qualifiers
source                  1..18
                        mol_type = unassigned DNA
                        organism = Homo sapiens
SEQUENCE: 309
tttttcgaat ttttgcgc                                                      18

SEQ ID NO: 310          moltype = DNA   length = 20
FEATURE                 Location/Qualifiers
source                  1..20
                        mol_type = unassigned DNA
                        organism = Homo sapiens
SEQUENCE: 310
aacacgctcc gactaacttc                                                    20

SEQ ID NO: 311          moltype = DNA   length = 24
FEATURE                 Location/Qualifiers
source                  1..24
                        mol_type = unassigned DNA
                        organism = Homo sapiens
SEQUENCE: 311
ggttgttttt tcgaattttt gcgc                                               24

SEQ ID NO: 312          moltype = DNA   length = 22
FEATURE                 Location/Qualifiers
source                  1..22
                        mol_type = unassigned DNA
                        organism = Homo sapiens
SEQUENCE: 312
taaacacgct ccgactaact tc                                                 22

SEQ ID NO: 313          moltype = DNA   length = 19
FEATURE                 Location/Qualifiers
source                  1..19
                        mol_type = unassigned DNA
                        organism = Homo sapiens
SEQUENCE: 313
cgttcgcgtt attatttgc                                                     19

SEQ ID NO: 314          moltype = DNA   length = 18
```

-continued

```
FEATURE                    Location/Qualifiers
source                     1..18
                           mol_type = unassigned DNA
                           organism = Homo sapiens
SEQUENCE: 314
cgcccaataa caactcgt                                                    18

SEQ ID NO: 315             moltype = DNA   length = 24
FEATURE                    Location/Qualifiers
source                     1..24
                           mol_type = unassigned DNA
                           organism = Homo sapiens
SEQUENCE: 315
attatcgttc gcgttattat ttgc                                             24

SEQ ID NO: 316             moltype = DNA   length = 21
FEATURE                    Location/Qualifiers
source                     1..21
                           mol_type = unassigned DNA
                           organism = Homo sapiens
SEQUENCE: 316
cctcgcccaa taacaactcg t                                                21

SEQ ID NO: 317             moltype = DNA   length = 20
FEATURE                    Location/Qualifiers
source                     1..20
                           mol_type = unassigned DNA
                           organism = Homo sapiens
SEQUENCE: 317
gtcgagtcgt cgttacgatc                                                  20

SEQ ID NO: 318             moltype = DNA   length = 21
FEATURE                    Location/Qualifiers
source                     1..21
                           mol_type = unassigned DNA
                           organism = Homo sapiens
SEQUENCE: 318
ctaccctcct cgaactctac g                                                21

SEQ ID NO: 319             moltype = DNA   length = 22
FEATURE                    Location/Qualifiers
source                     1..22
                           mol_type = unassigned DNA
                           organism = Homo sapiens
SEQUENCE: 319
gttttcggat gggaaatttt ag                                               22

SEQ ID NO: 320             moltype = DNA   length = 22
FEATURE                    Location/Qualifiers
source                     1..22
                           mol_type = unassigned DNA
                           organism = Homo sapiens
SEQUENCE: 320
aaaccatcta catcgaaatc gc                                               22

SEQ ID NO: 321             moltype = DNA   length = 25
FEATURE                    Location/Qualifiers
source                     1..25
                           mol_type = unassigned DNA
                           organism = Homo sapiens
SEQUENCE: 321
gtggttttcg gatgggaaat tttag                                            25

SEQ ID NO: 322             moltype = DNA   length = 26
FEATURE                    Location/Qualifiers
source                     1..26
                           mol_type = unassigned DNA
                           organism = Homo sapiens
SEQUENCE: 322
aacaaaacca tctacatcga aatcgc                                           26

SEQ ID NO: 323             moltype = DNA   length = 25
FEATURE                    Location/Qualifiers
source                     1..25
                           mol_type = unassigned DNA
                           organism = Homo sapiens
SEQUENCE: 323
tttttaggag taagtatttt gtgtg                                            25
```

-continued

```
SEQ ID NO: 324          moltype = DNA   length = 21
FEATURE                 Location/Qualifiers
source                  1..21
                        mol_type = unassigned DNA
                        organism = Homo sapiens
SEQUENCE: 324
ccctcttcct cccctactaa t                                          21

SEQ ID NO: 325          moltype = DNA   length = 19
FEATURE                 Location/Qualifiers
source                  1..19
                        mol_type = unassigned DNA
                        organism = Homo sapiens
SEQUENCE: 325
taggtatatt tcggtcggc                                             19

SEQ ID NO: 326          moltype = DNA   length = 18
FEATURE                 Location/Qualifiers
source                  1..18
                        mol_type = unassigned DNA
                        organism = Homo sapiens
SEQUENCE: 326
aactcgaaac ctcatccg                                              18

SEQ ID NO: 327          moltype = DNA   length = 19
FEATURE                 Location/Qualifiers
source                  1..19
                        mol_type = unassigned DNA
                        organism = Homo sapiens
SEQUENCE: 327
acgggagggt aaatttagc                                             19

SEQ ID NO: 328          moltype = DNA   length = 20
FEATURE                 Location/Qualifiers
source                  1..20
                        mol_type = unassigned DNA
                        organism = Homo sapiens
SEQUENCE: 328
taccaaacaa ttcgacgtta                                            20

SEQ ID NO: 329          moltype = DNA   length = 18
FEATURE                 Location/Qualifiers
source                  1..18
                        mol_type = unassigned DNA
                        organism = Homo sapiens
SEQUENCE: 329
gcgtacgtcg gtttattc                                              18

SEQ ID NO: 330          moltype = DNA   length = 18
FEATURE                 Location/Qualifiers
source                  1..18
                        mol_type = unassigned DNA
                        organism = Homo sapiens
SEQUENCE: 330
acgctctacg cgatcaaa                                              18

SEQ ID NO: 331          moltype = DNA   length = 22
FEATURE                 Location/Qualifiers
source                  1..22
                        mol_type = unassigned DNA
                        organism = Homo sapiens
SEQUENCE: 331
aagtgcgtac gtcggtttat tc                                         22

SEQ ID NO: 332          moltype = DNA   length = 21
FEATURE                 Location/Qualifiers
source                  1..21
                        mol_type = unassigned DNA
                        organism = Homo sapiens
SEQUENCE: 332
gcgacgctct acgcgatcaa a                                          21

SEQ ID NO: 333          moltype = DNA   length = 20
FEATURE                 Location/Qualifiers
source                  1..20
                        mol_type = unassigned DNA
                        organism = Homo sapiens
SEQUENCE: 333
cgagcgattg tggggttaga                                            20
```

-continued

```
SEQ ID NO: 334          moltype = DNA  length = 19
FEATURE                 Location/Qualifiers
source                  1..19
                        mol_type = unassigned DNA
                        organism = Homo sapiens
SEQUENCE: 334
caactcgcga ccgcctaaa                                            19

SEQ ID NO: 335          moltype = DNA  length = 20
FEATURE                 Location/Qualifiers
source                  1..20
                        mol_type = unassigned DNA
                        organism = Homo sapiens
SEQUENCE: 335
ttcgggcgtt tatagagttc                                           20

SEQ ID NO: 336          moltype = DNA  length = 18
FEATURE                 Location/Qualifiers
source                  1..18
                        mol_type = unassigned DNA
                        organism = Homo sapiens
SEQUENCE: 336
aaaatcaaaa cgcgaacg                                             18

SEQ ID NO: 337          moltype = DNA  length = 19
FEATURE                 Location/Qualifiers
source                  1..19
                        mol_type = unassigned DNA
                        organism = Homo sapiens
SEQUENCE: 337
tagcgtcgcg ttagaaagc                                            19

SEQ ID NO: 338          moltype = DNA  length = 20
FEATURE                 Location/Qualifiers
source                  1..20
                        mol_type = unassigned DNA
                        organism = Homo sapiens
SEQUENCE: 338
atcgctcaaa acctaacgaa                                           20

SEQ ID NO: 339          moltype = DNA  length = 22
FEATURE                 Location/Qualifiers
source                  1..22
                        mol_type = unassigned DNA
                        organism = Homo sapiens
SEQUENCE: 339
ttttagcgtc gcgttagaaa gc                                        22

SEQ ID NO: 340          moltype = DNA  length = 24
FEATURE                 Location/Qualifiers
source                  1..24
                        mol_type = unassigned DNA
                        organism = Homo sapiens
SEQUENCE: 340
aaaaatcgct caaaacctaa cgaa                                      24

SEQ ID NO: 341          moltype = DNA  length = 20
FEATURE                 Location/Qualifiers
source                  1..20
                        mol_type = unassigned DNA
                        organism = Homo sapiens
SEQUENCE: 341
aggtttagtt tcgaaatcgc                                           20

SEQ ID NO: 342          moltype = DNA  length = 18
FEATURE                 Location/Qualifiers
source                  1..18
                        mol_type = unassigned DNA
                        organism = Homo sapiens
SEQUENCE: 342
aaccgaacga ttccctaa                                             18

SEQ ID NO: 343          moltype = DNA  length = 24
FEATURE                 Location/Qualifiers
source                  1..24
                        mol_type = unassigned DNA
                        organism = Homo sapiens
SEQUENCE: 343
```

-continued

```
gttaaggttt agtttcgaaa tcgc                                                24

SEQ ID NO: 344          moltype = DNA   length = 24
FEATURE                 Location/Qualifiers
source                  1..24
                        mol_type = unassigned DNA
                        organism = Homo sapiens
SEQUENCE: 344
ctaaaaaacc gaacgattcc ctaa                                                24

SEQ ID NO: 345          moltype = DNA   length = 21
FEATURE                 Location/Qualifiers
source                  1..21
                        mol_type = unassigned DNA
                        organism = Homo sapiens
SEQUENCE: 345
gaatttttgg aaaagtcggg a                                                   21

SEQ ID NO: 346          moltype = DNA   length = 20
FEATURE                 Location/Qualifiers
source                  1..20
                        mol_type = unassigned DNA
                        organism = Homo sapiens
SEQUENCE: 346
ctcctacaaa aaaaactccc                                                     20

SEQ ID NO: 347          moltype = DNA   length = 25
FEATURE                 Location/Qualifiers
source                  1..25
                        mol_type = unassigned DNA
                        organism = Homo sapiens
SEQUENCE: 347
ttcggaattt ttggaaaagt cggga                                               25

SEQ ID NO: 348          moltype = DNA   length = 23
FEATURE                 Location/Qualifiers
source                  1..23
                        mol_type = unassigned DNA
                        organism = Homo sapiens
SEQUENCE: 348
cgactcctac aaaaaaaact ccc                                                 23

SEQ ID NO: 349          moltype = DNA   length = 18
FEATURE                 Location/Qualifiers
source                  1..18
                        mol_type = unassigned DNA
                        organism = Homo sapiens
SEQUENCE: 349
agaaggtggt cggtaagc                                                       18

SEQ ID NO: 350          moltype = DNA   length = 22
FEATURE                 Location/Qualifiers
source                  1..22
                        mol_type = unassigned DNA
                        organism = Homo sapiens
SEQUENCE: 350
acgtaattat aaaaaacacg cc                                                  22

SEQ ID NO: 351          moltype = DNA   length = 20
FEATURE                 Location/Qualifiers
source                  1..20
                        mol_type = unassigned DNA
                        organism = Homo sapiens
SEQUENCE: 351
ggagaaggtg gtcggtaagc                                                     20

SEQ ID NO: 352          moltype = DNA   length = 25
FEATURE                 Location/Qualifiers
source                  1..25
                        mol_type = unassigned DNA
                        organism = Homo sapiens
SEQUENCE: 352
aaaacgtaat tataaaaaac acgcc                                               25

SEQ ID NO: 353          moltype = DNA   length = 20
FEATURE                 Location/Qualifiers
source                  1..20
                        mol_type = unassigned DNA
                        organism = Homo sapiens
```

-continued

```
SEQUENCE: 353
tagtttttttg gagggagagg                                                    20

SEQ ID NO: 354          moltype = DNA  length = 21
FEATURE                 Location/Qualifiers
source                  1..21
                        mol_type = unassigned DNA
                        organism = Homo sapiens
SEQUENCE: 354
atcctcgtcc tcttaaaaaa c                                                    21

SEQ ID NO: 355          moltype = DNA  length = 20
FEATURE                 Location/Qualifiers
source                  1..20
                        mol_type = unassigned DNA
                        organism = Homo sapiens
SEQUENCE: 355
gtcgagtttg ggattttggt                                                     20

SEQ ID NO: 356          moltype = DNA  length = 21
FEATURE                 Location/Qualifiers
source                  1..21
                        mol_type = unassigned DNA
                        organism = Homo sapiens
SEQUENCE: 356
aaactcctac tcgccctaac c                                                    21

SEQ ID NO: 357          moltype = DNA  length = 23
FEATURE                 Location/Qualifiers
source                  1..23
                        mol_type = unassigned DNA
                        organism = Homo sapiens
SEQUENCE: 357
ggggtcgagt ttgggatttt ggt                                                  23

SEQ ID NO: 358          moltype = DNA  length = 23
FEATURE                 Location/Qualifiers
source                  1..23
                        mol_type = unassigned DNA
                        organism = Homo sapiens
SEQUENCE: 358
aaaaactcct actcgcccta acc                                                  23

SEQ ID NO: 359          moltype = DNA  length = 20
FEATURE                 Location/Qualifiers
source                  1..20
                        mol_type = unassigned DNA
                        organism = Homo sapiens
SEQUENCE: 359
tcgagttgga taaggcgtac                                                      20

SEQ ID NO: 360          moltype = DNA  length = 20
FEATURE                 Location/Qualifiers
source                  1..20
                        mol_type = unassigned DNA
                        organism = Homo sapiens
SEQUENCE: 360
ccgataacac gaccgacata                                                      20

SEQ ID NO: 361          moltype = DNA  length = 20
FEATURE                 Location/Qualifiers
source                  1..20
                        mol_type = unassigned DNA
                        organism = Homo sapiens
SEQUENCE: 361
tgtatgtcgg tcgtgttatc                                                      20

SEQ ID NO: 362          moltype = DNA  length = 20
FEATURE                 Location/Qualifiers
source                  1..20
                        mol_type = unassigned DNA
                        organism = Homo sapiens
SEQUENCE: 362
taaacgtact acctccgacc                                                      20

SEQ ID NO: 363          moltype = DNA  length = 25
FEATURE                 Location/Qualifiers
source                  1..25
                        mol_type = unassigned DNA
```

-continued

```
                             organism = Homo sapiens
SEQUENCE: 363
ggatgtggga ggttcggttc gggtg                                        25

SEQ ID NO: 364           moltype = DNA   length = 25
FEATURE                  Location/Qualifiers
source                   1..25
                         mol_type = unassigned DNA
                         organism = Homo sapiens
SEQUENCE: 364
ccgctcgccc ctcgctaaaa ctaca                                        25

SEQ ID NO: 365           moltype = DNA   length = 30
FEATURE                  Location/Qualifiers
source                   1..30
                         mol_type = unassigned DNA
                         organism = Homo sapiens
SEQUENCE: 365
ggcgcgaggt agttttagta cgtagttttt                                   30

SEQ ID NO: 366           moltype = DNA   length = 28
FEATURE                  Location/Qualifiers
source                   1..28
                         mol_type = unassigned DNA
                         organism = Homo sapiens
SEQUENCE: 366
ataacaacgt cgtcctttcc gcaaaacg                                     28

SEQ ID NO: 367           moltype = DNA   length = 28
FEATURE                  Location/Qualifiers
source                   1..28
                         mol_type = unassigned DNA
                         organism = Homo sapiens
SEQUENCE: 367
ggggattttg taagttcgcg cgtggttt                                     28

SEQ ID NO: 368           moltype = DNA   length = 28
FEATURE                  Location/Qualifiers
source                   1..28
                         mol_type = unassigned DNA
                         organism = Homo sapiens
SEQUENCE: 368
acactctccg cgcgacctat attaacga                                     28

SEQ ID NO: 369           moltype = DNA   length = 28
FEATURE                  Location/Qualifiers
source                   1..28
                         mol_type = unassigned DNA
                         organism = Homo sapiens
SEQUENCE: 369
ggagacggtt tgttatggtt gttgcgtt                                     28

SEQ ID NO: 370           moltype = DNA   length = 28
FEATURE                  Location/Qualifiers
source                   1..28
                         mol_type = unassigned DNA
                         organism = Homo sapiens
SEQUENCE: 370
acgccctttc taccgacctc acgaacta                                     28

SEQ ID NO: 371           moltype = DNA   length = 27
FEATURE                  Location/Qualifiers
source                   1..27
                         mol_type = unassigned DNA
                         organism = Homo sapiens
SEQUENCE: 371
tttttcgggg gcgtggtttg tatgttt                                      27

SEQ ID NO: 372           moltype = DNA   length = 28
FEATURE                  Location/Qualifiers
source                   1..28
                         mol_type = unassigned DNA
                         organism = Homo sapiens
SEQUENCE: 372
tacctaacga aacgctcact ccacctcg                                     28

SEQ ID NO: 373           moltype = DNA   length = 28
FEATURE                  Location/Qualifiers
source                   1..28
```

-continued

```
                              mol_type = unassigned DNA
                              organism = Homo sapiens
SEQUENCE: 373
ttttgcggtt aggtgaaggc gtagaggt                                          28

SEQ ID NO: 374          moltype = DNA   length = 28
FEATURE                 Location/Qualifiers
source                  1..28
                        mol_type = unassigned DNA
                        organism = Homo sapiens
SEQUENCE: 374
gaccgaatac cccgctttct ctctcgac                                          28

SEQ ID NO: 375          moltype = DNA   length = 28
FEATURE                 Location/Qualifiers
source                  1..28
                        mol_type = unassigned DNA
                        organism = Homo sapiens
SEQUENCE: 375
gaggtcgaga gagaaagcgg ggtattcg                                          28

SEQ ID NO: 376          moltype = DNA   length = 28
FEATURE                 Location/Qualifiers
source                  1..28
                        mol_type = unassigned DNA
                        organism = Homo sapiens
SEQUENCE: 376
aacgctctca acccaacccc taaactca                                          28

SEQ ID NO: 377          moltype = DNA   length = 28
FEATURE                 Location/Qualifiers
source                  1..28
                        mol_type = unassigned DNA
                        organism = Homo sapiens
SEQUENCE: 377
aggatagtag cggtgagtcg ttagcgtt                                          28

SEQ ID NO: 378          moltype = DNA   length = 28
FEATURE                 Location/Qualifiers
source                  1..28
                        mol_type = unassigned DNA
                        organism = Homo sapiens
SEQUENCE: 378
cgctcccact tttctccttt ctccctcc                                          28

SEQ ID NO: 379          moltype = DNA   length = 28
FEATURE                 Location/Qualifiers
source                  1..28
                        mol_type = unassigned DNA
                        organism = Homo sapiens
SEQUENCE: 379
ttttgataaa gtggggaggg cgtagggg                                          28

SEQ ID NO: 380          moltype = DNA   length = 28
FEATURE                 Location/Qualifiers
source                  1..28
                        mol_type = unassigned DNA
                        organism = Homo sapiens
SEQUENCE: 380
acactctcaa atacccgtcg cgctctat                                          28

SEQ ID NO: 381          moltype = DNA   length = 28
FEATURE                 Location/Qualifiers
source                  1..28
                        mol_type = unassigned DNA
                        organism = Homo sapiens
SEQUENCE: 381
ttttgataaa gtggggaggg cgtagggg                                          28

SEQ ID NO: 382          moltype = DNA   length = 28
FEATURE                 Location/Qualifiers
source                  1..28
                        mol_type = unassigned DNA
                        organism = Homo sapiens
SEQUENCE: 382
acactctcaa atacccgtcg cgctctat                                          28

SEQ ID NO: 383          moltype = DNA   length = 28
FEATURE                 Location/Qualifiers
```

```
source                      1..28
                            mol_type = unassigned DNA
                            organism = Homo sapiens
SEQUENCE: 383
agcgtagcgt agttggagta gttgcgaa                                                    28

SEQ ID NO: 384              moltype = DNA   length = 30
FEATURE                     Location/Qualifiers
source                      1..30
                            mol_type = unassigned DNA
                            organism = Homo sapiens
SEQUENCE: 384
cgacgactct cttcccaatc taaaacccca                                                  30

SEQ ID NO: 385              moltype = DNA   length = 28
FEATURE                     Location/Qualifiers
source                      1..28
                            mol_type = unassigned DNA
                            organism = Homo sapiens
SEQUENCE: 385
cggagtttag aagggcgttc ggttacgg                                                    28

SEQ ID NO: 386              moltype = DNA   length = 28
FEATURE                     Location/Qualifiers
source                      1..28
                            mol_type = unassigned DNA
                            organism = Homo sapiens
SEQUENCE: 386
ctccacgaat cgcatctttc aataccca                                                    28

SEQ ID NO: 387              moltype = DNA   length = 28
FEATURE                     Location/Qualifiers
source                      1..28
                            mol_type = unassigned DNA
                            organism = Homo sapiens
SEQUENCE: 387
aaaggtggtt cgagtgagga aattgcgg                                                    28

SEQ ID NO: 388              moltype = DNA   length = 28
FEATURE                     Location/Qualifiers
source                      1..28
                            mol_type = unassigned DNA
                            organism = Homo sapiens
SEQUENCE: 388
gcgtccctaa acgacacacg acgaaatc                                                    28

SEQ ID NO: 389              moltype = DNA   length = 28
FEATURE                     Location/Qualifiers
source                      1..28
                            mol_type = unassigned DNA
                            organism = Homo sapiens
SEQUENCE: 389
gtcgacggcg gttttatcgt attgtcgc                                                    28

SEQ ID NO: 390              moltype = DNA   length = 28
FEATURE                     Location/Qualifiers
source                      1..28
                            mol_type = unassigned DNA
                            organism = Homo sapiens
SEQUENCE: 390
ccttctcccg aaccttcctt cgtatcct                                                    28

SEQ ID NO: 391              moltype = DNA   length = 28
FEATURE                     Location/Qualifiers
source                      1..28
                            mol_type = unassigned DNA
                            organism = Homo sapiens
SEQUENCE: 391
ttagaggtat ggcggggttt ttgtgacg                                                    28

SEQ ID NO: 392              moltype = DNA   length = 28
FEATURE                     Location/Qualifiers
source                      1..28
                            mol_type = unassigned DNA
                            organism = Homo sapiens
SEQUENCE: 392
aatactccct aaacctccta accgcgcc                                                    28

SEQ ID NO: 393              moltype = DNA   length = 25
```

-continued

```
FEATURE              Location/Qualifiers
source               1..25
                     mol_type = unassigned DNA
                     organism = Homo sapiens
SEQUENCE: 393
gaggtttaat tgtttcgttg gtcgc                                           25

SEQ ID NO: 394       moltype = DNA   length = 23
FEATURE              Location/Qualifiers
source               1..23
                     mol_type = unassigned DNA
                     organism = Homo sapiens
SEQUENCE: 394
acgcaaaacc gcgtatatca cct                                             23

SEQ ID NO: 395       moltype = DNA   length = 28
FEATURE              Location/Qualifiers
source               1..28
                     mol_type = unassigned DNA
                     organism = Homo sapiens
SEQUENCE: 395
ggttttaggg acgcggttgg aatttggg                                        28

SEQ ID NO: 396       moltype = DNA   length = 29
FEATURE              Location/Qualifiers
source               1..29
                     mol_type = unassigned DNA
                     organism = Homo sapiens
SEQUENCE: 396
cccaacgcct cgaccatatt aaataactt                                       29

SEQ ID NO: 397       moltype = DNA   length = 28
FEATURE              Location/Qualifiers
source               1..28
                     mol_type = unassigned DNA
                     organism = Homo sapiens
SEQUENCE: 397
gcgattaagg cgtatcggtg ggtattgc                                        28

SEQ ID NO: 398       moltype = DNA   length = 28
FEATURE              Location/Qualifiers
source               1..28
                     mol_type = unassigned DNA
                     organism = Homo sapiens
SEQUENCE: 398
aacaccaccc gacgaactct cgactaac                                        28

SEQ ID NO: 399       moltype = DNA   length = 28
FEATURE              Location/Qualifiers
source               1..28
                     mol_type = unassigned DNA
                     organism = Homo sapiens
SEQUENCE: 399
taggacgttg tttggttcga agttcggg                                        28

SEQ ID NO: 400       moltype = DNA   length = 28
FEATURE              Location/Qualifiers
source               1..28
                     mol_type = unassigned DNA
                     organism = Homo sapiens
SEQUENCE: 400
ctccgaaccg accgaaaaac gcaacttt                                        28

SEQ ID NO: 401       moltype = DNA   length = 21
FEATURE              Location/Qualifiers
source               1..21
                     mol_type = unassigned DNA
                     organism = Homo sapiens
SEQUENCE: 401
ggcggggtat tgttttgttt c                                               21

SEQ ID NO: 402       moltype = DNA   length = 24
FEATURE              Location/Qualifiers
source               1..24
                     mol_type = unassigned DNA
                     organism = Homo sapiens
SEQUENCE: 402
tctaccgata tcataacacc gact                                            24
```

-continued

```
SEQ ID NO: 403            moltype = DNA   length = 28
FEATURE                   Location/Qualifiers
source                    1..28
                          mol_type = unassigned DNA
                          organism = Homo sapiens
SEQUENCE: 403
aaaggtagag ggaaggagag ttgttttt                                       28

SEQ ID NO: 404            moltype = DNA   length = 29
FEATURE                   Location/Qualifiers
source                    1..29
                          mol_type = unassigned DNA
                          organism = Homo sapiens
SEQUENCE: 404
actcctacct cctccgaatc ctaaaacct                                      29

SEQ ID NO: 405            moltype = DNA   length = 28
FEATURE                   Location/Qualifiers
source                    1..28
                          mol_type = unassigned DNA
                          organism = Homo sapiens
SEQUENCE: 405
cggaatgaag gtgtttcgta ggaaggcg                                       28

SEQ ID NO: 406            moltype = DNA   length = 27
FEATURE                   Location/Qualifiers
source                    1..27
                          mol_type = unassigned DNA
                          organism = Homo sapiens
SEQUENCE: 406
gctacgacac ccaacgaccc atcgaaa                                        27

SEQ ID NO: 407            moltype = DNA   length = 28
FEATURE                   Location/Qualifiers
source                    1..28
                          mol_type = unassigned DNA
                          organism = Homo sapiens
SEQUENCE: 407
aatgattttg ttgggttcgg tggagcgg                                       28

SEQ ID NO: 408            moltype = DNA   length = 28
FEATURE                   Location/Qualifiers
source                    1..28
                          mol_type = unassigned DNA
                          organism = Homo sapiens
SEQUENCE: 408
ccgacaactt ccgcgccatc tcttaaac                                       28

SEQ ID NO: 409            moltype = DNA   length = 28
FEATURE                   Location/Qualifiers
source                    1..28
                          mol_type = unassigned DNA
                          organism = Homo sapiens
SEQUENCE: 409
ttgtgttttg agcgtaggtt gcgcgtag                                       28

SEQ ID NO: 410            moltype = DNA   length = 28
FEATURE                   Location/Qualifiers
source                    1..28
                          mol_type = unassigned DNA
                          organism = Homo sapiens
SEQUENCE: 410
gccttcccgt cgtaaaacaa ctccgaca                                       28

SEQ ID NO: 411            moltype = DNA   length = 29
FEATURE                   Location/Qualifiers
source                    1..29
                          mol_type = unassigned DNA
                          organism = Homo sapiens
SEQUENCE: 411
gttttagggg gttgggggtt tgttaggga                                      29

SEQ ID NO: 412            moltype = DNA   length = 28
FEATURE                   Location/Qualifiers
source                    1..28
                          mol_type = unassigned DNA
                          organism = Homo sapiens
SEQUENCE: 412
aacccgaaac gaaactatac accccgca                                       28
```

```
SEQ ID NO: 413           moltype = DNA  length = 28
FEATURE                  Location/Qualifiers
source                   1..28
                         mol_type = unassigned DNA
                         organism = Homo sapiens
SEQUENCE: 413
tcgatgttcg tagtgttgtt gtagcggt                                      28

SEQ ID NO: 414           moltype = DNA  length = 28
FEATURE                  Location/Qualifiers
source                   1..28
                         mol_type = unassigned DNA
                         organism = Homo sapiens
SEQUENCE: 414
ccatccccgc ctaacgaaaa ctaaccct                                      28

SEQ ID NO: 415           moltype = DNA  length = 28
FEATURE                  Location/Qualifiers
source                   1..28
                         mol_type = unassigned DNA
                         organism = Homo sapiens
SEQUENCE: 415
cgtttcgaga agaagtttcg cggttggt                                      28

SEQ ID NO: 416           moltype = DNA  length = 28
FEATURE                  Location/Qualifiers
source                   1..28
                         mol_type = unassigned DNA
                         organism = Homo sapiens
SEQUENCE: 416
atctaaaccc aaatcgaaaa ccgccgcc                                      28

SEQ ID NO: 417           moltype = DNA  length = 28
FEATURE                  Location/Qualifiers
source                   1..28
                         mol_type = unassigned DNA
                         organism = Homo sapiens
SEQUENCE: 417
ttggagttgt cgtagatcgt cgtggtgg                                      28

SEQ ID NO: 418           moltype = DNA  length = 28
FEATURE                  Location/Qualifiers
source                   1..28
                         mol_type = unassigned DNA
                         organism = Homo sapiens
SEQUENCE: 418
aaatcgcccc actaccgcat ccttactc                                      28

SEQ ID NO: 419           moltype = DNA  length = 28
FEATURE                  Location/Qualifiers
source                   1..28
                         mol_type = unassigned DNA
                         organism = Homo sapiens
SEQUENCE: 419
gcggttaggt gtggtaaagt agttggcg                                      28

SEQ ID NO: 420           moltype = DNA  length = 28
FEATURE                  Location/Qualifiers
source                   1..28
                         mol_type = unassigned DNA
                         organism = Homo sapiens
SEQUENCE: 420
gcgcacaacc aacctataaa ctccgacg                                      28

SEQ ID NO: 421           moltype = DNA  length = 22
FEATURE                  Location/Qualifiers
source                   1..22
                         mol_type = unassigned DNA
                         organism = Homo sapiens
SEQUENCE: 421
gggatttgtg aaggcggatt tg                                            22

SEQ ID NO: 422           moltype = DNA  length = 27
FEATURE                  Location/Qualifiers
source                   1..27
                         mol_type = unassigned DNA
                         organism = Homo sapiens
SEQUENCE: 422
```

-continued

```
aatattccgt cgataccgaa aacccga                                              27

SEQ ID NO: 423          moltype = DNA   length = 27
FEATURE                 Location/Qualifiers
source                  1..27
                        mol_type = unassigned DNA
                        organism = Homo sapiens
SEQUENCE: 423
cggttggagc gcgttttcga gaagaat                                              27

SEQ ID NO: 424          moltype = DNA   length = 28
FEATURE                 Location/Qualifiers
source                  1..28
                        mol_type = unassigned DNA
                        organism = Homo sapiens
SEQUENCE: 424
aacgcaaaac aaaccgcgac cgaaaata                                             28

SEQ ID NO: 425          moltype = DNA   length = 22
FEATURE                 Location/Qualifiers
source                  1..22
                        mol_type = unassigned DNA
                        organism = Homo sapiens
SEQUENCE: 425
aggagaagtc gtagcgggcg tc                                                   22

SEQ ID NO: 426          moltype = DNA   length = 24
FEATURE                 Location/Qualifiers
source                  1..24
                        mol_type = unassigned DNA
                        organism = Homo sapiens
SEQUENCE: 426
gactaaacct tctaccgccc accg                                                 24

SEQ ID NO: 427          moltype = DNA   length = 28
FEATURE                 Location/Qualifiers
source                  1..28
                        mol_type = unassigned DNA
                        organism = Homo sapiens
SEQUENCE: 427
tagttgcgat ggggtgggaa gttacgtt                                             28

SEQ ID NO: 428          moltype = DNA   length = 28
FEATURE                 Location/Qualifiers
source                  1..28
                        mol_type = unassigned DNA
                        organism = Homo sapiens
SEQUENCE: 428
aaaaccatcg ccatccacga aaacgaca                                             28

SEQ ID NO: 429          moltype = DNA   length = 30
FEATURE                 Location/Qualifiers
source                  1..30
                        mol_type = unassigned DNA
                        organism = Homo sapiens
SEQUENCE: 429
aggaggatga tagtttagaa agaagagggt                                           30

SEQ ID NO: 430          moltype = DNA   length = 28
FEATURE                 Location/Qualifiers
source                  1..28
                        mol_type = unassigned DNA
                        organism = Homo sapiens
SEQUENCE: 430
cgcgaccgcg acgataacga taaaaact                                             28

SEQ ID NO: 431          moltype = DNA   length = 28
FEATURE                 Location/Qualifiers
source                  1..28
                        mol_type = unassigned DNA
                        organism = Homo sapiens
SEQUENCE: 431
gaaacgtgta ggcgtcggcg tttatgag                                             28

SEQ ID NO: 432          moltype = DNA   length = 28
FEATURE                 Location/Qualifiers
source                  1..28
                        mol_type = unassigned DNA
                        organism = Homo sapiens
```

-continued

```
SEQUENCE: 432
cgacctctcg aacgcctcct acaaacaa                                                       28

SEQ ID NO: 433            moltype = DNA   length = 21
FEATURE                   Location/Qualifiers
source                    1..21
                          mol_type = unassigned DNA
                          organism = Homo sapiens
SEQUENCE: 433
gtggaggagg aagttcgttt c                                                              21

SEQ ID NO: 434            moltype = DNA   length = 24
FEATURE                   Location/Qualifiers
source                    1..24
                          mol_type = unassigned DNA
                          organism = Homo sapiens
SEQUENCE: 434
aactactacc aaacacgaaa cgca                                                           24

SEQ ID NO: 435            moltype = DNA   length = 23
FEATURE                   Location/Qualifiers
source                    1..23
                          mol_type = unassigned DNA
                          organism = Homo sapiens
SEQUENCE: 435
ggttagagtc ggttgcgtag ttt                                                            23

SEQ ID NO: 436            moltype = DNA   length = 27
FEATURE                   Location/Qualifiers
source                    1..27
                          mol_type = unassigned DNA
                          organism = Homo sapiens
SEQUENCE: 436
tttttgttag gcgaagtata gagagcg                                                        27

SEQ ID NO: 437            moltype = DNA   length = 27
FEATURE                   Location/Qualifiers
source                    1..27
                          mol_type = unassigned DNA
                          organism = Homo sapiens
SEQUENCE: 437
tttttcgatt ggtcgacggc gagagag                                                        27

SEQ ID NO: 438            moltype = DNA   length = 28
FEATURE                   Location/Qualifiers
source                    1..28
                          mol_type = unassigned DNA
                          organism = Homo sapiens
SEQUENCE: 438
tttccgaact acaaacgcac actaaaac                                                       28

SEQ ID NO: 439            moltype = DNA   length = 26
FEATURE                   Location/Qualifiers
source                    1..26
                          mol_type = unassigned DNA
                          organism = Homo sapiens
SEQUENCE: 439
gattcgtatg ggttttatcg agtttc                                                         26

SEQ ID NO: 440            moltype = DNA   length = 25
FEATURE                   Location/Qualifiers
source                    1..25
                          mol_type = unassigned DNA
                          organism = Homo sapiens
SEQUENCE: 440
acttaaaaat aaactcgccc gtacg                                                          25

SEQ ID NO: 441            moltype = DNA   length = 28
FEATURE                   Location/Qualifiers
source                    1..28
                          mol_type = unassigned DNA
                          organism = Homo sapiens
SEQUENCE: 441
tcgttggtga aggtgtagtg ttcgttcg                                                       28

SEQ ID NO: 442            moltype = DNA   length = 28
FEATURE                   Location/Qualifiers
source                    1..28
                          mol_type = unassigned DNA
```

-continued

```
                            organism = Homo sapiens
SEQUENCE: 442
taacgcgcgc gctcacaaat aaaacgac                                  28

SEQ ID NO: 443          moltype = DNA   length = 28
FEATURE                 Location/Qualifiers
source                  1..28
                        mol_type = unassigned DNA
                        organism = Homo sapiens
SEQUENCE: 443
tttttagtgg ttcgagcgtt tgcgttgc                                  28

SEQ ID NO: 444          moltype = DNA   length = 29
FEATURE                 Location/Qualifiers
source                  1..29
                        mol_type = unassigned DNA
                        organism = Homo sapiens
SEQUENCE: 444
tccgtcctcg aaataattct aaccgacgc                                 29

SEQ ID NO: 445          moltype = DNA   length = 25
FEATURE                 Location/Qualifiers
source                  1..25
                        mol_type = unassigned DNA
                        organism = Homo sapiens
SEQUENCE: 445
cgtggtatag ttaatcgcgc ggcgt                                     25

SEQ ID NO: 446          moltype = DNA   length = 28
FEATURE                 Location/Qualifiers
source                  1..28
                        mol_type = unassigned DNA
                        organism = Homo sapiens
SEQUENCE: 446
tacaacccca acgccataac tcgccaat                                  28

SEQ ID NO: 447          moltype = DNA   length = 28
FEATURE                 Location/Qualifiers
source                  1..28
                        mol_type = unassigned DNA
                        organism = Homo sapiens
SEQUENCE: 447
tgtcgtcgtc gtcggggttt tgttattt                                  28

SEQ ID NO: 448          moltype = DNA   length = 28
FEATURE                 Location/Qualifiers
source                  1..28
                        mol_type = unassigned DNA
                        organism = Homo sapiens
SEQUENCE: 448
acgacgataa actcccgcta aacccgaa                                  28

SEQ ID NO: 449          moltype = DNA   length = 27
FEATURE                 Location/Qualifiers
source                  1..27
                        mol_type = unassigned DNA
                        organism = Homo sapiens
SEQUENCE: 449
gaacgaggat ttgcgttttt ggatcgc                                   27

SEQ ID NO: 450          moltype = DNA   length = 29
FEATURE                 Location/Qualifiers
source                  1..29
                        mol_type = unassigned DNA
                        organism = Homo sapiens
SEQUENCE: 450
cctaaactcc tctacatatt cctctacct                                 29

SEQ ID NO: 451          moltype = DNA   length = 27
FEATURE                 Location/Qualifiers
source                  1..27
                        mol_type = unassigned DNA
                        organism = Homo sapiens
SEQUENCE: 451
gaatggttgc gatatggggt tcgacgg                                   27

SEQ ID NO: 452          moltype = DNA   length = 27
FEATURE                 Location/Qualifiers
source                  1..27
```

```
                              mol_type = unassigned DNA
                              organism = Homo sapiens
SEQUENCE: 452
ccacgatatc cgccgcgatc caaaaac                                    27

SEQ ID NO: 453          moltype = DNA   length = 25
FEATURE                 Location/Qualifiers
source                  1..25
                        mol_type = unassigned DNA
                        organism = Homo sapiens
SEQUENCE: 453
taagggtcgg ttgttgtttt ttttc                                     25

SEQ ID NO: 454          moltype = DNA   length = 25
FEATURE                 Location/Qualifiers
source                  1..25
                        mol_type = unassigned DNA
                        organism = Homo sapiens
SEQUENCE: 454
accgacgcct tccttataaa atacg                                     25

SEQ ID NO: 455          moltype = DNA   length = 28
FEATURE                 Location/Qualifiers
source                  1..28
                        mol_type = unassigned DNA
                        organism = Homo sapiens
SEQUENCE: 455
tgtgggataa tttggcgaag ggagtaga                                  28

SEQ ID NO: 456          moltype = DNA   length = 28
FEATURE                 Location/Qualifiers
source                  1..28
                        mol_type = unassigned DNA
                        organism = Homo sapiens
SEQUENCE: 456
aactcgaaat taactacgaa cgcccgcc                                  28

SEQ ID NO: 457          moltype = DNA   length = 28
FEATURE                 Location/Qualifiers
source                  1..28
                        mol_type = unassigned DNA
                        organism = Homo sapiens
SEQUENCE: 457
ggcgggggta gtttttgtat taaggcga                                  28

SEQ ID NO: 458          moltype = DNA   length = 28
FEATURE                 Location/Qualifiers
source                  1..28
                        mol_type = unassigned DNA
                        organism = Homo sapiens
SEQUENCE: 458
cctacgctac tactcttctc gacccccg                                  28

SEQ ID NO: 459          moltype = DNA   length = 27
FEATURE                 Location/Qualifiers
source                  1..27
                        mol_type = unassigned DNA
                        organism = Homo sapiens
SEQUENCE: 459
cgtttcgttc gtcggtcgta gcgattg                                   27

SEQ ID NO: 460          moltype = DNA   length = 28
FEATURE                 Location/Qualifiers
source                  1..28
                        mol_type = unassigned DNA
                        organism = Homo sapiens
SEQUENCE: 460
ccgacgaaac attttcgcac cacaacac                                  28

SEQ ID NO: 461          moltype = DNA   length = 28
FEATURE                 Location/Qualifiers
source                  1..28
                        mol_type = unassigned DNA
                        organism = Homo sapiens
SEQUENCE: 461
cgcggtttcg gggtatacgg agtttttg                                  28

SEQ ID NO: 462          moltype = DNA   length = 28
FEATURE                 Location/Qualifiers
```

-continued

```
source                   1..28
                         mol_type = unassigned DNA
                         organism = Homo sapiens
SEQUENCE: 462
gcaattcaat cgctacgacc gacgaacg                                    28

SEQ ID NO: 463           moltype = DNA   length = 28
FEATURE                  Location/Qualifiers
source                   1..28
                         mol_type = unassigned DNA
                         organism = Homo sapiens
SEQUENCE: 463
cgtcgtagcg ggtacggtta acgagttg                                    28

SEQ ID NO: 464           moltype = DNA   length = 27
FEATURE                  Location/Qualifiers
source                   1..27
                         mol_type = unassigned DNA
                         organism = Homo sapiens
SEQUENCE: 464
tttctccact cgaaacgccc gacaacc                                     27

SEQ ID NO: 465           moltype = DNA   length = 28
FEATURE                  Location/Qualifiers
source                   1..28
                         mol_type = unassigned DNA
                         organism = Homo sapiens
SEQUENCE: 465
cgggggagaa cggtttgagt ttcgagta                                    28

SEQ ID NO: 466           moltype = DNA   length = 28
FEATURE                  Location/Qualifiers
source                   1..28
                         mol_type = unassigned DNA
                         organism = Homo sapiens
SEQUENCE: 466
tcatatttca acctcgccgc cgctaaac                                    28

SEQ ID NO: 467           moltype = DNA   length = 28
FEATURE                  Location/Qualifiers
source                   1..28
                         mol_type = unassigned DNA
                         organism = Homo sapiens
SEQUENCE: 467
agtagggatg gtcgttcgtt gttcggtg                                    28

SEQ ID NO: 468           moltype = DNA   length = 28
FEATURE                  Location/Qualifiers
source                   1..28
                         mol_type = unassigned DNA
                         organism = Homo sapiens
SEQUENCE: 468
gacaaacgac cgaaaatact cgcgcaac                                    28

SEQ ID NO: 469           moltype = DNA   length = 28
FEATURE                  Location/Qualifiers
source                   1..28
                         mol_type = unassigned DNA
                         organism = Homo sapiens
SEQUENCE: 469
ttttacggtc ggggcgatag ttgaaggt                                    28

SEQ ID NO: 470           moltype = DNA   length = 28
FEATURE                  Location/Qualifiers
source                   1..28
                         mol_type = unassigned DNA
                         organism = Homo sapiens
SEQUENCE: 470
tcacgccaat acccgctaat ccctccta                                    28

SEQ ID NO: 471           moltype = DNA   length = 27
FEATURE                  Location/Qualifiers
source                   1..27
                         mol_type = unassigned DNA
                         organism = Homo sapiens
SEQUENCE: 471
ggggatggat aatttttagg cgttaac                                     27

SEQ ID NO: 472           moltype = DNA   length = 22
```

```
FEATURE            Location/Qualifiers
source             1..22
                   mol_type = unassigned DNA
                   organism = Homo sapiens
SEQUENCE: 472
taacctcgtc tttatccccg cg                                                        22

SEQ ID NO: 473     moltype = DNA   length = 29
FEATURE            Location/Qualifiers
source             1..29
                   mol_type = unassigned DNA
                   organism = Homo sapiens
SEQUENCE: 473
agtgtgtagt cgtttgtggg tgaggagtt                                                 29

SEQ ID NO: 474     moltype = DNA   length = 28
FEATURE            Location/Qualifiers
source             1..28
                   mol_type = unassigned DNA
                   organism = Homo sapiens
SEQUENCE: 474
caccgcgaaa aacgcccaca atcttacc                                                  28

SEQ ID NO: 475     moltype = DNA   length = 29
FEATURE            Location/Qualifiers
source             1..29
                   mol_type = unassigned DNA
                   organism = Homo sapiens
SEQUENCE: 475
cgcggggag tttatttttg aggattcgg                                                  29

SEQ ID NO: 476     moltype = DNA   length = 28
FEATURE            Location/Qualifiers
source             1..28
                   mol_type = unassigned DNA
                   organism = Homo sapiens
SEQUENCE: 476
actcctcacc cacaaacgac tacacact                                                  28

SEQ ID NO: 477     moltype = DNA   length = 29
FEATURE            Location/Qualifiers
source             1..29
                   mol_type = unassigned DNA
                   organism = Homo sapiens
SEQUENCE: 477
tagtatttgt acggagtttt tcggcggtc                                                 29

SEQ ID NO: 478     moltype = DNA   length = 29
FEATURE            Location/Qualifiers
source             1..29
                   mol_type = unassigned DNA
                   organism = Homo sapiens
SEQUENCE: 478
tacgacgcaa ccaacgatac tatcaccaa                                                 29

SEQ ID NO: 479     moltype = DNA   length = 27
FEATURE            Location/Qualifiers
source             1..27
                   mol_type = unassigned DNA
                   organism = Homo sapiens
SEQUENCE: 479
tagtgattgg ttatttgggc gcggggc                                                   27

SEQ ID NO: 480     moltype = DNA   length = 28
FEATURE            Location/Qualifiers
source             1..28
                   mol_type = unassigned DNA
                   organism = Homo sapiens
SEQUENCE: 480
aaacgacatc catcatctcc ctcgaccc                                                  28

SEQ ID NO: 481     moltype = DNA   length = 20
FEATURE            Location/Qualifiers
source             1..20
                   mol_type = unassigned DNA
                   organism = Homo sapiens
SEQUENCE: 481
aggtcgcgtt ttggtcgtgc                                                           20
```

-continued

```
SEQ ID NO: 482          moltype = DNA   length = 25
FEATURE                 Location/Qualifiers
source                  1..25
                        mol_type = unassigned DNA
                        organism = Homo sapiens
SEQUENCE: 482
acttaaaaat aaactcgccc gtacg                                          25

SEQ ID NO: 483          moltype = DNA   length = 28
FEATURE                 Location/Qualifiers
source                  1..28
                        mol_type = unassigned DNA
                        organism = Homo sapiens
SEQUENCE: 483
attttacgta gggtggggtt gagggcgt                                       28

SEQ ID NO: 484          moltype = DNA   length = 28
FEATURE                 Location/Qualifiers
source                  1..28
                        mol_type = unassigned DNA
                        organism = Homo sapiens
SEQUENCE: 484
atcctaaccg tcccgcctca aaaccgta                                       28

SEQ ID NO: 485          moltype = DNA   length = 26
FEATURE                 Location/Qualifiers
source                  1..26
                        mol_type = unassigned DNA
                        organism = Homo sapiens
SEQUENCE: 485
cgtcgtagta tttggcggcg cgtttc                                         26

SEQ ID NO: 486          moltype = DNA   length = 28
FEATURE                 Location/Qualifiers
source                  1..28
                        mol_type = unassigned DNA
                        organism = Homo sapiens
SEQUENCE: 486
aacgtaccta atccccaaac ccactcct                                       28

SEQ ID NO: 487          moltype = DNA   length = 29
FEATURE                 Location/Qualifiers
source                  1..29
                        mol_type = unassigned DNA
                        organism = Homo sapiens
SEQUENCE: 487
tcgttgtgcg cgtttcgttt gttggatta                                      29

SEQ ID NO: 488          moltype = DNA   length = 28
FEATURE                 Location/Qualifiers
source                  1..28
                        mol_type = unassigned DNA
                        organism = Homo sapiens
SEQUENCE: 488
tcgataatat ctccgtcgcc tccgcaaa                                       28

SEQ ID NO: 489          moltype = DNA   length = 28
FEATURE                 Location/Qualifiers
source                  1..28
                        mol_type = unassigned DNA
                        organism = Homo sapiens
SEQUENCE: 489
gcgcgtttaa tcgtgggatt tttgggag                                       28

SEQ ID NO: 490          moltype = DNA   length = 27
FEATURE                 Location/Qualifiers
source                  1..27
                        mol_type = unassigned DNA
                        organism = Homo sapiens
SEQUENCE: 490
caaattcgcg acaccctacc ccaacac                                        27

SEQ ID NO: 491          moltype = DNA   length = 21
FEATURE                 Location/Qualifiers
source                  1..21
                        mol_type = unassigned DNA
                        organism = Homo sapiens
SEQUENCE: 491
gggtgtcgcg aatttggggt a                                              21
```

-continued

```
SEQ ID NO: 492            moltype = DNA   length = 28
FEATURE                   Location/Qualifiers
source                    1..28
                          mol_type = unassigned DNA
                          organism = Homo sapiens
SEQUENCE: 492
ctaaacctct cccctcccaa atttacct                                      28

SEQ ID NO: 493            moltype = DNA   length = 28
FEATURE                   Location/Qualifiers
source                    1..28
                          mol_type = unassigned DNA
                          organism = Homo sapiens
SEQUENCE: 493
atcgagtttt tagcggtttt tggggcgg                                      28

SEQ ID NO: 494            moltype = DNA   length = 28
FEATURE                   Location/Qualifiers
source                    1..28
                          mol_type = unassigned DNA
                          organism = Homo sapiens
SEQUENCE: 494
actaacatcg cgcacttaaa tctttccg                                      28

SEQ ID NO: 495            moltype = DNA   length = 21
FEATURE                   Location/Qualifiers
source                    1..21
                          mol_type = unassigned DNA
                          organism = Homo sapiens
SEQUENCE: 495
ggtagcggcg ggtaaaaagt c                                             21

SEQ ID NO: 496            moltype = DNA   length = 22
FEATURE                   Location/Qualifiers
source                    1..22
                          mol_type = unassigned DNA
                          organism = Homo sapiens
SEQUENCE: 496
tacaactttt tacctccgcc gc                                            22

SEQ ID NO: 497            moltype = DNA   length = 28
FEATURE                   Location/Qualifiers
source                    1..28
                          mol_type = unassigned DNA
                          organism = Homo sapiens
SEQUENCE: 497
cgtcgatttg cggaatttcg tcgtcgtt                                      28

SEQ ID NO: 498            moltype = DNA   length = 28
FEATURE                   Location/Qualifiers
source                    1..28
                          mol_type = unassigned DNA
                          organism = Homo sapiens
SEQUENCE: 498
acatccgcgt aaactcgccc tttaacac                                      28

SEQ ID NO: 499            moltype = DNA   length = 28
FEATURE                   Location/Qualifiers
source                    1..28
                          mol_type = unassigned DNA
                          organism = Homo sapiens
SEQUENCE: 499
tttcgggatt agggtttcgg agggtgtc                                      28

SEQ ID NO: 500            moltype = DNA   length = 28
FEATURE                   Location/Qualifiers
source                    1..28
                          mol_type = unassigned DNA
                          organism = Homo sapiens
SEQUENCE: 500
cgtatcgatc cgtccctccc gcttaaaa                                      28

SEQ ID NO: 501            moltype = DNA   length = 26
FEATURE                   Location/Qualifiers
source                    1..26
                          mol_type = unassigned DNA
                          organism = Homo sapiens
SEQUENCE: 501
```

-continued

```
cggttttggt ggtagttttg gtaatc                                      26

SEQ ID NO: 502          moltype = DNA   length = 28
FEATURE                 Location/Qualifiers
source                  1..28
                        mol_type = unassigned DNA
                        organism = Homo sapiens
SEQUENCE: 502
aaaacctccc gaacgacgaa ataatcca                                    28

SEQ ID NO: 503          moltype = DNA   length = 21
FEATURE                 Location/Qualifiers
source                  1..21
                        mol_type = unassigned DNA
                        organism = Homo sapiens
SEQUENCE: 503
gtaggcggtc ggaacgtgaa c                                           21

SEQ ID NO: 504          moltype = DNA   length = 29
FEATURE                 Location/Qualifiers
source                  1..29
                        mol_type = unassigned DNA
                        organism = Homo sapiens
SEQUENCE: 504
cgataaaaac tacaataact cgacaacca                                   29

SEQ ID NO: 505          moltype = DNA   length = 24
FEATURE                 Location/Qualifiers
source                  1..24
                        mol_type = unassigned DNA
                        organism = Homo sapiens
SEQUENCE: 505
gttgtgaggg ttttcggcgg tatc                                        24

SEQ ID NO: 506          moltype = DNA   length = 21
FEATURE                 Location/Qualifiers
source                  1..21
                        mol_type = unassigned DNA
                        organism = Homo sapiens
SEQUENCE: 506
cataacaacg cgcgacccct a                                           21

SEQ ID NO: 507          moltype = DNA   length = 29
FEATURE                 Location/Qualifiers
source                  1..29
                        mol_type = unassigned DNA
                        organism = Homo sapiens
SEQUENCE: 507
tgattataaa ttaggggtt tggtcgtcg                                    29

SEQ ID NO: 508          moltype = DNA   length = 28
FEATURE                 Location/Qualifiers
source                  1..28
                        mol_type = unassigned DNA
                        organism = Homo sapiens
SEQUENCE: 508
aaaccctcca ccctcgcaat actactcc                                    28

SEQ ID NO: 509          moltype = DNA   length = 28
FEATURE                 Location/Qualifiers
source                  1..28
                        mol_type = unassigned DNA
                        organism = Homo sapiens
SEQUENCE: 509
tgtaggagat aatgggagtg aagaggga                                    28

SEQ ID NO: 510          moltype = DNA   length = 28
FEATURE                 Location/Qualifiers
source                  1..28
                        mol_type = unassigned DNA
                        organism = Homo sapiens
SEQUENCE: 510
ttccacgaaa cgcgcgactt cctaacta                                    28

SEQ ID NO: 511          moltype = DNA   length = 24
FEATURE                 Location/Qualifiers
source                  1..24
                        mol_type = unassigned DNA
                        organism = Homo sapiens
```

-continued

```
SEQUENCE: 511
gttgagttag gagaggtcga tagc                                                    24

SEQ ID NO: 512          moltype = DNA   length = 28
FEATURE                 Location/Qualifiers
source                  1..28
                        mol_type = unassigned DNA
                        organism = Homo sapiens
SEQUENCE: 512
cccgaaaaca acgactatcg aaatccaa                                                28

SEQ ID NO: 513          moltype = DNA   length = 28
FEATURE                 Location/Qualifiers
source                  1..28
                        mol_type = unassigned DNA
                        organism = Homo sapiens
SEQUENCE: 513
ataaggtttg gtggaagcgt aggagcgt                                                28

SEQ ID NO: 514          moltype = DNA   length = 28
FEATURE                 Location/Qualifiers
source                  1..28
                        mol_type = unassigned DNA
                        organism = Homo sapiens
SEQUENCE: 514
acgccgaata aaaatcccgc aaccacaa                                                28

SEQ ID NO: 515          moltype = DNA   length = 28
FEATURE                 Location/Qualifiers
source                  1..28
                        mol_type = unassigned DNA
                        organism = Homo sapiens
SEQUENCE: 515
ggaggggagg agatagcgtt atttaggg                                                28

SEQ ID NO: 516          moltype = DNA   length = 28
FEATURE                 Location/Qualifiers
source                  1..28
                        mol_type = unassigned DNA
                        organism = Homo sapiens
SEQUENCE: 516
aaacaaaacc cgaaacccca cctacacc                                                28

SEQ ID NO: 517          moltype = DNA   length = 28
FEATURE                 Location/Qualifiers
source                  1..28
                        mol_type = unassigned DNA
                        organism = Homo sapiens
SEQUENCE: 517
gcgtggtagt tgaggatgta gacgtggt                                                28

SEQ ID NO: 518          moltype = DNA   length = 28
FEATURE                 Location/Qualifiers
source                  1..28
                        mol_type = unassigned DNA
                        organism = Homo sapiens
SEQUENCE: 518
tccgaactac ttaaaaatcc ccgccgcc                                                28

SEQ ID NO: 519          moltype = DNA   length = 28
FEATURE                 Location/Qualifiers
source                  1..28
                        mol_type = unassigned DNA
                        organism = Homo sapiens
SEQUENCE: 519
tcgttggttg tgatttttat gcgggcgt                                                28

SEQ ID NO: 520          moltype = DNA   length = 28
FEATURE                 Location/Qualifiers
source                  1..28
                        mol_type = unassigned DNA
                        organism = Homo sapiens
SEQUENCE: 520
acctctccga taaaccaaat cctccgcc                                                28

SEQ ID NO: 521          moltype = DNA   length = 28
FEATURE                 Location/Qualifiers
source                  1..28
                        mol_type = unassigned DNA
```

-continued

```
                        organism = Homo sapiens
SEQUENCE: 521
cgggtgaggt ttgtggttaa tttcgcgt                                            28

SEQ ID NO: 522           moltype = DNA   length = 28
FEATURE                  Location/Qualifiers
source                   1..28
                         mol_type = unassigned DNA
                         organism = Homo sapiens
SEQUENCE: 522
ctcaaccaaa ctacaacgtt cccgcctc                                            28

SEQ ID NO: 523           moltype = DNA   length = 28
FEATURE                  Location/Qualifiers
source                   1..28
                         mol_type = unassigned DNA
                         organism = Homo sapiens
SEQUENCE: 523
aatggaggcg tagattaacg agcggtgt                                            28

SEQ ID NO: 524           moltype = DNA   length = 28
FEATURE                  Location/Qualifiers
source                   1..28
                         mol_type = unassigned DNA
                         organism = Homo sapiens
SEQUENCE: 524
atccttaaca accccgccga ctaacgtc                                            28

SEQ ID NO: 525           moltype = DNA   length = 28
FEATURE                  Location/Qualifiers
source                   1..28
                         mol_type = unassigned DNA
                         organism = Homo sapiens
SEQUENCE: 525
acgggtacgg agaaacgtcg gatttagt                                            28

SEQ ID NO: 526           moltype = DNA   length = 28
FEATURE                  Location/Qualifiers
source                   1..28
                         mol_type = unassigned DNA
                         organism = Homo sapiens
SEQUENCE: 526
tccccgcgac actctaccta taacgtcc                                            28

SEQ ID NO: 527           moltype = DNA   length = 22
FEATURE                  Location/Qualifiers
source                   1..22
                         mol_type = unassigned DNA
                         organism = Homo sapiens
SEQUENCE: 527
cgtttggcgg gtattgttgt tc                                                  22

SEQ ID NO: 528           moltype = DNA   length = 20
FEATURE                  Location/Qualifiers
source                   1..20
                         mol_type = unassigned DNA
                         organism = Homo sapiens
SEQUENCE: 528
cccgacgcaa actccctctc                                                     20

SEQ ID NO: 529           moltype = DNA   length = 25
FEATURE                  Location/Qualifiers
source                   1..25
                         mol_type = unassigned DNA
                         organism = Homo sapiens
SEQUENCE: 529
gaagttgttt tttaggggtt tgcgc                                               25

SEQ ID NO: 530           moltype = DNA   length = 25
FEATURE                  Location/Qualifiers
source                   1..25
                         mol_type = unassigned DNA
                         organism = Homo sapiens
SEQUENCE: 530
actcaaatct accctcgctt caacg                                               25

SEQ ID NO: 531           moltype = DNA   length = 28
FEATURE                  Location/Qualifiers
source                   1..28
```

-continued

```
                        mol_type = unassigned DNA
                        organism = Homo sapiens
SEQUENCE: 531
gcgcgggggt attttggagg gttagtta                                         28

SEQ ID NO: 532          moltype = DNA   length = 28
FEATURE                 Location/Qualifiers
source                  1..28
                        mol_type = unassigned DNA
                        organism = Homo sapiens
SEQUENCE: 532
tccctactcg cccgctacga ctataaca                                         28

SEQ ID NO: 533          moltype = DNA   length = 28
FEATURE                 Location/Qualifiers
source                  1..28
                        mol_type = unassigned DNA
                        organism = Homo sapiens
SEQUENCE: 533
cggattttgt tttcgggagt cgttcggg                                         28

SEQ ID NO: 534          moltype = DNA   length = 28
FEATURE                 Location/Qualifiers
source                  1..28
                        mol_type = unassigned DNA
                        organism = Homo sapiens
SEQUENCE: 534
aactaaacgc ctaacccttc cctcccac                                         28

SEQ ID NO: 535          moltype = DNA   length = 28
FEATURE                 Location/Qualifiers
source                  1..28
                        mol_type = unassigned DNA
                        organism = Homo sapiens
SEQUENCE: 535
ttcgttttgt ttttcggttg gagcgggt                                         28

SEQ ID NO: 536          moltype = DNA   length = 28
FEATURE                 Location/Qualifiers
source                  1..28
                        mol_type = unassigned DNA
                        organism = Homo sapiens
SEQUENCE: 536
tataacctaa cccttcaacc gcgcctcg                                         28

SEQ ID NO: 537          moltype = DNA   length = 28
FEATURE                 Location/Qualifiers
source                  1..28
                        mol_type = unassigned DNA
                        organism = Homo sapiens
SEQUENCE: 537
aggcggcggt ttttggcgat tgtttttc                                         28

SEQ ID NO: 538          moltype = DNA   length = 27
FEATURE                 Location/Qualifiers
source                  1..27
                        mol_type = unassigned DNA
                        organism = Homo sapiens
SEQUENCE: 538
ttccgttacc ataaaactac ccgcccc                                          27

SEQ ID NO: 539          moltype = DNA   length = 21
FEATURE                 Location/Qualifiers
source                  1..21
                        mol_type = unassigned DNA
                        organism = Homo sapiens
SEQUENCE: 539
gatttcgcgt atcgtcgtgt c                                                21

SEQ ID NO: 540          moltype = DNA   length = 21
FEATURE                 Location/Qualifiers
source                  1..21
                        mol_type = unassigned DNA
                        organism = Homo sapiens
SEQUENCE: 540
taatatcccc cgtaccccc g                                                 21

SEQ ID NO: 541          moltype = DNA   length = 28
FEATURE                 Location/Qualifiers
```

-continued

```
source                1..28
                      mol_type = unassigned DNA
                      organism = Homo sapiens
SEQUENCE: 541
tttcgataat agcgtttttg cggcgtgg                                      28

SEQ ID NO: 542        moltype = DNA   length = 28
FEATURE               Location/Qualifiers
source                1..28
                      mol_type = unassigned DNA
                      organism = Homo sapiens
SEQUENCE: 542
caaaaacacg cgacctacgc cctcctaa                                      28

SEQ ID NO: 543        moltype = DNA   length = 28
FEATURE               Location/Qualifiers
source                1..28
                      mol_type = unassigned DNA
                      organism = Homo sapiens
SEQUENCE: 543
cgagtcggag tgagcgttaa gtgagggg                                      28

SEQ ID NO: 544        moltype = DNA   length = 28
FEATURE               Location/Qualifiers
source                1..28
                      mol_type = unassigned DNA
                      organism = Homo sapiens
SEQUENCE: 544
cctatcaacg accacccaac tactccct                                      28

SEQ ID NO: 545        moltype = DNA   length = 28
FEATURE               Location/Qualifiers
source                1..28
                      mol_type = unassigned DNA
                      organism = Homo sapiens
SEQUENCE: 545
tcgggtttag cgtcgtttgt agtttcgg                                      28

SEQ ID NO: 546        moltype = DNA   length = 28
FEATURE               Location/Qualifiers
source                1..28
                      mol_type = unassigned DNA
                      organism = Homo sapiens
SEQUENCE: 546
aaaaacgtct ccttaattcc ccgcgctt                                      28

SEQ ID NO: 547        moltype = DNA   length = 30
FEATURE               Location/Qualifiers
source                1..30
                      mol_type = unassigned DNA
                      organism = Homo sapiens
SEQUENCE: 547
gcggttggag tagaagtgtt agcggttaga                                    30

SEQ ID NO: 548        moltype = DNA   length = 28
FEATURE               Location/Qualifiers
source                1..28
                      mol_type = unassigned DNA
                      organism = Homo sapiens
SEQUENCE: 548
tcaccctaca aaaccgata accgacga                                       28

SEQ ID NO: 549        moltype = DNA   length = 28
FEATURE               Location/Qualifiers
source                1..28
                      mol_type = unassigned DNA
                      organism = Homo sapiens
SEQUENCE: 549
agttggttat aggcggcgaa ttgggttt                                      28

SEQ ID NO: 550        moltype = DNA   length = 28
FEATURE               Location/Qualifiers
source                1..28
                      mol_type = unassigned DNA
                      organism = Homo sapiens
SEQUENCE: 550
tcaacacccc ctctcctaac ctctccaa                                      28

SEQ ID NO: 551        moltype = DNA   length = 28
```

-continued

```
FEATURE                 Location/Qualifiers
source                  1..28
                        mol_type = unassigned DNA
                        organism = Homo sapiens
SEQUENCE: 551
cggggaagag tttcggttcg cgttttag                                              28

SEQ ID NO: 552          moltype = DNA   length = 28
FEATURE                 Location/Qualifiers
source                  1..28
                        mol_type = unassigned DNA
                        organism = Homo sapiens
SEQUENCE: 552
ccctcctata accccgacct acccgaaa                                              28

SEQ ID NO: 553          moltype = DNA   length = 28
FEATURE                 Location/Qualifiers
source                  1..28
                        mol_type = unassigned DNA
                        organism = Homo sapiens
SEQUENCE: 553
gcgcggtagg tgtttttcgg gttgtaaa                                              28

SEQ ID NO: 554          moltype = DNA   length = 28
FEATURE                 Location/Qualifiers
source                  1..28
                        mol_type = unassigned DNA
                        organism = Homo sapiens
SEQUENCE: 554
acctttacct aactacactc ccatccaa                                              28

SEQ ID NO: 555          moltype = DNA   length = 21
FEATURE                 Location/Qualifiers
source                  1..21
                        mol_type = unassigned DNA
                        organism = Homo sapiens
SEQUENCE: 555
agagtaggtc gtgggggatt c                                                     21

SEQ ID NO: 556          moltype = DNA   length = 21
FEATURE                 Location/Qualifiers
source                  1..21
                        mol_type = unassigned DNA
                        organism = Homo sapiens
SEQUENCE: 556
cgcgctaacc gcgataaaaa c                                                     21

SEQ ID NO: 557          moltype = DNA   length = 28
FEATURE                 Location/Qualifiers
source                  1..28
                        mol_type = unassigned DNA
                        organism = Homo sapiens
SEQUENCE: 557
aggagcggga gagggaaaaa tagttaag                                              28

SEQ ID NO: 558          moltype = DNA   length = 27
FEATURE                 Location/Qualifiers
source                  1..27
                        mol_type = unassigned DNA
                        organism = Homo sapiens
SEQUENCE: 558
actacgccca aaactcaact actaaat                                               27

SEQ ID NO: 559          moltype = DNA   length = 28
FEATURE                 Location/Qualifiers
source                  1..28
                        mol_type = unassigned DNA
                        organism = Homo sapiens
SEQUENCE: 559
tgggaacggg atagggacgc gttttaat                                              28

SEQ ID NO: 560          moltype = DNA   length = 28
FEATURE                 Location/Qualifiers
source                  1..28
                        mol_type = unassigned DNA
                        organism = Homo sapiens
SEQUENCE: 560
gaatcccta aactacccgc catcccac                                               28
```

-continued

```
SEQ ID NO: 561          moltype = DNA   length = 29
FEATURE                 Location/Qualifiers
source                  1..29
                        mol_type = unassigned DNA
                        organism = Homo sapiens
SEQUENCE: 561
tgtacgcgta tttttggagg gtggtttgc                                         29

SEQ ID NO: 562          moltype = DNA   length = 28
FEATURE                 Location/Qualifiers
source                  1..28
                        mol_type = unassigned DNA
                        organism = Homo sapiens
SEQUENCE: 562
cgatctaatc gaccacctcc tctcctcc                                          28

SEQ ID NO: 563          moltype = DNA   length = 28
FEATURE                 Location/Qualifiers
source                  1..28
                        mol_type = unassigned DNA
                        organism = Homo sapiens
SEQUENCE: 563
aagtttcgtc gagttggggt cgttggtt                                          28

SEQ ID NO: 564          moltype = DNA   length = 27
FEATURE                 Location/Qualifiers
source                  1..27
                        mol_type = unassigned DNA
                        organism = Homo sapiens
SEQUENCE: 564
gacccttccc gacaaccatc tcgaaca                                           27

SEQ ID NO: 565          moltype = DNA   length = 28
FEATURE                 Location/Qualifiers
source                  1..28
                        mol_type = unassigned DNA
                        organism = Homo sapiens
SEQUENCE: 565
gaaaattgcg cggttgggtt agtagggg                                          28

SEQ ID NO: 566          moltype = DNA   length = 28
FEATURE                 Location/Qualifiers
source                  1..28
                        mol_type = unassigned DNA
                        organism = Homo sapiens
SEQUENCE: 566
acctacaaat accgtcccca cccgaaac                                          28

SEQ ID NO: 567          moltype = DNA   length = 28
FEATURE                 Location/Qualifiers
source                  1..28
                        mol_type = unassigned DNA
                        organism = Homo sapiens
SEQUENCE: 567
aagagggtg tgattcgcga gtttagat                                           28

SEQ ID NO: 568          moltype = DNA   length = 23
FEATURE                 Location/Qualifiers
source                  1..23
                        mol_type = unassigned DNA
                        organism = Homo sapiens
SEQUENCE: 568
ccgcgcgcga ctcgaacgaa aaa                                               23

SEQ ID NO: 569          moltype = DNA   length = 28
FEATURE                 Location/Qualifiers
source                  1..28
                        mol_type = unassigned DNA
                        organism = Homo sapiens
SEQUENCE: 569
aagggtgcga tgttttcgtt taggatcg                                          28

SEQ ID NO: 570          moltype = DNA   length = 29
FEATURE                 Location/Qualifiers
source                  1..29
                        mol_type = unassigned DNA
                        organism = Homo sapiens
SEQUENCE: 570
taactaacta aaaccgcgat aaaacgact                                         29
```

-continued

```
SEQ ID NO: 571            moltype = DNA  length = 28
FEATURE                   Location/Qualifiers
source                    1..28
                          mol_type = unassigned DNA
                          organism = Homo sapiens
SEQUENCE: 571
tggtaatcgc gtaggtgtgt gatagggc                                       28

SEQ ID NO: 572            moltype = DNA  length = 28
FEATURE                   Location/Qualifiers
source                    1..28
                          mol_type = unassigned DNA
                          organism = Homo sapiens
SEQUENCE: 572
aaaatacaaa atacgccccc gaccccga                                       28

SEQ ID NO: 573            moltype = DNA  length = 28
FEATURE                   Location/Qualifiers
source                    1..28
                          mol_type = unassigned DNA
                          organism = Homo sapiens
SEQUENCE: 573
tgaggagaga ttcggagtag ttagtaga                                       28

SEQ ID NO: 574            moltype = DNA  length = 28
FEATURE                   Location/Qualifiers
source                    1..28
                          mol_type = unassigned DNA
                          organism = Homo sapiens
SEQUENCE: 574
ccctatcaca cacctacgcg attaccaa                                       28

SEQ ID NO: 575            moltype = DNA  length = 28
FEATURE                   Location/Qualifiers
source                    1..28
                          mol_type = unassigned DNA
                          organism = Homo sapiens
SEQUENCE: 575
tttcgaaaag ttggtagtcg gcggttgg                                       28

SEQ ID NO: 576            moltype = DNA  length = 28
FEATURE                   Location/Qualifiers
source                    1..28
                          mol_type = unassigned DNA
                          organism = Homo sapiens
SEQUENCE: 576
cattctactc ccccgaatcg aaaccccc                                       28

SEQ ID NO: 577            moltype = DNA  length = 28
FEATURE                   Location/Qualifiers
source                    1..28
                          mol_type = unassigned DNA
                          organism = Homo sapiens
SEQUENCE: 577
aagaggaaga gttcgcgcgt cgagttta                                       28

SEQ ID NO: 578            moltype = DNA  length = 28
FEATURE                   Location/Qualifiers
source                    1..28
                          mol_type = unassigned DNA
                          organism = Homo sapiens
SEQUENCE: 578
gaaatcgcgc gcccacgata ctacaaaa                                       28

SEQ ID NO: 579            moltype = DNA  length = 25
FEATURE                   Location/Qualifiers
source                    1..25
                          mol_type = unassigned DNA
                          organism = Homo sapiens
SEQUENCE: 579
ttattagtag gcggcgtcgg gggtt                                          25

SEQ ID NO: 580            moltype = DNA  length = 29
FEATURE                   Location/Qualifiers
source                    1..29
                          mol_type = unassigned DNA
                          organism = Homo sapiens
SEQUENCE: 580
```

-continued

```
cgaaaacccc tactccgaaa aatcgtccg                                   29

SEQ ID NO: 581          moltype = DNA   length = 28
FEATURE                 Location/Qualifiers
source                  1..28
                        mol_type = unassigned DNA
                        organism = Homo sapiens
SEQUENCE: 581
gttgagatat cgaggggttc gggttagg                                    28

SEQ ID NO: 582          moltype = DNA   length = 30
FEATURE                 Location/Qualifiers
source                  1..30
                        mol_type = unassigned DNA
                        organism = Homo sapiens
SEQUENCE: 582
cgccaacaac gataaaataa ataccgcgcc                                  30

SEQ ID NO: 583          moltype = DNA   length = 29
FEATURE                 Location/Qualifiers
source                  1..29
                        mol_type = unassigned DNA
                        organism = Homo sapiens
SEQUENCE: 583
cgtttgttcg atcgggtcg tacgagtat                                    29

SEQ ID NO: 584          moltype = DNA   length = 28
FEATURE                 Location/Qualifiers
source                  1..28
                        mol_type = unassigned DNA
                        organism = Homo sapiens
SEQUENCE: 584
tttccgcctc ctaccttcta acccgact                                    28

SEQ ID NO: 585          moltype = DNA   length = 28
FEATURE                 Location/Qualifiers
source                  1..28
                        mol_type = unassigned DNA
                        organism = Homo sapiens
SEQUENCE: 585
ggttggggga gtgggaggta aattcgtt                                    28

SEQ ID NO: 586          moltype = DNA   length = 28
FEATURE                 Location/Qualifiers
source                  1..28
                        mol_type = unassigned DNA
                        organism = Homo sapiens
SEQUENCE: 586
ctaaacgctc cctcacgcct taccttca                                    28

SEQ ID NO: 587          moltype = DNA   length = 28
FEATURE                 Location/Qualifiers
source                  1..28
                        mol_type = unassigned DNA
                        organism = Homo sapiens
SEQUENCE: 587
ttgagggaaa cgcggtggga atcgtttt                                    28

SEQ ID NO: 588          moltype = DNA   length = 28
FEATURE                 Location/Qualifiers
source                  1..28
                        mol_type = unassigned DNA
                        organism = Homo sapiens
SEQUENCE: 588
ccgtaactcg cccgaaaaac taaccgaa                                    28

SEQ ID NO: 589          moltype = DNA   length = 22
FEATURE                 Location/Qualifiers
source                  1..22
                        mol_type = unassigned DNA
                        organism = Homo sapiens
SEQUENCE: 589
tgattggttg cggggtagtt tc                                          22

SEQ ID NO: 590          moltype = DNA   length = 24
FEATURE                 Location/Qualifiers
source                  1..24
                        mol_type = unassigned DNA
                        organism = Homo sapiens
```

-continued

```
SEQUENCE: 590
acacccgctt taaaataccg ctaa                                           24

SEQ ID NO: 591          moltype = DNA  length = 28
FEATURE                 Location/Qualifiers
source                  1..28
                        mol_type = unassigned DNA
                        organism = Homo sapiens
SEQUENCE: 591
gcgtttcggg tcgttcgttt tatttcgc                                       28

SEQ ID NO: 592          moltype = DNA  length = 28
FEATURE                 Location/Qualifiers
source                  1..28
                        mol_type = unassigned DNA
                        organism = Homo sapiens
SEQUENCE: 592
cgacaaccta cgccgaatat acgcacct                                       28

SEQ ID NO: 593          moltype = DNA  length = 28
FEATURE                 Location/Qualifiers
source                  1..28
                        mol_type = unassigned DNA
                        organism = Homo sapiens
SEQUENCE: 593
gaagggatga ggttgaggtt ggaggtcg                                       28

SEQ ID NO: 594          moltype = DNA  length = 29
FEATURE                 Location/Qualifiers
source                  1..29
                        mol_type = unassigned DNA
                        organism = Homo sapiens
SEQUENCE: 594
acctcctacc caccaattcc gaaaaacaa                                      29

SEQ ID NO: 595          moltype = DNA  length = 24
FEATURE                 Location/Qualifiers
source                  1..24
                        mol_type = unassigned DNA
                        organism = Homo sapiens
SEQUENCE: 595
ttacggagtt ttaggcggcg ttac                                           24

SEQ ID NO: 596          moltype = DNA  length = 23
FEATURE                 Location/Qualifiers
source                  1..23
                        mol_type = unassigned DNA
                        organism = Homo sapiens
SEQUENCE: 596
catttccctc tctacgcgcg aac                                            23

SEQ ID NO: 597          moltype = DNA  length = 28
FEATURE                 Location/Qualifiers
source                  1..28
                        mol_type = unassigned DNA
                        organism = Homo sapiens
SEQUENCE: 597
cgtaggtttt gttggagcga gagatcgg                                       28

SEQ ID NO: 598          moltype = DNA  length = 29
FEATURE                 Location/Qualifiers
source                  1..29
                        mol_type = unassigned DNA
                        organism = Homo sapiens
SEQUENCE: 598
acatataaaa ccgcgctacc cgaaaaccg                                      29

SEQ ID NO: 599          moltype = DNA  length = 28
FEATURE                 Location/Qualifiers
source                  1..28
                        mol_type = unassigned DNA
                        organism = Homo sapiens
SEQUENCE: 599
tgaaaggggga gagggggaatg ttattgtt                                     28

SEQ ID NO: 600          moltype = DNA  length = 28
FEATURE                 Location/Qualifiers
source                  1..28
                        mol_type = unassigned DNA
```

-continued

```
                             organism = Homo sapiens
SEQUENCE: 600
aatattctcg caaacccacc gccaaacc                                        28

SEQ ID NO: 601          moltype = DNA  length = 28
FEATURE                 Location/Qualifiers
source                  1..28
                        mol_type = unassigned DNA
                        organism = Homo sapiens
SEQUENCE: 601
aaagagattc gtgttgcggc ggatgaag                                        28

SEQ ID NO: 602          moltype = DNA  length = 28
FEATURE                 Location/Qualifiers
source                  1..28
                        mol_type = unassigned DNA
                        organism = Homo sapiens
SEQUENCE: 602
gatcaacact cgaacccgaa ctttccgc                                        28

SEQ ID NO: 603          moltype = DNA  length = 28
FEATURE                 Location/Qualifiers
source                  1..28
                        mol_type = unassigned DNA
                        organism = Homo sapiens
SEQUENCE: 603
aagggaggag ggtggatcga aagcgtta                                        28

SEQ ID NO: 604          moltype = DNA  length = 29
FEATURE                 Location/Qualifiers
source                  1..29
                        mol_type = unassigned DNA
                        organism = Homo sapiens
SEQUENCE: 604
cgaaaacctt tacacgcgca caaactacg                                       29

SEQ ID NO: 605          moltype = DNA  length = 28
FEATURE                 Location/Qualifiers
source                  1..28
                        mol_type = unassigned DNA
                        organism = Homo sapiens
SEQUENCE: 605
tatgggttgc gtcgagggta aggtagtg                                        28

SEQ ID NO: 606          moltype = DNA  length = 29
FEATURE                 Location/Qualifiers
source                  1..29
                        mol_type = unassigned DNA
                        organism = Homo sapiens
SEQUENCE: 606
accatcgccg ttcttacctt tcgtctaca                                       29

SEQ ID NO: 607          moltype = DNA  length = 28
FEATURE                 Location/Qualifiers
source                  1..28
                        mol_type = unassigned DNA
                        organism = Homo sapiens
SEQUENCE: 607
tttttaattc ggttcggcgt tgatttgt                                        28

SEQ ID NO: 608          moltype = DNA  length = 21
FEATURE                 Location/Qualifiers
source                  1..21
                        mol_type = unassigned DNA
                        organism = Homo sapiens
SEQUENCE: 608
acaaccgcgc gctcccgata c                                               21

SEQ ID NO: 609          moltype = DNA  length = 27
FEATURE                 Location/Qualifiers
source                  1..27
                        mol_type = unassigned DNA
                        organism = Homo sapiens
SEQUENCE: 609
tagcgcggaa gttgtgagtt taaggcg                                         27

SEQ ID NO: 610          moltype = DNA  length = 29
FEATURE                 Location/Qualifiers
source                  1..29
```

-continued

```
                              mol_type = unassigned DNA
                              organism = Homo sapiens
SEQUENCE: 610
tcctctaaac accatcgaaa cccccgaac                                    29

SEQ ID NO: 611       moltype = DNA   length = 28
FEATURE              Location/Qualifiers
source               1..28
                     mol_type = unassigned DNA
                     organism = Homo sapiens
SEQUENCE: 611
agtggcgttc gttgagatta gggaaggg                                     28

SEQ ID NO: 612       moltype = DNA   length = 28
FEATURE              Location/Qualifiers
source               1..28
                     mol_type = unassigned DNA
                     organism = Homo sapiens
SEQUENCE: 612
accgtacgct accgaaacga cctttaca                                     28

SEQ ID NO: 613       moltype = DNA   length = 22
FEATURE              Location/Qualifiers
source               1..22
                     mol_type = unassigned DNA
                     organism = Homo sapiens
SEQUENCE: 613
gtttgtaatt ggtatgagcg gc                                           22

SEQ ID NO: 614       moltype = DNA   length = 18
FEATURE              Location/Qualifiers
source               1..18
                     mol_type = unassigned DNA
                     organism = Homo sapiens
SEQUENCE: 614
ataacgaaac gacgcctc                                                18

SEQ ID NO: 615       moltype = DNA   length = 20
FEATURE              Location/Qualifiers
source               1..20
                     mol_type = unassigned DNA
                     organism = Homo sapiens
SEQUENCE: 615
gtaattggta tgagcggcgt                                              20

SEQ ID NO: 616       moltype = DNA   length = 21
FEATURE              Location/Qualifiers
source               1..21
                     mol_type = unassigned DNA
                     organism = Homo sapiens
SEQUENCE: 616
gcctccgcga aataaaacca t                                            21

SEQ ID NO: 617       moltype = DNA   length = 21
FEATURE              Location/Qualifiers
source               1..21
                     mol_type = unassigned DNA
                     organism = Homo sapiens
SEQUENCE: 617
agttagagtg ggttagggga t                                            21

SEQ ID NO: 618       moltype = DNA   length = 20
FEATURE              Location/Qualifiers
source               1..20
                     mol_type = unassigned DNA
                     organism = Homo sapiens
SEQUENCE: 618
acgcgtaaca caaacacgac                                              20

SEQ ID NO: 619       moltype = DNA   length = 20
FEATURE              Location/Qualifiers
source               1..20
                     mol_type = unassigned DNA
                     organism = Homo sapiens
SEQUENCE: 619
gggggatttt aaagatcgtc                                              20

SEQ ID NO: 620       moltype = DNA   length = 18
FEATURE              Location/Qualifiers
```

-continued

```
source                  1..18
                        mol_type = unassigned DNA
                        organism = Homo sapiens
SEQUENCE: 620
gacgaacgca atccacaa                                                  18

SEQ ID NO: 621          moltype = DNA   length = 20
FEATURE                 Location/Qualifiers
source                  1..20
                        mol_type = unassigned DNA
                        organism = Homo sapiens
SEQUENCE: 621
tggtggagtt gtggattgcg                                                20

SEQ ID NO: 622          moltype = DNA   length = 20
FEATURE                 Location/Qualifiers
source                  1..20
                        mol_type = unassigned DNA
                        organism = Homo sapiens
SEQUENCE: 622
tcccacccaa acctctctct                                                20

SEQ ID NO: 623          moltype = DNA   length = 18
FEATURE                 Location/Qualifiers
source                  1..18
                        mol_type = unassigned DNA
                        organism = Homo sapiens
SEQUENCE: 623
ggtgcgttta cgggtttc                                                  18

SEQ ID NO: 624          moltype = DNA   length = 21
FEATURE                 Location/Qualifiers
source                  1..21
                        mol_type = unassigned DNA
                        organism = Homo sapiens
SEQUENCE: 624
acctaatccg atatttcccg a                                              21

SEQ ID NO: 625          moltype = DNA   length = 20
FEATURE                 Location/Qualifiers
source                  1..20
                        mol_type = unassigned DNA
                        organism = Homo sapiens
SEQUENCE: 625
ggtagggttt cggttgcgta                                                20

SEQ ID NO: 626          moltype = DNA   length = 24
FEATURE                 Location/Qualifiers
source                  1..24
                        mol_type = unassigned DNA
                        organism = Homo sapiens
SEQUENCE: 626
tatttcccga aaactccaca tcca                                           24

SEQ ID NO: 627          moltype = DNA   length = 20
FEATURE                 Location/Qualifiers
source                  1..20
                        mol_type = unassigned DNA
                        organism = Homo sapiens
SEQUENCE: 627
tcccgaaaac tccacatcca                                                20

SEQ ID NO: 628          moltype = DNA   length = 20
FEATURE                 Location/Qualifiers
source                  1..20
                        mol_type = unassigned DNA
                        organism = Homo sapiens
SEQUENCE: 628
atttggatgt ttcgcgtttc                                                20

SEQ ID NO: 629          moltype = DNA   length = 20
FEATURE                 Location/Qualifiers
source                  1..20
                        mol_type = unassigned DNA
                        organism = Homo sapiens
SEQUENCE: 629
tatcgctacg acccgactaa                                                20

SEQ ID NO: 630          moltype = DNA   length = 24
```

-continued

```
FEATURE            Location/Qualifiers
source             1..24
                   mol_type = unassigned DNA
                   organism = Homo sapiens
SEQUENCE: 630
gttaatttgg atgtttcgcg tttc                                    24

SEQ ID NO: 631     moltype = DNA  length = 23
FEATURE            Location/Qualifiers
source             1..23
                   mol_type = unassigned DNA
                   organism = Homo sapiens
SEQUENCE: 631
gtttatcgct acgacccgac taa                                     23

SEQ ID NO: 632     moltype = DNA  length = 20
FEATURE            Location/Qualifiers
source             1..20
                   mol_type = unassigned DNA
                   organism = Homo sapiens
SEQUENCE: 632
aggggagtcg cgtttttagg                                         20

SEQ ID NO: 633     moltype = DNA  length = 20
FEATURE            Location/Qualifiers
source             1..20
                   mol_type = unassigned DNA
                   organism = Homo sapiens
SEQUENCE: 633
tcccgaccga aacccaaatc                                         20

SEQ ID NO: 634     moltype = DNA  length = 22
FEATURE            Location/Qualifiers
source             1..22
                   mol_type = unassigned DNA
                   organism = Homo sapiens
SEQUENCE: 634
gaataacggc gtaagttttt ac                                      22

SEQ ID NO: 635     moltype = DNA  length = 18
FEATURE            Location/Qualifiers
source             1..18
                   mol_type = unassigned DNA
                   organism = Homo sapiens
SEQUENCE: 635
atcctcccga acgcaata                                           18

SEQ ID NO: 636     moltype = DNA  length = 21
FEATURE            Location/Qualifiers
source             1..21
                   mol_type = unassigned DNA
                   organism = Homo sapiens
SEQUENCE: 636
ttgtacgttt gtgggtgtgg a                                       21

SEQ ID NO: 637     moltype = DNA  length = 21
FEATURE            Location/Qualifiers
source             1..21
                   mol_type = unassigned DNA
                   organism = Homo sapiens
SEQUENCE: 637
tcctcccgaa cgcaataatc g                                       21

SEQ ID NO: 638     moltype = DNA  length = 21
FEATURE            Location/Qualifiers
source             1..21
                   mol_type = unassigned DNA
                   organism = Homo sapiens
SEQUENCE: 638
ttaacggtta ggttagatcg c                                       21

SEQ ID NO: 639     moltype = DNA  length = 20
FEATURE            Location/Qualifiers
source             1..20
                   mol_type = unassigned DNA
                   organism = Homo sapiens
SEQUENCE: 639
caatctctaa aacgcgacac                                         20
```

-continued

```
SEQ ID NO: 640            moltype = DNA   length = 21
FEATURE                   Location/Qualifiers
source                    1..21
                          mol_type = unassigned DNA
                          organism = Homo sapiens
SEQUENCE: 640
cgggtgtcgc gttttagaga t                                              21

SEQ ID NO: 641            moltype = DNA   length = 21
FEATURE                   Location/Qualifiers
source                    1..21
                          mol_type = unassigned DNA
                          organism = Homo sapiens
SEQUENCE: 641
ttctccgatc tcataccccc t                                              21

SEQ ID NO: 642            moltype = DNA   length = 19
FEATURE                   Location/Qualifiers
source                    1..19
                          mol_type = unassigned DNA
                          organism = Homo sapiens
SEQUENCE: 642
gagaaaagtt gtttcggtc                                                 19

SEQ ID NO: 643            moltype = DNA   length = 20
FEATURE                   Location/Qualifiers
source                    1..20
                          mol_type = unassigned DNA
                          organism = Homo sapiens
SEQUENCE: 643
gctacgtctc tactatccga                                                20

SEQ ID NO: 644            moltype = DNA   length = 22
FEATURE                   Location/Qualifiers
source                    1..22
                          mol_type = unassigned DNA
                          organism = Homo sapiens
SEQUENCE: 644
cgggagaaaa gttgtttcgg tc                                             22

SEQ ID NO: 645            moltype = DNA   length = 22
FEATURE                   Location/Qualifiers
source                    1..22
                          mol_type = unassigned DNA
                          organism = Homo sapiens
SEQUENCE: 645
ccgctacgtc tctactatcc ga                                             22

SEQ ID NO: 646            moltype = DNA   length = 18
FEATURE                   Location/Qualifiers
source                    1..18
                          mol_type = unassigned DNA
                          organism = Homo sapiens
SEQUENCE: 646
ttcggggtga gggtagtc                                                  18

SEQ ID NO: 647            moltype = DNA   length = 18
FEATURE                   Location/Qualifiers
source                    1..18
                          mol_type = unassigned DNA
                          organism = Homo sapiens
SEQUENCE: 647
ccgacgccca actaaaaa                                                  18

SEQ ID NO: 648            moltype = DNA   length = 21
FEATURE                   Location/Qualifiers
source                    1..21
                          mol_type = unassigned DNA
                          organism = Homo sapiens
SEQUENCE: 648
gagttcgggg tgagggtagt c                                              21

SEQ ID NO: 649            moltype = DNA   length = 23
FEATURE                   Location/Qualifiers
source                    1..23
                          mol_type = unassigned DNA
                          organism = Homo sapiens
SEQUENCE: 649
gaatcccgac gcccaactaa aaa                                            23
```

-continued

```
SEQ ID NO: 650            moltype = DNA  length = 20
FEATURE                   Location/Qualifiers
source                    1..20
                          mol_type = unassigned DNA
                          organism = Homo sapiens
SEQUENCE: 650
ttttcgggtt acgggtcgtt                                         20

SEQ ID NO: 651            moltype = DNA  length = 20
FEATURE                   Location/Qualifiers
source                    1..20
                          mol_type = unassigned DNA
                          organism = Homo sapiens
SEQUENCE: 651
acgactcctc cgaaaatccg                                         20

SEQ ID NO: 652            moltype = DNA  length = 19
FEATURE                   Location/Qualifiers
source                    1..19
                          mol_type = unassigned DNA
                          organism = Homo sapiens
SEQUENCE: 652
gtcgattttt gttttgagc                                          19

SEQ ID NO: 653            moltype = DNA  length = 22
FEATURE                   Location/Qualifiers
source                    1..22
                          mol_type = unassigned DNA
                          organism = Homo sapiens
SEQUENCE: 653
taaaaataat ctaccgaatc gc                                      22

SEQ ID NO: 654            moltype = DNA  length = 20
FEATURE                   Location/Qualifiers
source                    1..20
                          mol_type = unassigned DNA
                          organism = Homo sapiens
SEQUENCE: 654
ggcgttagcg gggatttaga                                         20

SEQ ID NO: 655            moltype = DNA  length = 20
FEATURE                   Location/Qualifiers
source                    1..20
                          mol_type = unassigned DNA
                          organism = Homo sapiens
SEQUENCE: 655
cgcatcaaac gaaaccctcc                                         20

SEQ ID NO: 656            moltype = DNA  length = 28
FEATURE                   Location/Qualifiers
source                    1..28
                          mol_type = unassigned DNA
                          organism = Homo sapiens
SEQUENCE: 656
cgggaaggtg ttcgtttaat ggttcggt                                28

SEQ ID NO: 657            moltype = DNA  length = 28
FEATURE                   Location/Qualifiers
source                    1..28
                          mol_type = unassigned DNA
                          organism = Homo sapiens
SEQUENCE: 657
gtttccgctc taaatccccg ctaacgcc                                28

SEQ ID NO: 658            moltype = DNA  length = 28
FEATURE                   Location/Qualifiers
source                    1..28
                          mol_type = unassigned DNA
                          organism = Homo sapiens
SEQUENCE: 658
ggaaaaagga ggaggataag aagcgcgg                                28

SEQ ID NO: 659            moltype = DNA  length = 28
FEATURE                   Location/Qualifiers
source                    1..28
                          mol_type = unassigned DNA
                          organism = Homo sapiens
SEQUENCE: 659
```

-continued

```
ctcgccgaaa atcacgacgc aatcctac                                       28

SEQ ID NO: 660          moltype = DNA   length = 19
FEATURE                 Location/Qualifiers
source                  1..19
                        mol_type = unassigned DNA
                        organism = Homo sapiens
SEQUENCE: 660
taggggaggc gtcgagttc                                                 19

SEQ ID NO: 661          moltype = DNA   length = 20
FEATURE                 Location/Qualifiers
source                  1..20
                        mol_type = unassigned DNA
                        organism = Homo sapiens
SEQUENCE: 661
actcgctaaa cgtcccaacc                                                20

SEQ ID NO: 662          moltype = DNA   length = 18
FEATURE                 Location/Qualifiers
source                  1..18
                        mol_type = unassigned DNA
                        organism = Homo sapiens
SEQUENCE: 662
gagtttaggg gtcgcgtc                                                  18

SEQ ID NO: 663          moltype = DNA   length = 20
FEATURE                 Location/Qualifiers
source                  1..20
                        mol_type = unassigned DNA
                        organism = Homo sapiens
SEQUENCE: 663
caataccgcc gcctctacta                                                20

SEQ ID NO: 664          moltype = DNA   length = 20
FEATURE                 Location/Qualifiers
source                  1..20
                        mol_type = unassigned DNA
                        organism = Homo sapiens
SEQUENCE: 664
gagagagtag gagcggatcg                                                20

SEQ ID NO: 665          moltype = DNA   length = 20
FEATURE                 Location/Qualifiers
source                  1..20
                        mol_type = unassigned DNA
                        organism = Homo sapiens
SEQUENCE: 665
acaaatcaac cccgccctaa                                                20

SEQ ID NO: 666          moltype = DNA   length = 20
FEATURE                 Location/Qualifiers
source                  1..20
                        mol_type = unassigned DNA
                        organism = Homo sapiens
SEQUENCE: 666
agtgagtgtt cgggagtttc                                                20

SEQ ID NO: 667          moltype = DNA   length = 20
FEATURE                 Location/Qualifiers
source                  1..20
                        mol_type = unassigned DNA
                        organism = Homo sapiens
SEQUENCE: 667
tcatttatta aaaacgcgcg                                                20

SEQ ID NO: 668          moltype = DNA   length = 22
FEATURE                 Location/Qualifiers
source                  1..22
                        mol_type = unassigned DNA
                        organism = Homo sapiens
SEQUENCE: 668
gcagtgagtg ctcgggagcc cc                                             22

SEQ ID NO: 669          moltype = DNA   length = 25
FEATURE                 Location/Qualifiers
source                  1..25
                        mol_type = unassigned DNA
                        organism = Homo sapiens
```

```
SEQUENCE: 669
ggttttcatt tgttagaggc gcgcg                                      25

SEQ ID NO: 670          moltype = DNA  length = 20
FEATURE                 Location/Qualifiers
source                  1..20
                        mol_type = unassigned DNA
                        organism = Homo sapiens
SEQUENCE: 670
cgggttcgcg taggattagg                                            20

SEQ ID NO: 671          moltype = DNA  length = 20
FEATURE                 Location/Qualifiers
source                  1..20
                        mol_type = unassigned DNA
                        organism = Homo sapiens
SEQUENCE: 671
actcctcatc ccaacaccct                                            20

SEQ ID NO: 672          moltype = DNA  length = 19
FEATURE                 Location/Qualifiers
source                  1..19
                        mol_type = unassigned DNA
                        organism = Homo sapiens
SEQUENCE: 672
gttcgtagtt cgcggtttc                                             19

SEQ ID NO: 673          moltype = DNA  length = 18
FEATURE                 Location/Qualifiers
source                  1..18
                        mol_type = unassigned DNA
                        organism = Homo sapiens
SEQUENCE: 673
cgatactctc ctcgccct                                              18

SEQ ID NO: 674          moltype = DNA  length = 22
FEATURE                 Location/Qualifiers
source                  1..22
                        mol_type = unassigned DNA
                        organism = Homo sapiens
SEQUENCE: 674
tcggttcgta gttcgcggtt tc                                         22

SEQ ID NO: 675          moltype = DNA  length = 21
FEATURE                 Location/Qualifiers
source                  1..21
                        mol_type = unassigned DNA
                        organism = Homo sapiens
SEQUENCE: 675
gcacgatact ctcctcgccc t                                          21

SEQ ID NO: 676          moltype = DNA  length = 19
FEATURE                 Location/Qualifiers
source                  1..19
                        mol_type = unassigned DNA
                        organism = Homo sapiens
SEQUENCE: 676
ttgggcgagt gatagtttc                                             19

SEQ ID NO: 677          moltype = DNA  length = 18
FEATURE                 Location/Qualifiers
source                  1..18
                        mol_type = unassigned DNA
                        organism = Homo sapiens
SEQUENCE: 677
gaccgctact acacccga                                              18

SEQ ID NO: 678          moltype = DNA  length = 23
FEATURE                 Location/Qualifiers
source                  1..23
                        mol_type = unassigned DNA
                        organism = Homo sapiens
SEQUENCE: 678
cggtagaaga acgtgtatga ggt                                        23

SEQ ID NO: 679          moltype = DNA  length = 20
FEATURE                 Location/Qualifiers
source                  1..20
                        mol_type = unassigned DNA
```

```
                              organism = Homo sapiens
SEQUENCE: 679
gctaccctcg aaaacccgaa                                                          20

SEQ ID NO: 680        moltype = DNA   length = 20
FEATURE               Location/Qualifiers
source                1..20
                      mol_type = unassigned DNA
                      organism = Homo sapiens
SEQUENCE: 680
gatttttttt aaggtcgcgc                                                          20

SEQ ID NO: 681        moltype = DNA   length = 24
FEATURE               Location/Qualifiers
source                1..24
                      mol_type = unassigned DNA
                      organism = Homo sapiens
SEQUENCE: 681
ttacgatttt ttttaaggtc gcgc                                                     24

SEQ ID NO: 682        moltype = DNA   length = 22
FEATURE               Location/Qualifiers
source                1..22
                      mol_type = unassigned DNA
                      organism = Homo sapiens
SEQUENCE: 682
actataccta cctaccgccg tc                                                       22

SEQ ID NO: 683        moltype = DNA   length = 20
FEATURE               Location/Qualifiers
source                1..20
                      mol_type = unassigned DNA
                      organism = Homo sapiens
SEQUENCE: 683
atttcgaaga aggcgggtcg                                                          20

SEQ ID NO: 684        moltype = DNA   length = 20
FEATURE               Location/Qualifiers
source                1..20
                      mol_type = unassigned DNA
                      organism = Homo sapiens
SEQUENCE: 684
ctccaaacga tacgccaacg                                                          20

SEQ ID NO: 685        moltype = DNA   length = 18
FEATURE               Location/Qualifiers
source                1..18
                      mol_type = unassigned DNA
                      organism = Homo sapiens
SEQUENCE: 685
ttttgcgggt aagcgttc                                                            18

SEQ ID NO: 686        moltype = DNA   length = 19
FEATURE               Location/Qualifiers
source                1..19
                      mol_type = unassigned DNA
                      organism = Homo sapiens
SEQUENCE: 686
ccacaactct ctcgacgac                                                           19

SEQ ID NO: 687        moltype = DNA   length = 22
FEATURE               Location/Qualifiers
source                1..22
                      mol_type = unassigned DNA
                      organism = Homo sapiens
SEQUENCE: 687
tgttttttgc gggtaagcgt tc                                                       22

SEQ ID NO: 688        moltype = DNA   length = 21
FEATURE               Location/Qualifiers
source                1..21
                      mol_type = unassigned DNA
                      organism = Homo sapiens
SEQUENCE: 688
gcccacaact ctctcgacga c                                                        21

SEQ ID NO: 689        moltype = DNA   length = 20
FEATURE               Location/Qualifiers
source                1..20
```

-continued

```
                              mol_type = unassigned DNA
                              organism = Homo sapiens
SEQUENCE: 689
atttcgggaa agggtgggtc                                            20

SEQ ID NO: 690          moltype = DNA   length = 20
FEATURE                 Location/Qualifiers
source                  1..20
                        mol_type = unassigned DNA
                        organism = Homo sapiens
SEQUENCE: 690
accctaatcc cccttcacca                                            20

SEQ ID NO: 691          moltype = DNA   length = 20
FEATURE                 Location/Qualifiers
source                  1..20
                        mol_type = unassigned DNA
                        organism = Homo sapiens
SEQUENCE: 691
tttcgtttcg tttcggtcgc                                            20

SEQ ID NO: 692          moltype = DNA   length = 20
FEATURE                 Location/Qualifiers
source                  1..20
                        mol_type = unassigned DNA
                        organism = Homo sapiens
SEQUENCE: 692
aacccgcccg aactcaaata                                            20

SEQ ID NO: 693          moltype = DNA   length = 21
FEATURE                 Location/Qualifiers
source                  1..21
                        mol_type = unassigned DNA
                        organism = Homo sapiens
SEQUENCE: 693
attaggagcg tacgtttatt c                                          21

SEQ ID NO: 694          moltype = DNA   length = 18
FEATURE                 Location/Qualifiers
source                  1..18
                        mol_type = unassigned DNA
                        organism = Homo sapiens
SEQUENCE: 694
tacgcactcg aaacacaa                                              18

SEQ ID NO: 695          moltype = DNA   length = 20
FEATURE                 Location/Qualifiers
source                  1..20
                        mol_type = unassigned DNA
                        organism = Homo sapiens
SEQUENCE: 695
cggcgcgttt taagggtttt                                            20

SEQ ID NO: 696          moltype = DNA   length = 20
FEATURE                 Location/Qualifiers
source                  1..20
                        mol_type = unassigned DNA
                        organism = Homo sapiens
SEQUENCE: 696
attactctca cctccgcacg                                            20

SEQ ID NO: 697          moltype = DNA   length = 19
FEATURE                 Location/Qualifiers
source                  1..19
                        mol_type = unassigned DNA
                        organism = Homo sapiens
SEQUENCE: 697
gattgcggga agaaggtac                                             19

SEQ ID NO: 698          moltype = DNA   length = 19
FEATURE                 Location/Qualifiers
source                  1..19
                        mol_type = unassigned DNA
                        organism = Homo sapiens
SEQUENCE: 698
aaacgaaacc aaacgacaa                                             19

SEQ ID NO: 699          moltype = DNA   length = 21
FEATURE                 Location/Qualifiers
```

-continued

```
source                        1..21
                              mol_type = unassigned DNA
                              organism = Homo sapiens
SEQUENCE: 699
cggattgcgg gaagaaggta c                                                       21

SEQ ID NO: 700           moltype = DNA   length = 23
FEATURE                  Location/Qualifiers
source                   1..23
                         mol_type = unassigned DNA
                         organism = Homo sapiens
SEQUENCE: 700
gacgaaacga aaccaaacga caa                                                     23

SEQ ID NO: 701           moltype = DNA   length = 20
FEATURE                  Location/Qualifiers
source                   1..20
                         mol_type = unassigned DNA
                         organism = Homo sapiens
SEQUENCE: 701
ttttcgagtt tgaagcgttc                                                         20

SEQ ID NO: 702           moltype = DNA   length = 19
FEATURE                  Location/Qualifiers
source                   1..19
                         mol_type = unassigned DNA
                         organism = Homo sapiens
SEQUENCE: 702
cgactctcac ctaatccgc                                                          19

SEQ ID NO: 703           moltype = DNA   length = 23
FEATURE                  Location/Qualifiers
source                   1..23
                         mol_type = unassigned DNA
                         organism = Homo sapiens
SEQUENCE: 703
cggttttcga gtttgaagcg ttc                                                     23

SEQ ID NO: 704           moltype = DNA   length = 22
FEATURE                  Location/Qualifiers
source                   1..22
                         mol_type = unassigned DNA
                         organism = Homo sapiens
SEQUENCE: 704
taccgactct cacctaatcc gc                                                      22

SEQ ID NO: 705           moltype = DNA   length = 20
FEATURE                  Location/Qualifiers
source                   1..20
                         mol_type = unassigned DNA
                         organism = Homo sapiens
SEQUENCE: 705
ttacgacggg gagttcgttc                                                         20

SEQ ID NO: 706           moltype = DNA   length = 24
FEATURE                  Location/Qualifiers
source                   1..24
                         mol_type = unassigned DNA
                         organism = Homo sapiens
SEQUENCE: 706
cttaacaacg ttcgcaaatc acga                                                    24

SEQ ID NO: 707           moltype = DNA   length = 20
FEATURE                  Location/Qualifiers
source                   1..20
                         mol_type = unassigned DNA
                         organism = Homo sapiens
SEQUENCE: 707
acaacgttcg caaatcacga                                                         20

SEQ ID NO: 708           moltype = DNA   length = 19
FEATURE                  Location/Qualifiers
source                   1..19
                         mol_type = unassigned DNA
                         organism = Homo sapiens
SEQUENCE: 708
gttcgttatt tcggaattc                                                          19

SEQ ID NO: 709           moltype = DNA   length = 21
```

-continued

```
FEATURE              Location/Qualifiers
source               1..21
                     mol_type = unassigned DNA
                     organism = Homo sapiens
SEQUENCE: 709
ccgaccgata aaatataatt c                                      21

SEQ ID NO: 710       moltype = DNA   length = 20
FEATURE              Location/Qualifiers
source               1..20
                     mol_type = unassigned DNA
                     organism = Homo sapiens
SEQUENCE: 710
gggagggatt taagcgggag                                        20

SEQ ID NO: 711       moltype = DNA   length = 20
FEATURE              Location/Qualifiers
source               1..20
                     mol_type = unassigned DNA
                     organism = Homo sapiens
SEQUENCE: 711
cccccttcac taatcccgac                                        20

SEQ ID NO: 712       moltype = DNA   length = 18
FEATURE              Location/Qualifiers
source               1..18
                     mol_type = unassigned DNA
                     organism = Homo sapiens
SEQUENCE: 712
agtgttgaga gtcgacgc                                          18

SEQ ID NO: 713       moltype = DNA   length = 20
FEATURE              Location/Qualifiers
source               1..20
                     mol_type = unassigned DNA
                     organism = Homo sapiens
SEQUENCE: 713
aataaaataa cccgaaccgc                                        20

SEQ ID NO: 714       moltype = DNA   length = 20
FEATURE              Location/Qualifiers
source               1..20
                     mol_type = unassigned DNA
                     organism = Homo sapiens
SEQUENCE: 714
gggttacggt ttcgggttgt                                        20

SEQ ID NO: 715       moltype = DNA   length = 20
FEATURE              Location/Qualifiers
source               1..20
                     mol_type = unassigned DNA
                     organism = Homo sapiens
SEQUENCE: 715
cgcgtcgact ctcaacacta                                        20

SEQ ID NO: 716       moltype = DNA   length = 19
FEATURE              Location/Qualifiers
source               1..19
                     mol_type = unassigned DNA
                     organism = Homo sapiens
SEQUENCE: 716
ggtcgagtcg agtcgttac                                         19

SEQ ID NO: 717       moltype = DNA   length = 18
FEATURE              Location/Qualifiers
source               1..18
                     mol_type = unassigned DNA
                     organism = Homo sapiens
SEQUENCE: 717
aaaacgcctc ctaacgaa                                          18

SEQ ID NO: 718       moltype = DNA   length = 22
FEATURE              Location/Qualifiers
source               1..22
                     mol_type = unassigned DNA
                     organism = Homo sapiens
SEQUENCE: 718
attggtcgag tcgagtcgtt ac                                     22
```

-continued

```
SEQ ID NO: 719          moltype = DNA   length = 23
FEATURE                 Location/Qualifiers
source                  1..23
                        mol_type = unassigned DNA
                        organism = Homo sapiens
SEQUENCE: 719
acaaaaaaac gcctcctaac gaa                                          23

SEQ ID NO: 720          moltype = DNA   length = 21
FEATURE                 Location/Qualifiers
source                  1..21
                        mol_type = unassigned DNA
                        organism = Homo sapiens
SEQUENCE: 720
tatttttggg cgaaggcgtt g                                            21

SEQ ID NO: 721          moltype = DNA   length = 20
FEATURE                 Location/Qualifiers
source                  1..20
                        mol_type = unassigned DNA
                        organism = Homo sapiens
SEQUENCE: 721
gtaacgactc gactcgacca                                              20

SEQ ID NO: 722          moltype = DNA   length = 18
FEATURE                 Location/Qualifiers
source                  1..18
                        mol_type = unassigned DNA
                        organism = Homo sapiens
SEQUENCE: 722
tcggcgtttt cgtttttc                                                18

SEQ ID NO: 723          moltype = DNA   length = 22
FEATURE                 Location/Qualifiers
source                  1..22
                        mol_type = unassigned DNA
                        organism = Homo sapiens
SEQUENCE: 723
cgacgacaca accataaact tt                                           22

SEQ ID NO: 724          moltype = DNA   length = 20
FEATURE                 Location/Qualifiers
source                  1..20
                        mol_type = unassigned DNA
                        organism = Homo sapiens
SEQUENCE: 724
aaggttttgt agttgcggcg                                              20

SEQ ID NO: 725          moltype = DNA   length = 18
FEATURE                 Location/Qualifiers
source                  1..18
                        mol_type = unassigned DNA
                        organism = Homo sapiens
SEQUENCE: 725
tctcacgcgc aaccgaat                                                18

SEQ ID NO: 726          moltype = DNA   length = 19
FEATURE                 Location/Qualifiers
source                  1..19
                        mol_type = unassigned DNA
                        organism = Homo sapiens
SEQUENCE: 726
gtggagtttt aggtagcgc                                               19

SEQ ID NO: 727          moltype = DNA   length = 19
FEATURE                 Location/Qualifiers
source                  1..19
                        mol_type = unassigned DNA
                        organism = Homo sapiens
SEQUENCE: 727
acccgcgata aactaaacc                                               19

SEQ ID NO: 728          moltype = DNA   length = 22
FEATURE                 Location/Qualifiers
source                  1..22
                        mol_type = unassigned DNA
                        organism = Homo sapiens
SEQUENCE: 728
agggtggagt tttaggtagc gc                                           22
```

-continued

```
SEQ ID NO: 729          moltype = DNA   length = 23
FEATURE                 Location/Qualifiers
source                  1..23
                        mol_type = unassigned DNA
                        organism = Homo sapiens
SEQUENCE: 729
aacaacccgc gataaactaa acc                                      23

SEQ ID NO: 730          moltype = DNA   length = 20
FEATURE                 Location/Qualifiers
source                  1..20
                        mol_type = unassigned DNA
                        organism = Homo sapiens
SEQUENCE: 730
tgtagtcgtg gttgtcgtgg                                          20

SEQ ID NO: 731          moltype = DNA   length = 20
FEATURE                 Location/Qualifiers
source                  1..20
                        mol_type = unassigned DNA
                        organism = Homo sapiens
SEQUENCE: 731
ccaaataaac gacgtcccgc                                          20

SEQ ID NO: 732          moltype = DNA   length = 22
FEATURE                 Location/Qualifiers
source                  1..22
                        mol_type = unassigned DNA
                        organism = Homo sapiens
SEQUENCE: 732
attttatagt cgcgttaaaa gc                                       22

SEQ ID NO: 733          moltype = DNA   length = 20
FEATURE                 Location/Qualifiers
source                  1..20
                        mol_type = unassigned DNA
                        organism = Homo sapiens
SEQUENCE: 733
acttttatta ctcgcgatcc                                          20

SEQ ID NO: 734          moltype = DNA   length = 20
FEATURE                 Location/Qualifiers
source                  1..20
                        mol_type = unassigned DNA
                        organism = Homo sapiens
SEQUENCE: 734
ggtagggtga gtttggtcgg                                          20

SEQ ID NO: 735          moltype = DNA   length = 20
FEATURE                 Location/Qualifiers
source                  1..20
                        mol_type = unassigned DNA
                        organism = Homo sapiens
SEQUENCE: 735
cgccgaacca cgtaaaaact                                          20

SEQ ID NO: 736          moltype = DNA   length = 20
FEATURE                 Location/Qualifiers
source                  1..20
                        mol_type = unassigned DNA
                        organism = Homo sapiens
SEQUENCE: 736
atttggggcg tttatgtttc                                          20

SEQ ID NO: 737          moltype = DNA   length = 18
FEATURE                 Location/Qualifiers
source                  1..18
                        mol_type = unassigned DNA
                        organism = Homo sapiens
SEQUENCE: 737
ccctcgaaaa acgactcc                                            18

SEQ ID NO: 738          moltype = DNA   length = 18
FEATURE                 Location/Qualifiers
source                  1..18
                        mol_type = unassigned DNA
                        organism = Homo sapiens
SEQUENCE: 738
```

-continued

```
aggggttgta gggtcggg                                                  18

SEQ ID NO: 739              moltype = DNA   length = 21
FEATURE                     Location/Qualifiers
source                      1..21
                            mol_type = unassigned DNA
                            organism = Homo sapiens
SEQUENCE: 739
tttaggggtt gtagggtcgg g                                              21

SEQ ID NO: 740              moltype = DNA   length = 22
FEATURE                     Location/Qualifiers
source                      1..22
                            mol_type = unassigned DNA
                            organism = Homo sapiens
SEQUENCE: 740
attttacatt tccctccccc gc                                             22

SEQ ID NO: 741              moltype = DNA   length = 18
FEATURE                     Location/Qualifiers
source                      1..18
                            mol_type = unassigned DNA
                            organism = Homo sapiens
SEQUENCE: 741
agaataaaag taggcggc                                                  18

SEQ ID NO: 742              moltype = DNA   length = 20
FEATURE                     Location/Qualifiers
source                      1..20
                            mol_type = unassigned DNA
                            organism = Homo sapiens
SEQUENCE: 742
tctcgaaacc aaaataaacg                                                20

SEQ ID NO: 743              moltype = DNA   length = 20
FEATURE                     Location/Qualifiers
source                      1..20
                            mol_type = unassigned DNA
                            organism = Homo sapiens
SEQUENCE: 743
agtaggcggc ggatttgtag                                                20

SEQ ID NO: 744              moltype = DNA   length = 22
FEATURE                     Location/Qualifiers
source                      1..22
                            mol_type = unassigned DNA
                            organism = Homo sapiens
SEQUENCE: 744
ccgaaaatac gcgaaatcaa cc                                             22

SEQ ID NO: 745              moltype = DNA   length = 19
FEATURE                     Location/Qualifiers
source                      1..19
                            mol_type = unassigned DNA
                            organism = Homo sapiens
SEQUENCE: 745
gaggagataa aggtgtcgc                                                 19

SEQ ID NO: 746              moltype = DNA   length = 20
FEATURE                     Location/Qualifiers
source                      1..20
                            mol_type = unassigned DNA
                            organism = Homo sapiens
SEQUENCE: 746
aacgtaccta acccgaaaac                                                20

SEQ ID NO: 747              moltype = DNA   length = 22
FEATURE                     Location/Qualifiers
source                      1..22
                            mol_type = unassigned DNA
                            organism = Homo sapiens
SEQUENCE: 747
tcggaggaga taaaggtgtc gc                                             22

SEQ ID NO: 748              moltype = DNA   length = 22
FEATURE                     Location/Qualifiers
source                      1..22
                            mol_type = unassigned DNA
                            organism = Homo sapiens
```

```
SEQUENCE: 748
ccaacgtacc taacccgaaa ac                                             22

SEQ ID NO: 749         moltype = DNA   length = 18
FEATURE                Location/Qualifiers
source                 1..18
                       mol_type = unassigned DNA
                       organism = Homo sapiens
SEQUENCE: 749
gacggtttcg gtagggtc                                                  18

SEQ ID NO: 750         moltype = DNA   length = 20
FEATURE                Location/Qualifiers
source                 1..20
                       mol_type = unassigned DNA
                       organism = Homo sapiens
SEQUENCE: 750
ccgaaccgaa tataaaacga                                                20

SEQ ID NO: 751         moltype = DNA   length = 20
FEATURE                Location/Qualifiers
source                 1..20
                       mol_type = unassigned DNA
                       organism = Homo sapiens
SEQUENCE: 751
cggacggttt cggtagggtc                                                20

SEQ ID NO: 752         moltype = DNA   length = 23
FEATURE                Location/Qualifiers
source                 1..23
                       mol_type = unassigned DNA
                       organism = Homo sapiens
SEQUENCE: 752
gcgccgaacc gaatataaaa cga                                            23

SEQ ID NO: 753         moltype = DNA   length = 19
FEATURE                Location/Qualifiers
source                 1..19
                       mol_type = unassigned DNA
                       organism = Homo sapiens
SEQUENCE: 753
ttaggttcgt aaagagggc                                                 19

SEQ ID NO: 754         moltype = DNA   length = 19
FEATURE                Location/Qualifiers
source                 1..19
                       mol_type = unassigned DNA
                       organism = Homo sapiens
SEQUENCE: 754
ttaaaaccac gtccgaata                                                 19

SEQ ID NO: 755         moltype = DNA   length = 20
FEATURE                Location/Qualifiers
source                 1..20
                       mol_type = unassigned DNA
                       organism = Homo sapiens
SEQUENCE: 755
tttcgggcgg gagttatagg                                                20

SEQ ID NO: 756         moltype = DNA   length = 20
FEATURE                Location/Qualifiers
source                 1..20
                       mol_type = unassigned DNA
                       organism = Homo sapiens
SEQUENCE: 756
acgcgctcta aactcaaccg                                                20

SEQ ID NO: 757         moltype = DNA   length = 26
FEATURE                Location/Qualifiers
source                 1..26
                       mol_type = unassigned DNA
                       organism = Homo sapiens
SEQUENCE: 757
gcgcgtgggg ttcgtagcgt tttaag                                         26

SEQ ID NO: 758         moltype = DNA   length = 25
FEATURE                Location/Qualifiers
source                 1..25
                       mol_type = unassigned DNA
```

-continued

```
                         organism = Homo sapiens
SEQUENCE: 758
ttacccgaaa caccccgcgc ccttc                                                 25

SEQ ID NO: 759           moltype = DNA   length = 28
FEATURE                  Location/Qualifiers
source                   1..28
                         mol_type = unassigned DNA
                         organism = Homo sapiens
SEQUENCE: 759
agatacggag atttagcgcg agatcggt                                              28

SEQ ID NO: 760           moltype = DNA   length = 28
FEATURE                  Location/Qualifiers
source                   1..28
                         mol_type = unassigned DNA
                         organism = Homo sapiens
SEQUENCE: 760
aaattaaccg ccgaacactc acaatacg                                              28

SEQ ID NO: 761           moltype = DNA   length = 28
FEATURE                  Location/Qualifiers
source                   1..28
                         mol_type = unassigned DNA
                         organism = Homo sapiens
SEQUENCE: 761
ttgtagtgtc gcgttgcgag tcgattgt                                              28

SEQ ID NO: 762           moltype = DNA   length = 29
FEATURE                  Location/Qualifiers
source                   1..29
                         mol_type = unassigned DNA
                         organism = Homo sapiens
SEQUENCE: 762
acaataacgt aacgcccata aaccgaacg                                             29

SEQ ID NO: 763           moltype = DNA   length = 28
FEATURE                  Location/Qualifiers
source                   1..28
                         mol_type = unassigned DNA
                         organism = Homo sapiens
SEQUENCE: 763
gaggacgggt tgaatcgtgg tttgttgg                                              28

SEQ ID NO: 764           moltype = DNA   length = 28
FEATURE                  Location/Qualifiers
source                   1..28
                         mol_type = unassigned DNA
                         organism = Homo sapiens
SEQUENCE: 764
actacgataa tcaaaacgct ccacgcga                                              28

SEQ ID NO: 765           moltype = DNA   length = 27
FEATURE                  Location/Qualifiers
source                   1..27
                         mol_type = unassigned DNA
                         organism = Homo sapiens
SEQUENCE: 765
gtgcgcgttt tagtagggcg agaatgg                                               27

SEQ ID NO: 766           moltype = DNA   length = 28
FEATURE                  Location/Qualifiers
source                   1..28
                         mol_type = unassigned DNA
                         organism = Homo sapiens
SEQUENCE: 766
cgaaaaccaa atccgaacca ccgtctcc                                              28

SEQ ID NO: 767           moltype = DNA   length = 28
FEATURE                  Location/Qualifiers
source                   1..28
                         mol_type = unassigned DNA
                         organism = Homo sapiens
SEQUENCE: 767
tgatttgggt ggatgtagag gttgtggt                                              28

SEQ ID NO: 768           moltype = DNA   length = 28
FEATURE                  Location/Qualifiers
source                   1..28
```

```
                          mol_type = unassigned DNA
                          organism = Homo sapiens
SEQUENCE: 768
tttcgaataa cgctactccg aaccgcga                                    28

SEQ ID NO: 769           moltype = DNA   length = 28
FEATURE                  Location/Qualifiers
source                   1..28
                          mol_type = unassigned DNA
                          organism = Homo sapiens
SEQUENCE: 769
ttgagagtag ggattgtggt gcgtcgtc                                    28

SEQ ID NO: 770           moltype = DNA   length = 28
FEATURE                  Location/Qualifiers
source                   1..28
                          mol_type = unassigned DNA
                          organism = Homo sapiens
SEQUENCE: 770
ctaactcccg aacgctacat tcgctcca                                    28

SEQ ID NO: 771           moltype = DNA   length = 27
FEATURE                  Location/Qualifiers
source                   1..27
                          mol_type = unassigned DNA
                          organism = Homo sapiens
SEQUENCE: 771
ggttgtggtg agtttggttt acgggcg                                     27

SEQ ID NO: 772           moltype = DNA   length = 26
FEATURE                  Location/Qualifiers
source                   1..26
                          mol_type = unassigned DNA
                          organism = Homo sapiens
SEQUENCE: 772
cgtaaaacgc gaccaccgcc aacata                                      26

SEQ ID NO: 773           moltype = DNA   length = 28
FEATURE                  Location/Qualifiers
source                   1..28
                          mol_type = unassigned DNA
                          organism = Homo sapiens
SEQUENCE: 773
gggaggttat tcgtaggatt tggcgcgg                                    28

SEQ ID NO: 774           moltype = DNA   length = 28
FEATURE                  Location/Qualifiers
source                   1..28
                          mol_type = unassigned DNA
                          organism = Homo sapiens
SEQUENCE: 774
atcctaacga ctacgcacta cttccgca                                    28

SEQ ID NO: 775           moltype = DNA   length = 24
FEATURE                  Location/Qualifiers
source                   1..24
                          mol_type = unassigned DNA
                          organism = Homo sapiens
SEQUENCE: 775
gagttcgttt agttcgtcgg cgtc                                        24

SEQ ID NO: 776           moltype = DNA   length = 27
FEATURE                  Location/Qualifiers
source                   1..27
                          mol_type = unassigned DNA
                          organism = Homo sapiens
SEQUENCE: 776
aaccccgata aactccgata acgacct                                     27

SEQ ID NO: 777           moltype = DNA   length = 28
FEATURE                  Location/Qualifiers
source                   1..28
                          mol_type = unassigned DNA
                          organism = Homo sapiens
SEQUENCE: 777
agagttgggg gcggtatagt tagggtgt                                    28

SEQ ID NO: 778           moltype = DNA   length = 28
FEATURE                  Location/Qualifiers
```

```
source                      1..28
                            mol_type = unassigned DNA
                            organism = Homo sapiens
SEQUENCE: 778
ttcaatccct acgaccccaa cgcctaaa                                              28

SEQ ID NO: 779              moltype = DNA   length = 28
FEATURE                     Location/Qualifiers
source                      1..28
                            mol_type = unassigned DNA
                            organism = Homo sapiens
SEQUENCE: 779
cgtggatacg agttttggcg gcgattat                                             28

SEQ ID NO: 780              moltype = DNA   length = 28
FEATURE                     Location/Qualifiers
source                      1..28
                            mol_type = unassigned DNA
                            organism = Homo sapiens
SEQUENCE: 780
gccaccaacc ctacctcctt ccatatcc                                             28

SEQ ID NO: 781              moltype = DNA   length = 28
FEATURE                     Location/Qualifiers
source                      1..28
                            mol_type = unassigned DNA
                            organism = Homo sapiens
SEQUENCE: 781
tttttcggtt tgagttatcg tggcggga                                             28

SEQ ID NO: 782              moltype = DNA   length = 28
FEATURE                     Location/Qualifiers
source                      1..28
                            mol_type = unassigned DNA
                            organism = Homo sapiens
SEQUENCE: 782
cgaaccgtac ttccaaccaa acgcaact                                             28

SEQ ID NO: 783              moltype = DNA   length = 28
FEATURE                     Location/Qualifiers
source                      1..28
                            mol_type = unassigned DNA
                            organism = Homo sapiens
SEQUENCE: 783
taggaagggg tcgatgttgg tttgggtt                                             28

SEQ ID NO: 784              moltype = DNA   length = 28
FEATURE                     Location/Qualifiers
source                      1..28
                            mol_type = unassigned DNA
                            organism = Homo sapiens
SEQUENCE: 784
tctcaccaac tcccatcgaa ttcgcaca                                             28

SEQ ID NO: 785              moltype = DNA   length = 28
FEATURE                     Location/Qualifiers
source                      1..28
                            mol_type = unassigned DNA
                            organism = Homo sapiens
SEQUENCE: 785
gttttggttt cgtttcggag cgcgtaga                                             28

SEQ ID NO: 786              moltype = DNA   length = 28
FEATURE                     Location/Qualifiers
source                      1..28
                            mol_type = unassigned DNA
                            organism = Homo sapiens
SEQUENCE: 786
tttctctacc gactcaactc cccctccc                                             28

SEQ ID NO: 787              moltype = DNA   length = 28
FEATURE                     Location/Qualifiers
source                      1..28
                            mol_type = unassigned DNA
                            organism = Homo sapiens
SEQUENCE: 787
tcggttgcgt aaatcgcgtt tttggttg                                            28

SEQ ID NO: 788              moltype = DNA   length = 28
```

-continued

```
FEATURE              Location/Qualifiers
source               1..28
                     mol_type = unassigned DNA
                     organism = Homo sapiens
SEQUENCE: 788
ttctcgataa tatctccgtc gcctccgc                                           28

SEQ ID NO: 789       moltype = DNA  length = 27
FEATURE              Location/Qualifiers
source               1..27
                     mol_type = unassigned DNA
                     organism = Homo sapiens
SEQUENCE: 789
gtttaggggt ggaggtcggg gttttga                                           27

SEQ ID NO: 790       moltype = DNA  length = 28
FEATURE              Location/Qualifiers
source               1..28
                     mol_type = unassigned DNA
                     organism = Homo sapiens
SEQUENCE: 790
ccgaaccccg cgcaaataaa aacaacct                                          28

SEQ ID NO: 791       moltype = DNA  length = 28
FEATURE              Location/Qualifiers
source               1..28
                     mol_type = unassigned DNA
                     organism = Homo sapiens
SEQUENCE: 791
ggggcgcgtt tttatggaaa gttagggt                                          28

SEQ ID NO: 792       moltype = DNA  length = 28
FEATURE              Location/Qualifiers
source               1..28
                     mol_type = unassigned DNA
                     organism = Homo sapiens
SEQUENCE: 792
ctacgcccta aaacacgcct cgacttct                                          28

SEQ ID NO: 793       moltype = DNA  length = 28
FEATURE              Location/Qualifiers
source               1..28
                     mol_type = unassigned DNA
                     organism = Homo sapiens
SEQUENCE: 793
tgtgcgaaag agacgcgggg tttagtta                                          28

SEQ ID NO: 794       moltype = DNA  length = 28
FEATURE              Location/Qualifiers
source               1..28
                     mol_type = unassigned DNA
                     organism = Homo sapiens
SEQUENCE: 794
cccgtaatcg ctaaaacatc cgccctta                                          28

SEQ ID NO: 795       moltype = DNA  length = 26
FEATURE              Location/Qualifiers
source               1..26
                     mol_type = unassigned DNA
                     organism = Homo sapiens
SEQUENCE: 795
cgtcgggcga tgttggtttg ttcgtg                                            26

SEQ ID NO: 796       moltype = DNA  length = 29
FEATURE              Location/Qualifiers
source               1..29
                     mol_type = unassigned DNA
                     organism = Homo sapiens
SEQUENCE: 796
gcgacgctcc accgtaaacc caatattta                                         29

SEQ ID NO: 797       moltype = DNA  length = 27
FEATURE              Location/Qualifiers
source               1..27
                     mol_type = unassigned DNA
                     organism = Homo sapiens
SEQUENCE: 797
cggggagggt cgagggtttt gtttgag                                           27
```

```
SEQ ID NO: 798          moltype = DNA   length = 28
FEATURE                 Location/Qualifiers
source                  1..28
                        mol_type = unassigned DNA
                        organism = Homo sapiens
SEQUENCE: 798
gcgtcccaaa cttcattcaa ccgacgac                                              28

SEQ ID NO: 799          moltype = DNA   length = 28
FEATURE                 Location/Qualifiers
source                  1..28
                        mol_type = unassigned DNA
                        organism = Homo sapiens
SEQUENCE: 799
gcggacgtag taatggatta aacgggga                                              28

SEQ ID NO: 800          moltype = DNA   length = 28
FEATURE                 Location/Qualifiers
source                  1..28
                        mol_type = unassigned DNA
                        organism = Homo sapiens
SEQUENCE: 800
aaatccgact ccctacactc ccgacttt                                              28

SEQ ID NO: 801          moltype = DNA   length = 29
FEATURE                 Location/Qualifiers
source                  1..29
                        mol_type = unassigned DNA
                        organism = Homo sapiens
SEQUENCE: 801
gggggttgtg ttagttgttt gtttagcga                                             29

SEQ ID NO: 802          moltype = DNA   length = 28
FEATURE                 Location/Qualifiers
source                  1..28
                        mol_type = unassigned DNA
                        organism = Homo sapiens
SEQUENCE: 802
cgaaactatt tcccgccaaa ccgaaccc                                              28

SEQ ID NO: 803          moltype = DNA   length = 28
FEATURE                 Location/Qualifiers
source                  1..28
                        mol_type = unassigned DNA
                        organism = Homo sapiens
SEQUENCE: 803
tttcgggcgg gagtatcggg ttttgtag                                             28

SEQ ID NO: 804          moltype = DNA   length = 28
FEATURE                 Location/Qualifiers
source                  1..28
                        mol_type = unassigned DNA
                        organism = Homo sapiens
SEQUENCE: 804
gctcctttac cccttctcga ccaactcc                                             28

SEQ ID NO: 805          moltype = DNA   length = 30
FEATURE                 Location/Qualifiers
source                  1..30
                        mol_type = unassigned DNA
                        organism = Homo sapiens
SEQUENCE: 805
ttacggattt tatttgtatt cggaatcgta                                           30

SEQ ID NO: 806          moltype = DNA   length = 29
FEATURE                 Location/Qualifiers
source                  1..29
                        mol_type = unassigned DNA
                        organism = Homo sapiens
SEQUENCE: 806
acgcatcaaa ctcgacacaa aatttcatc                                            29

SEQ ID NO: 807          moltype = DNA   length = 28
FEATURE                 Location/Qualifiers
source                  1..28
                        mol_type = unassigned DNA
                        organism = Homo sapiens
SEQUENCE: 807
ggtgttttcg taagacgggg tagtgggt                                             28
```

```
SEQ ID NO: 808          moltype = DNA   length = 28
FEATURE                 Location/Qualifiers
source                  1..28
                        mol_type = unassigned DNA
                        organism = Homo sapiens
SEQUENCE: 808
ttctcctccg ctaaaaatcc gaatacga                                  28

SEQ ID NO: 809          moltype = DNA   length = 28
FEATURE                 Location/Qualifiers
source                  1..28
                        mol_type = unassigned DNA
                        organism = Homo sapiens
SEQUENCE: 809
agggattgta tttcgaggtg gtcgaggt                                  28

SEQ ID NO: 810          moltype = DNA   length = 28
FEATURE                 Location/Qualifiers
source                  1..28
                        mol_type = unassigned DNA
                        organism = Homo sapiens
SEQUENCE: 810
ccgacaaatc gaaaccttcg cccgaaac                                  28

SEQ ID NO: 811          moltype = DNA   length = 28
FEATURE                 Location/Qualifiers
source                  1..28
                        mol_type = unassigned DNA
                        organism = Homo sapiens
SEQUENCE: 811
tcgcgggtta taaatatttg gttgcggc                                  28

SEQ ID NO: 812          moltype = DNA   length = 28
FEATURE                 Location/Qualifiers
source                  1..28
                        mol_type = unassigned DNA
                        organism = Homo sapiens
SEQUENCE: 812
gaccgccact acctcgaaaa catttccc                                  28

SEQ ID NO: 813          moltype = DNA   length = 28
FEATURE                 Location/Qualifiers
source                  1..28
                        mol_type = unassigned DNA
                        organism = Homo sapiens
SEQUENCE: 813
ggtaacggaa aagcgcggga attataga                                  28

SEQ ID NO: 814          moltype = DNA   length = 26
FEATURE                 Location/Qualifiers
source                  1..26
                        mol_type = unassigned DNA
                        organism = Homo sapiens
SEQUENCE: 814
cccacaacct atcccccgtc caaaaa                                    26

SEQ ID NO: 815          moltype = DNA   length = 28
FEATURE                 Location/Qualifiers
source                  1..28
                        mol_type = unassigned DNA
                        organism = Homo sapiens
SEQUENCE: 815
ttttgtacgt tgggttacgg gggtttgg                                  28

SEQ ID NO: 816          moltype = DNA   length = 28
FEATURE                 Location/Qualifiers
source                  1..28
                        mol_type = unassigned DNA
                        organism = Homo sapiens
SEQUENCE: 816
taaacgcgat aaacccctac gacccca                                   28

SEQ ID NO: 817          moltype = DNA   length = 28
FEATURE                 Location/Qualifiers
source                  1..28
                        mol_type = unassigned DNA
                        organism = Homo sapiens
SEQUENCE: 817
```

-continued

```
tatcggtttt cgtagttgcg ggaggagg                                            28

SEQ ID NO: 818          moltype = DNA   length = 28
FEATURE                 Location/Qualifiers
source                  1..28
                        mol_type = unassigned DNA
                        organism = Homo sapiens
SEQUENCE: 818
ccgaataaat accaaactcg cccgacgc                                            28

SEQ ID NO: 819          moltype = DNA   length = 28
FEATURE                 Location/Qualifiers
source                  1..28
                        mol_type = unassigned DNA
                        organism = Homo sapiens
SEQUENCE: 819
cgggtagagg ggaggtagga attggaga                                            28

SEQ ID NO: 820          moltype = DNA   length = 28
FEATURE                 Location/Qualifiers
source                  1..28
                        mol_type = unassigned DNA
                        organism = Homo sapiens
SEQUENCE: 820
ccgaataaac gtcacccta cacaccgc                                             28

SEQ ID NO: 821          moltype = DNA   length = 28
FEATURE                 Location/Qualifiers
source                  1..28
                        mol_type = unassigned DNA
                        organism = Homo sapiens
SEQUENCE: 821
ttttgcggtt aggtgaaggc gtagaggt                                            28

SEQ ID NO: 822          moltype = DNA   length = 28
FEATURE                 Location/Qualifiers
source                  1..28
                        mol_type = unassigned DNA
                        organism = Homo sapiens
SEQUENCE: 822
gaccgaatac cccgctttct ctctcgac                                            28

SEQ ID NO: 823          moltype = DNA   length = 27
FEATURE                 Location/Qualifiers
source                  1..27
                        mol_type = unassigned DNA
                        organism = Homo sapiens
SEQUENCE: 823
aggagtagta ttgcgagggt ggagggt                                             27

SEQ ID NO: 824          moltype = DNA   length = 28
FEATURE                 Location/Qualifiers
source                  1..28
                        mol_type = unassigned DNA
                        organism = Homo sapiens
SEQUENCE: 824
taaacccgaa aaacaacgcc aatcccgc                                            28

SEQ ID NO: 825          moltype = DNA   length = 28
FEATURE                 Location/Qualifiers
source                  1..28
                        mol_type = unassigned DNA
                        organism = Homo sapiens
SEQUENCE: 825
ggggatttgt tgtagagtcg taggagaa                                            28

SEQ ID NO: 826          moltype = DNA   length = 25
FEATURE                 Location/Qualifiers
source                  1..25
                        mol_type = unassigned DNA
                        organism = Homo sapiens
SEQUENCE: 826
ccgcatccca ccctttaaaa ctcta                                               25

SEQ ID NO: 827          moltype = DNA   length = 28
FEATURE                 Location/Qualifiers
source                  1..28
                        mol_type = unassigned DNA
                        organism = Homo sapiens
```

-continued

```
SEQUENCE: 827
tatgggttgc gtcgagggta aggtagtg                                                28

SEQ ID NO: 828          moltype = DNA  length = 28
FEATURE                 Location/Qualifiers
source                  1..28
                        mol_type = unassigned DNA
                        organism = Homo sapiens
SEQUENCE: 828
tacgacgacc atcgccgttc ttaccttt                                                28

SEQ ID NO: 829          moltype = DNA  length = 28
FEATURE                 Location/Qualifiers
source                  1..28
                        mol_type = unassigned DNA
                        organism = Homo sapiens
SEQUENCE: 829
aaatttggat tgggggaggg acgaggtt                                                28

SEQ ID NO: 830          moltype = DNA  length = 28
FEATURE                 Location/Qualifiers
source                  1..28
                        mol_type = unassigned DNA
                        organism = Homo sapiens
SEQUENCE: 830
cttcgcaacc gaactactca cccccgac                                                28

SEQ ID NO: 831          moltype = DNA  length = 28
FEATURE                 Location/Qualifiers
source                  1..28
                        mol_type = unassigned DNA
                        organism = Homo sapiens
SEQUENCE: 831
ggtcgttgga gtggtcgttt cggtttag                                                28

SEQ ID NO: 832          moltype = DNA  length = 28
FEATURE                 Location/Qualifiers
source                  1..28
                        mol_type = unassigned DNA
                        organism = Homo sapiens
SEQUENCE: 832
cctcaaaccc ccgaacgcgc taaataaa                                                28

SEQ ID NO: 833          moltype = DNA  length = 28
FEATURE                 Location/Qualifiers
source                  1..28
                        mol_type = unassigned DNA
                        organism = Homo sapiens
SEQUENCE: 833
gttcggggag ggagggagat tcgttttg                                                28

SEQ ID NO: 834          moltype = DNA  length = 28
FEATURE                 Location/Qualifiers
source                  1..28
                        mol_type = unassigned DNA
                        organism = Homo sapiens
SEQUENCE: 834
aactcccgac tttaacctcc caacccaa                                                28

SEQ ID NO: 835          moltype = DNA  length = 28
FEATURE                 Location/Qualifiers
source                  1..28
                        mol_type = unassigned DNA
                        organism = Homo sapiens
SEQUENCE: 835
gttgtagggg tgtttggtcg ggttggta                                                28

SEQ ID NO: 836          moltype = DNA  length = 28
FEATURE                 Location/Qualifiers
source                  1..28
                        mol_type = unassigned DNA
                        organism = Homo sapiens
SEQUENCE: 836
atcaactact ccgtacccca cgtaaccg                                                28

SEQ ID NO: 837          moltype = DNA  length = 25
FEATURE                 Location/Qualifiers
source                  1..25
                        mol_type = unassigned DNA
```

-continued

```
                                      organism = Homo sapiens
SEQUENCE: 837
agtcggggtt ggttggtgga agagg                                                  25

SEQ ID NO: 838           moltype = DNA   length = 28
FEATURE                  Location/Qualifiers
source                   1..28
                         mol_type = unassigned DNA
                         organism = Homo sapiens
SEQUENCE: 838
ccctctcaac tcgattcaaa attccccc                                               28

SEQ ID NO: 839           moltype = DNA   length = 28
FEATURE                  Location/Qualifiers
source                   1..28
                         mol_type = unassigned DNA
                         organism = Homo sapiens
SEQUENCE: 839
aaagtaataa gtggtttcgg gcggagtc                                               28

SEQ ID NO: 840           moltype = DNA   length = 28
FEATURE                  Location/Qualifiers
source                   1..28
                         mol_type = unassigned DNA
                         organism = Homo sapiens
SEQUENCE: 840
accccgcata cctacgaaaa cgaaaacc                                               28

SEQ ID NO: 841           moltype = DNA   length = 27
FEATURE                  Location/Qualifiers
source                   1..27
                         mol_type = unassigned DNA
                         organism = Homo sapiens
SEQUENCE: 841
cgggattatg gaggggtaga gcggtcg                                                27

SEQ ID NO: 842           moltype = DNA   length = 28
FEATURE                  Location/Qualifiers
source                   1..28
                         mol_type = unassigned DNA
                         organism = Homo sapiens
SEQUENCE: 842
acgtccttaa cgaacaccta caacaacg                                               28

SEQ ID NO: 843           moltype = DNA   length = 28
FEATURE                  Location/Qualifiers
source                   1..28
                         mol_type = unassigned DNA
                         organism = Homo sapiens
SEQUENCE: 843
aggttttgta gtagtaggcg gacgaggc                                               28

SEQ ID NO: 844           moltype = DNA   length = 28
FEATURE                  Location/Qualifiers
source                   1..28
                         mol_type = unassigned DNA
                         organism = Homo sapiens
SEQUENCE: 844
acgaatacga aacccgaaac cgaaacgc                                               28

SEQ ID NO: 845           moltype = DNA   length = 25
FEATURE                  Location/Qualifiers
source                   1..25
                         mol_type = unassigned DNA
                         organism = Homo sapiens
SEQUENCE: 845
cgtggtatag ttaatcgcgc ggcgt                                                  25

SEQ ID NO: 846           moltype = DNA   length = 28
FEATURE                  Location/Qualifiers
source                   1..28
                         mol_type = unassigned DNA
                         organism = Homo sapiens
SEQUENCE: 846
tacaacccca acgccataac tcgccaat                                               28

SEQ ID NO: 847           moltype = DNA   length = 28
FEATURE                  Location/Qualifiers
source                   1..28
```

-continued

```
                          mol_type = unassigned DNA
                          organism = Homo sapiens
SEQUENCE: 847
tagcggggat ttattagggg agaggtgg                                              28

SEQ ID NO: 848          moltype = DNA   length = 28
FEATURE                 Location/Qualifiers
source                  1..28
                        mol_type = unassigned DNA
                        organism = Homo sapiens
SEQUENCE: 848
atcacctacg aacactatcc ctcacccg                                             28

SEQ ID NO: 849          moltype = DNA   length = 28
FEATURE                 Location/Qualifiers
source                  1..28
                        mol_type = unassigned DNA
                        organism = Homo sapiens
SEQUENCE: 849
gcggaatagt tcgcggtttt ggaatgtt                                             28

SEQ ID NO: 850          moltype = DNA   length = 28
FEATURE                 Location/Qualifiers
source                  1..28
                        mol_type = unassigned DNA
                        organism = Homo sapiens
SEQUENCE: 850
aaacgtttcc gctccccgaa aaacgaat                                             28

SEQ ID NO: 851          moltype = DNA   length = 28
FEATURE                 Location/Qualifiers
source                  1..28
                        mol_type = unassigned DNA
                        organism = Homo sapiens
SEQUENCE: 851
ggagatagtt ttgagagggg gaggtcgc                                             28

SEQ ID NO: 852          moltype = DNA   length = 28
FEATURE                 Location/Qualifiers
source                  1..28
                        mol_type = unassigned DNA
                        organism = Homo sapiens
SEQUENCE: 852
cgctacctac gccgatcgta aatcccaa                                             28

SEQ ID NO: 853          moltype = DNA   length = 28
FEATURE                 Location/Qualifiers
source                  1..28
                        mol_type = unassigned DNA
                        organism = Homo sapiens
SEQUENCE: 853
gaatggttgc gatatggggt tcgacgga                                             28

SEQ ID NO: 854          moltype = DNA   length = 28
FEATURE                 Location/Qualifiers
source                  1..28
                        mol_type = unassigned DNA
                        organism = Homo sapiens
SEQUENCE: 854
cgcgatccaa aaacgcaaat cctcgttc                                             28

SEQ ID NO: 855          moltype = DNA   length = 28
FEATURE                 Location/Qualifiers
source                  1..28
                        mol_type = unassigned DNA
                        organism = Homo sapiens
SEQUENCE: 855
ggttttggtc gagatttggg cgggtgag                                             28

SEQ ID NO: 856          moltype = DNA   length = 28
FEATURE                 Location/Qualifiers
source                  1..28
                        mol_type = unassigned DNA
                        organism = Homo sapiens
SEQUENCE: 856
cccgaatcct acgccccaac caaataaa                                             28

SEQ ID NO: 857          moltype = DNA   length = 28
FEATURE                 Location/Qualifiers
```

-continued

```
source                   1..28
                         mol_type = unassigned DNA
                         organism = Homo sapiens
SEQUENCE: 857
tgagtgattt cggttcgggg cgtagatt                                         28

SEQ ID NO: 858          moltype = DNA   length = 29
FEATURE                 Location/Qualifiers
source                  1..29
                        mol_type = unassigned DNA
                        organism = Homo sapiens
SEQUENCE: 858
cgaaatctc tacaaatccc gcaacctcg                                        29

SEQ ID NO: 859          moltype = DNA   length = 28
FEATURE                 Location/Qualifiers
source                  1..28
                        mol_type = unassigned DNA
                        organism = Homo sapiens
SEQUENCE: 859
atggtttcgg ggtgtttagc ggcgattg                                        28

SEQ ID NO: 860          moltype = DNA   length = 28
FEATURE                 Location/Qualifiers
source                  1..28
                        mol_type = unassigned DNA
                        organism = Homo sapiens
SEQUENCE: 860
aacgaaaccg aacgaacccc aatccgta                                        28

SEQ ID NO: 861          moltype = DNA   length = 27
FEATURE                 Location/Qualifiers
source                  1..27
                        mol_type = unassigned DNA
                        organism = Homo sapiens
SEQUENCE: 861
gagtcggagt gagcgttaag tgagggg                                         27

SEQ ID NO: 862          moltype = DNA   length = 28
FEATURE                 Location/Qualifiers
source                  1..28
                        mol_type = unassigned DNA
                        organism = Homo sapiens
SEQUENCE: 862
tccctccgac cgacccaaaa taactacg                                        28

SEQ ID NO: 863          moltype = DNA   length = 28
FEATURE                 Location/Qualifiers
source                  1..28
                        mol_type = unassigned DNA
                        organism = Homo sapiens
SEQUENCE: 863
ttcgttgttc gttttgggta aagggaag                                        28

SEQ ID NO: 864          moltype = DNA   length = 28
FEATURE                 Location/Qualifiers
source                  1..28
                        mol_type = unassigned DNA
                        organism = Homo sapiens
SEQUENCE: 864
aaactcgctt cccaaacttc taaaaatc                                        28

SEQ ID NO: 865          moltype = DNA   length = 28
FEATURE                 Location/Qualifiers
source                  1..28
                        mol_type = unassigned DNA
                        organism = Homo sapiens
SEQUENCE: 865
ggggaggcgt cgagttcgga gtttatta                                        28

SEQ ID NO: 866          moltype = DNA   length = 28
FEATURE                 Location/Qualifiers
source                  1..28
                        mol_type = unassigned DNA
                        organism = Homo sapiens
SEQUENCE: 866
aaaactcgct aaacgtccca accgcatc                                        28

SEQ ID NO: 867          moltype = DNA   length = 30
```

-continued

```
FEATURE              Location/Qualifiers
source               1..30
                     mol_type = unassigned DNA
                     organism = Homo sapiens
SEQUENCE: 867
cgggtattgt tggtttaggt tgtagtaggt                                    30

SEQ ID NO: 868       moltype = DNA   length = 28
FEATURE              Location/Qualifiers
source               1..28
                     mol_type = unassigned DNA
                     organism = Homo sapiens
SEQUENCE: 868
cgaccctaac caaccccgaa actcgaaa                                      28

SEQ ID NO: 869       moltype = DNA   length = 28
FEATURE              Location/Qualifiers
source               1..28
                     mol_type = unassigned DNA
                     organism = Homo sapiens
SEQUENCE: 869
agggtagaaa ggaagcggta gtagaaaa                                      28

SEQ ID NO: 870       moltype = DNA   length = 28
FEATURE              Location/Qualifiers
source               1..28
                     mol_type = unassigned DNA
                     organism = Homo sapiens
SEQUENCE: 870
acaacaactc ctcccttcga acccaacc                                      28

SEQ ID NO: 871       moltype = DNA   length = 28
FEATURE              Location/Qualifiers
source               1..28
                     mol_type = unassigned DNA
                     organism = Homo sapiens
SEQUENCE: 871
tgtgggaggg aagggaaatc gagattgg                                      28

SEQ ID NO: 872       moltype = DNA   length = 29
FEATURE              Location/Qualifiers
source               1..29
                     mol_type = unassigned DNA
                     organism = Homo sapiens
SEQUENCE: 872
acgacaaaac gaaacccaca atcctaccc                                     29

SEQ ID NO: 873       moltype = DNA   length = 28
FEATURE              Location/Qualifiers
source               1..28
                     mol_type = unassigned DNA
                     organism = Homo sapiens
SEQUENCE: 873
attcggattg gttagttttt gcggaagt                                      28

SEQ ID NO: 874       moltype = DNA   length = 28
FEATURE              Location/Qualifiers
source               1..28
                     mol_type = unassigned DNA
                     organism = Homo sapiens
SEQUENCE: 874
ttcgccacgc aacaacctaa aacgctac                                      28

SEQ ID NO: 875       moltype = DNA   length = 28
FEATURE              Location/Qualifiers
source               1..28
                     mol_type = unassigned DNA
                     organism = Homo sapiens
SEQUENCE: 875
ggttgcggcg tttatttagc gggaagtc                                      28

SEQ ID NO: 876       moltype = DNA   length = 26
FEATURE              Location/Qualifiers
source               1..26
                     mol_type = unassigned DNA
                     organism = Homo sapiens
SEQUENCE: 876
ctcgccgaac ccgcgacgaa atctac                                        26
```

-continued

```
SEQ ID NO: 877          moltype = DNA   length = 28
FEATURE                 Location/Qualifiers
source                  1..28
                        mol_type = unassigned DNA
                        organism = Homo sapiens
SEQUENCE: 877
tagaggaatt taaagtgtgg gttggggg                                          28

SEQ ID NO: 878          moltype = DNA   length = 28
FEATURE                 Location/Qualifiers
source                  1..28
                        mol_type = unassigned DNA
                        organism = Homo sapiens
SEQUENCE: 878
accaacttct ctccctttac gccttttt                                          28

SEQ ID NO: 879          moltype = DNA   length = 29
FEATURE                 Location/Qualifiers
source                  1..29
                        mol_type = unassigned DNA
                        organism = Homo sapiens
SEQUENCE: 879
tgggttaagt atttgttatg tgttacgga                                         29

SEQ ID NO: 880          moltype = DNA   length = 24
FEATURE                 Location/Qualifiers
source                  1..24
                        mol_type = unassigned DNA
                        organism = Homo sapiens
SEQUENCE: 880
cgctatccac ccgaatacgc aact                                              24

SEQ ID NO: 881          moltype = DNA   length = 26
FEATURE                 Location/Qualifiers
source                  1..26
                        mol_type = unassigned DNA
                        organism = Homo sapiens
SEQUENCE: 881
gcgcggcgtt ttgttatcgg tggatt                                           26

SEQ ID NO: 882          moltype = DNA   length = 30
FEATURE                 Location/Qualifiers
source                  1..30
                        mol_type = unassigned DNA
                        organism = Homo sapiens
SEQUENCE: 882
tctaaaataa cccgcaccaa acaaactaca                                       30

SEQ ID NO: 883          moltype = DNA   length = 28
FEATURE                 Location/Qualifiers
source                  1..28
                        mol_type = unassigned DNA
                        organism = Homo sapiens
SEQUENCE: 883
ttataaaggt cggaagcggt tacggggg                                          28

SEQ ID NO: 884          moltype = DNA   length = 28
FEATURE                 Location/Qualifiers
source                  1..28
                        mol_type = unassigned DNA
                        organism = Homo sapiens
SEQUENCE: 884
aacccctttc gctcccttcc taaaacga                                          28

SEQ ID NO: 885          moltype = DNA   length = 28
FEATURE                 Location/Qualifiers
source                  1..28
                        mol_type = unassigned DNA
                        organism = Homo sapiens
SEQUENCE: 885
gtatggttgc gatttggggt tggaaggg                                          28

SEQ ID NO: 886          moltype = DNA   length = 28
FEATURE                 Location/Qualifiers
source                  1..28
                        mol_type = unassigned DNA
                        organism = Homo sapiens
SEQUENCE: 886
gccgcgatcc aaaaacgcaa atcctaat                                          28
```

```
SEQ ID NO: 887          moltype = DNA  length = 27
FEATURE                 Location/Qualifiers
source                  1..27
                        mol_type = unassigned DNA
                        organism = Homo sapiens
SEQUENCE: 887
tagggaatgt ttggttgcga tttgggg                                     27

SEQ ID NO: 888          moltype = DNA  length = 28
FEATURE                 Location/Qualifiers
source                  1..28
                        mol_type = unassigned DNA
                        organism = Homo sapiens
SEQUENCE: 888
tccttaccgt cgtaaacata ctactcat                                    28

SEQ ID NO: 889          moltype = DNA  length = 25
FEATURE                 Location/Qualifiers
source                  1..25
                        mol_type = unassigned DNA
                        organism = Homo sapiens
SEQUENCE: 889
gcgtaagtgc gaggttgtcg gtagc                                       25

SEQ ID NO: 890          moltype = DNA  length = 26
FEATURE                 Location/Qualifiers
source                  1..26
                        mol_type = unassigned DNA
                        organism = Homo sapiens
SEQUENCE: 890
tttcccgcaa ctctttcccc ctctct                                      26

SEQ ID NO: 891          moltype = DNA  length = 28
FEATURE                 Location/Qualifiers
source                  1..28
                        mol_type = unassigned DNA
                        organism = Homo sapiens
SEQUENCE: 891
tgcggttaaa gaattcgttc gcgttcgg                                    28

SEQ ID NO: 892          moltype = DNA  length = 28
FEATURE                 Location/Qualifiers
source                  1..28
                        mol_type = unassigned DNA
                        organism = Homo sapiens
SEQUENCE: 892
ctaaacgctc ccgcgaaacc tccaaatc                                    28

SEQ ID NO: 893          moltype = DNA  length = 28
FEATURE                 Location/Qualifiers
source                  1..28
                        mol_type = unassigned DNA
                        organism = Homo sapiens
SEQUENCE: 893
ttcgggtatt ttgaggttgt cgtcggga                                    28

SEQ ID NO: 894          moltype = DNA  length = 26
FEATURE                 Location/Qualifiers
source                  1..26
                        mol_type = unassigned DNA
                        organism = Homo sapiens
SEQUENCE: 894
gacgacgacg cgtccgacga atttta                                      26

SEQ ID NO: 895          moltype = DNA  length = 28
FEATURE                 Location/Qualifiers
source                  1..28
                        mol_type = unassigned DNA
                        organism = Homo sapiens
SEQUENCE: 895
gttttggtcg gggcgtcgtg gatatttt                                    28

SEQ ID NO: 896          moltype = DNA  length = 28
FEATURE                 Location/Qualifiers
source                  1..28
                        mol_type = unassigned DNA
                        organism = Homo sapiens
SEQUENCE: 896
```

-continued

```
aaaaaccaac taaaccccctt cccgctcg                                        28

SEQ ID NO: 897          moltype = DNA   length = 28
FEATURE                 Location/Qualifiers
source                  1..28
                        mol_type = unassigned DNA
                        organism = Homo sapiens
SEQUENCE: 897
gtgtggaaag ggtttggcgg ttgttagg                                         28

SEQ ID NO: 898          moltype = DNA   length = 28
FEATURE                 Location/Qualifiers
source                  1..28
                        mol_type = unassigned DNA
                        organism = Homo sapiens
SEQUENCE: 898
ctcgccaaat acgtccaccc aaaaacga                                         28

SEQ ID NO: 899          moltype = DNA   length = 28
FEATURE                 Location/Qualifiers
source                  1..28
                        mol_type = unassigned DNA
                        organism = Homo sapiens
SEQUENCE: 899
taggagggga cgtagagttt acggcgaa                                         28

SEQ ID NO: 900          moltype = DNA   length = 27
FEATURE                 Location/Qualifiers
source                  1..27
                        mol_type = unassigned DNA
                        organism = Homo sapiens
SEQUENCE: 900
gaatacccga cccgacccat ccatcac                                          27

SEQ ID NO: 901          moltype = DNA   length = 28
FEATURE                 Location/Qualifiers
source                  1..28
                        mol_type = unassigned DNA
                        organism = Homo sapiens
SEQUENCE: 901
tgcgtttgta ggagaagtcg ggttggtt                                         28

SEQ ID NO: 902          moltype = DNA   length = 28
FEATURE                 Location/Qualifiers
source                  1..28
                        mol_type = unassigned DNA
                        organism = Homo sapiens
SEQUENCE: 902
actcttcctc gcctcgcact actaccta                                         28

SEQ ID NO: 903          moltype = DNA   length = 28
FEATURE                 Location/Qualifiers
source                  1..28
                        mol_type = unassigned DNA
                        organism = Homo sapiens
SEQUENCE: 903
gtgcgattcg gggtttcgaa aagttggt                                         28

SEQ ID NO: 904          moltype = DNA   length = 28
FEATURE                 Location/Qualifiers
source                  1..28
                        mol_type = unassigned DNA
                        organism = Homo sapiens
SEQUENCE: 904
gaaactacgc gcgaacttac aacgcctc                                         28

SEQ ID NO: 905          moltype = DNA   length = 22
FEATURE                 Location/Qualifiers
source                  1..22
                        mol_type = unassigned DNA
                        organism = Homo sapiens
SEQUENCE: 905
gagcgtagag cgttgagcgg gg                                               22

SEQ ID NO: 906          moltype = DNA   length = 22
FEATURE                 Location/Qualifiers
source                  1..22
                        mol_type = unassigned DNA
                        organism = Homo sapiens
```

```
SEQUENCE: 906
cgccgccgaa taacacgccc ac                                                      22

SEQ ID NO: 907         moltype = DNA   length = 28
FEATURE                Location/Qualifiers
source                 1..28
                       mol_type = unassigned DNA
                       organism = Homo sapiens
SEQUENCE: 907
agcgggatt ttcggagttg gagagttt                                                 28

SEQ ID NO: 908         moltype = DNA   length = 28
FEATURE                Location/Qualifiers
source                 1..28
                       mol_type = unassigned DNA
                       organism = Homo sapiens
SEQUENCE: 908
ctccatccgc ccgacctaac cctaaaaa                                                28

SEQ ID NO: 909         moltype = DNA   length = 28
FEATURE                Location/Qualifiers
source                 1..28
                       mol_type = unassigned DNA
                       organism = Homo sapiens
SEQUENCE: 909
gggaagtggc gtagtgggcg tttgtatc                                                28

SEQ ID NO: 910         moltype = DNA   length = 28
FEATURE                Location/Qualifiers
source                 1..28
                       mol_type = unassigned DNA
                       organism = Homo sapiens
SEQUENCE: 910
tacctccaac gaccacgccc acaaaata                                                28

SEQ ID NO: 911         moltype = DNA   length = 28
FEATURE                Location/Qualifiers
source                 1..28
                       mol_type = unassigned DNA
                       organism = Homo sapiens
SEQUENCE: 911
tggagcgttg agtcgaagtt ttgatttt                                                28

SEQ ID NO: 912         moltype = DNA   length = 28
FEATURE                Location/Qualifiers
source                 1..28
                       mol_type = unassigned DNA
                       organism = Homo sapiens
SEQUENCE: 912
tcttacccga actttaaccc caaccgct                                                28

SEQ ID NO: 913         moltype = DNA   length = 28
FEATURE                Location/Qualifiers
source                 1..28
                       mol_type = unassigned DNA
                       organism = Homo sapiens
SEQUENCE: 913
ggttgggagt tcggagttgt agtagagg                                                28

SEQ ID NO: 914         moltype = DNA   length = 28
FEATURE                Location/Qualifiers
source                 1..28
                       mol_type = unassigned DNA
                       organism = Homo sapiens
SEQUENCE: 914
ctttaaccga ttcaaacaac aaacgcct                                                28

SEQ ID NO: 915         moltype = DNA   length = 26
FEATURE                Location/Qualifiers
source                 1..26
                       mol_type = unassigned DNA
                       organism = Homo sapiens
SEQUENCE: 915
gtagggcgcg gggtttcgtt agtttc                                                  26

SEQ ID NO: 916         moltype = DNA   length = 28
FEATURE                Location/Qualifiers
source                 1..28
                       mol_type = unassigned DNA
```

-continued

```
                            organism = Homo sapiens
SEQUENCE: 916
atctaccgtt ctatcctcgt aaccgccg                                          28

SEQ ID NO: 917            moltype = DNA   length = 28
FEATURE                   Location/Qualifiers
source                    1..28
                          mol_type = unassigned DNA
                          organism = Homo sapiens
SEQUENCE: 917
tcgtttggga gggatcgttt ttgggaga                                          28

SEQ ID NO: 918            moltype = DNA   length = 28
FEATURE                   Location/Qualifiers
source                    1..28
                          mol_type = unassigned DNA
                          organism = Homo sapiens
SEQUENCE: 918
aacccgaata ctatccaact accgccgc                                          28

SEQ ID NO: 919            moltype = DNA   length = 28
FEATURE                   Location/Qualifiers
source                    1..28
                          mol_type = unassigned DNA
                          organism = Homo sapiens
SEQUENCE: 919
cgagcgtggg tattaagtcg gtagtgga                                          28

SEQ ID NO: 920            moltype = DNA   length = 28
FEATURE                   Location/Qualifiers
source                    1..28
                          mol_type = unassigned DNA
                          organism = Homo sapiens
SEQUENCE: 920
gacctcaacc ccctacgcct aacctact                                          28

SEQ ID NO: 921            moltype = DNA   length = 28
FEATURE                   Location/Qualifiers
source                    1..28
                          mol_type = unassigned DNA
                          organism = Homo sapiens
SEQUENCE: 921
gtagatcgcg gttttgtagg ggcgtttg                                          28

SEQ ID NO: 922            moltype = DNA   length = 28
FEATURE                   Location/Qualifiers
source                    1..28
                          mol_type = unassigned DNA
                          organism = Homo sapiens
SEQUENCE: 922
ctaatttcga tttttccacc cccgccgc                                          28

SEQ ID NO: 923            moltype = DNA   length = 28
FEATURE                   Location/Qualifiers
source                    1..28
                          mol_type = unassigned DNA
                          organism = Homo sapiens
SEQUENCE: 923
gagtgtttgt cgagaaggtt gagtaaat                                          28

SEQ ID NO: 924            moltype = DNA   length = 28
FEATURE                   Location/Qualifiers
source                    1..28
                          mol_type = unassigned DNA
                          organism = Homo sapiens
SEQUENCE: 924
caccgcccaa cgcattcgtt ctaaaata                                          28

SEQ ID NO: 925            moltype = DNA   length = 26
FEATURE                   Location/Qualifiers
source                    1..26
                          mol_type = unassigned DNA
                          organism = Homo sapiens
SEQUENCE: 925
ataaaagtgg ggtgggtggc ggaggg                                            26

SEQ ID NO: 926            moltype = DNA   length = 28
FEATURE                   Location/Qualifiers
source                    1..28
```

-continued

```
                              mol_type = unassigned DNA
                              organism = Homo sapiens
SEQUENCE: 926
gcgccgaaat aacaacccaa cctaccaa                                    28

SEQ ID NO: 927          moltype = DNA   length = 28
FEATURE                 Location/Qualifiers
source                  1..28
                        mol_type = unassigned DNA
                        organism = Homo sapiens
SEQUENCE: 927
tttatcgggg aagttttcga gggtgggc                                    28

SEQ ID NO: 928          moltype = DNA   length = 28
FEATURE                 Location/Qualifiers
source                  1..28
                        mol_type = unassigned DNA
                        organism = Homo sapiens
SEQUENCE: 928
tcccaactac ctcctacgca cgaacgat                                    28

SEQ ID NO: 929          moltype = DNA   length = 29
FEATURE                 Location/Qualifiers
source                  1..29
                        mol_type = unassigned DNA
                        organism = Homo sapiens
SEQUENCE: 929
atgaaatgtg gttcgtggaa ggtgtttgt                                   29

SEQ ID NO: 930          moltype = DNA   length = 28
FEATURE                 Location/Qualifiers
source                  1..28
                        mol_type = unassigned DNA
                        organism = Homo sapiens
SEQUENCE: 930
acgacccgaa cgttaatcct cttactac                                    28

SEQ ID NO: 931          moltype = DNA   length = 29
FEATURE                 Location/Qualifiers
source                  1..29
                        mol_type = unassigned DNA
                        organism = Homo sapiens
SEQUENCE: 931
acgtagtttt cgagttagtg tcgttagaa                                   29

SEQ ID NO: 932          moltype = DNA   length = 23
FEATURE                 Location/Qualifiers
source                  1..23
                        mol_type = unassigned DNA
                        organism = Homo sapiens
SEQUENCE: 932
gacaaacgcc tcaaacccga ccg                                         23

SEQ ID NO: 933          moltype = DNA   length = 28
FEATURE                 Location/Qualifiers
source                  1..28
                        mol_type = unassigned DNA
                        organism = Homo sapiens
SEQUENCE: 933
aggagcggga gagggaaaaa tagttaag                                    28

SEQ ID NO: 934          moltype = DNA   length = 26
FEATURE                 Location/Qualifiers
source                  1..26
                        mol_type = unassigned DNA
                        organism = Homo sapiens
SEQUENCE: 934
cgctccaaac tacgcccaaa actcaa                                      26

SEQ ID NO: 935          moltype = DNA   length = 28
FEATURE                 Location/Qualifiers
source                  1..28
                        mol_type = unassigned DNA
                        organism = Homo sapiens
SEQUENCE: 935
attagagttg ttttgcgtat tgcggcgg                                    28

SEQ ID NO: 936          moltype = DNA   length = 28
FEATURE                 Location/Qualifiers
```

-continued

```
source                    1..28
                          mol_type = unassigned DNA
                          organism = Homo sapiens
SEQUENCE: 936
caaataccc gtacacccgc taccccaa                                              28

SEQ ID NO: 937            moltype = DNA   length = 28
FEATURE                   Location/Qualifiers
source                    1..28
                          mol_type = unassigned DNA
                          organism = Homo sapiens
SEQUENCE: 937
gggagttgag gtttacgcgg tttcgttg                                             28

SEQ ID NO: 938            moltype = DNA   length = 27
FEATURE                   Location/Qualifiers
source                    1..27
                          mol_type = unassigned DNA
                          organism = Homo sapiens
SEQUENCE: 938
gaccgccaac gcgatccacc cattaac                                              27

SEQ ID NO: 939            moltype = DNA   length = 28
FEATURE                   Location/Qualifiers
source                    1..28
                          mol_type = unassigned DNA
                          organism = Homo sapiens
SEQUENCE: 939
agttttggaa gtagattcgg tgcgggtg                                             28

SEQ ID NO: 940            moltype = DNA   length = 24
FEATURE                   Location/Qualifiers
source                    1..24
                          mol_type = unassigned DNA
                          organism = Homo sapiens
SEQUENCE: 940
gccgcgcaat cgcctctttt tcac                                                 24

SEQ ID NO: 941            moltype = DNA   length = 28
FEATURE                   Location/Qualifiers
source                    1..28
                          mol_type = unassigned DNA
                          organism = Homo sapiens
SEQUENCE: 941
agacgataga tggcgggtag gaagggag                                             28

SEQ ID NO: 942            moltype = DNA   length = 28
FEATURE                   Location/Qualifiers
source                    1..28
                          mol_type = unassigned DNA
                          organism = Homo sapiens
SEQUENCE: 942
gccgcctaca accgacgaac tacaaatc                                             28

SEQ ID NO: 943            moltype = DNA   length = 28
FEATURE                   Location/Qualifiers
source                    1..28
                          mol_type = unassigned DNA
                          organism = Homo sapiens
SEQUENCE: 943
tcgcgggtga ggtttgtggt taatttcg                                             28

SEQ ID NO: 944            moltype = DNA   length = 28
FEATURE                   Location/Qualifiers
source                    1..28
                          mol_type = unassigned DNA
                          organism = Homo sapiens
SEQUENCE: 944
gctcaaccaa actacaacgt tcccgcct                                             28

SEQ ID NO: 945            moltype = DNA   length = 28
FEATURE                   Location/Qualifiers
source                    1..28
                          mol_type = unassigned DNA
                          organism = Homo sapiens
SEQUENCE: 945
tgagaggcgt attttgttgg ttacggtt                                             28

SEQ ID NO: 946            moltype = DNA   length = 28
```

-continued

```
FEATURE               Location/Qualifiers
source                1..28
                      mol_type = unassigned DNA
                      organism = Homo sapiens
SEQUENCE: 946
cgaaaccat tccgctaccc ttccaact                                    28

SEQ ID NO: 947        moltype = DNA   length = 29
FEATURE               Location/Qualifiers
source                1..29
                      mol_type = unassigned DNA
                      organism = Homo sapiens
SEQUENCE: 947
ggggcgttgg gttatggaga ttacgtttt                                  29

SEQ ID NO: 948        moltype = DNA   length = 28
FEATURE               Location/Qualifiers
source                1..28
                      mol_type = unassigned DNA
                      organism = Homo sapiens
SEQUENCE: 948
gtcccgcgct taacgaattc tacgaacg                                   28

SEQ ID NO: 949        moltype = DNA   length = 22
FEATURE               Location/Qualifiers
source                1..22
                      mol_type = unassigned DNA
                      organism = Homo sapiens
SEQUENCE: 949
gttcgggtag gggtcggggg tc                                         22

SEQ ID NO: 950        moltype = DNA   length = 28
FEATURE               Location/Qualifiers
source                1..28
                      mol_type = unassigned DNA
                      organism = Homo sapiens
SEQUENCE: 950
cccgaaacga cgtacttaac gacccgaa                                   28

SEQ ID NO: 951        moltype = DNA   length = 28
FEATURE               Location/Qualifiers
source                1..28
                      mol_type = unassigned DNA
                      organism = Homo sapiens
SEQUENCE: 951
gggaggtttg agcgtcgaag ttttcgtt                                   28

SEQ ID NO: 952        moltype = DNA   length = 28
FEATURE               Location/Qualifiers
source                1..28
                      mol_type = unassigned DNA
                      organism = Homo sapiens
SEQUENCE: 952
gcccactacc ccgcgaaacc ttatcaac                                   28

SEQ ID NO: 953        moltype = DNA   length = 28
FEATURE               Location/Qualifiers
source                1..28
                      mol_type = unassigned DNA
                      organism = Homo sapiens
SEQUENCE: 953
agtcgttagg ttgttaaggc gcgttgtg                                   28

SEQ ID NO: 954        moltype = DNA   length = 29
FEATURE               Location/Qualifiers
source                1..29
                      mol_type = unassigned DNA
                      organism = Homo sapiens
SEQUENCE: 954
acaaaaataa aatcgaacct aaccccacg                                  29

SEQ ID NO: 955        moltype = DNA   length = 25
FEATURE               Location/Qualifiers
source                1..25
                      mol_type = unassigned DNA
                      organism = Homo sapiens
SEQUENCE: 955
cgtattaagg gttaagcggc gcggt                                      25
```

-continued

```
SEQ ID NO: 956          moltype = DNA  length = 29
FEATURE                 Location/Qualifiers
source                  1..29
                        mol_type = unassigned DNA
                        organism = Homo sapiens
SEQUENCE: 956
aactttctcg aacgactcga taaacctaa                                    29

SEQ ID NO: 957          moltype = DNA  length = 28
FEATURE                 Location/Qualifiers
source                  1..28
                        mol_type = unassigned DNA
                        organism = Homo sapiens
SEQUENCE: 957
aggttttggg aatttggaag ttcgcggg                                     28

SEQ ID NO: 958          moltype = DNA  length = 28
FEATURE                 Location/Qualifiers
source                  1..28
                        mol_type = unassigned DNA
                        organism = Homo sapiens
SEQUENCE: 958
aaaaacgctc gaacccaacc aatcgacg                                     28

SEQ ID NO: 959          moltype = DNA  length = 27
FEATURE                 Location/Qualifiers
source                  1..27
                        mol_type = unassigned DNA
                        organism = Homo sapiens
SEQUENCE: 959
aaaggaagat cgtgggtagt tcgtgcg                                      27

SEQ ID NO: 960          moltype = DNA  length = 28
FEATURE                 Location/Qualifiers
source                  1..28
                        mol_type = unassigned DNA
                        organism = Homo sapiens
SEQUENCE: 960
actacaactc acgtttcccc tccaacac                                     28

SEQ ID NO: 961          moltype = DNA  length = 29
FEATURE                 Location/Qualifiers
source                  1..29
                        mol_type = unassigned DNA
                        organism = Homo sapiens
SEQUENCE: 961
aggtttattt gacgttttag gtcgatagt                                    29

SEQ ID NO: 962          moltype = DNA  length = 28
FEATURE                 Location/Qualifiers
source                  1..28
                        mol_type = unassigned DNA
                        organism = Homo sapiens
SEQUENCE: 962
cgatctctcc ctttcttccg cttcctaa                                     28

SEQ ID NO: 963          moltype = DNA  length = 22
FEATURE                 Location/Qualifiers
source                  1..22
                        mol_type = unassigned DNA
                        organism = Homo sapiens
SEQUENCE: 963
ggcgtcggtt gcggttttag at                                           22

SEQ ID NO: 964          moltype = DNA  length = 30
FEATURE                 Location/Qualifiers
source                  1..30
                        mol_type = unassigned DNA
                        organism = Homo sapiens
SEQUENCE: 964
acgcgaaaat ctacctttta attacgaacc                                   30

SEQ ID NO: 965          moltype = DNA  length = 23
FEATURE                 Location/Qualifiers
source                  1..23
                        mol_type = unassigned DNA
                        organism = Homo sapiens
SEQUENCE: 965
tcgtcggtgg tcggcgcgtt ttt                                          23
```

-continued

```
SEQ ID NO: 966          moltype = DNA   length = 28
FEATURE                 Location/Qualifiers
source                  1..28
                        mol_type = unassigned DNA
                        organism = Homo sapiens
SEQUENCE: 966
aacccgcacc aaacaaacta cacgcaaa                                         28

SEQ ID NO: 967          moltype = DNA   length = 28
FEATURE                 Location/Qualifiers
source                  1..28
                        mol_type = unassigned DNA
                        organism = Homo sapiens
SEQUENCE: 967
gaatggtagc gagaggttgc gggttagg                                         28

SEQ ID NO: 968          moltype = DNA   length = 28
FEATURE                 Location/Qualifiers
source                  1..28
                        mol_type = unassigned DNA
                        organism = Homo sapiens
SEQUENCE: 968
ctctaccctc aaaatcgcga cgcaaacg                                         28

SEQ ID NO: 969          moltype = DNA   length = 28
FEATURE                 Location/Qualifiers
source                  1..28
                        mol_type = unassigned DNA
                        organism = Homo sapiens
SEQUENCE: 969
aggagtagta ttgcgagggt ggagggtt                                         28

SEQ ID NO: 970          moltype = DNA   length = 28
FEATURE                 Location/Qualifiers
source                  1..28
                        mol_type = unassigned DNA
                        organism = Homo sapiens
SEQUENCE: 970
cgccaatccc gctccgacac tataacaa                                         28

SEQ ID NO: 971          moltype = DNA   length = 28
FEATURE                 Location/Qualifiers
source                  1..28
                        mol_type = unassigned DNA
                        organism = Homo sapiens
SEQUENCE: 971
ataaggtttg gtggaagcgt aggagcgt                                         28

SEQ ID NO: 972          moltype = DNA   length = 28
FEATURE                 Location/Qualifiers
source                  1..28
                        mol_type = unassigned DNA
                        organism = Homo sapiens
SEQUENCE: 972
acgatattct aacctccgcc gcgaaact                                         28

SEQ ID NO: 973          moltype = DNA   length = 28
FEATURE                 Location/Qualifiers
source                  1..28
                        mol_type = unassigned DNA
                        organism = Homo sapiens
SEQUENCE: 973
ggtagaggga tagggaagag tttggcgt                                         28

SEQ ID NO: 974          moltype = DNA   length = 28
FEATURE                 Location/Qualifiers
source                  1..28
                        mol_type = unassigned DNA
                        organism = Homo sapiens
SEQUENCE: 974
attcaaaacg cgcgcgacga aattcaac                                         28

SEQ ID NO: 975          moltype = DNA   length = 28
FEATURE                 Location/Qualifiers
source                  1..28
                        mol_type = unassigned DNA
                        organism = Homo sapiens
SEQUENCE: 975
```

-continued

```
gcggagtggg agggttatat tgggagag                                    28

SEQ ID NO: 976          moltype = DNA   length = 28
FEATURE                 Location/Qualifiers
source                  1..28
                        mol_type = unassigned DNA
                        organism = Homo sapiens
SEQUENCE: 976
ccgaacaaaa ctacgacacc gccgaaaa                                    28

SEQ ID NO: 977          moltype = DNA   length = 28
FEATURE                 Location/Qualifiers
source                  1..28
                        mol_type = unassigned DNA
                        organism = Homo sapiens
SEQUENCE: 977
acgacgggtt gagataggtg gttggatt                                    28

SEQ ID NO: 978          moltype = DNA   length = 28
FEATURE                 Location/Qualifiers
source                  1..28
                        mol_type = unassigned DNA
                        organism = Homo sapiens
SEQUENCE: 978
cccgacgcga aacaacgaac taaaacga                                    28

SEQ ID NO: 979          moltype = DNA   length = 28
FEATURE                 Location/Qualifiers
source                  1..28
                        mol_type = unassigned DNA
                        organism = Homo sapiens
SEQUENCE: 979
tttttgtacg ttttcggggt cggaggag                                    28

SEQ ID NO: 980          moltype = DNA   length = 28
FEATURE                 Location/Qualifiers
source                  1..28
                        mol_type = unassigned DNA
                        organism = Homo sapiens
SEQUENCE: 980
aatcgccgtc taaacaaatc gcgaacta                                    28

SEQ ID NO: 981          moltype = DNA   length = 29
FEATURE                 Location/Qualifiers
source                  1..29
                        mol_type = unassigned DNA
                        organism = Homo sapiens
SEQUENCE: 981
cggcggtcgc ggtttgtagt ttagaattg                                   29

SEQ ID NO: 982          moltype = DNA   length = 28
FEATURE                 Location/Qualifiers
source                  1..28
                        mol_type = unassigned DNA
                        organism = Homo sapiens
SEQUENCE: 982
acgcgcttcc actccgacta acaaatta                                    28

SEQ ID NO: 983          moltype = DNA   length = 27
FEATURE                 Location/Qualifiers
source                  1..27
                        mol_type = unassigned DNA
                        organism = Homo sapiens
SEQUENCE: 983
ggcgtcgttc gggttaagtt tggttgt                                     27

SEQ ID NO: 984          moltype = DNA   length = 28
FEATURE                 Location/Qualifiers
source                  1..28
                        mol_type = unassigned DNA
                        organism = Homo sapiens
SEQUENCE: 984
cacaacttac gcgaaacaac aacctcgc                                    28

SEQ ID NO: 985          moltype = DNA   length = 28
FEATURE                 Location/Qualifiers
source                  1..28
                        mol_type = unassigned DNA
                        organism = Homo sapiens
```

-continued

```
SEQUENCE: 985
tgggttggtg tcgcgcgaat ttttgttt                                              28

SEQ ID NO: 986          moltype = DNA   length = 28
FEATURE                 Location/Qualifiers
source                  1..28
                        mol_type = unassigned DNA
                        organism = Homo sapiens
SEQUENCE: 986
cctcctcccg caactacgaa aaccgata                                              28

SEQ ID NO: 987          moltype = DNA   length = 28
FEATURE                 Location/Qualifiers
source                  1..28
                        mol_type = unassigned DNA
                        organism = Homo sapiens
SEQUENCE: 987
gttgggggtt atgtttggcg cggaatag                                              28

SEQ ID NO: 988          moltype = DNA   length = 28
FEATURE                 Location/Qualifiers
source                  1..28
                        mol_type = unassigned DNA
                        organism = Homo sapiens
SEQUENCE: 988
cgcctatata aaacgtcgac gcgcgaaa                                              28

SEQ ID NO: 989          moltype = DNA   length = 28
FEATURE                 Location/Qualifiers
source                  1..28
                        mol_type = unassigned DNA
                        organism = Homo sapiens
SEQUENCE: 989
gttcgggcgt cgcggtcgtt tttatatt                                              28

SEQ ID NO: 990          moltype = DNA   length = 28
FEATURE                 Location/Qualifiers
source                  1..28
                        mol_type = unassigned DNA
                        organism = Homo sapiens
SEQUENCE: 990
aaaacgccca ttatacccgc gccaattc                                              28

SEQ ID NO: 991          moltype = DNA   length = 28
FEATURE                 Location/Qualifiers
source                  1..28
                        mol_type = unassigned DNA
                        organism = Homo sapiens
SEQUENCE: 991
taagaatcgg cggtagttag taggcggg                                             28

SEQ ID NO: 992          moltype = DNA   length = 28
FEATURE                 Location/Qualifiers
source                  1..28
                        mol_type = unassigned DNA
                        organism = Homo sapiens
SEQUENCE: 992
tcctacgccg cgacgaaaac aaaaactc                                              28

SEQ ID NO: 993          moltype = DNA   length = 28
FEATURE                 Location/Qualifiers
source                  1..28
                        mol_type = unassigned DNA
                        organism = Homo sapiens
SEQUENCE: 993
aggtggggcg cgtttattag tttaggggg                                            28

SEQ ID NO: 994          moltype = DNA   length = 28
FEATURE                 Location/Qualifiers
source                  1..28
                        mol_type = unassigned DNA
                        organism = Homo sapiens
SEQUENCE: 994
acctctccat cgctaatacc ctaccgct                                              28

SEQ ID NO: 995          moltype = DNA   length = 28
FEATURE                 Location/Qualifiers
source                  1..28
                        mol_type = unassigned DNA
```

-continued

```
                                organism = Homo sapiens
SEQUENCE: 995
gagtgtttcg agggtaggag gttgtcgg                                    28

SEQ ID NO: 996           moltype = DNA  length = 28
FEATURE                  Location/Qualifiers
source                   1..28
                         mol_type = unassigned DNA
                         organism = Homo sapiens
SEQUENCE: 996
caaaaaccgc ccgcaaaacg aaacctaa                                    28

SEQ ID NO: 997           moltype = DNA  length = 28
FEATURE                  Location/Qualifiers
source                   1..28
                         mol_type = unassigned DNA
                         organism = Homo sapiens
SEQUENCE: 997
acggatcgat cgcggttttg gtaaggat                                    28

SEQ ID NO: 998           moltype = DNA  length = 28
FEATURE                  Location/Qualifiers
source                   1..28
                         mol_type = unassigned DNA
                         organism = Homo sapiens
SEQUENCE: 998
cgcaaaaacg aaaaactacg tacgcgct                                    28

SEQ ID NO: 999           moltype = DNA  length = 27
FEATURE                  Location/Qualifiers
source                   1..27
                         mol_type = unassigned DNA
                         organism = Homo sapiens
SEQUENCE: 999
gttgtttgag gacgggtcgt ttagcgg                                     27

SEQ ID NO: 1000          moltype = DNA  length = 28
FEATURE                  Location/Qualifiers
source                   1..28
                         mol_type = unassigned DNA
                         organism = Homo sapiens
SEQUENCE: 1000
acccctatcc tacaaccta cgaacgca                                     28

SEQ ID NO: 1001          moltype = DNA  length = 28
FEATURE                  Location/Qualifiers
source                   1..28
                         mol_type = unassigned DNA
                         organism = Homo sapiens
SEQUENCE: 1001
tttcgggagg tgtggttacg tttggaga                                    28

SEQ ID NO: 1002          moltype = DNA  length = 28
FEATURE                  Location/Qualifiers
source                   1..28
                         mol_type = unassigned DNA
                         organism = Homo sapiens
SEQUENCE: 1002
cccctcctcc caacacccaa cactaaaa                                    28

SEQ ID NO: 1003          moltype = DNA  length = 30
FEATURE                  Location/Qualifiers
source                   1..30
                         mol_type = unassigned DNA
                         organism = Homo sapiens
SEQUENCE: 1003
ggttgtggtt tttaaaaggg aaaattcggg                                  30

SEQ ID NO: 1004          moltype = DNA  length = 28
FEATURE                  Location/Qualifiers
source                   1..28
                         mol_type = unassigned DNA
                         organism = Homo sapiens
SEQUENCE: 1004
taaacgccga aacccgaacg taacaacc                                    28

SEQ ID NO: 1005          moltype = DNA  length = 28
FEATURE                  Location/Qualifiers
source                   1..28
```

-continued

```
                          mol_type = unassigned DNA
                          organism = Homo sapiens
SEQUENCE: 1005
aggtgattag aagggagagg gggaggtt                                    28

SEQ ID NO: 1006          moltype = DNA  length = 28
FEATURE                  Location/Qualifiers
source                   1..28
                          mol_type = unassigned DNA
                          organism = Homo sapiens
SEQUENCE: 1006
tcattataca cgacgcgccc ctccaaat                                    28

SEQ ID NO: 1007          moltype = DNA  length = 28
FEATURE                  Location/Qualifiers
source                   1..28
                          mol_type = unassigned DNA
                          organism = Homo sapiens
SEQUENCE: 1007
tacgtgggtg taggttaggt cgggttga                                    28

SEQ ID NO: 1008          moltype = DNA  length = 29
FEATURE                  Location/Qualifiers
source                   1..29
                          mol_type = unassigned DNA
                          organism = Homo sapiens
SEQUENCE: 1008
accacgcgac taccgtataa acaaccgaa                                   29
```